(12) United States Patent
Chen et al.

(10) Patent No.: US 7,449,447 B2
(45) Date of Patent: Nov. 11, 2008

(54) PEPTIDOMIMETIC NS3-SERINE PROTEASE INHIBITORS OF HEPATITIS C VIRUS

(75) Inventors: Kevin X. Chen, Edison, NJ (US); F. George Njoroge, Warren, NJ (US); Weiying Yang, Edison, NJ (US); Bancha Vibulbhan, Kenilworth, NJ (US); Viyyoor M. Girijavallabhan, Parsippany, NJ (US); Srikanth Venkatraman, Woodbridge, NJ (US); Francisco Velazquez, Clinton, NJ (US)

(73) Assignee: Schering Corporation, Kenilworth, NJ (US)

( * ) Notice: Subject to any disclaimer, the term of this patent is extended or adjusted under 35 U.S.C. 154(b) by 493 days.

(21) Appl. No.: 10/925,329

(22) Filed: Aug. 24, 2004

(65) Prior Publication Data

US 2005/0085425 A1 Apr. 21, 2005

Related U.S. Application Data

(60) Provisional application No. 60/497,749, filed on Aug. 26, 2003.

(51) Int. Cl.
*A61K 38/06* (2006.01)
*C07K 5/08* (2006.01)
*C07D 209/02* (2006.01)

(52) U.S. Cl. .................. 514/18; 530/331; 548/452; 548/465; 546/200; 546/276.7

(58) Field of Classification Search .............. 514/18, 514/323; 530/331; 546/200, 276.7; 548/452, 548/465

See application file for complete search history.

(56) References Cited

U.S. PATENT DOCUMENTS 5,712,145 A 1/1998 Houghton et al.

FOREIGN PATENT DOCUMENTS

| EP | 0 381 216 B1 | 12/1995 |
|---|---|---|
| WO | WO 89/04669 | 6/1989 |
| WO | WO 98/14181 | 4/1998 |
| WO | WO 98/17679 | 4/1998 |
| WO | WO 98/22496 | 5/1998 |
| WO | WO 99/07734 | 2/1999 |
| WO | WO 00/09543 | 2/2000 |
| WO | WO 00/09558 | 2/2000 |
| WO | WO 01/77113 A2 | 10/2001 |
| WO | WO 01/81325 A2 | 11/2001 |
| WO | WO 02/08187 A1 | 1/2002 |
| WO | WO 02/08198 A2 | 1/2002 |
| WO | WO 02/08244 A2 | 1/2002 |
| WO | WO 02/08251 A2 | 1/2002 |
| WO | WO 02/08256 A2 | 1/2002 |
| WO | WO 02/48172 A2 | 6/2002 |
| WO | WO 02/079234 A1 | 10/2002 |

OTHER PUBLICATIONS

Berenguer, Marina, et al., "Hepatitis B and . . . ," Proceedings of the Association of American Physicians, 110(2):98-112 (1998).
Dimasi, Nazzareno, et al., "Characterization of Engineered . . . ," Journal of Virology 71(10):7461-7469 (Oct. 1997).
Elzouki, Abdul-Nasser, et al., "Serine protease inhibitors . . . ," Journal of Hepatology 27:42-48 (1997).
Failla, Cristina Maria, et al., "Redesigning the substrate . . . ," Folding & Design 1(1):35-42 (Jan. 10, 1996).
Han, Wei, et al., "Alpha-Ketoamides, Alpha-Ketoesters . . . ," Bioorganic & Medicinal Chemistry Letters 10:711-713 (2000).
Hoofnagle, Jay H., et al., "The Treatment of Chronic Viral Hepatitis," The New England Journal of Medicine 336(5):347-356 (Jan. 30, 1997).
Ingallinella, Paolo, et al, "Potent Peptide Inhibitors . . . ," Biochemistry 37:8906-8914 (1998).
Kolykhalov, Alexander A., et al., "Specificity of the . . . ," Journal of Virology 68(11):7525-7533 (Nov. 1994).
Komoda, Yasumasa, et al., "Substrate Requirements of . . . ," Journal of Virology 68(11):7351-7357 (Nov. 1994).
Landro, James A., et al., "Mechanistic Role of . . . ," Biochemistry 36:9340-9348 (1997).
Llinas-Brunet, Montse, et al., "Peptide-Based Inhibitors . . . ," Bioorganic & Medicinal Chemistry Letters 8:1713-1718 (1998).
Marchetti, Antonella, et al., "Synthesis of Two . . . ," Synlett S1:1000-1002 (1999).
Martin, F., et al., "Affinity selection of a . . . ," Protein Engineering 10(5):607-614 (1997).
Martin, Franck, et al., "Design of Selective . . . ," Biochemistry 37:11459-11468 (1998).

(Continued)

*Primary Examiner*—Charanjit S Aulakh
(74) *Attorney, Agent, or Firm*—Palaiyur S. Kalyanaraman; Serena Farquharson-Torres

(57) ABSTRACT

The present application discloses a compound, or enantiomers, stereoisomers, rotamers, tautomers, racemates or prodrug of said compound, or pharmaceutically acceptable salts or solvates of said compound, or of said prodrug, said compound having the general structure shown in Formula 1:

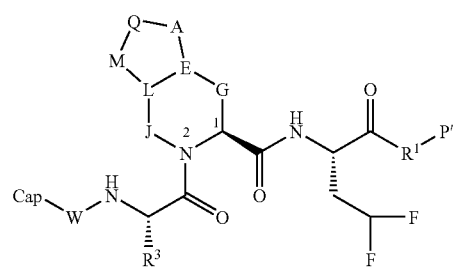

Formula 1 useful in the treatment or prevention or amelioration of one or more symptoms of hepatitis C.

41 Claims, No Drawings

OTHER PUBLICATIONS

Orvieto, Federica, et al., "Novel, Potent Phenethylamide . . . ," Bioorganic & Medicinal Chemistry Letters 13:2745-2748 (2003).
Pizzi, Elisabetta, et al., "Molecular model of . . . ," Proc. Natl. Acad. Sci. USA 91:888-892 (Feb. 1994).
BioWorld Today, 9(217):4 (Nov. 10, 1998).
U.S. Appl. No. 10/052,386, filed Jan. 18, 2002.
Orvieto, Federica, et al., "Novel, Potent Phenethylamide Inhibitors . . .", Bioorganic & Medicinal Chemistry Letters, 13:2745-2748 (2003).
PCT International Search Report dated Jul. 19, 2005 for corresponding PCT Application No. PCT/US2004/027422.

PEPTIDOMIMETIC NS3-SERINE PROTEASE INHIBITORS OF HEPATITIS C VIRUS

FIELD OF INVENTION

The present invention relates to novel hepatitis C virus ("HCV") protease inhibitors, pharmaceutical compositions containing one or more such inhibitors, methods of preparing such inhibitors and methods of using such inhibitors to treat hepatitis C and related disorders. This invention specifically discloses novel peptidomimetic compounds as inhibitors of the HCV NS3/NS4a serine protease. This application claims the benefit of priority from U.S. provisional patent application Ser. No. 60/497,749, filed Aug. 26, 2003.

BACKGROUND OF THE INVENTION

Hepatitis C virus (HCV) is a (+)-sense single-stranded RNA virus that has been implicated as the major causative agent in non-A, non-B hepatitis (NANBH), particularly in blood-associated NANBH (BB-NANBH) (see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliar cirrhosis.

Recently, an HCV protease necessary for polypeptide processing and viral replication has been identified, cloned and expressed; (see, e.g., U.S. Pat. No. 5,712,145). This approximately 3000 amino acid polyprotein contains, from the amino terminus to the carboxy terminus, a nucleocapsid protein (C), envelope proteins (E1 and E2) and several non-structural proteins (NS1, 2, 3, 4a, 5a and 5b). NS3 is an approximately 68 kda protein, encoded by approximately 1893 nucleotides of the HCV genome, and has two distinct domains: (a) a serine protease domain consisting of approximately 200 of the N-terminal amino acids; and (b) an RNA-dependent ATPase domain at the C-terminus of the protein. The NS3 protease is considered a member of the chymotrypsin family because of similarities in protein sequence, overall three-dimensional structure and mechanism of catalysis. Other chymotrypsin-like enzymes are elastase, factor Xa, thrombin, trypsin, plasmin, urokinase, tPA and PSA. The HCV NS3 serine protease is responsible for proteolysis of the polypeptide (polyprotein) at the NS3/NS4a, NS4a/NS4b, NS4b/NS5a and NS5a/NS5b junctions and is thus responsible for generating four viral proteins during viral replication. This has made the HCV NS3 serine protease an attractive target for antiviral chemotherapy. The inventive compounds can inhibit such protease. They can also modulate the processing of hepatitis C virus (HCV) polypeptide.

It has been determined that the NS4a protein, an approximately 6 kda polypeptide, is a co-factor for the serine protease activity of NS3. Autocleavage of the NS3/NS4a junction by the NS3/NS4a serine protease occurs intramolecularly (i.e., cis) while the other cleavage sites are processed intermolecularly (i.e., trans).

Analysis of the natural cleavage sites for HCV protease revealed the presence of cysteine at P1 and serine at P1' and that these residues are strictly conserved in the NS4a/NS4b, NS4b/NS5a and NS5a/NS5b junctions. The NS3/NS4a junction contains a threonine at P1 and a serine at P1'. The Cys→Thr substitution at NS3/NS4a is postulated to account for the requirement of cis rather than trans processing at this junction. See, e.g., Pizzi et al. (1994) Proc. Natl. Acad. Sci (USA) 91:888-892, Failla et al. (1996) Folding & Design 1:35-42. The NS3/NS4a cleavage site is also more tolerant of mutagenesis than the other sites. See, e.g., Kollykhalov et al. (1994) J. Virol. 68:7525-7533. It has also been found that acidic residues in the region upstream of the cleavage site are required for efficient cleavage. See, e.g., Komoda et al. (1994) J. Virol. 68:7351-7357.

Inhibitors of HCV protease that have been reported include antioxidants (see, International Patent Application Publication No. WO 98/14181), certain peptides and peptide analogs (see, International Patent Application Publication No. WO 98/17679, Landro et al. (1997) Biochem. 36:9340-9348, Ingallinella et al. (1998) Biochem. 37:8906-8914, Llinàs-Brunet et al. (1998) Bioorg. Med. Chem. Lett. 8:1713-1718), inhibitors based on the 70-amino acid polypeptide eglin c (Martin et al. (1998) Biochem. 37:11459-11468, inhibitors affinity selected from human pancreatic secretory trypsin inhibitor (hPSTI-C3) and minibody repertoires (MBip) (Dimasi et al. (1997) J. Virol. 71:7461-7469), $cV_HE2$ (a "camelized" variable domain antibody fragment) (Martin et al. (1997) Protein Eng. 10:607-614), and α1-antichymotrypsin (ACT) (Elzouki et a.) (1997) J. Hepat. 27:42-28). A ribozyme designed to selectively destroy hepatitis C virus RNA has recently been disclosed (see, BioWorld Today 9(217): 4 (Nov. 10, 1998)).

Reference is also made to the PCT Publications, No. WO 98/17679, published Apr. 30, 1998 (Vertex Pharmaceuticals Incorporated); WO 98/22496, published May 28, 1998 (F. Hoffmann-La Roche AG); and WO 99/07734, published Feb. 18, 1999 (Boehringer Ingelheim Canada Ltd.).

HCV has been implicated in cirrhosis of the liver and in induction of hepatocellular carcinoma. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10-30%, whereas those with localized unresectable hepatocellular carcinoma have a five-year survival rate of less than 1%.

Reference is made to A. Marchetti et al, Synlett, S1, 1000-1002 (1999) describing the synthesis of bicylic analogs of an inhibitor of HCV NS3 protease. A compound disclosed therein has the formula:

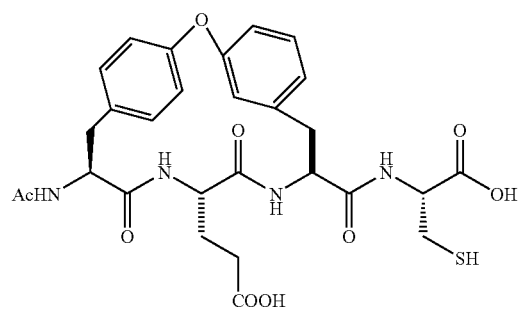

Reference is also made to W. Han et al, Bioorganic & Medicinal Chem. Lett, (2000) 10, 711-713, which describes the preparation of certain α-ketoamides, α-ketoesters and α-diketones containing allyl and ethyl functionalities.

Reference is also made to WO 00/09558 (Assignee: Boehringer Ingelheim Limited; Published Feb. 24, 2000) which discloses peptide derivatives of the formula:

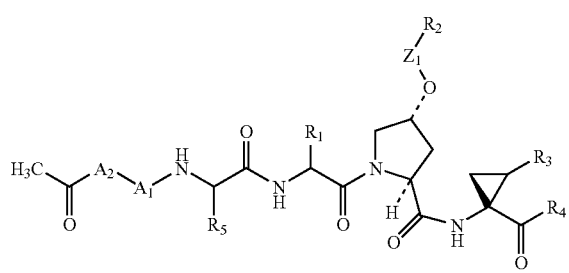

where the various elements are defined therein. An illustrative compound of that series is:

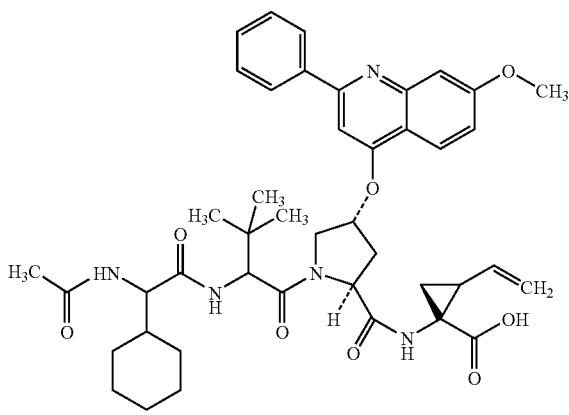

Reference is also made to WO 00/09543 (Assignee: Boehringer Ingelheim Limited; Published Feb. 24, 2000) which discloses peptide derivatives of the formula:

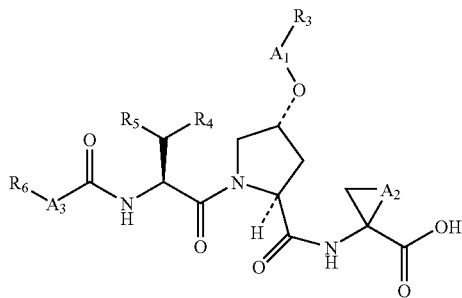

where the various elements are defined therein. An illustrative compound of that series is:

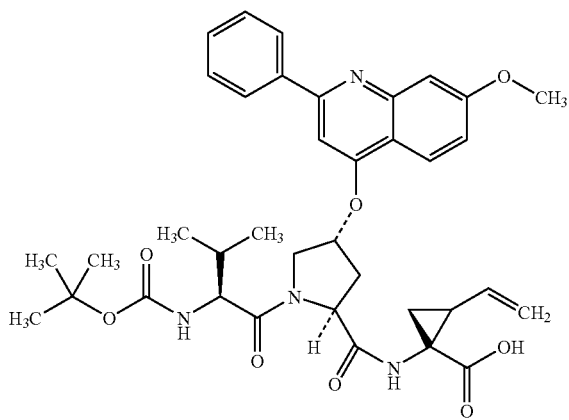

Reference is also made to a recent publication by F. Orvieto et al, *Bioorganic & Medicinal Chem. Lett.*, (2003), 13, 2745, which describes HCV NS3 Protease inhibitors an example of which is shown by the formula:

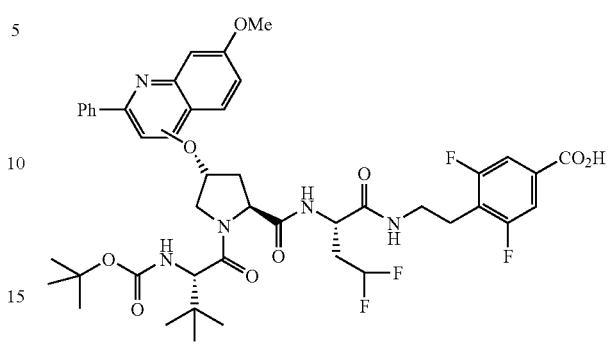

Reference is also made to WO2002079234 by S. Colarusso et al, which discloses the compound of the formula:

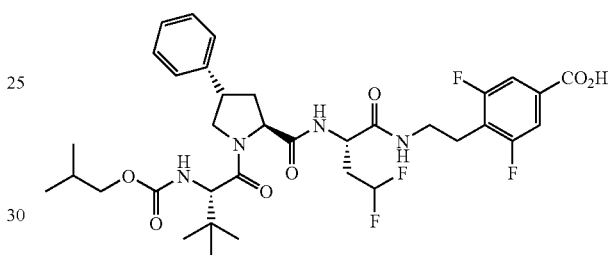

Current therapies for hepatitis C include interferon-α (INF$_\alpha$) and combination therapy with ribavirin and interferon. See, e.g., Beremguer et al. (1998) *Proc. Assoc. Am. Physicians* 110(2):98-112. These therapies suffer from a low sustained response rate and frequent side effects. See, e.g., Hoofnagle et al. (1997) *N. Engl. J. Med.* 336:347. Currently, no vaccine is available for HCV infection.

PCT Publications WO 01/77113; WO 01/081325; WO 02/08198; WO 02/08256; WO 02/08187; WO 02/08244; WO 02/48172; WO 02/08251; and pending U.S. patent application Ser. No. 10/052,386 filed Jan. 18, 2002 disclose various types of peptides and/or other compounds as NS-3 serine protease inhibitors of hepatitis C virus.

There is a need for new treatments and therapies for HCV infection. There is a need for compounds useful in the treatment or prevention or amelioration of one or more symptoms of hepatitis C.

There is a need for methods of treatment or prevention or amelioration of one or more symptoms of hepatitis C.

There is a need for methods for modulating the activity of serine proteases, particularly the HCV NS3/NS4a serine protease, using the compounds provided herein.

There is a need for methods of modulating the processing of the HCV polypeptide using the compounds provided herein.

SUMMARY OF THE INVENTION

In its many embodiments, the present invention provides a novel class of inhibitors of the HCV protease, pharmaceutical compositions containing one or more of the compounds, methods of preparing pharmaceutical formulations comprising one or more such compounds, and methods of treatment, prevention or amelioration of one or more of the symptoms of hepatitis C. Also provided are methods of modulating the interaction of an HCV polypeptide with HCV protease. The compounds provided herein can inhibit HCV NS3/NS4a serine protease activity. The present application discloses compounds having the general structure shown in Formula 1:

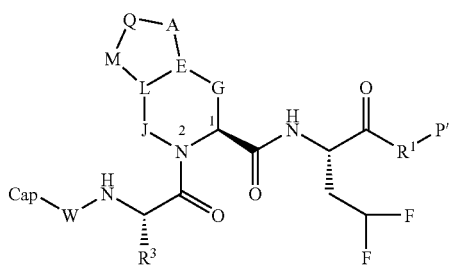

Formula 1 or pharmaceutically acceptable salts, solvates or esters of said compounds, wherein:

Cap and P' are independently H, alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arlylalkyloxy or heterocyclylamino, wherein each of said alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arlylalkyloxy or heterocyclylamino can be unsubstituted or optionally independently substituted with one or two substituents which can be the same or different and are independently selected from $X^1$ and $X^2$;

$X^1$ is alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl, or heteroarylalkyl, and $X^1$ can be unsubstituted or optionally independently substituted with one or more of $X^2$ moieties which can be the same or different and are independently selected;

$X^2$ is hydroxy, alkyl, aryl, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, keto, ester or nitro, wherein each of said alkyl, alkoxy, and aryl can be unsubstituted or optionally independently substituted with one or more moieties which can be the same or different and are independently selected from alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl and heteroarylalkyl;

W may be present or absent, and when W is present W is C(=O), C(=S), C(=NH), C(=N—OH), C(=N—CN), S(O) or S(O$_2$);

Q maybe present or absent, and when Q is present, Q is N(R), P(R), CR=CR', (CH$_2$)$_p$, (CHR)$_p$, (CRR')$_p$, (CHR—CHR')$_p$, O, S, S(O) or S(O$_2$); when Q is absent, M is (i) either directly linked to A or (ii) M is an independent substituent on L and A is an independent substituent on E, with said independent substituent being selected from —OR, —CH(R)(R'), S(O)$_{0-2}$R or —NRR'; when both Q and M are absent, A is either directly linked to L, or A is an independent substituent on E, selected from —OR, —CH(R)(R'), S(O)$_{0-2}$R or —NRR';

A is present or absent and if present A is O, O(R) CH$_2$, (CHR)$_p$, (CHR—CHR')$_p$, (CRR')$_p$, N(R), NRR', S, or S(O$_2$), and when Q is absent, A is —OR, —CH(R)(R') or —NRR'; and when A is absent, either Q and E are connected by a bond or Q is an independent substituent on M;

E is present or absent and if present E is CH, N, C(R);

G may be present or absent, and when G is present, G is (CH$_2$)$_p$, (CHR)$_p$, or (CRR')$_p$; when G is absent, J is present and E is directly connected to the carbon atom marked position 1;

J may be present or absent, and when J is present, J is (CH$_2$)$_p$, (CHR—CHR')$_p$, (CHR)$_p$, (CRR')$_p$, S(O$_2$), N(H), N(R) or 0; when J is absent and G is present, L is directly linked to the nitrogen atom marked position 2;

L may be present or absent, and when L is present, L is CH, N, or CR; when L is absent, M is present or absent; if M is present with L being absent, then M is directly and independently linked to E, and J is directly and independently linked to E;

M may be present or absent, and when M is present, M is O, N(R), S, S(O$_2$), (CH$_2$)$_p$, (CHR)$_p$, (CHR—CHR')$_p$, or (CRR')$_p$;

p is a number from 0 to 6;

R, R' and $R^3$ can be the same or different, each being independently selected from the group consisting of: H, $C_1$-$C_{10}$ alkyl, $C_2$-$C_{10}$ alkenyl, $C_3$-$C_8$ cycloalkyl, $C_3$-$C_8$ heterocyclyl, alkoxy, aryloxy, alkylthio, arylthio, amino, amido, arylthioamino, arylcarbonylamino, arylaminocarboxy, alkylaminocarboxy, heteroalkyl, heteroalkenyl, alkenyl, alkynyl, aryl-alkyl, heteroarylalkyl, ester, carboxylic acid, carbamate, urea, ketone, aldehyde, cyano, nitro, halogen, (cycloalkyl)alkyl, aryl, heteroaryl, alkyl-aryl, alkylheteroaryl, alkyl-heteroaryl and (heterocyclyl)alkyl;

R and R' in (CRR') can be linked together such that the combination forms a cycloalkyl or heterocyclyl moiety; and $R^1$ is N(R) or O.

A further feature of the invention is a pharmaceutical composition containing as active ingredient at least one compound of Formula I together with at least one pharmaceutically acceptable carrier or excipient.

The invention also provides methods for preparing compounds of Formula I, as well as methods for treating diseases such as, for example, HCV, AIDS (Acquired Immune Deficiency Syndrome), and related disorders. The methods for treating comprise administering to a patient suffering from said disease or diseases a therapeutically effective amount of at least one compound of Formula I or a pharmaceutical composition comprising at least one compound of Formula I.

Also disclosed is the use of a compound of Formula I for the manufacture of a medicament for treating HCV, AIDS, and related disorders.

Also disclosed is a method of treatment of a hepatitis C virus associated disorder, comprising administering an effective amount of one or more of the inventive compounds.

Also disclosed is a method of modulating the activity of hepatitis C virus (HCV) protease, comprising contacting HCV protease with one or more inventive compounds.

Also disclosed is a method of treating, preventing, or ameliorating one or more symptoms of hepatitis C, comprising administering an effective amount of one or more of the inventive compounds.

DETAILED DESCRIPTION OF THE INVENTION

As used above, and throughout the specification, the following terms, unless otherwise indicated, shall be understood to have the meanings described below.

"Acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alicyclic" means an aliphatic structure including a cyclic structure with from 3-15 carbon atoms, and/or including a chain of linear or branched aliphatic carbon atoms. The alicyclic group can be optionally substituted with one or more "ring system substituents" which may be the same or different, and are as defined herein.

"Aliphatic" means and includes straight or branched chains of paraffinic, olefinic or acetylenic carbon atoms. The aliphatic group can be optionally substituted by one or more substituents which may be the same or different, each substituent being independently selected from the group consisting of H, halo, halogen, alkyl, aryl, cycloalkyl, cycloalkylamino, alkenyl, heterocyclic, alkynyl, cycloalkylaminocarbonyl, hydroxyl, thio, cyano, hydroxy, alkoxy, alkylthio, amino, —NH(alkyl), —NH(cycloalkyl), —N(alkyl)$_2$, carboxyl, —C(O)O-alkyl, heteroaryl, aralkyl, alkylaryl, aralkenyl, heteroaralkyl, alkylheteroaryl, heteroaralkenyl, heteroalkyl, carbonyl, hydroxyalkyl, aryloxy, aralkoxy, acyl, aroyl, nitro, amino, amido, ester, carboxylic acid aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkenyl, heterocyclyl, heterocyclenyl, carbamate, urea, ketone, aldehyde, cyano, sulfonamide, sulfoxide, sulfone, sulfonyl urea, sulfonyl, hydrazide, hydroxamate, S(alkyl)$Y_1Y_2$N-alkyl-, $Y_1Y_2$NC(O)— and $Y_1Y_2$NSO$_2$—, wherein $Y_1$ and $Y_2$ can be the same or different and are independently selected from the group consisting of hydrogen, alkyl, aryl, and aralkyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The term "alkenyl" includes substituted alkenyl which means that the alkenyl group may be substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "alkyl" includes substituted alkyl which means that the alkyl group may be substituted by one or more substituents which may be the same or different, each substituent being independently selected from the group consisting of H, halo, halogen, alkyl, aryl, cycloalkyl, cycloalkylamino, alkenyl, heterocyclic, alkynyl, cycloalkylaminocarbonyl, hydroxyl, thio, cyano, hydroxy, alkoxy, alkylthio, amino, —NH(alkyl), —NH(cycloalkyl), —N(alkyl)$_2$, carboxyl, —C(O)O-alkyl, heteroaryl, aralkyl, alkylaryl, aralkenyl, heteroaralkyl, alkylheteroaryl, heteroaralkenyl, heteroalkyl, carbonyl, hydroxyalkyl, aryloxy, aralkoxy, acyl, aroyl, nitro, amino, amido, ester, carboxylic acid aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkenyl, heterocyclyl, heterocyclenyl, carbamate, urea, ketone, aldehyde, cyano, sulfonamide, sulfoxide, sulfone, sulfonyl urea, sulfonyl, hydrazide, hydroxamate, S(alkyl)$Y_1Y_2$N-alkyl-, $Y_1Y_2$NC(O)— and $Y_1Y_2$NSO$_2$—, wherein $Y_1$ and $Y_2$ can be the same or different and are independently selected from the group consisting of hydrogen, alkyl, aryl, and aralkyl. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkylamino" means an —NH$_2$ or —NH$_3^+$ group in which one or more of the hydrogen atoms on the nitrogen is replaced by an alkyl group as defined above.

"Alkylaminocarbonyl" means an alkyl group attached to a nitrogen atom, which is attached to a carbonyl group through which the substituent is boned to the parent moiety, the whole is referred as a substituted amide;

"Alkylaryl" means an alkyl-aryl-group in which the alkyl and aryl are as previously described. Preferred alkylaryls comprise a lower alkyl group. Non-limiting examples of suitable alkylaryl groups include o-tolyl, p-tolyl and xylyl. The bond to the parent moiety is through the aryl.

"Alkylheteroaryl" means an alkyl group attached to a parent moiety via a heteroaryl group.

"Alkylsulfonyl" means an alkyl-S(O$_2$)— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The term "alkynyl" includes substituted alkynyl which means that the alkynyl group may be substituted by one or more substituents which may be the same or different, each substituent being independently selected from the group consisting of alkyl, aryl and cycloalkyl.

"Alkylthio" means an alkyl-S— group in which the alkyl group is as previously described. Non-limiting examples of suitable alkylthio groups include methylthio, ethylthio, i-propylthio and heptylthio. The bond to the parent moiety is through the sulfur.

"Alkoxy" or "Alkyloxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Amide" represents an amino group attached to a carbonyl group.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Aralkylthio" means an aralkyl-S— group in which the aralkyl group is as previously described. Non-limiting example of a suitable aralkylthio group is benzylthio. The bond to the parent moiety is through the sulfur.

"Aroyl" means an aryl-C(O)— group in which the aryl group is as previously described. The bond to the parent moiety is through the carbonyl. Non-limiting examples of suitable groups include benzoyl and 1- and 2-naphthoyl.

"Aryl" (sometimes abbreviated "ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Arylamino" means an —NH$_2$ or —NH$_3^+$ group in which one or more of the hydrogen atoms on the nitrogen is replaced by an aryl group as defined above.

"Arylcarbonyl" means a carbonyl group in which one or more of the hydrogen atoms on the carbonyl is replaced by an aryl group as defined above and wherein the bond to the parent moiety is through the carbonyl.

"Aryloxy" means an aryl-O— group in which the aryl group is as previously described. Non-limiting examples of suitable aryloxy groups include phenoxy and naphthoxy. The bond to the parent moiety is through the ether oxygen.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Arylsulfonyl" means an aryl-S(O$_2$)— group. The bond to the parent moiety is through the sulfonyl.

"Arylsulfinyl" means an aryl-S(O)— group. The bond to the parent moiety is through the sulfinyl.

"Arylthio" means an aryl-S— group in which the aryl group is as previously described. Non-limiting examples of suitable arylthio groups include phenylthio and naphthylthio. The bond to the parent moiety is through the sulfur.

Carbamates and urea substituents refer to groups with oxygens and nitrogens respectively adjacent an amide; representative carbamate and urea substituents include the following:

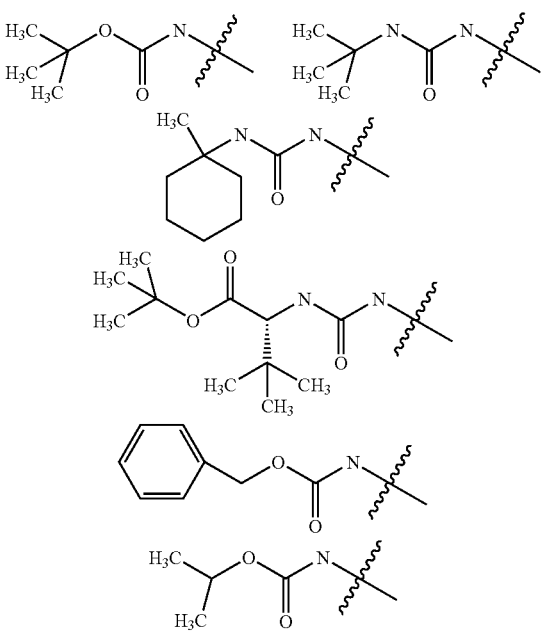

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl.

"Cycloalkylaminocarbonyl" means a cyclic alkyl group attached to a nitrogen atom, which is attached to a carbonyl group, the whole is referred as a substituted amide.

"Cycloalkoxycarbonyl" means a cyclic ring connected to an oxygen atom (e.g.—cyclohexyloxy), which is attached to a parent moiety via a carbonyl group, the whole is referred to as an ester linkage.

"Effective amount" or "therapeutically effective amount" is meant to describe an amount of compound or a composition of the present invention effective in inhibiting a hepatitis C virus ("HCV") protease and thus producing the desired therapeutic effect in a suitable patient.

"Ester" means an alkoxy group attached to a carbonyl group.

"Ether" means an oxygen atom attached, on both sides, to a carbon atom.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above.

"Heteroaliphatic" or "heteroalicyclic" means an otherwise aliphatic group or alicyclic group that contains at least one heteroatom (such as oxygen, nitrogen or sulfur). The terms heteroaliphatic and heteoalicyclic include substituted heteroaliphatic and heteroalicyclic.

"Heteroarylalkyl" means a heteroaryl substituent connected to a parent moiety via an alkyl moiety.

"Heteroalkenyl" means an alkenyl substituent connected to a heteroatom.

"Heterocyclic" means, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2- or 3-piperidinyl, 2- or 3-piperazinyl, 2- or 3-morpholinyl, or 2- or 3-thiomorpholinyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen, phosphorus, or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

Mammal means humans and other animals.

Patient includes both human and other mammals;

Prodrugs, esters and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The term "substituted" or "optionally substituted" means substitution or optional substitution with specified groups, or with one or more groups, moieties or radicals which can be the same or different, with each, for example, being independently selected.

"Ring system substituent" means a substituent attached to an aromatic or non-aromatic ring system which, for example, replaces an available hydrogen on the ring system. Ring system substituents may be the same or different, each being independently selected from the group consisting of H, halo, halogen, alkyl, aryl, cycloalkyl, cycloalkylamino, alkenyl, heterocyclic, alkynyl, cycloalkylaminocarbonyl, hydroxyl, thio, cyano, hydroxy, alkoxy, alkylthio, amino, —NH(alkyl), —NH(cycloalkyl), —N(alkyl)$_2$, carboxyl, —C(O)O-alkyl, heteroaryl, aralkyl, alkylaryl, aralkenyl, heteroaralkyl, alkylheteroaryl, heteroaralkenyl, heteroalkyl, carbonyl, hydroxyalkyl, aryloxy, aralkoxy, acyl, aroyl, nitro, amino, amido, ester, carboxylic acid aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkenyl, heterocyclyl, heterocyclenyl, carbamate, urea, ketone, aldehyde, cyano, sulfonamide, sulfoxide, sulfone, sulfonyl urea, sulfonyl, hydrazide, hydroxamate, $Y_1Y_2$N-alkyl-, $Y_1Y_2$NC(O)— and $Y_1Y_2$NSO$_2$—, wherein $Y_1$ and $Y_2$ can be the same or different and are independently selected from the group consisting of hydrogen, alkyl, aryl, and aralkyl. "Ring system substituent" also means a cyclic ring of 3 to 7 ring atoms of which 1-2 may be a heteroatom, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

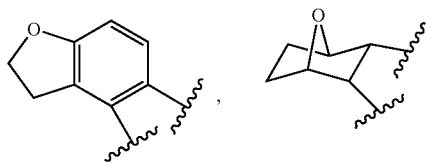

and the like.

The wavy line ～～～ as a bond generally indicates a mixture of, or either of, the possible isomers, e.g., containing (R)— and (S)— stereochemistry. For example,

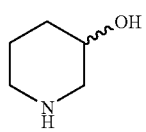

means containing both

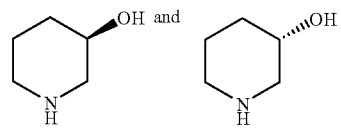

Lines drawn into the ring systems, such as, for example:

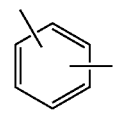

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

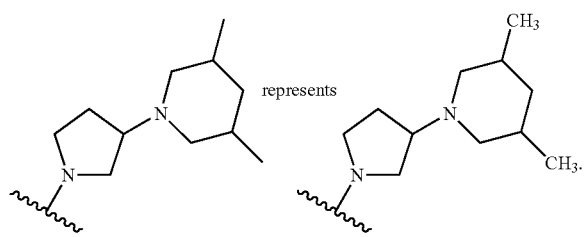

Further wherein the substituents listed above can be linked together in combinations to form one substituent. For example, an arylcycloakyl group would be a substituent comprising an aryl group attached to the parent moiety via a cycloalkyl group. Another example is an alkylthioamino group which is an alkyl group attached to a thio group which is attached to an amino group wherein the alkylthioamino substituent is connected to the parent moiety via the amino group. Also, the definitions above apply regardless of whether a term is used by itself or in combination with other terms. Hence the definition of "alkyl" applies to "alkyl" as well as to the "alkyl" portions of "alkoxy", "alkylamino" etc.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art.

As used herein, the term "composition" is intended to encompass a product comprising the specified ingredients in the specified amounts, as well as any product which results, directly or indirectly, from combination of the specified ingredients in the specified amounts.

It should also be noted that any Formula, compound, moiety or chemical illustration with unsatisfied valences in the present specification and/or claims herein is assumed to have the hydrogen atom to satisfy the valences.

When any variable (e.g., aryl, heterocycle, $R^2$, etc.) occurs more than one time in any constituent or in Formula 1 its definition on each occurrence is independent of its definition at every other occurrence. Also, combinations of substituents and/or variables are permissible only if such combinations result in stable compounds.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

Polymorphic forms of the compounds of Formula 1 and of the salts, esters, solvates and prodrugs of the compounds of Formula 1 are intended to be included in the present invention.

In one embodiment, the present invention discloses compounds of Formula 1 as inhibitors of HCV protease, especially the HCV NS3/NS4a serine protease, or a pharmaceutically acceptable derivative thereof, where the various definitions are given above.

In another embodiment, the present invention discloses compounds of Formula 1 wherein W is C=O and the portion of structural Formula 1 represented by Formula 2:

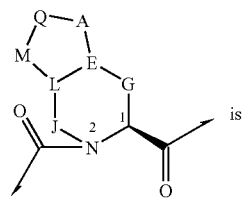

Formula 2 is

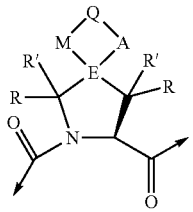

where the arrows ◄— and —► refer to points of connection of Formula 2 to the points shown in Formula 1. Similarly, in general, the arrows ◄— and —► on such Formulas elsewhere in this application too refer to the respective points of connection of the concerned Formula to the points shown in the structure of its parent Formula.

In an embodiment on the present invention, the portion represented by structural Formula 2 is selected from the group consisting of the following structures:

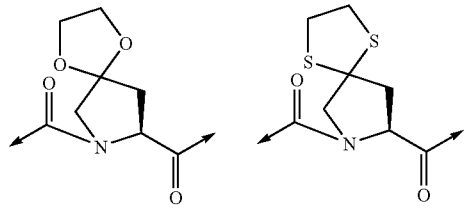

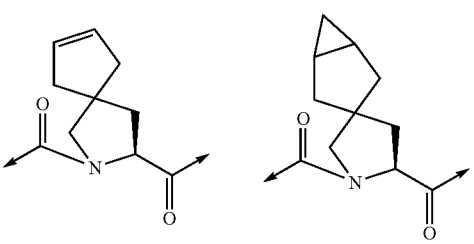

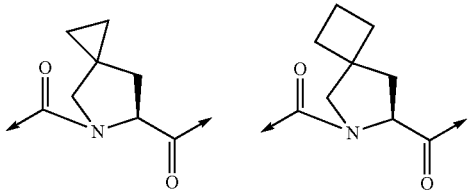

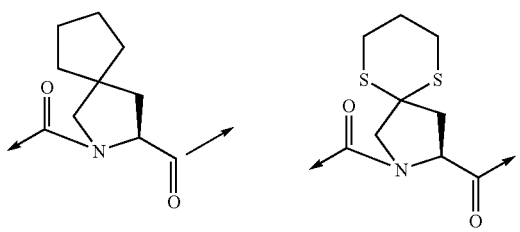

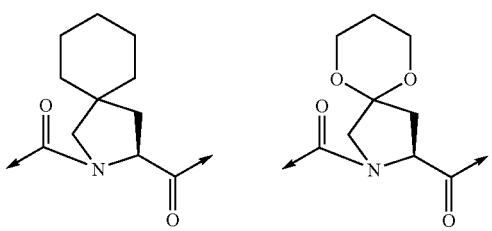

In another embodiment on the present invention, the portion represented by structural Formula 2 is selected from the group consisting of the following structures:

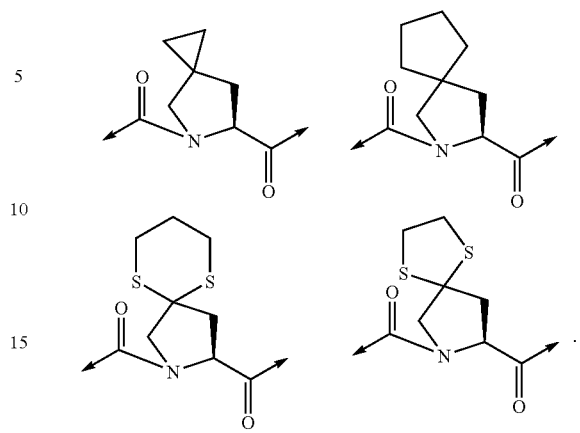

In another embodiment of the present invention, W is C=O and the portion represented by structural Formula 2:

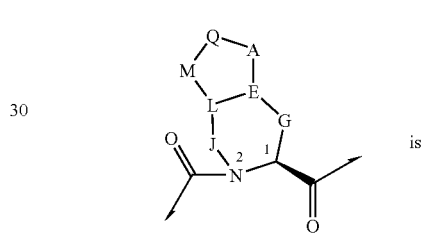

is

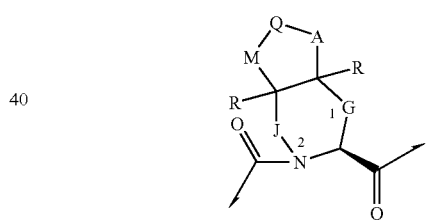

In another embodiment of the present invention, the portion represented by structural Formula 2 is selected from the group consisting of the following structures:

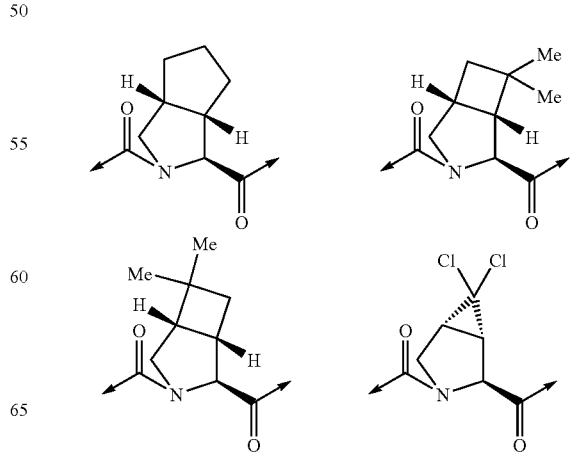

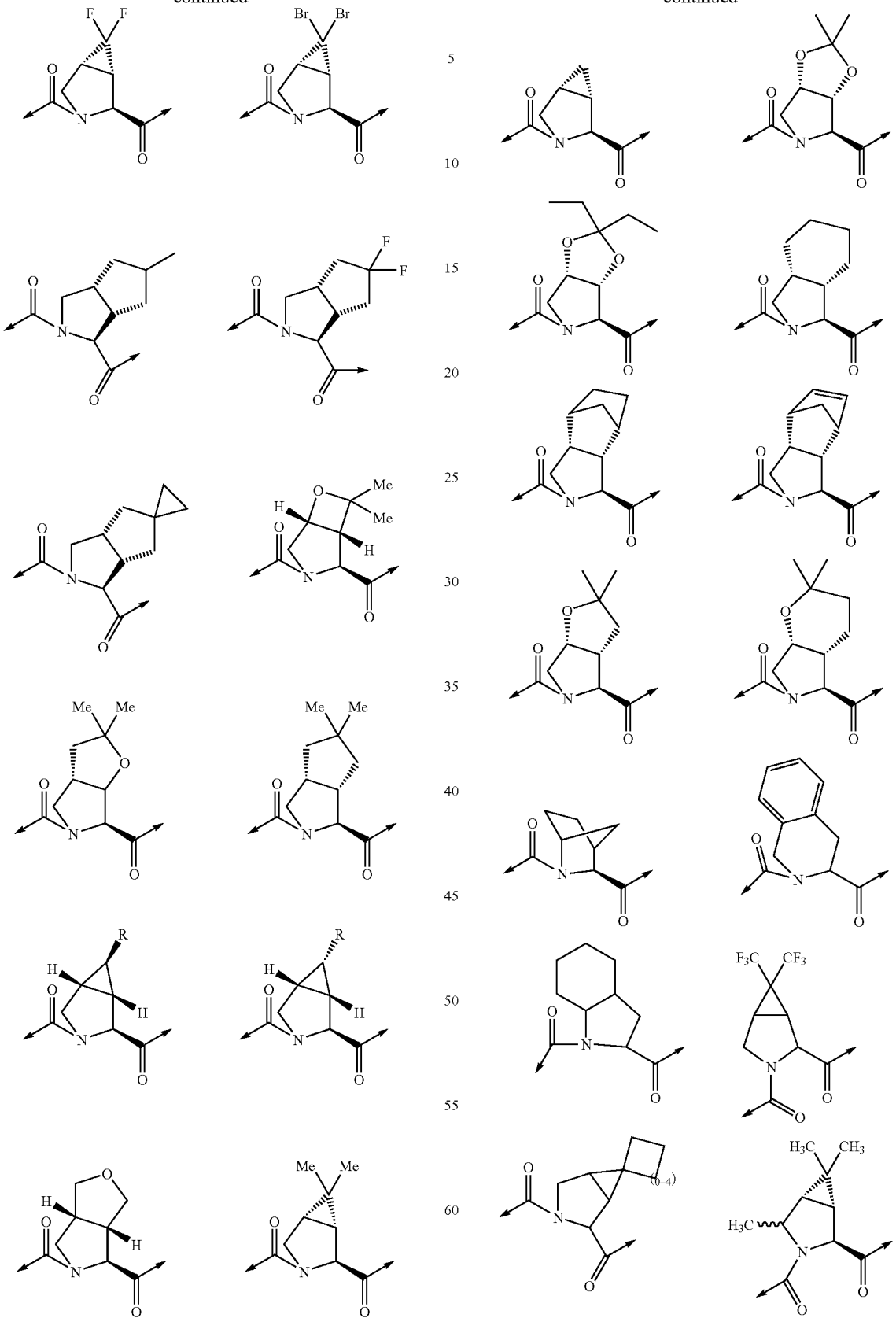

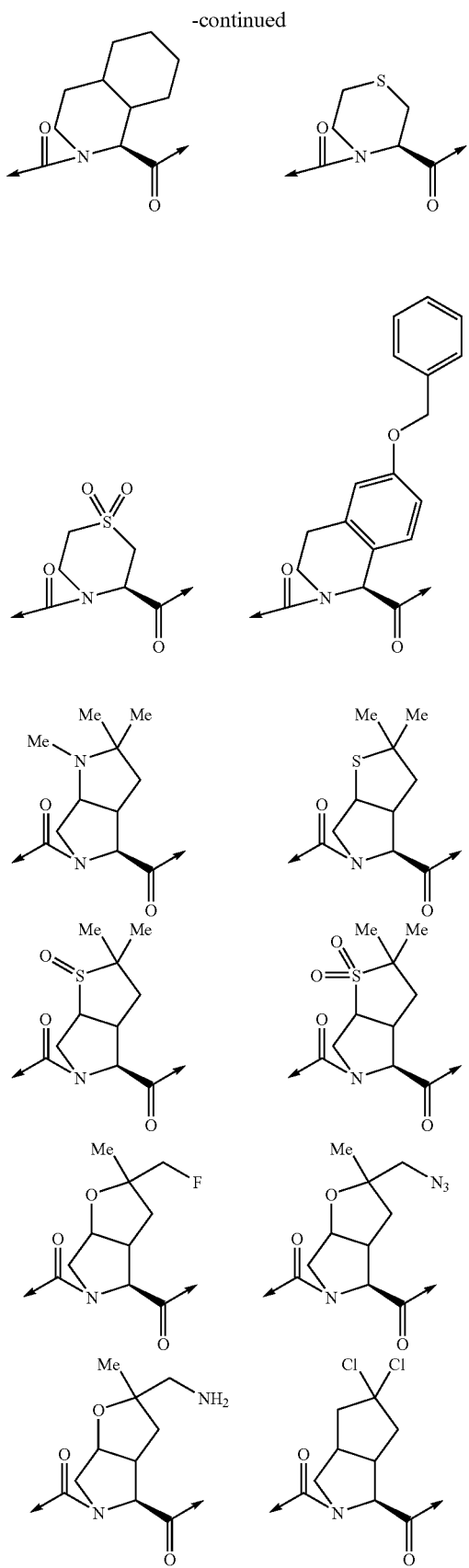
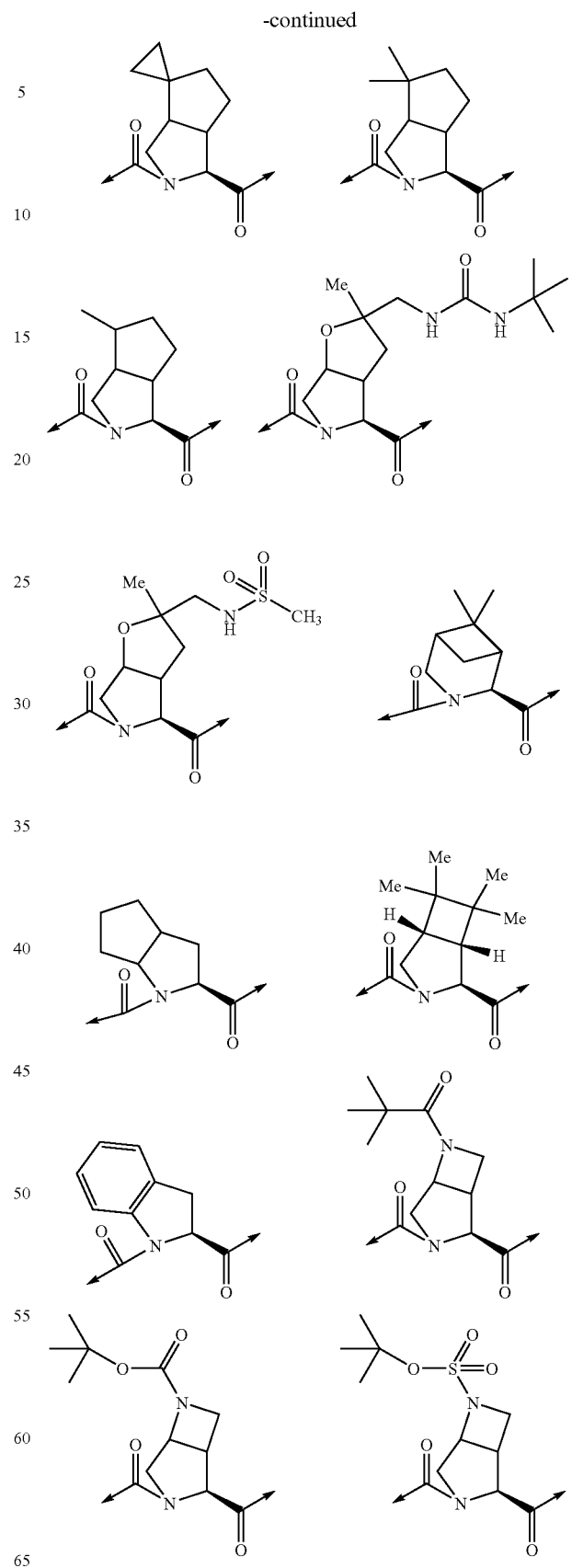

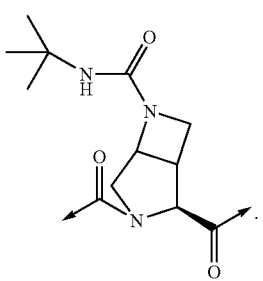
In another embodiment of the present invention, the portion represented by structural Formula 2 is selected from the group consisting of the following structures:
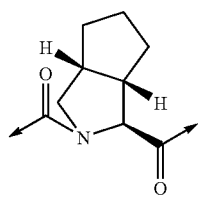 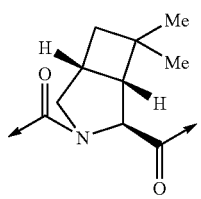
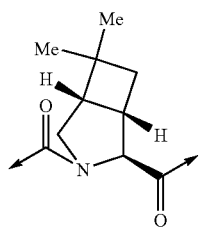 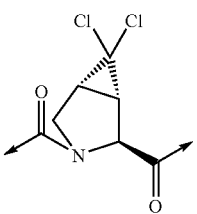
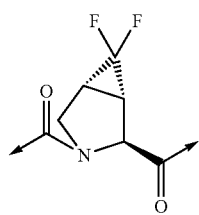 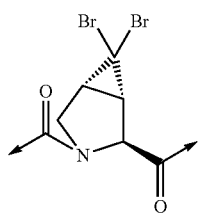
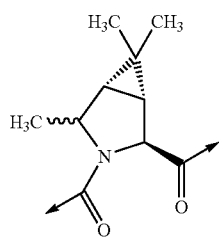 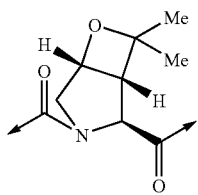
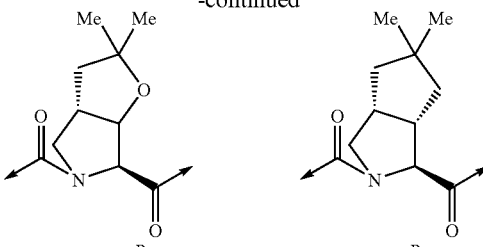
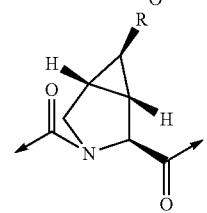
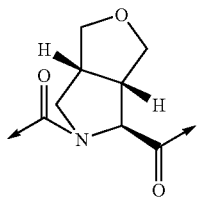 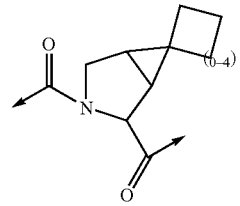
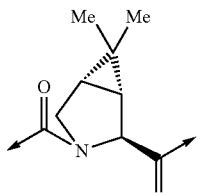 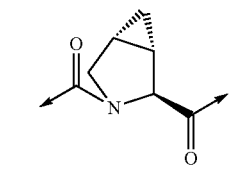
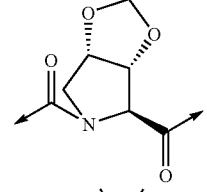 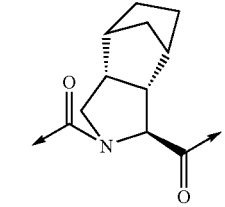
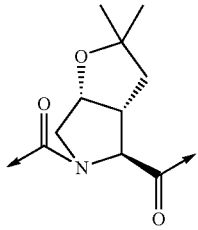 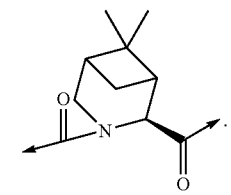
In another embodiment of the present invention, the portion represented by structural Formula 2 is selected from the group consisting of the following structures:
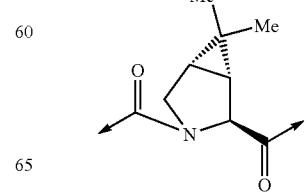 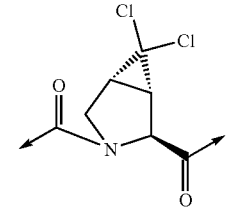

-continued

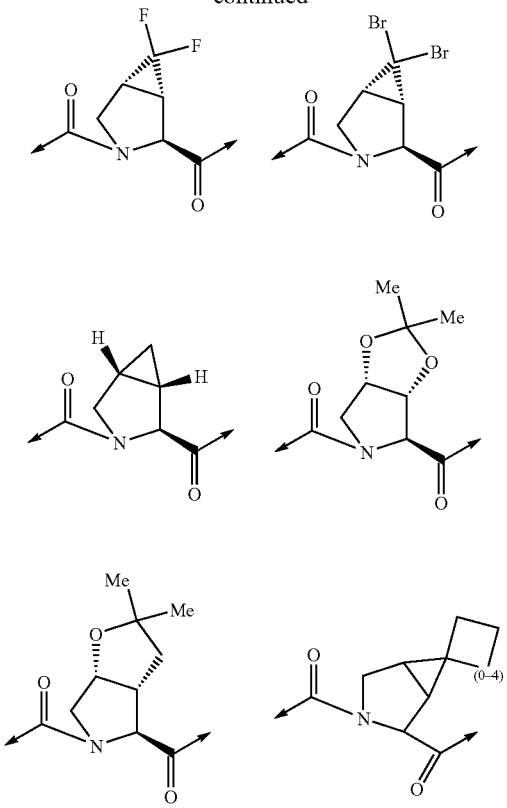

In another embodiment of the present invention, the portion represented by structural Formula 2 is selected from the group consisting of the following structures:

-continued

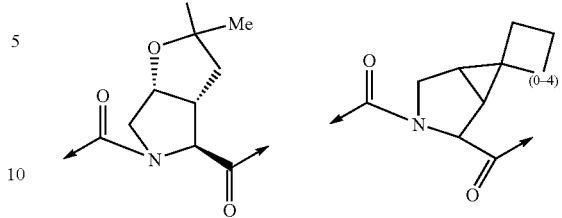

In another aspect of the present invention, W is C=O and the portion represented by structural Formula 2:

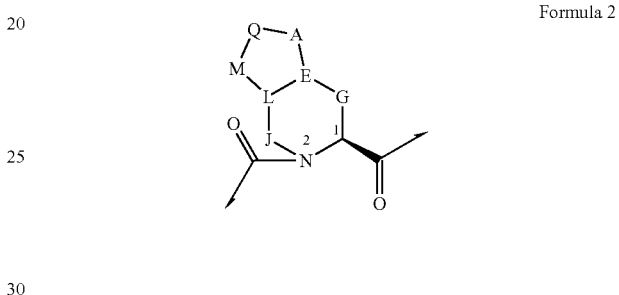

Formula 2 is selected from the following structures:

In another aspect of the present invention, the portion represented by structural Formula 2 is selected from the group consisting of the following structures:

-continued
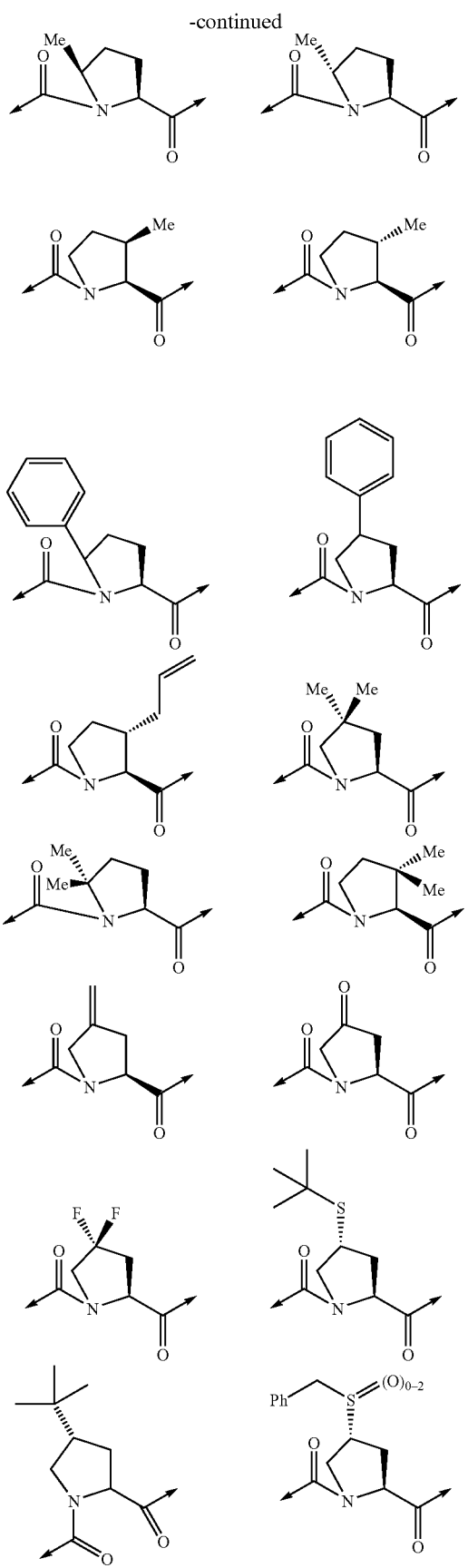
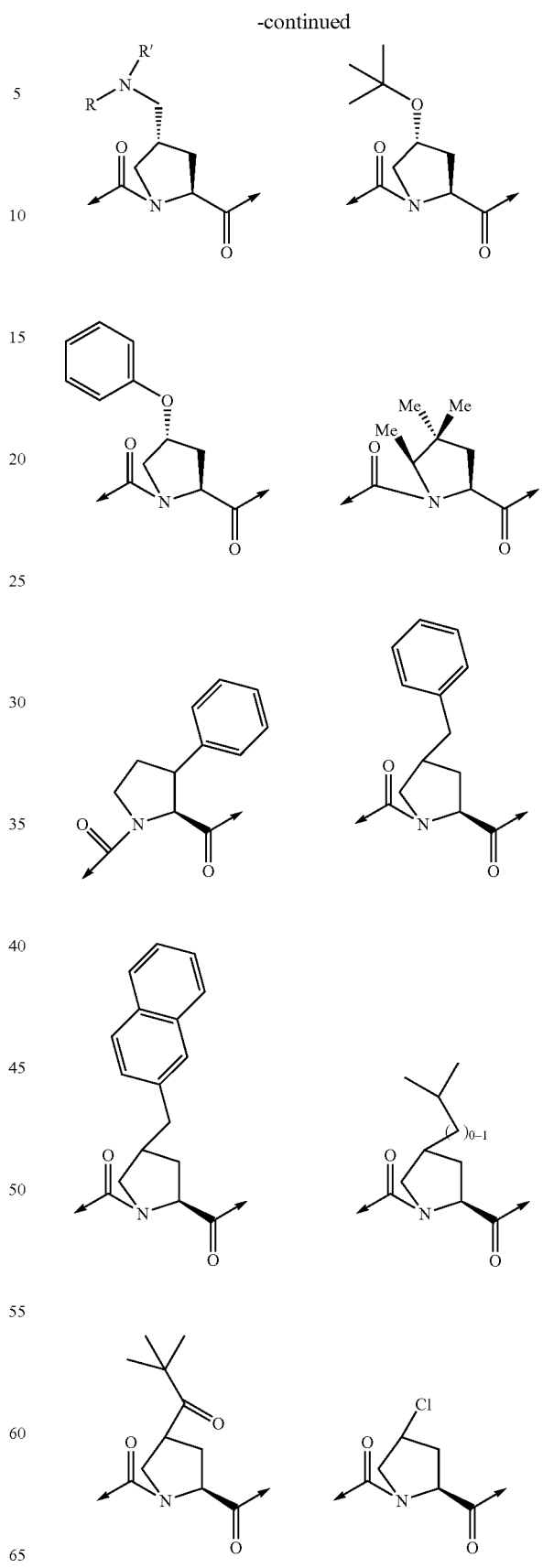

-continued
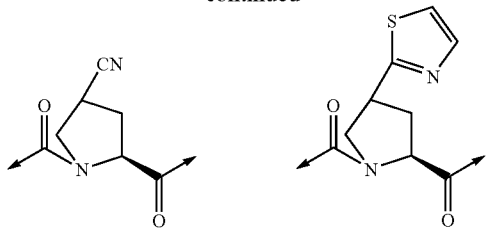
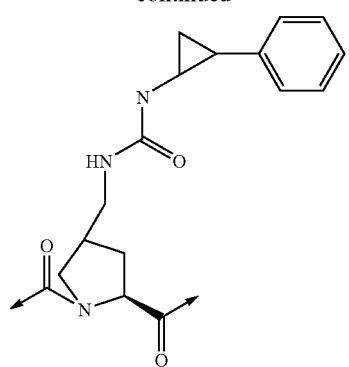
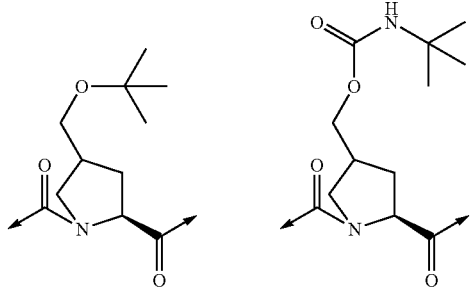
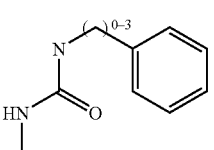
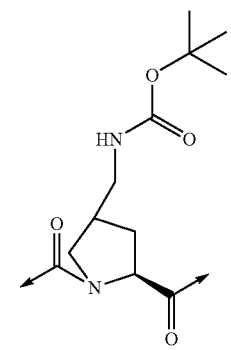
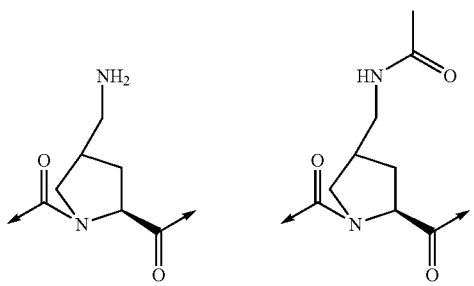
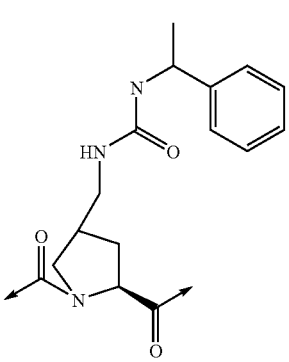
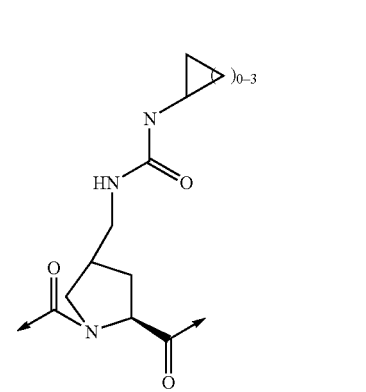
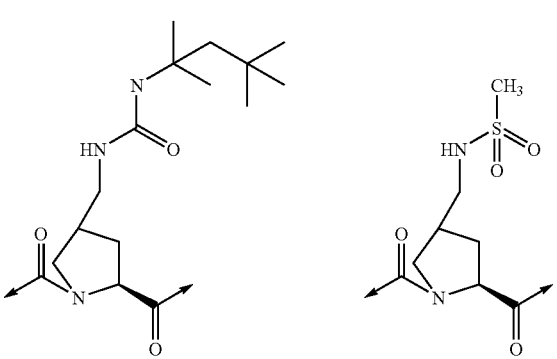

-continued

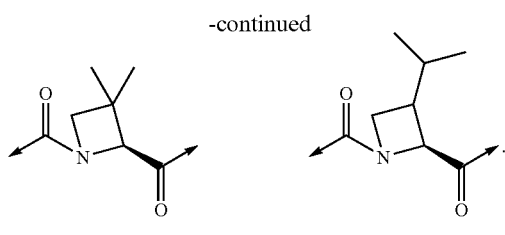

In another aspect of the present invention, the portion represented by structural Formula 2 is selected from the group consisting of the following structures:

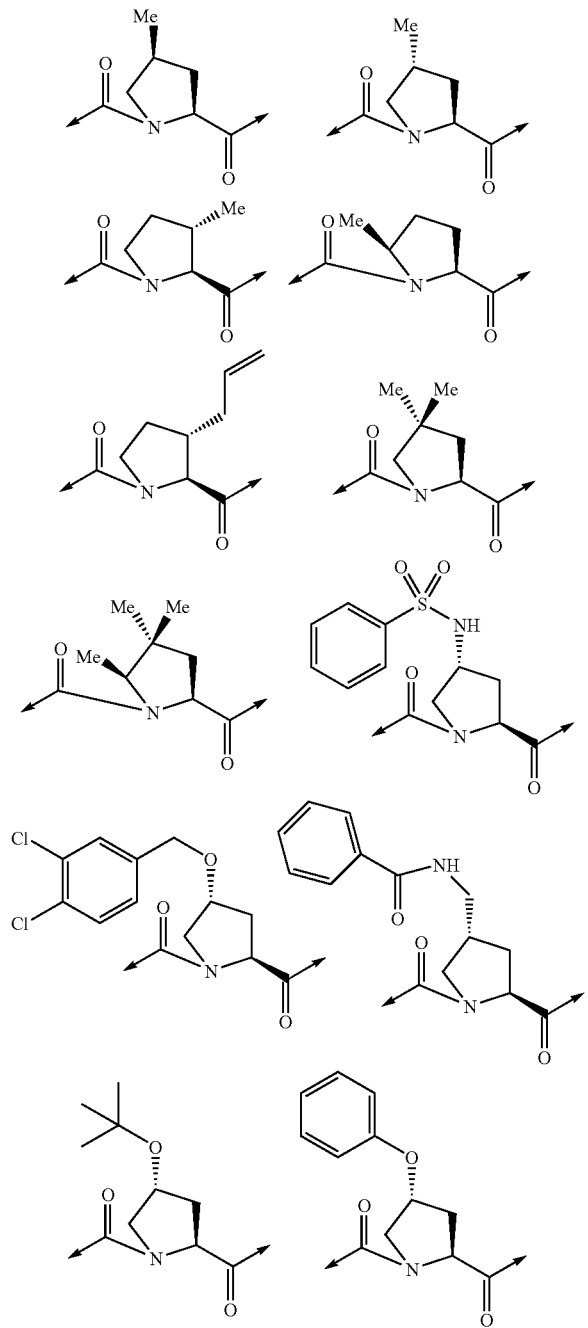

-continued

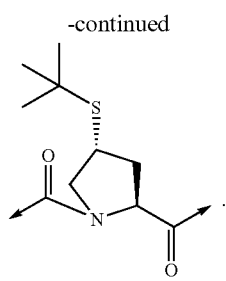

In another aspect of the present invention, W is C=O and the portion represented by structural Formula 2:

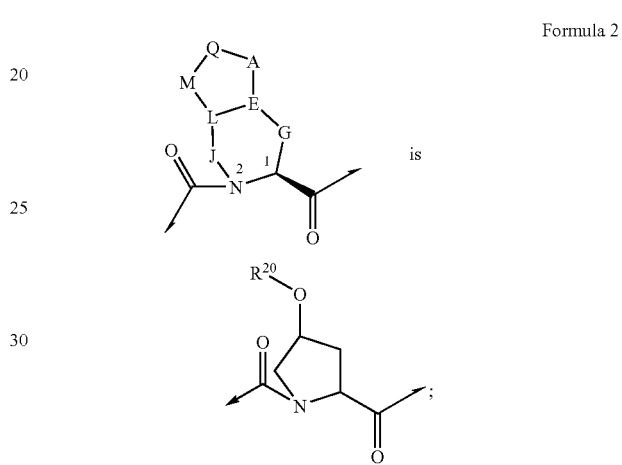

is where $R^{20}$ is selected from the group consisting of the following structures:

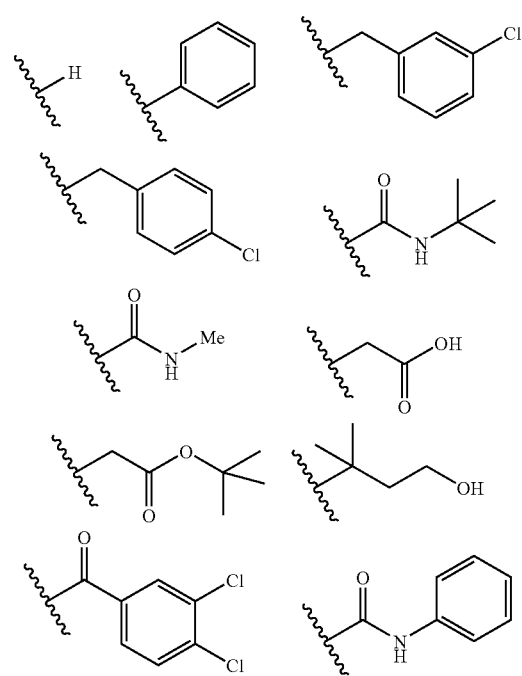

-continued

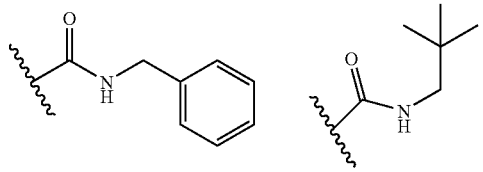

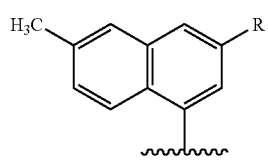

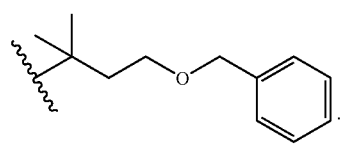

In another aspect of the present invention, the portion represented by structural Formula 2:

Formula 2

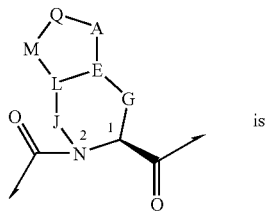

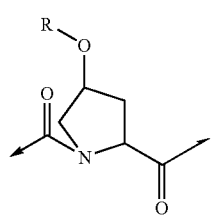

with the proviso that R is not a substituted or unsubstituted quinoline or quinoline derivative, and still more preferably wherein R is selected from the group consisting of: H, $C_1$-$C_{10}$ alkyl, $C_2$-$C_{10}$ alkenyl, $C_3$-$C_8$ cycloalkyl, $C_3$-$C_8$ heterocyclyl, alkoxy, aryloxy, alkylthio, arylthio, amino, amido, arylthioamino, arylcarbonylamino, arylaminocarboxy, alkylaminocarboxy, heteroalkyl, heteroalkenyl, alkenyl, alkynyl, arylalkyl, ester, carboxylic acid, carbamate, urea, ketone, aldehyde, cyano, nitro, halogen, (cycloalkyl)alkyl, aryl, alkyl-aryl, and (heterocyclyl)alkyl, wherein said cycloalkyl moieties are made of three to eight carbon atoms, and zero to six oxygen, nitrogen, sulfur, or phosphorus atoms.

In a still another aspect of the present invention, W is C=O and the portion represented by structural Formula 2:

Formula 2

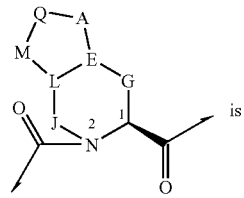
is

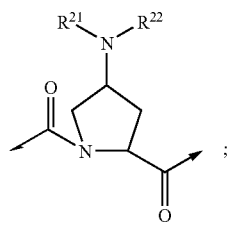
;

where $R^{21}$ and $R^{22}$ may be the same or different and are independently selected from the group consisting of the following structures:

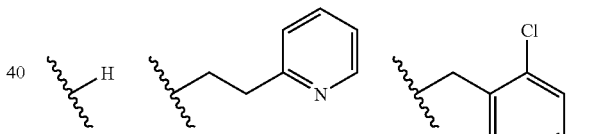

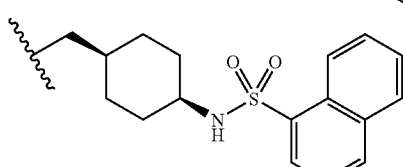

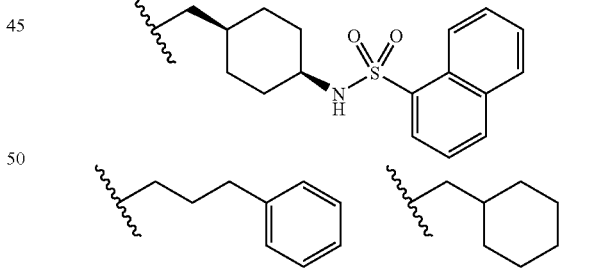

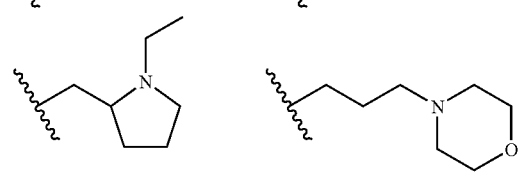

-continued

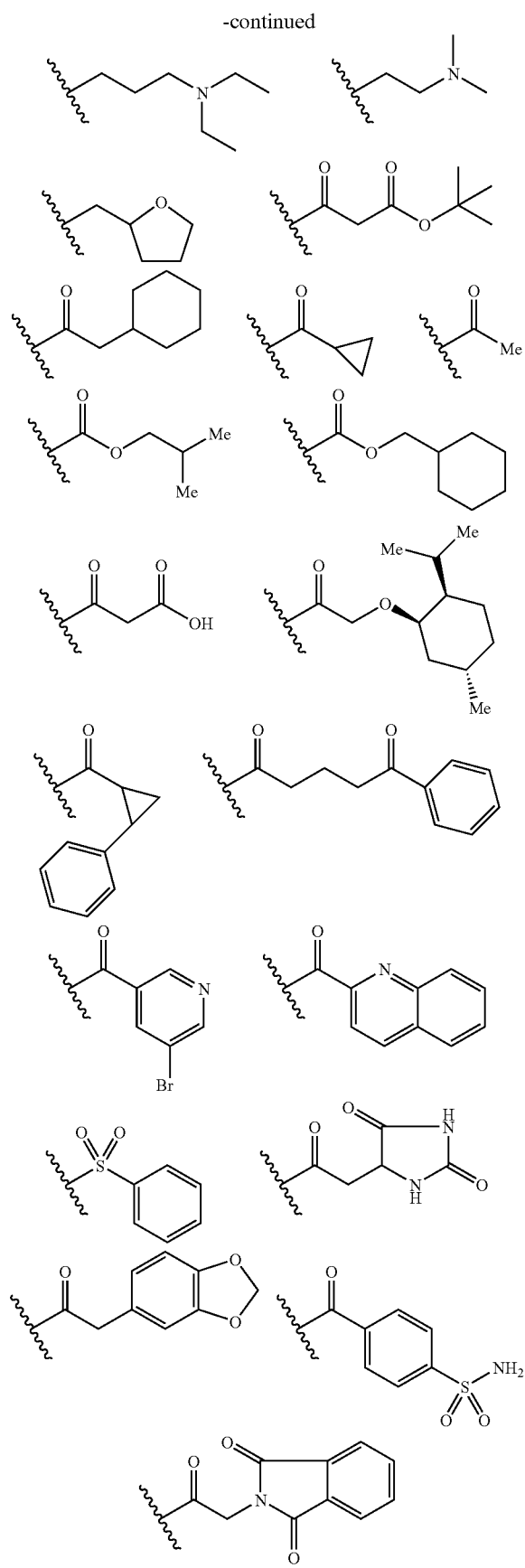

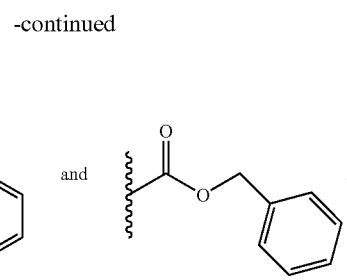

and

In another aspect of the present invention, the portion represented by structural Formula 2:

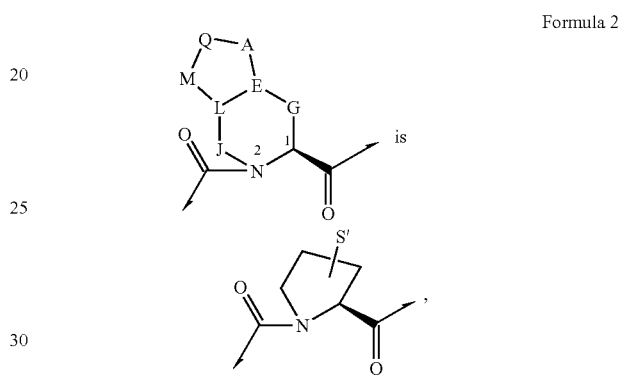

Formula 2 is with the proviso that the substituent S' on the five membered heterocycle immediately shown above numbers one or more, and if more than one, the S' substituents can be the same or different, each being independently selected from the group consisting of: $C_1$-$C_{10}$ alkyl, $C_2$-$C_{10}$ alkenyl, $C_3$-$C_8$ cycloalkyl, $C_3$-$C_8$ heterocyclyl, alkoxy, aryloxy, alkylthio, arylthio, amino, amido, arylthioamino, arylcarbonylamino, arylaminocarboxy, alkylaminocarboxy, heteroalkyl, heteroalkenyl, alkenyl, alkynyl, aryl-alkyl, heteroarylalkyl, ester, carboxylic acid, carbamate, urea, ketone, aldehyde, cyano, nitro, halogen, (cycloalkyl)alkyl, aryl, heteroaryl, alkyl-aryl, alkylheteroaryl, alkyl-heteroaryl and (heterocyclyl)alkyl. In another aspect of the present invention, W is C=O; and Cap is selected from the group consisting of the following structures:

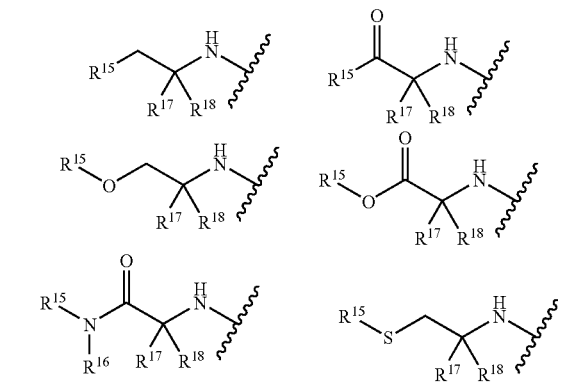

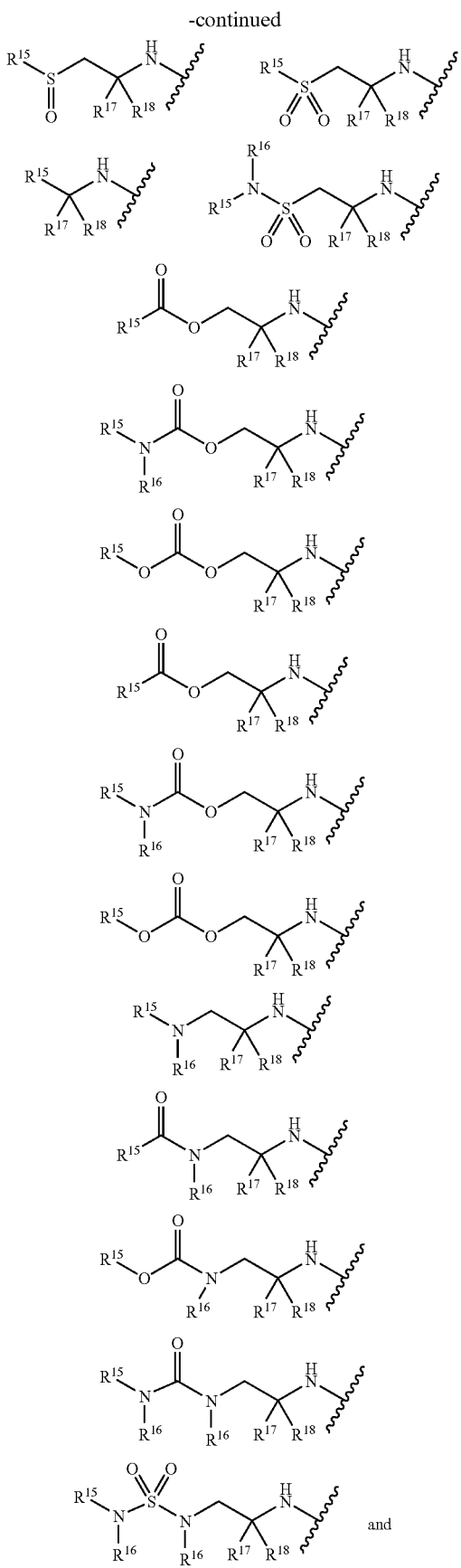

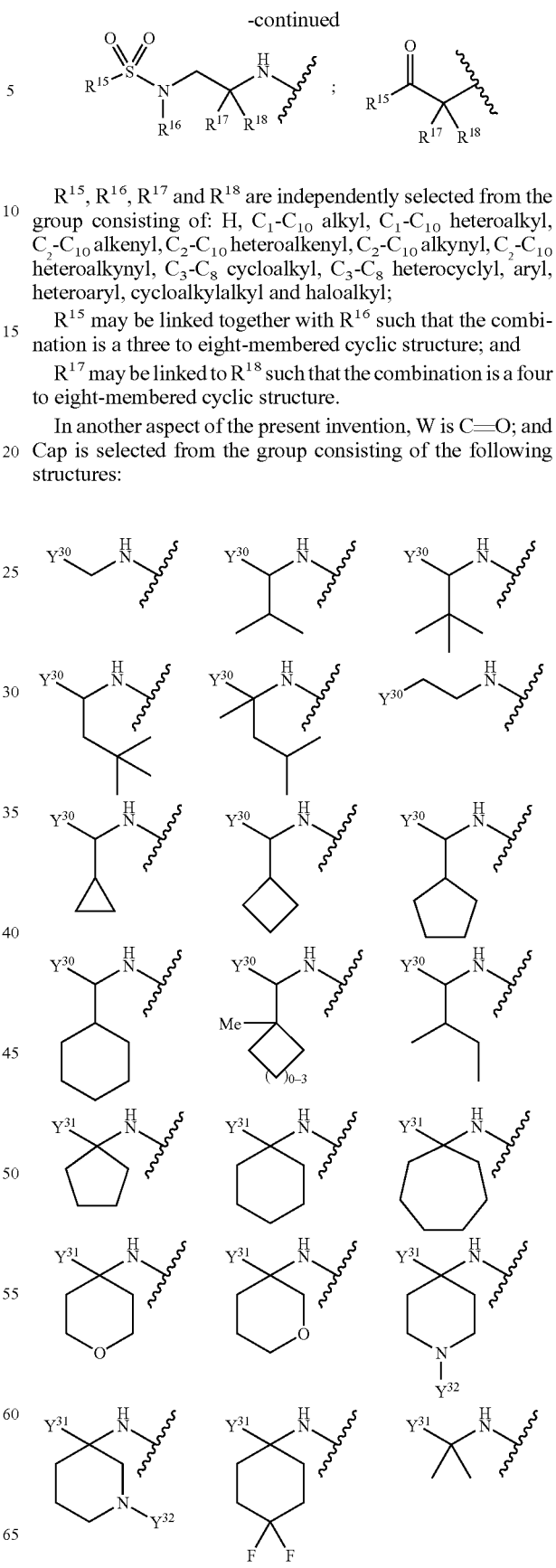

$R^{15}$, $R^{16}$, $R^{17}$ and $R^{18}$ are independently selected from the group consisting of: H, $C_1$-$C_{10}$ alkyl, $C_1$-$C_{10}$ heteroalkyl, $C_2$-$C_{10}$ alkenyl, $C_2$-$C_{10}$ heteroalkenyl, $C_2$-$C_{10}$ alkynyl, $C_2$-$C_{10}$ heteroalkynyl, $C_3$-$C_8$ cycloalkyl, $C_3$-$C_8$ heterocyclyl, aryl, heteroaryl, cycloalkylalkyl and haloalkyl;

$R^{15}$ may be linked together with $R^{16}$ such that the combination is a three to eight-membered cyclic structure; and $R^{17}$ may be linked to $R^{18}$ such that the combination is a four to eight-membered cyclic structure.

In another aspect of the present invention, W is C=O; and Cap is selected from the group consisting of the following structures:

-continued
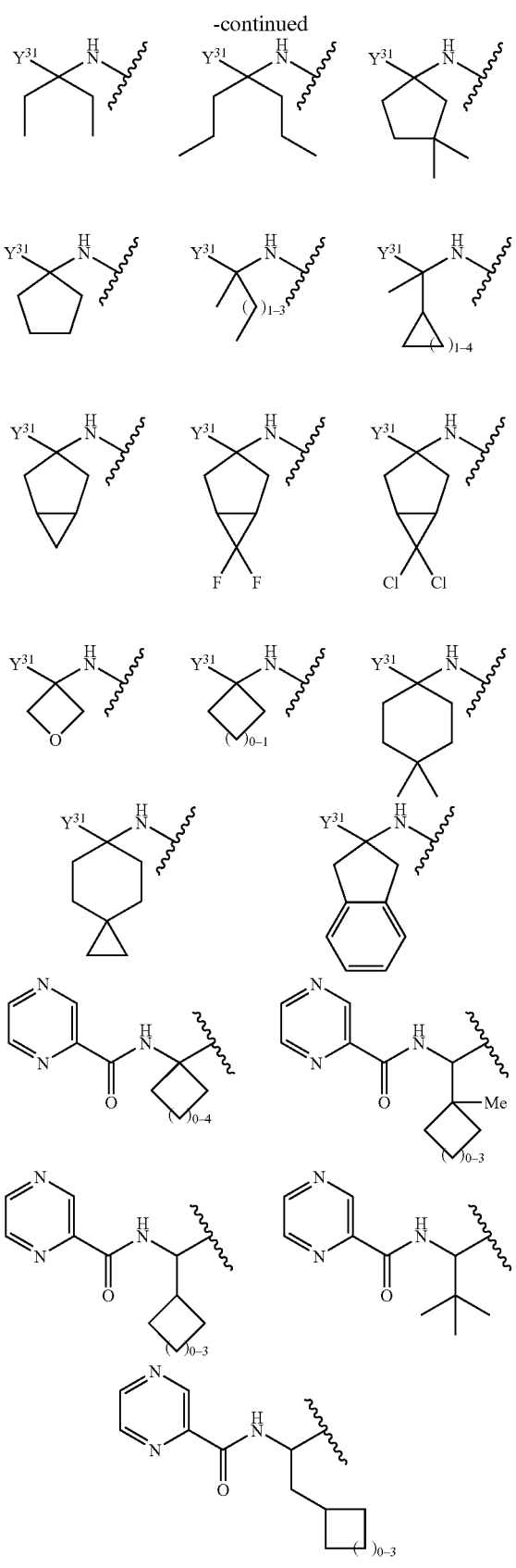
$Y^{30}$ is selected from the group consisting of the following structures:
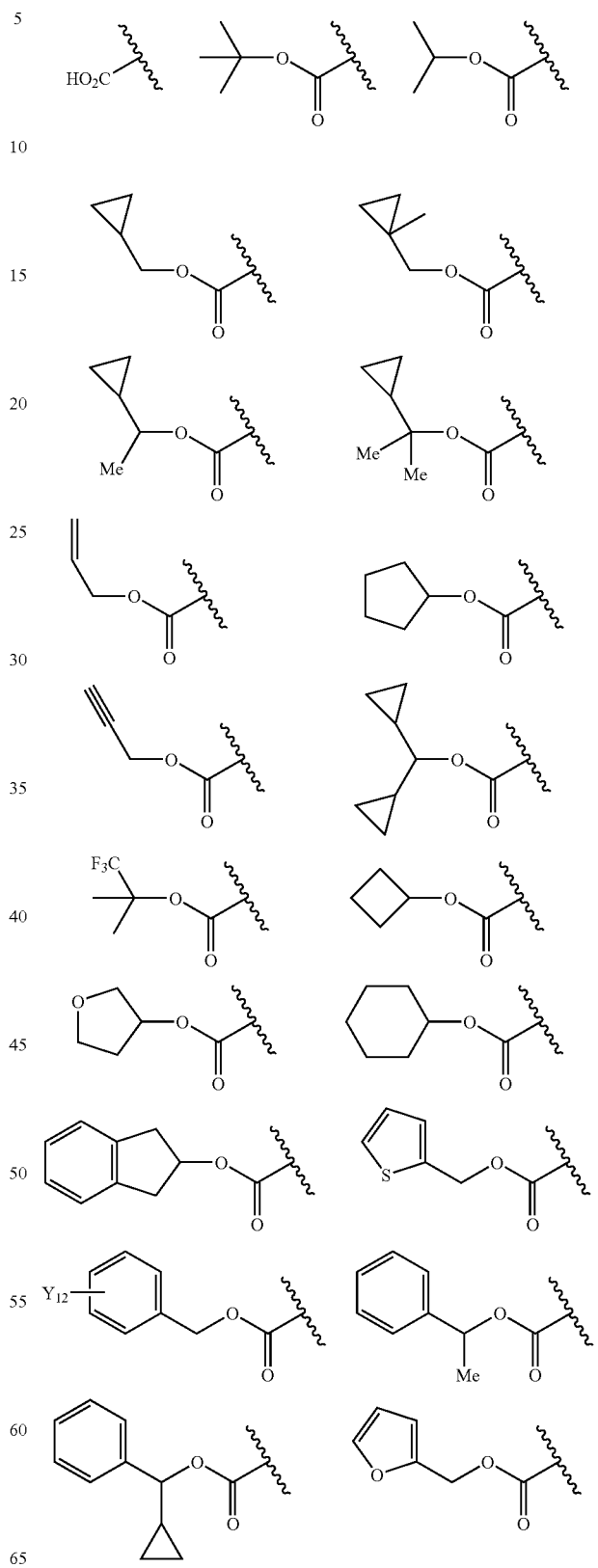

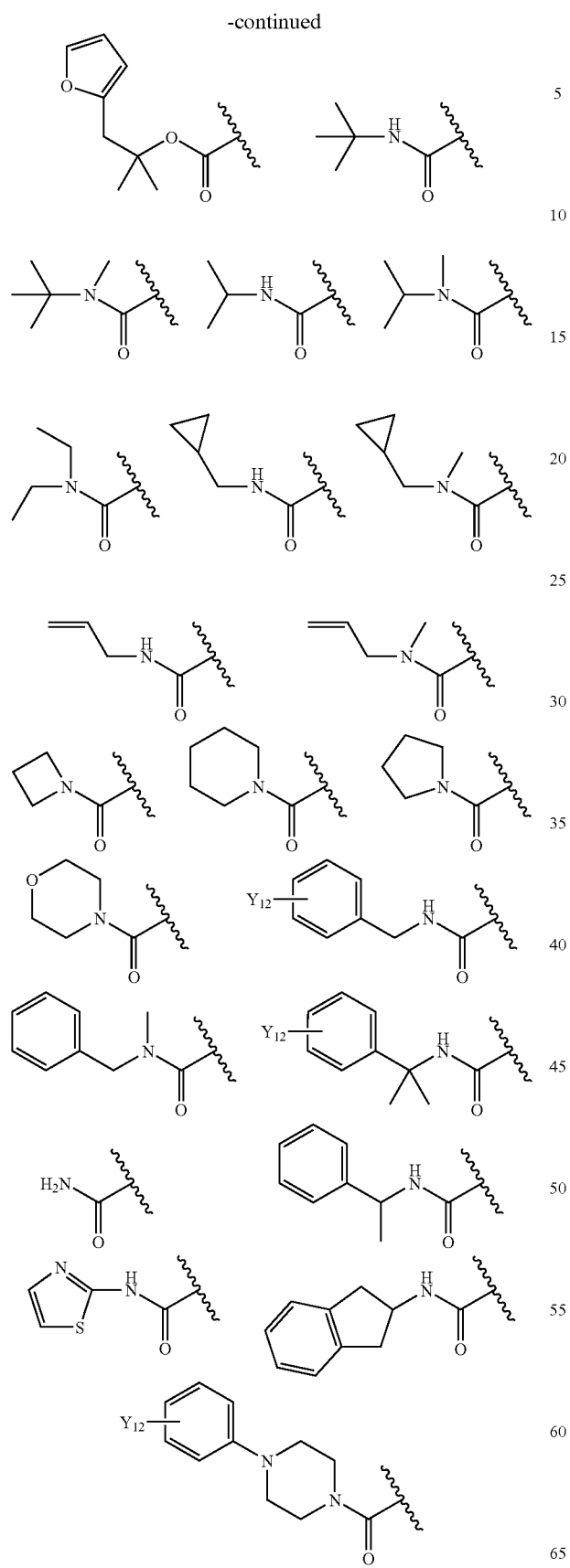
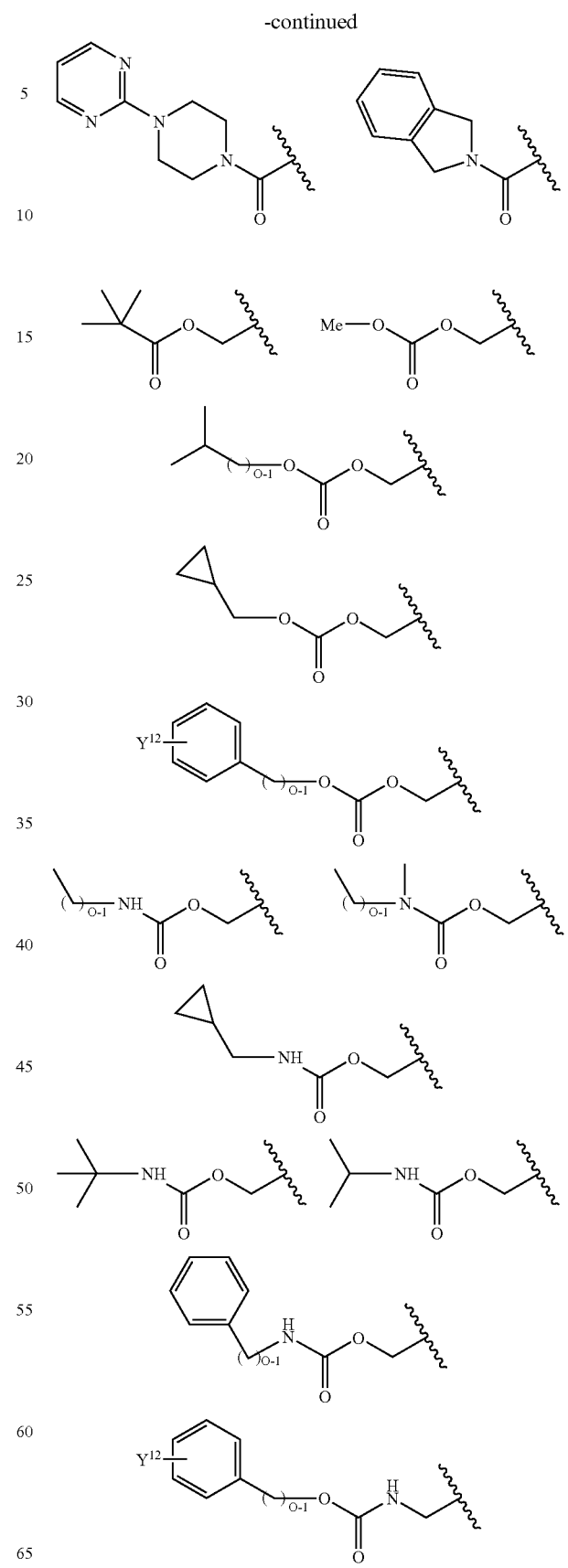

-continued
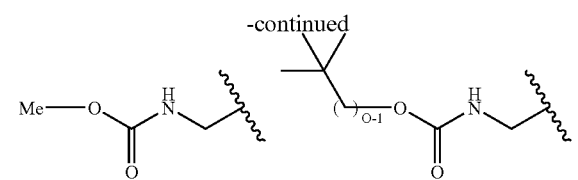
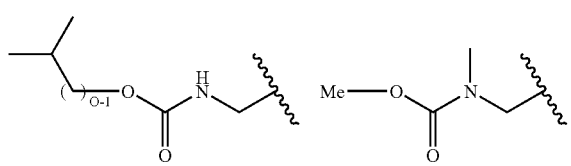
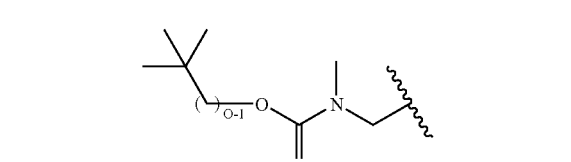
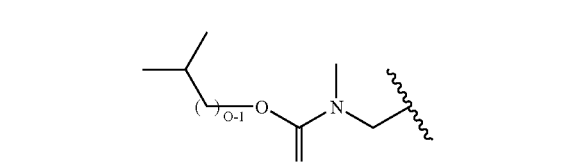
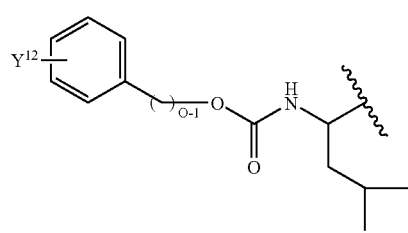
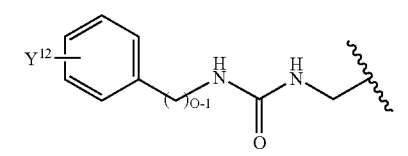
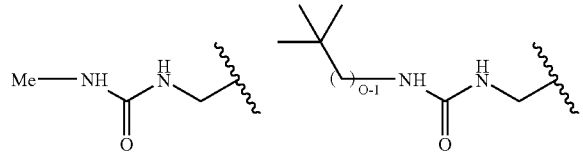
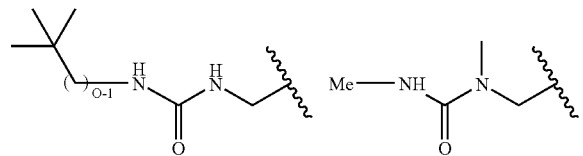
-continued
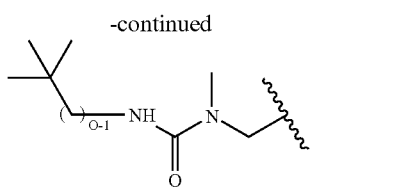
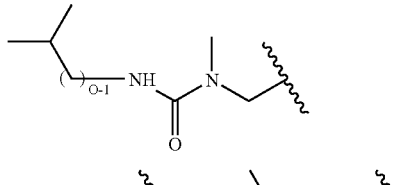
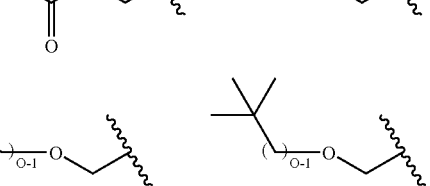
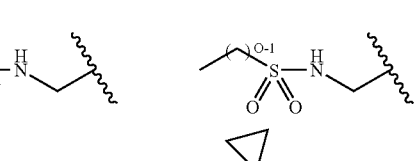
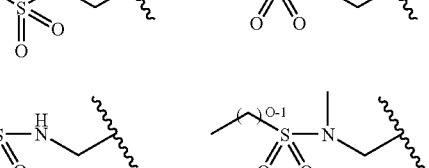
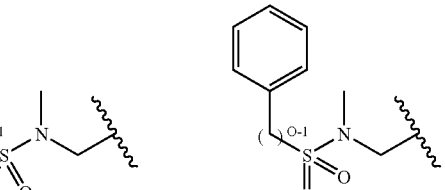
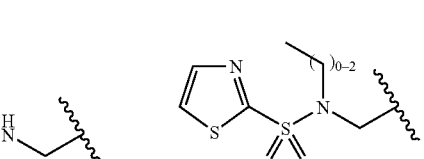
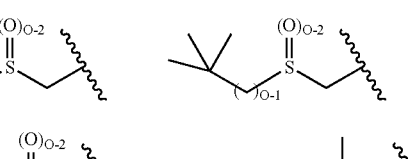

-continued
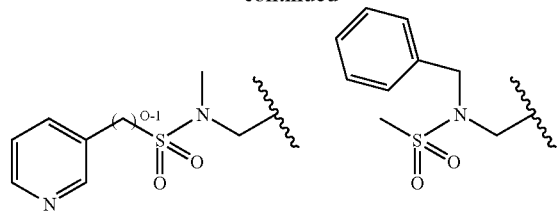
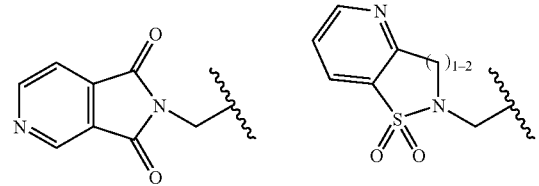
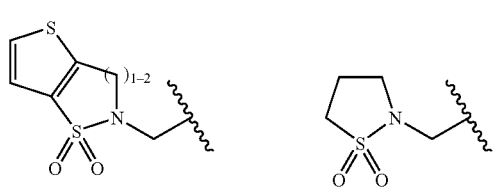
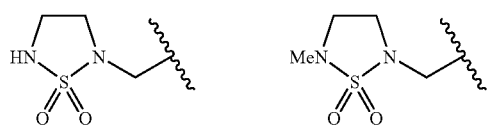
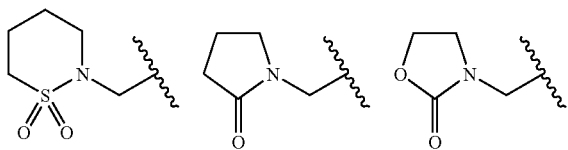
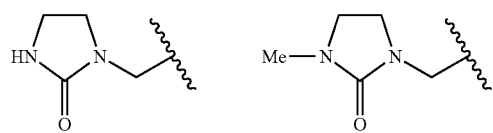
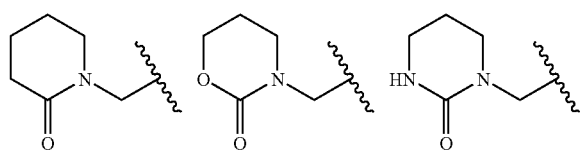
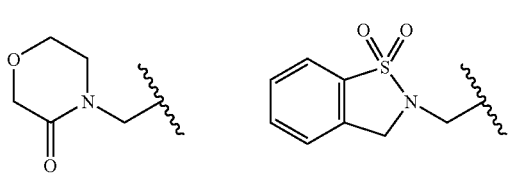
-continued
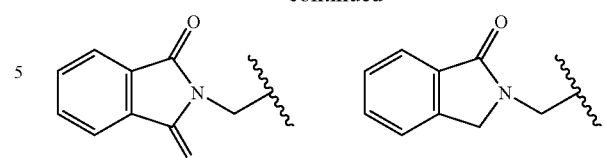
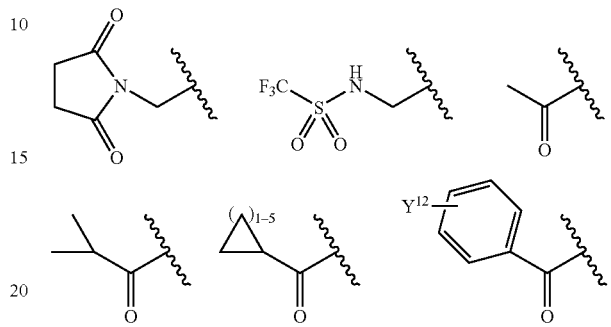
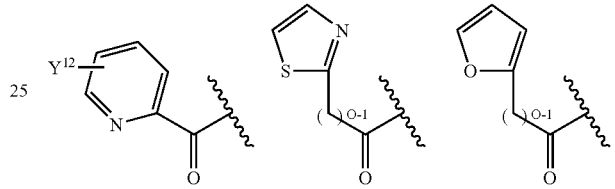
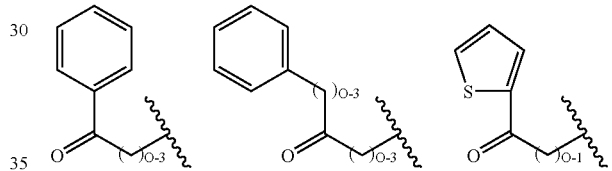
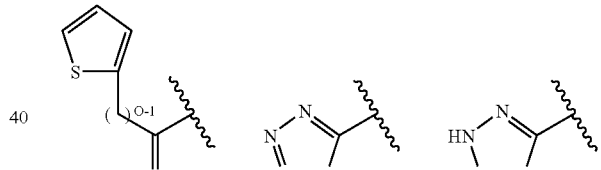
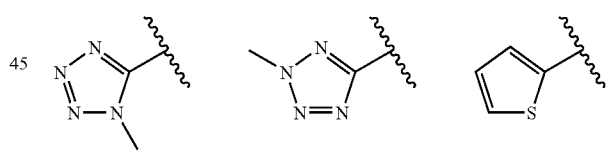
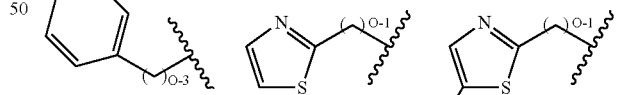
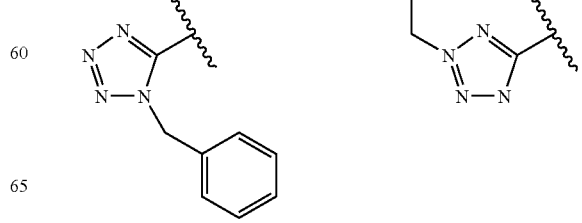

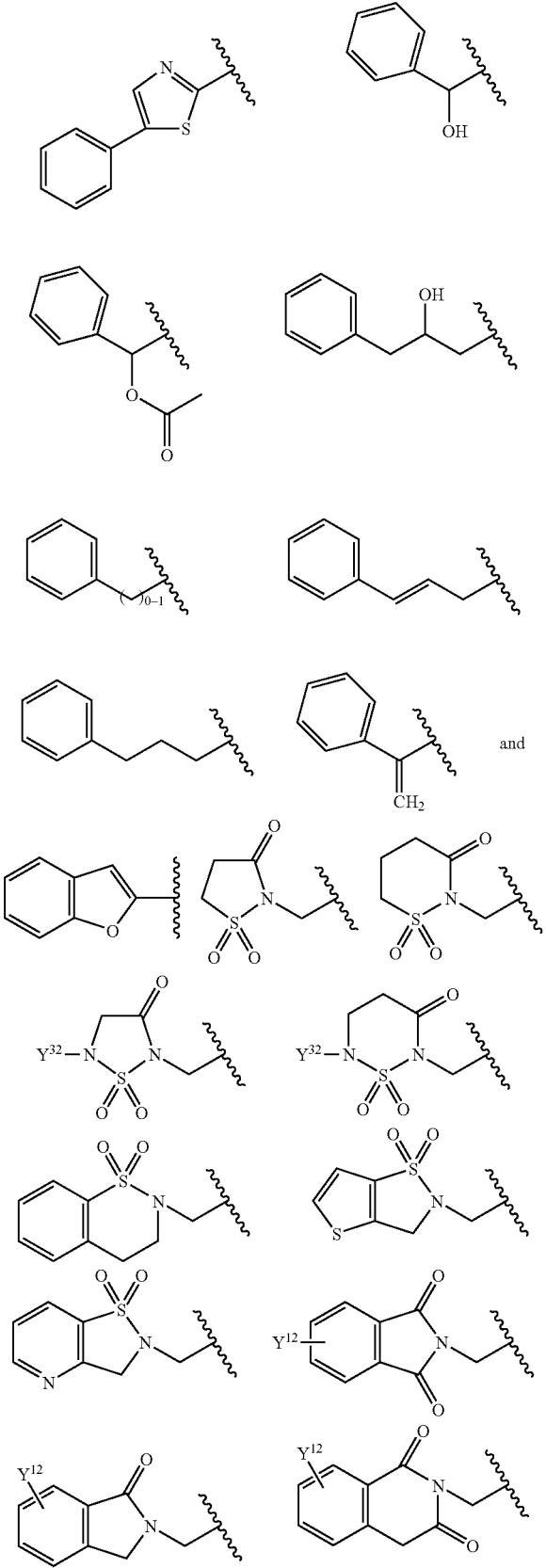
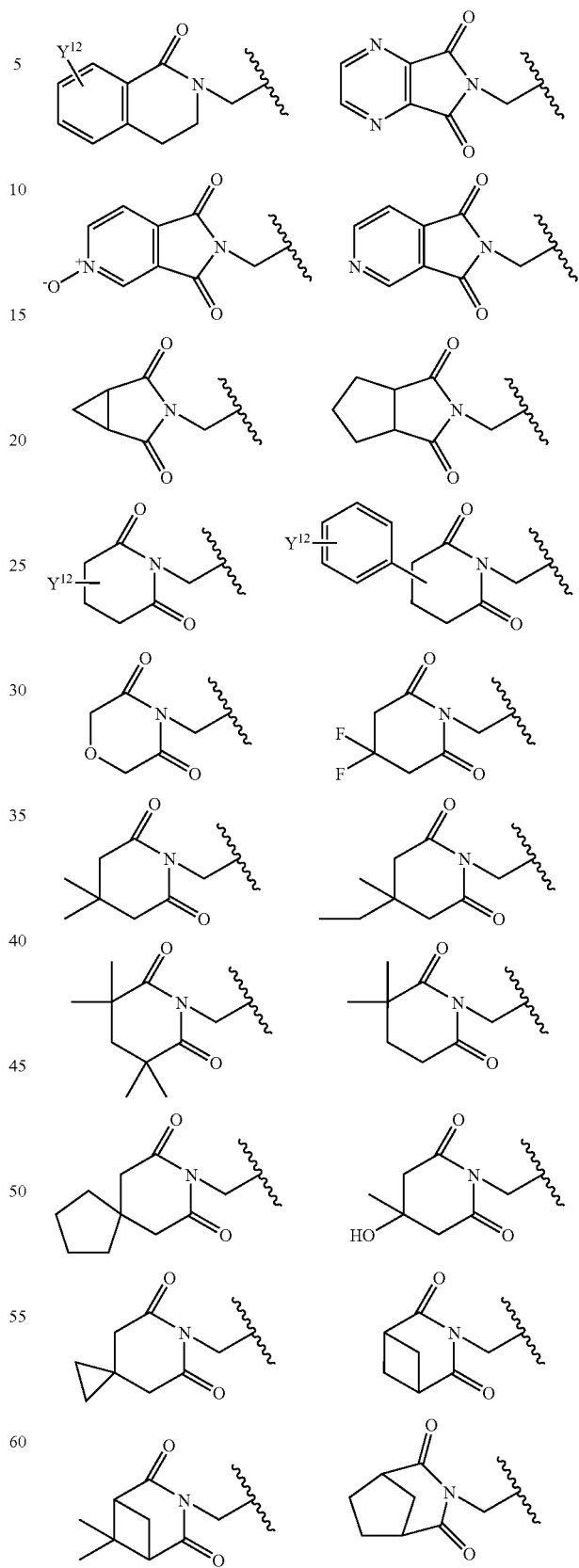

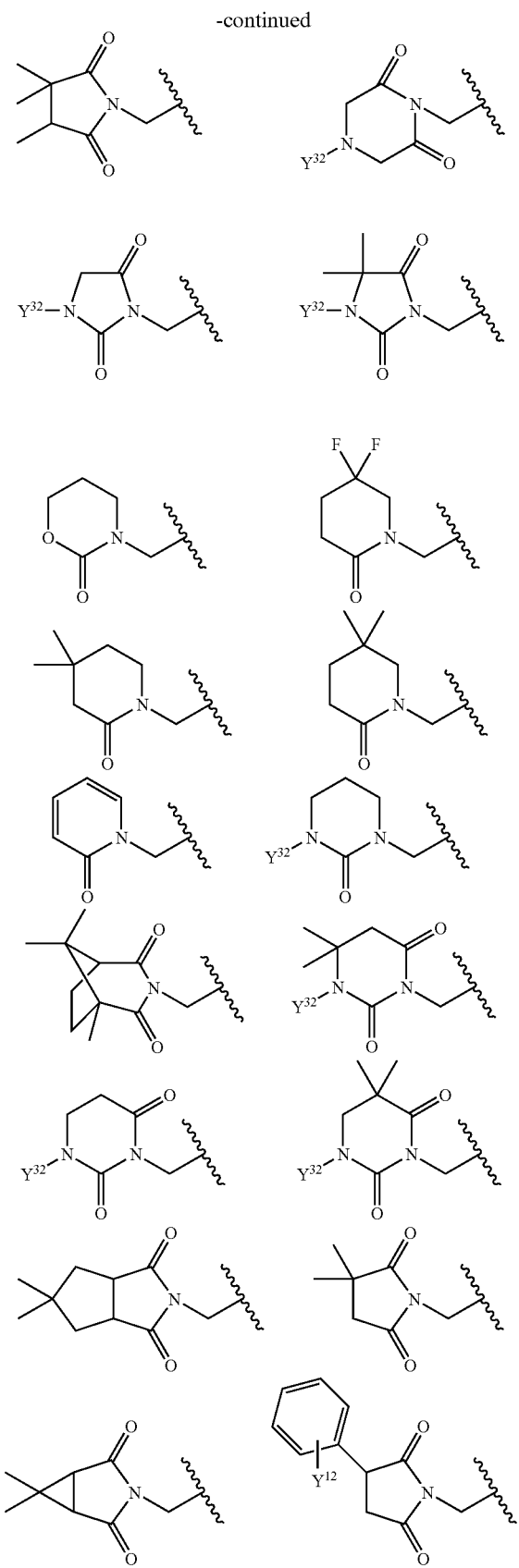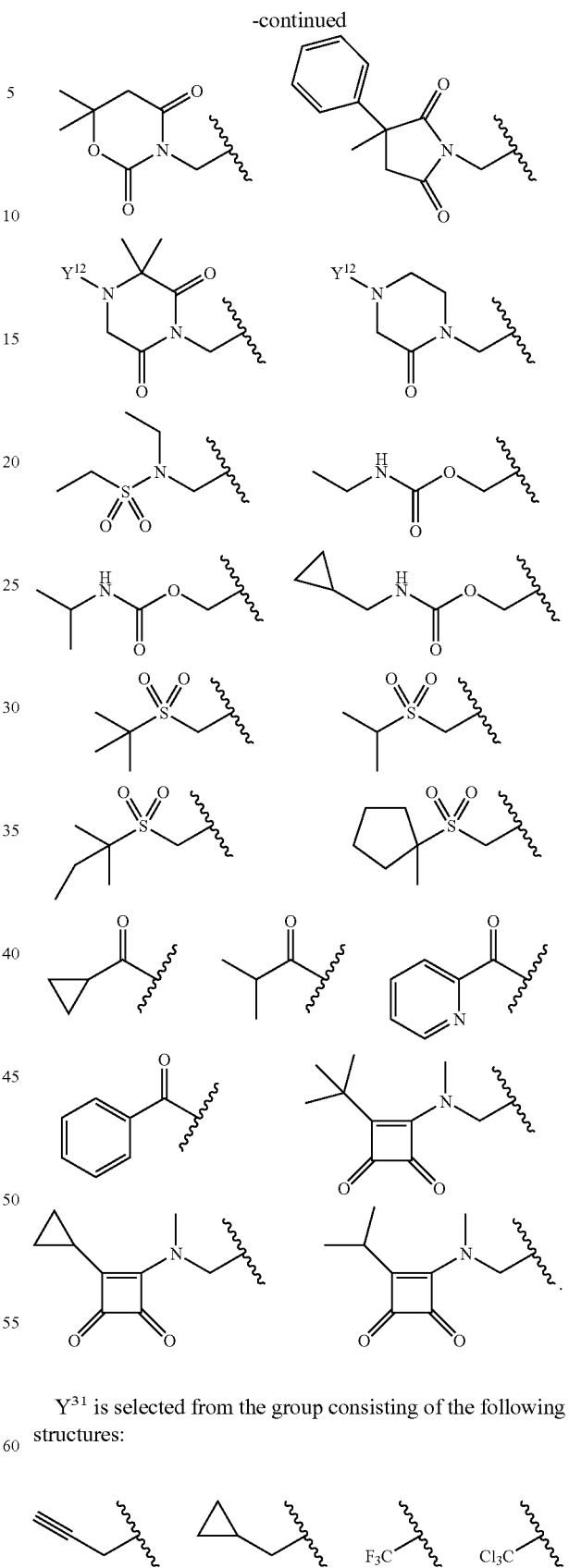

-continued
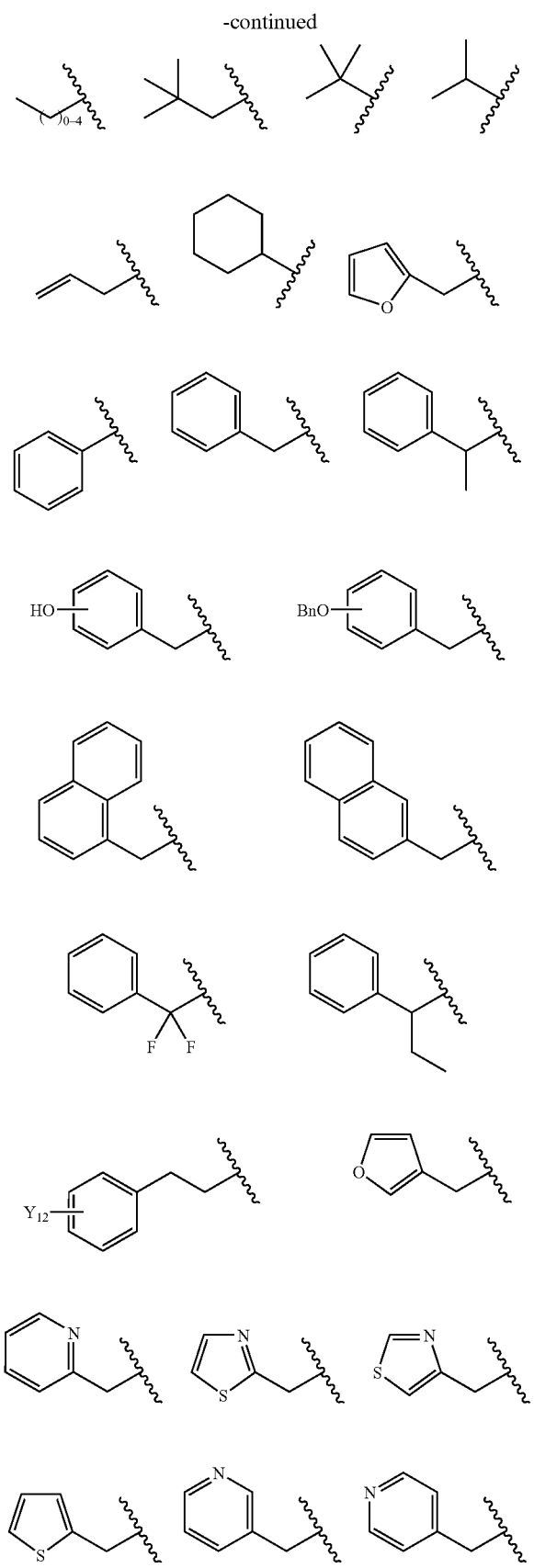
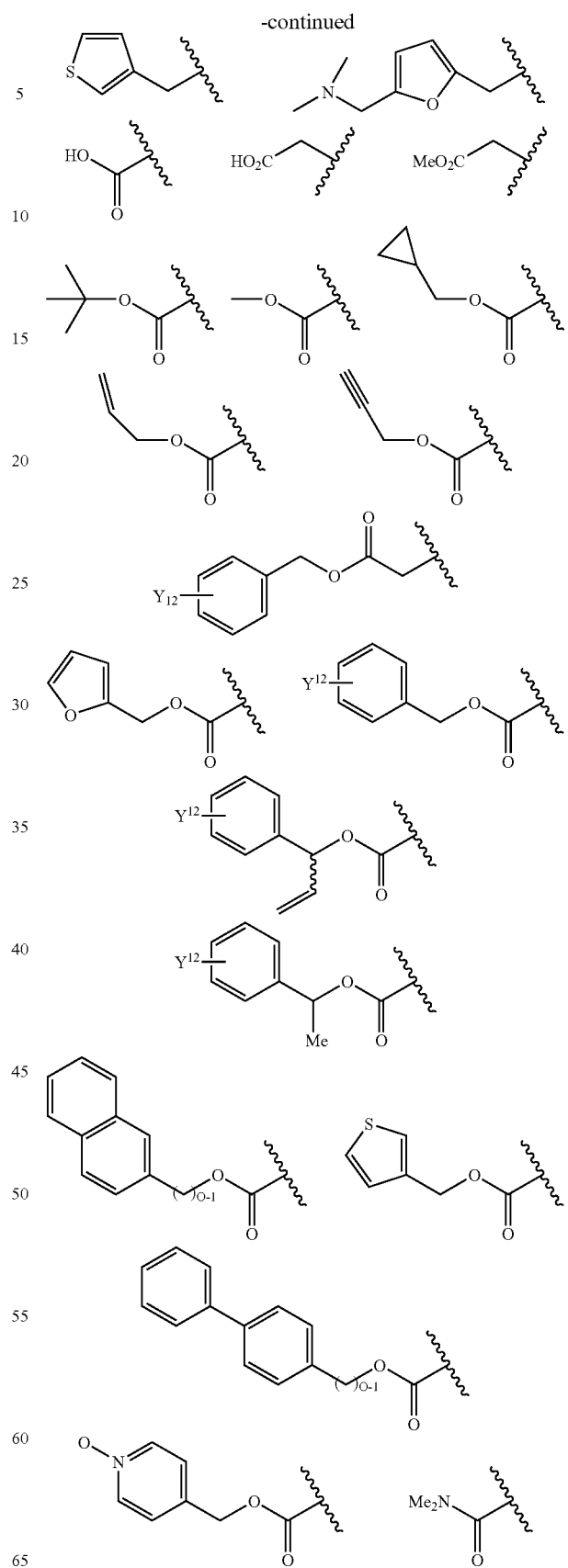

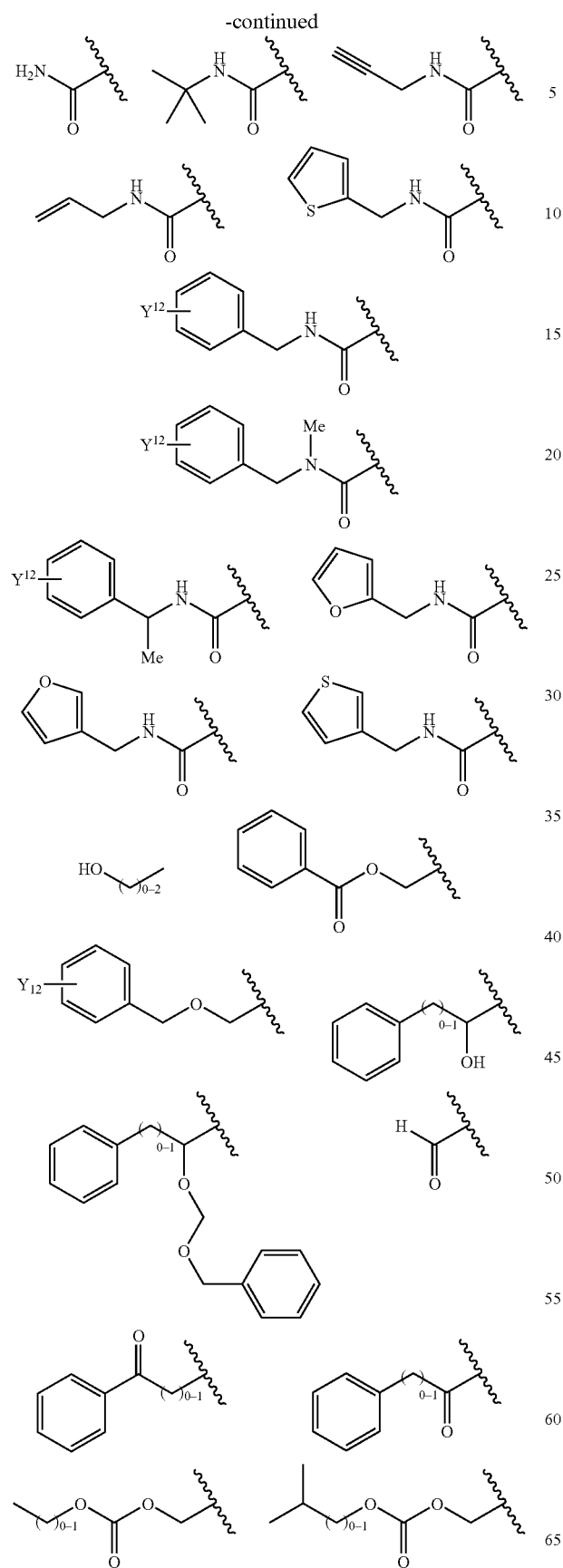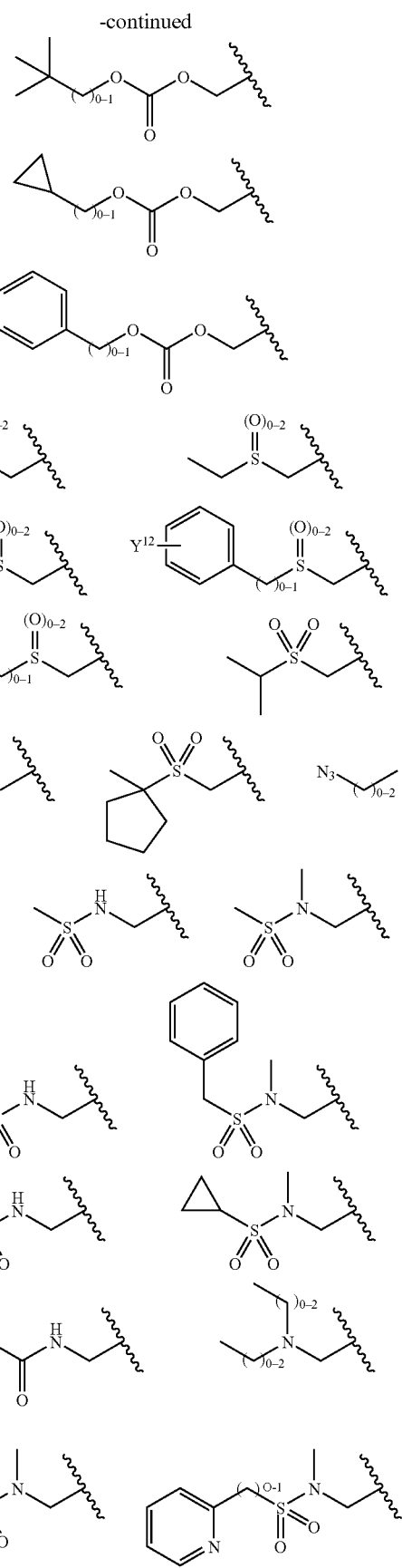

-continued

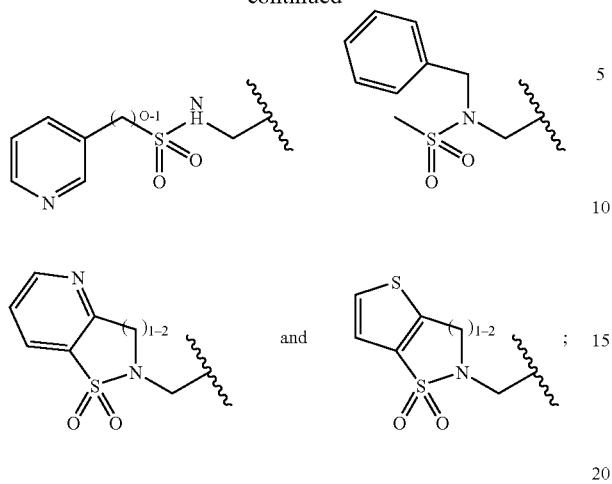

$Y^{32}$ is selected from the group consisting of the following structures:

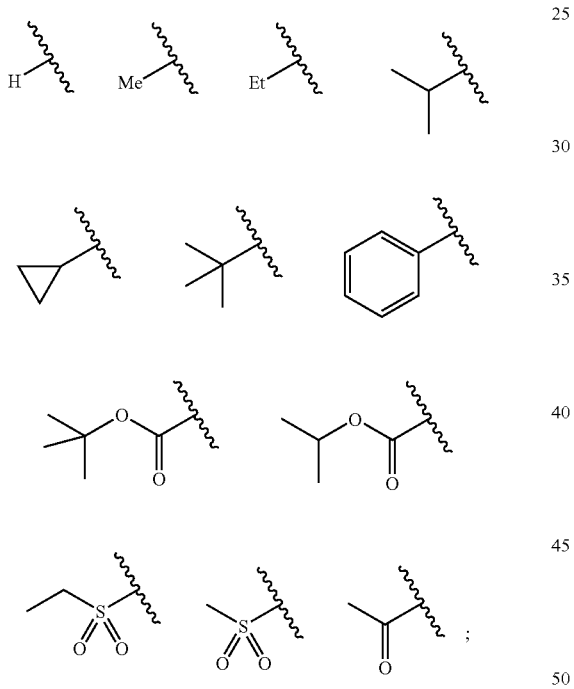

and $Y^{12}$ is selected from H, COOH, COOMe, OMe, F, Cl, Br, $NH_2$, $NHSO_2CH_3$, $NHCOCH_3$, $NO_2$, $SO_2NH_2$, $CF_3$, OH, $OCF_3$, $CONH_2$, Me, Et, isopropyl, cyclopropyl, tert-butyl.

In another aspect of the invention, W is C=O; and Cap is selected from the group consisting of the following structures:

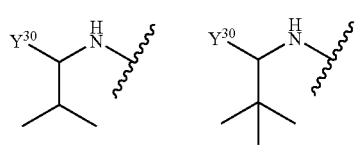

In a still another aspect of the present invention, Cap is selected from the group consisting of the following structures:

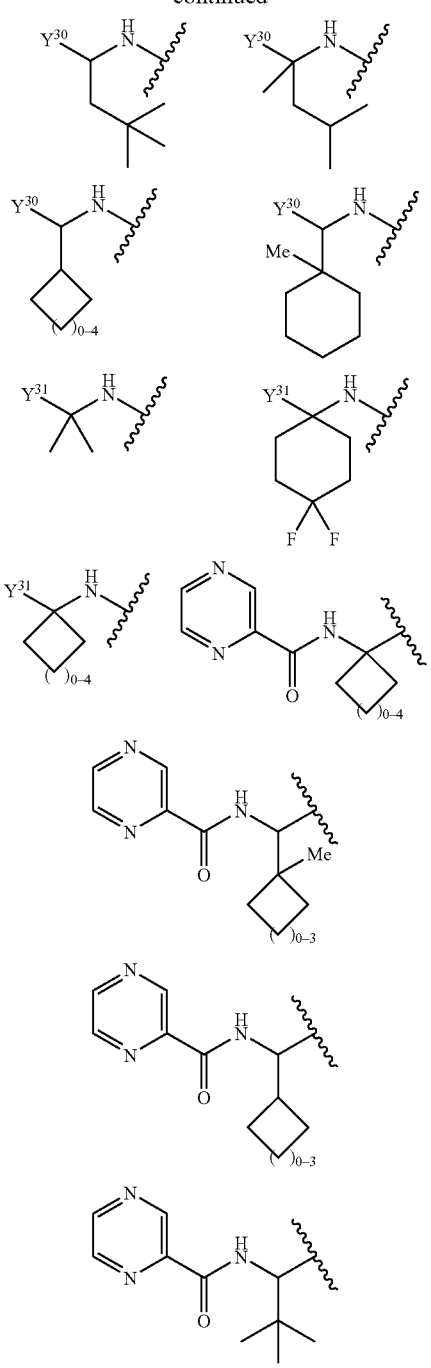

-continued
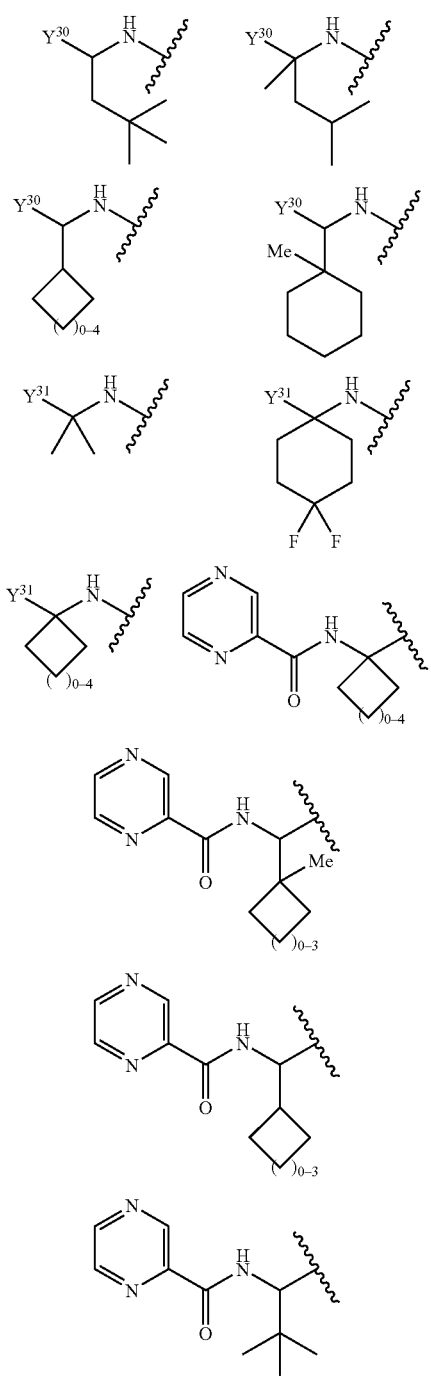
and
$Y^{30}$ is selected from the group consisting of the following structures:
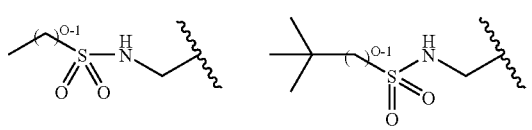
-continued
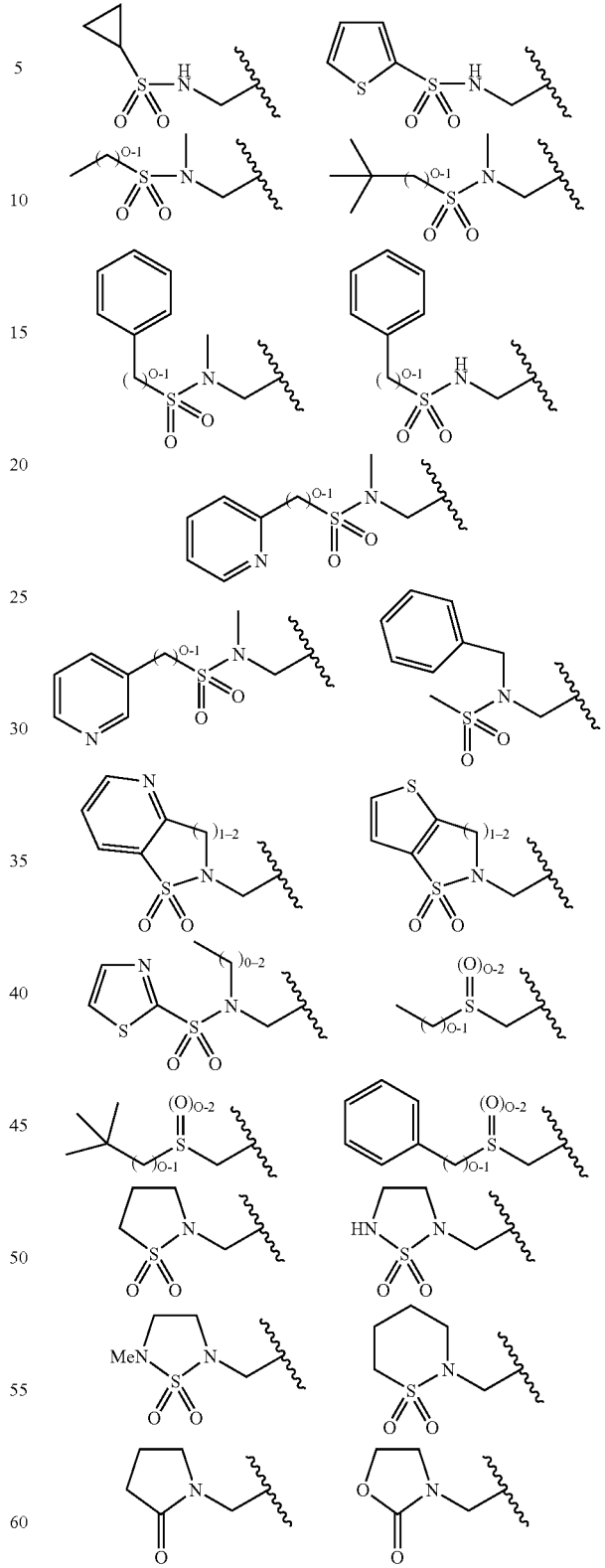

-continued
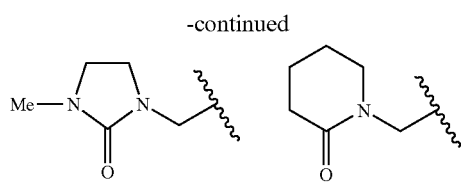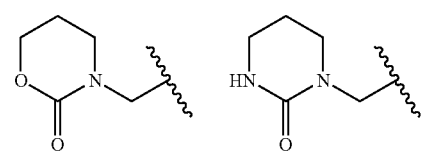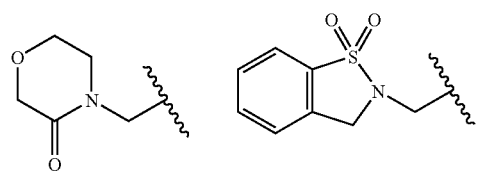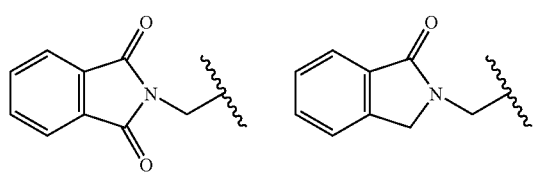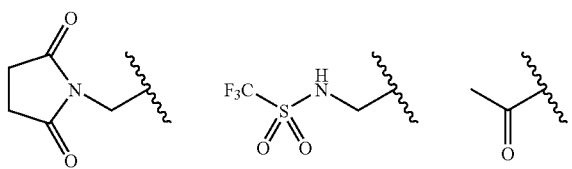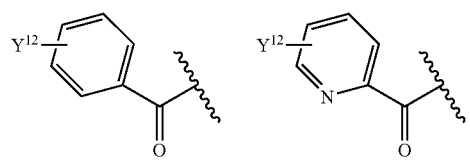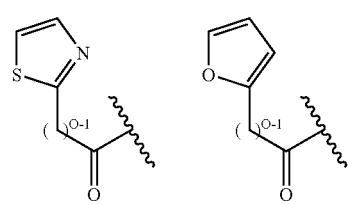
-continued
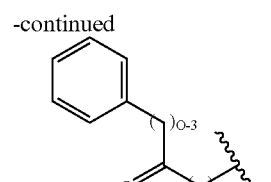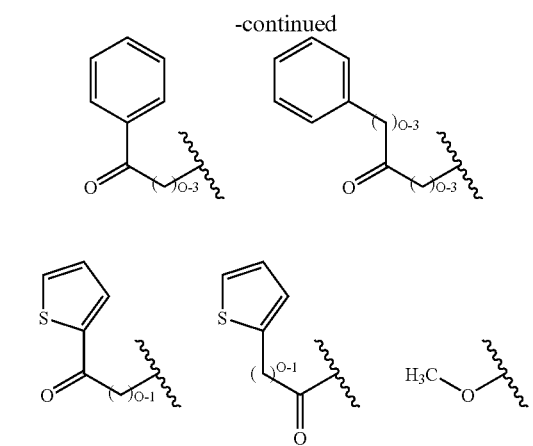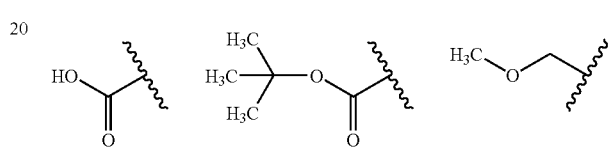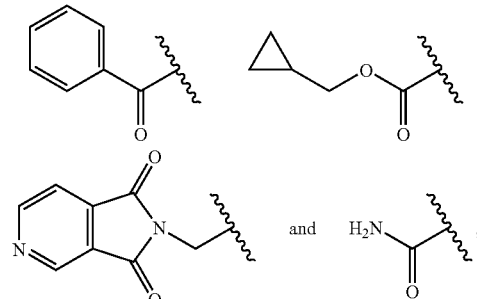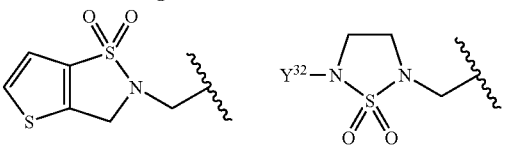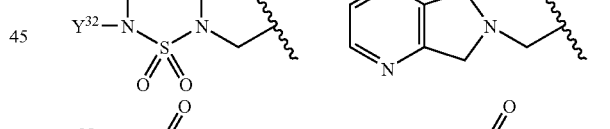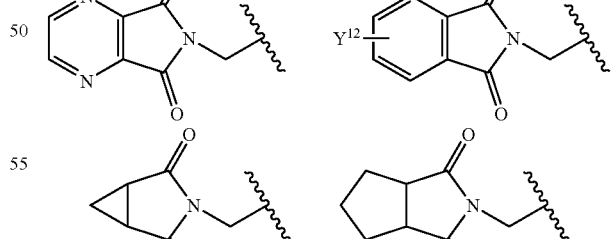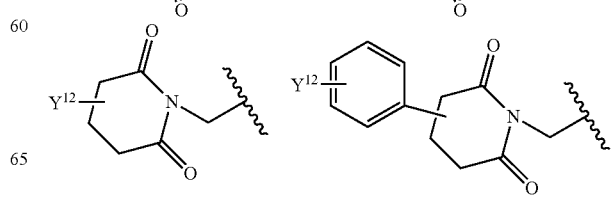

-continued
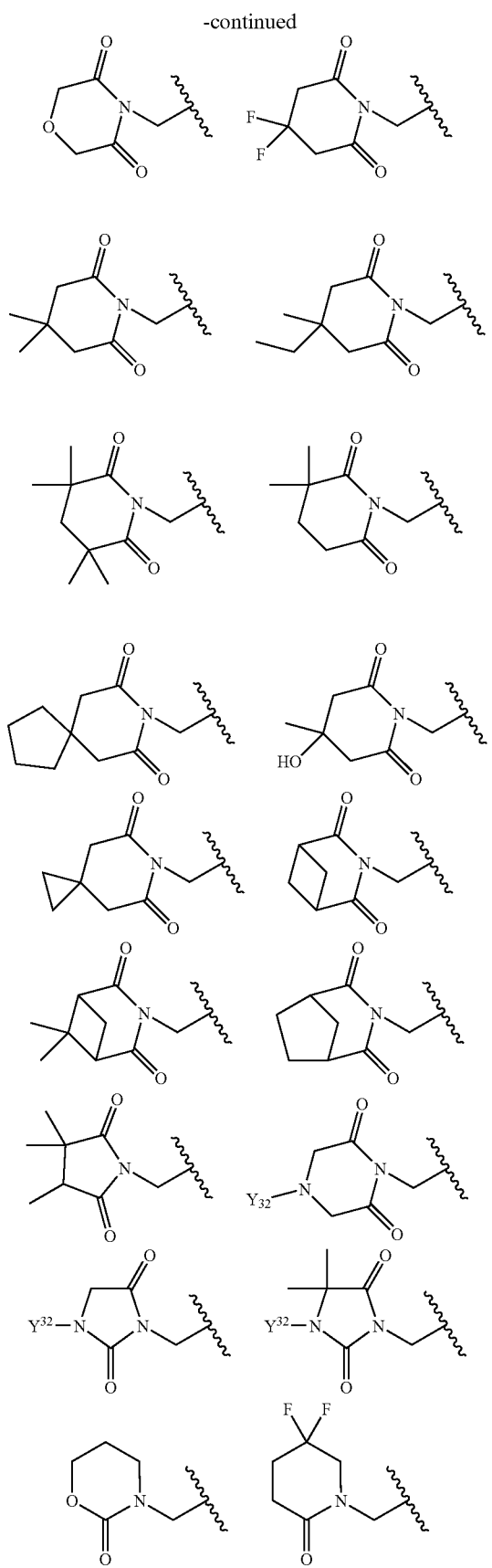
-continued
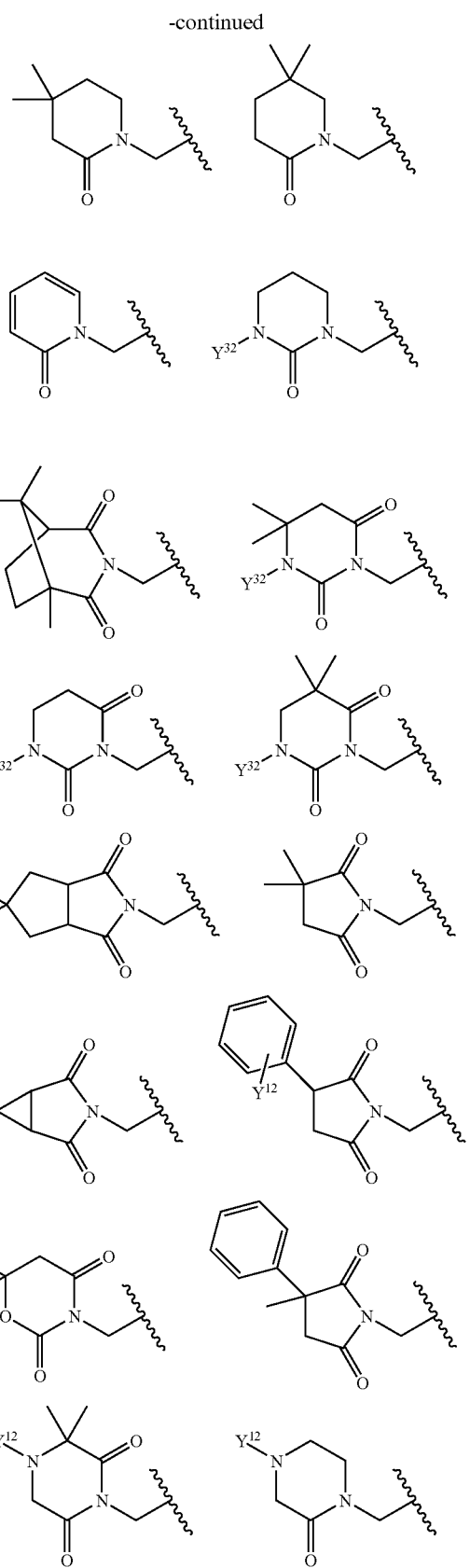

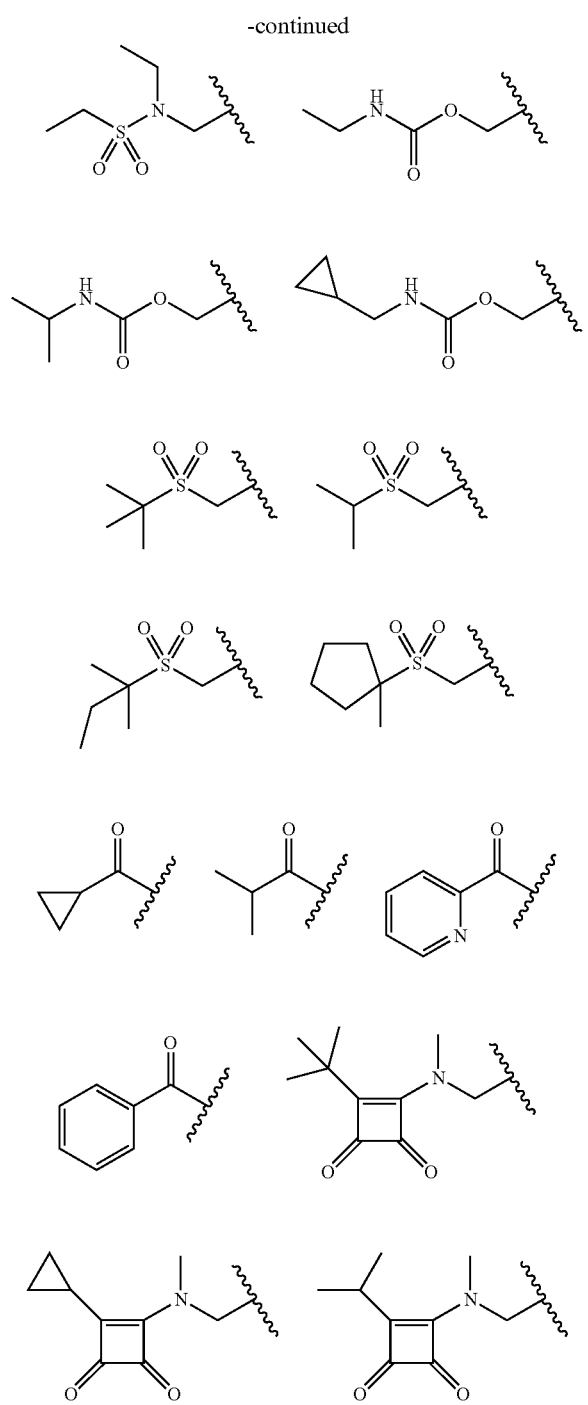
and Y³¹ is selected from the group consisting of the following structures:
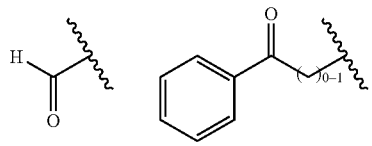
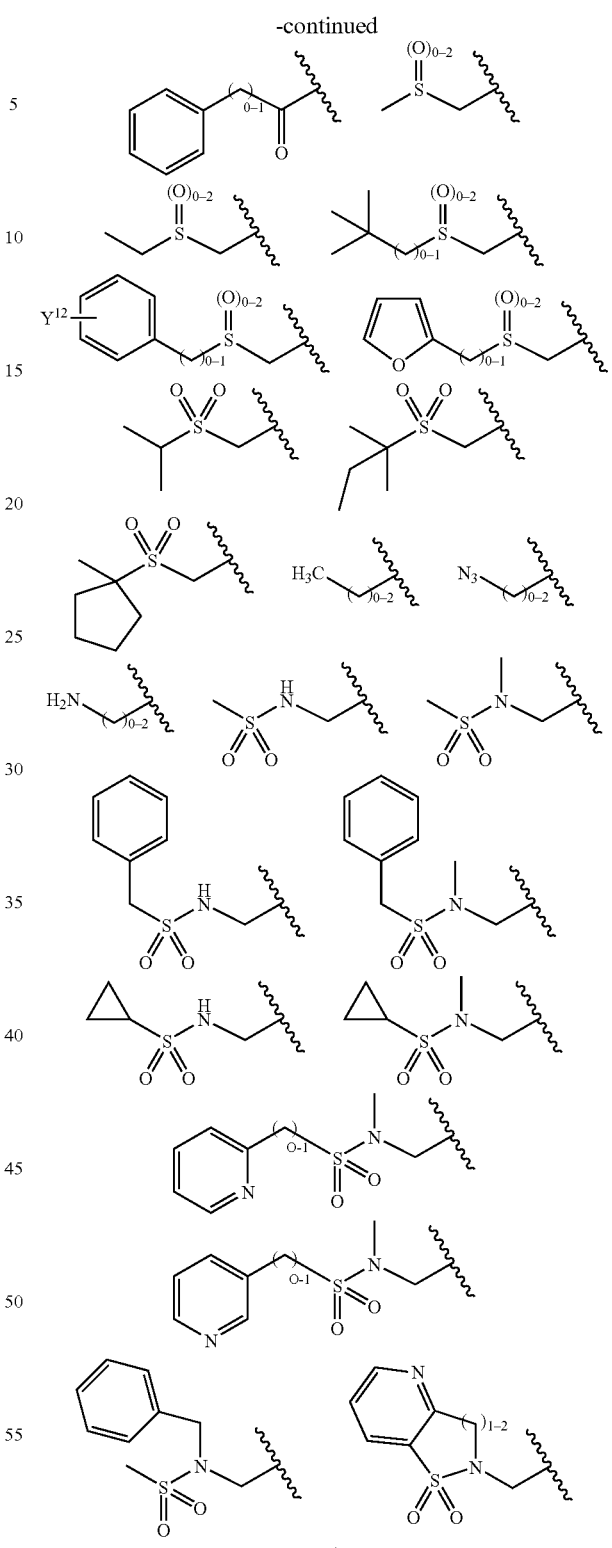
and
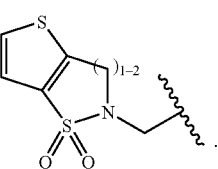

In another aspect of the invention, W is C=O; and $Y^{30}$ and $Y^{31}$ are independently selected from the group consisting of the following structures:
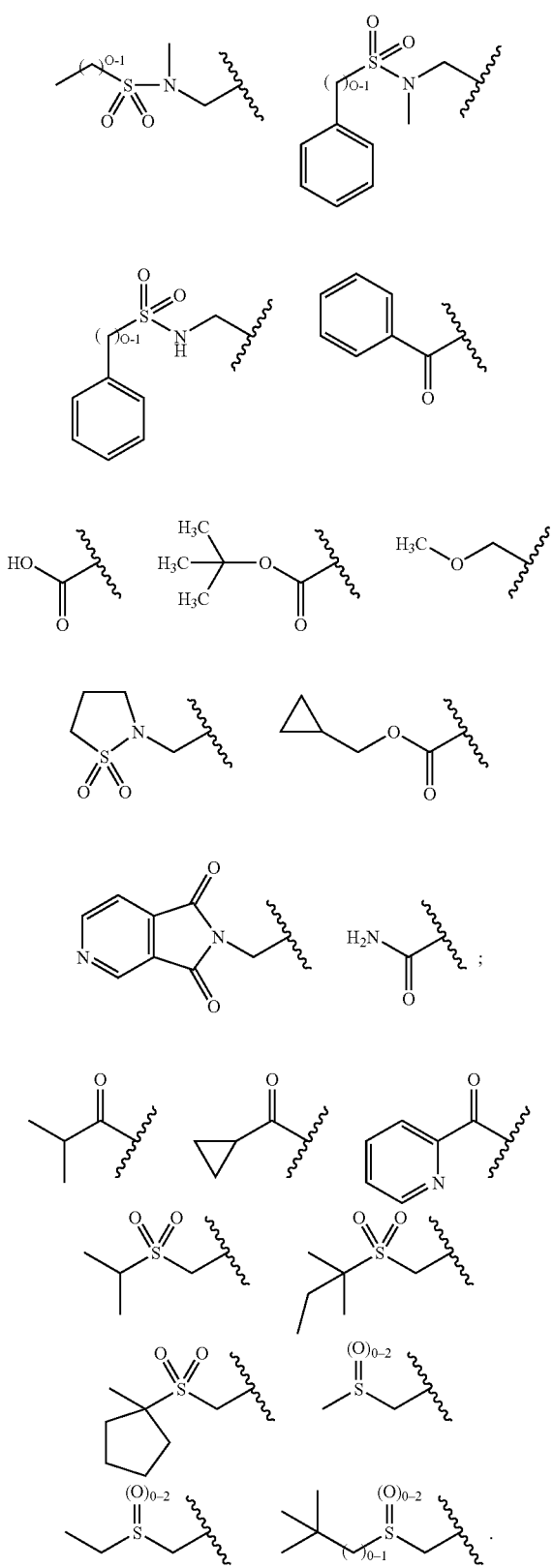
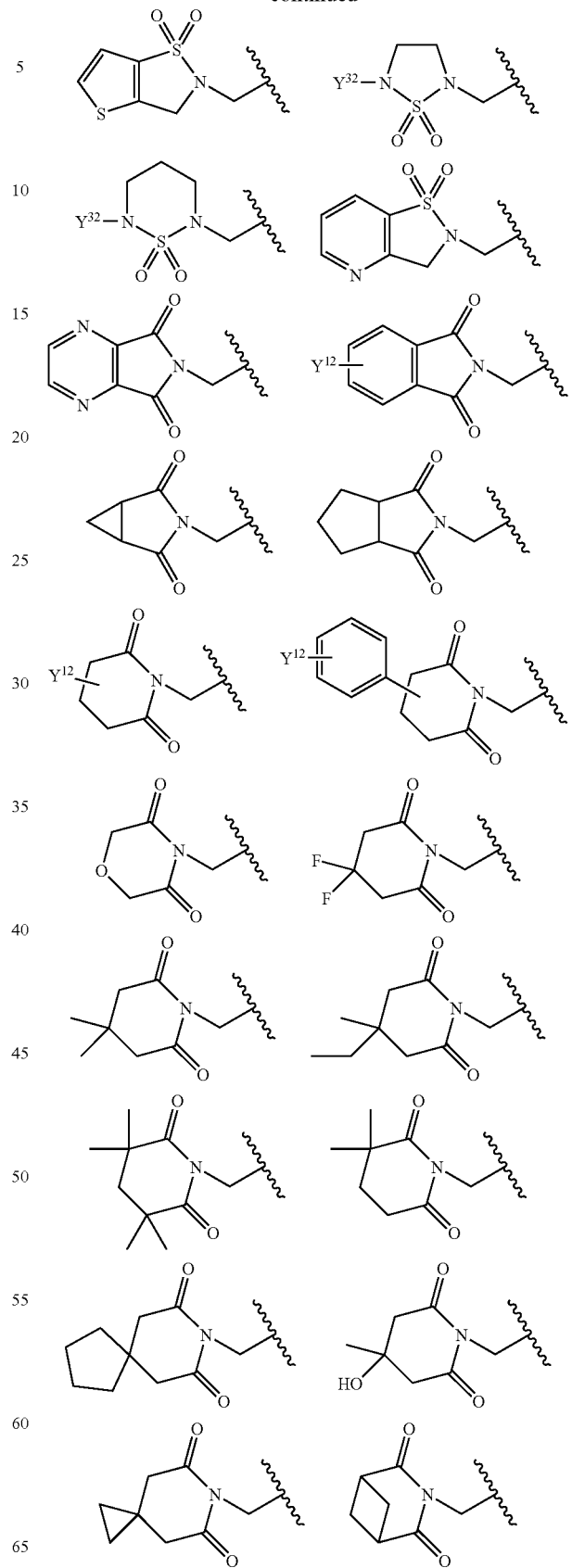

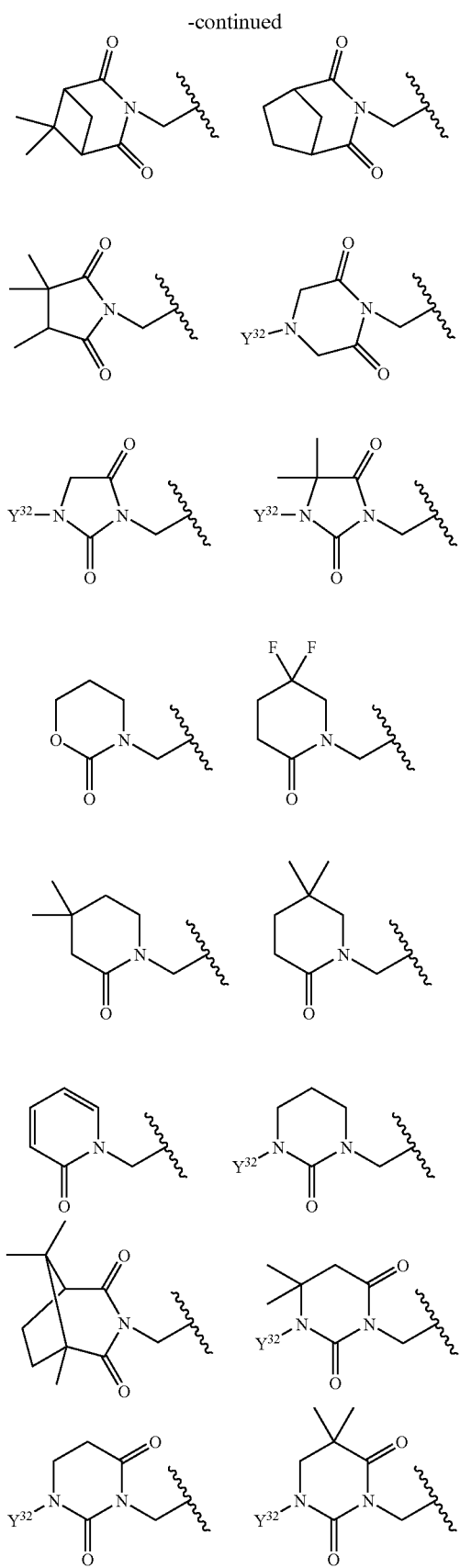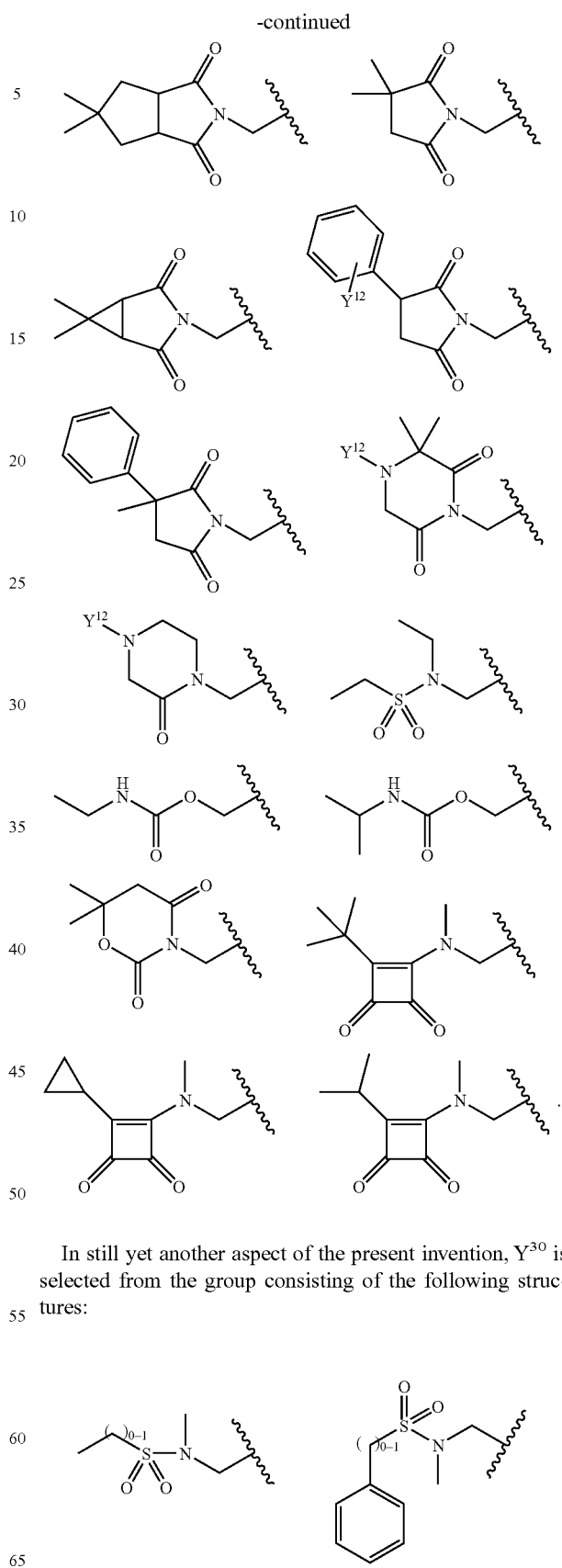
In still yet another aspect of the present invention, $Y^{30}$ is selected from the group consisting of the following structures:
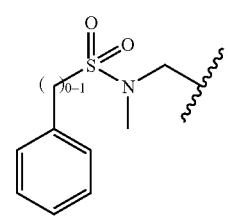

-continued and
$Y^{31}$ is selected from the group consisting of the following structures:

In one class of embodiments of the present invention, W is C=O; and Cap is selected from the group consisting of the following structures:

-continued
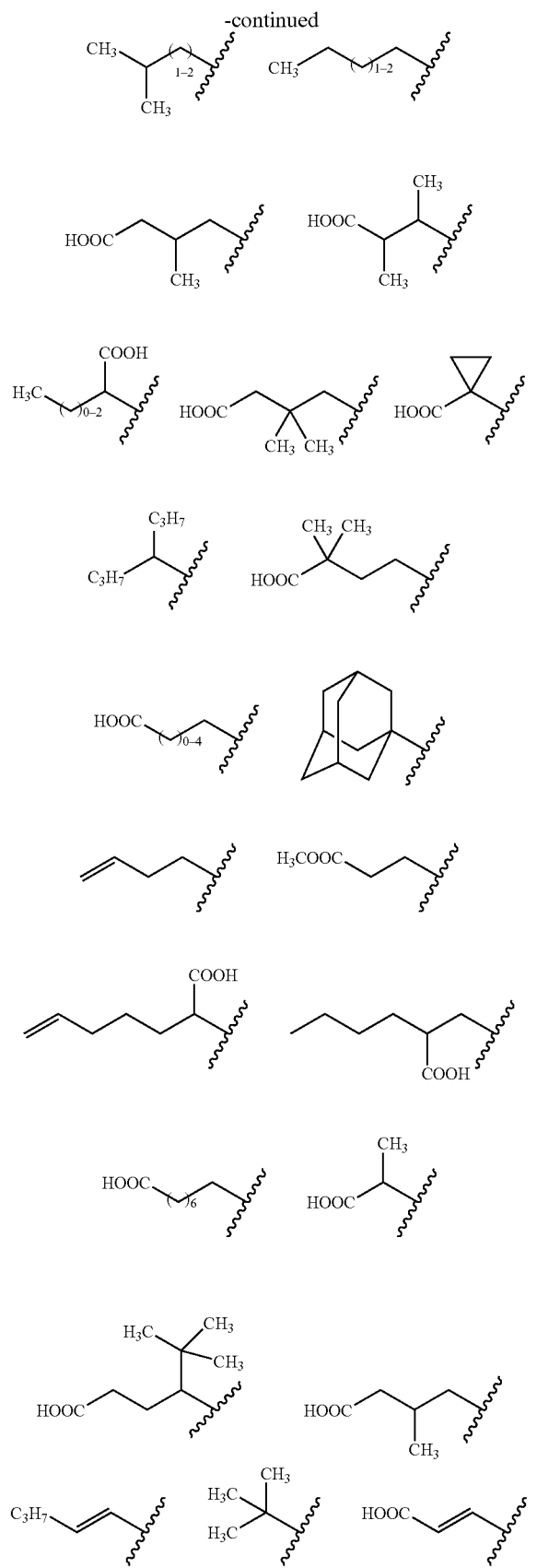
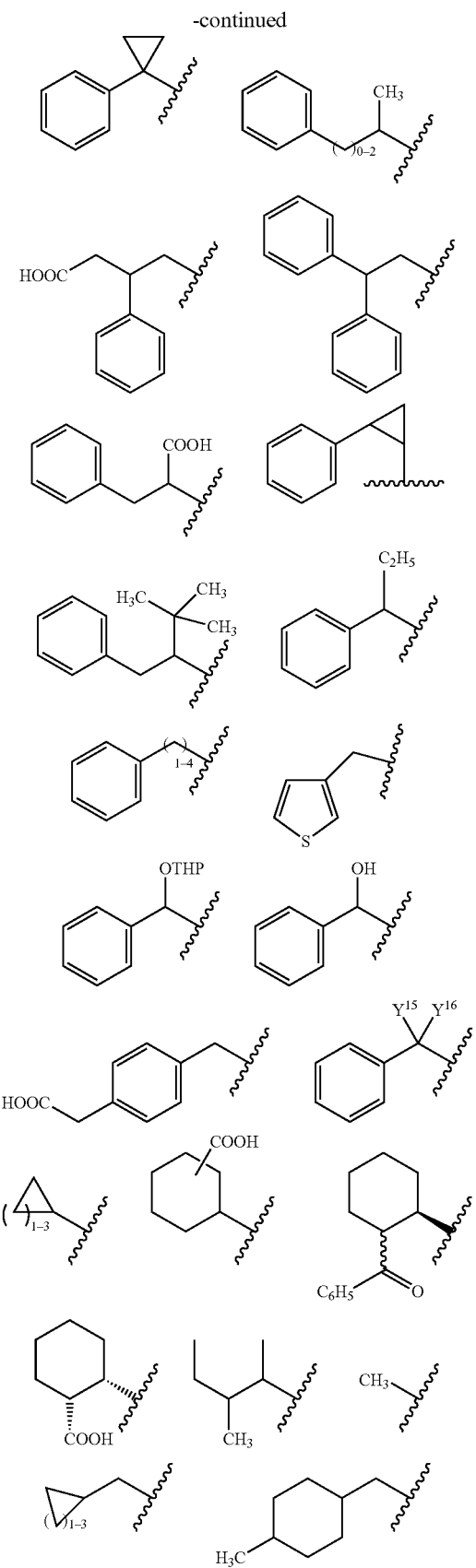

-continued
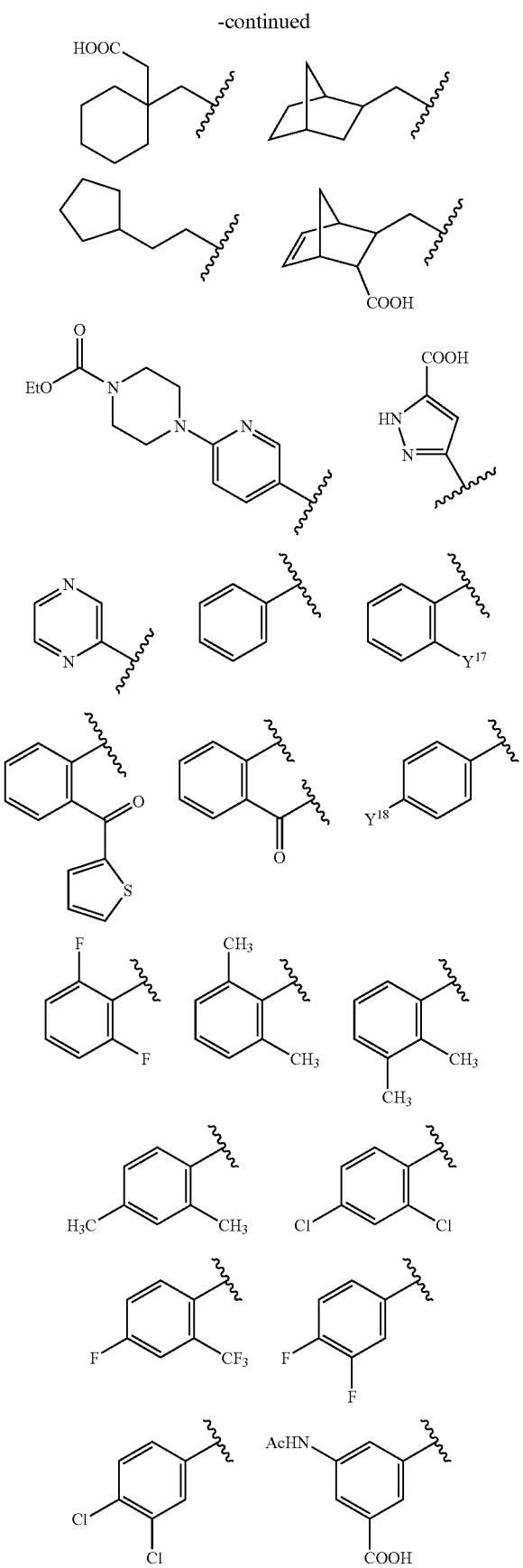
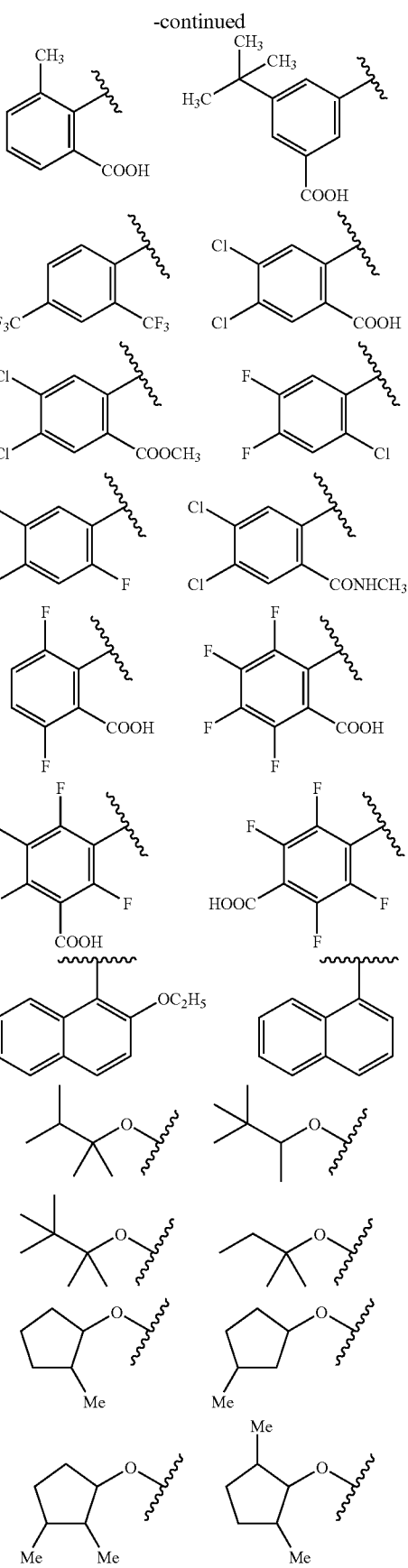

-continued
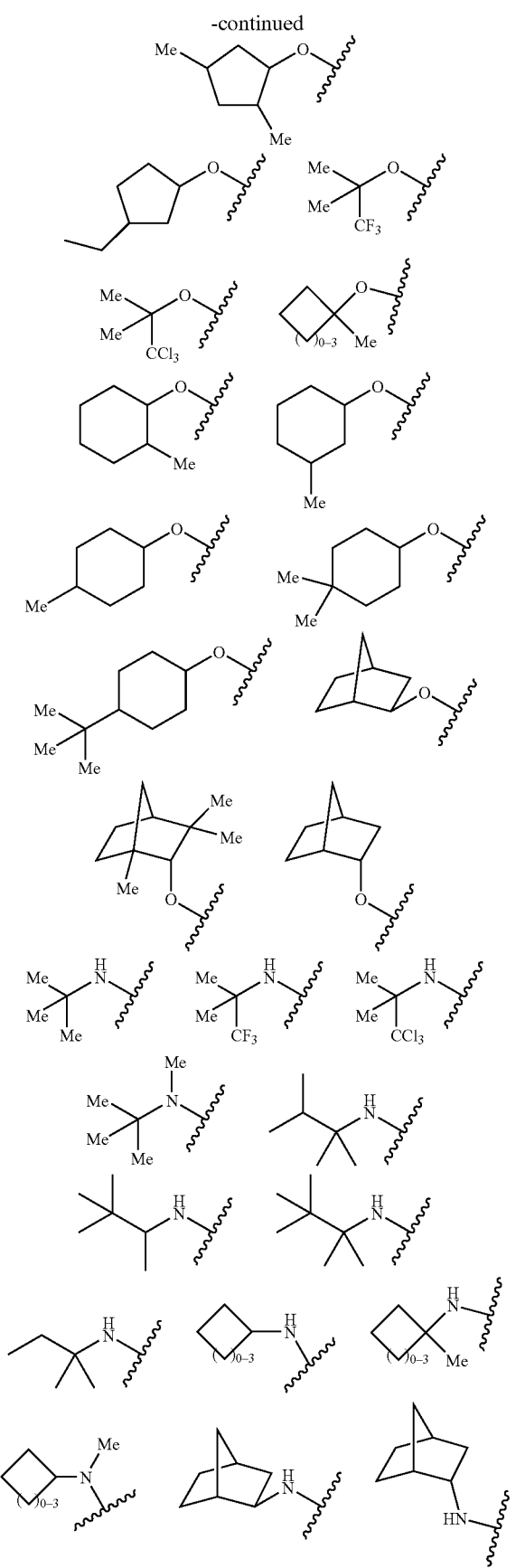
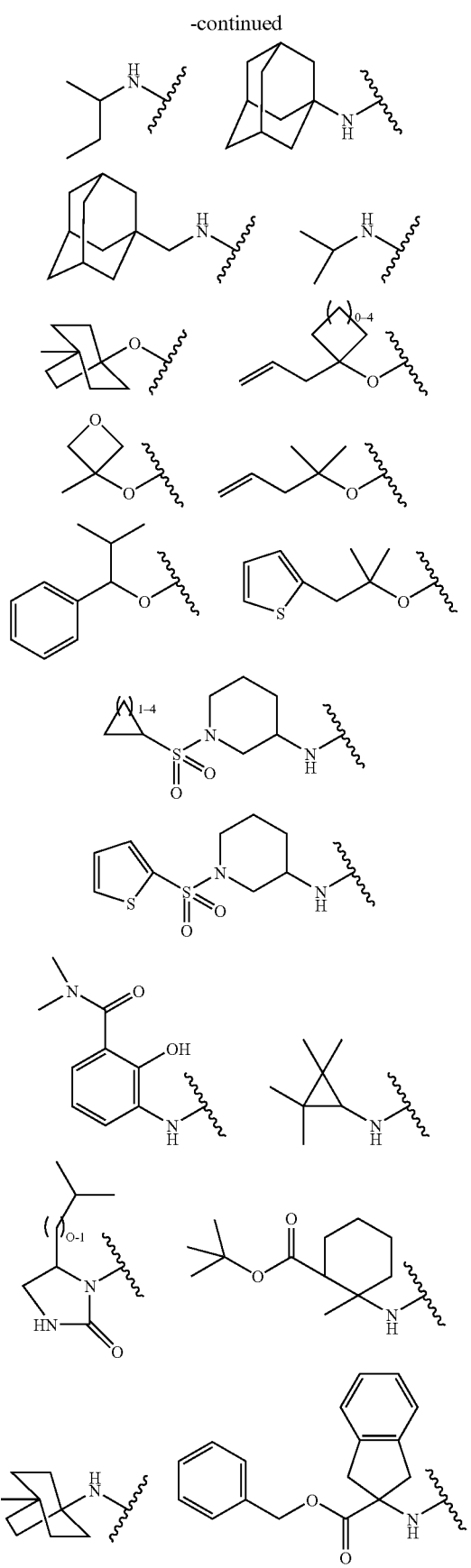

-continued
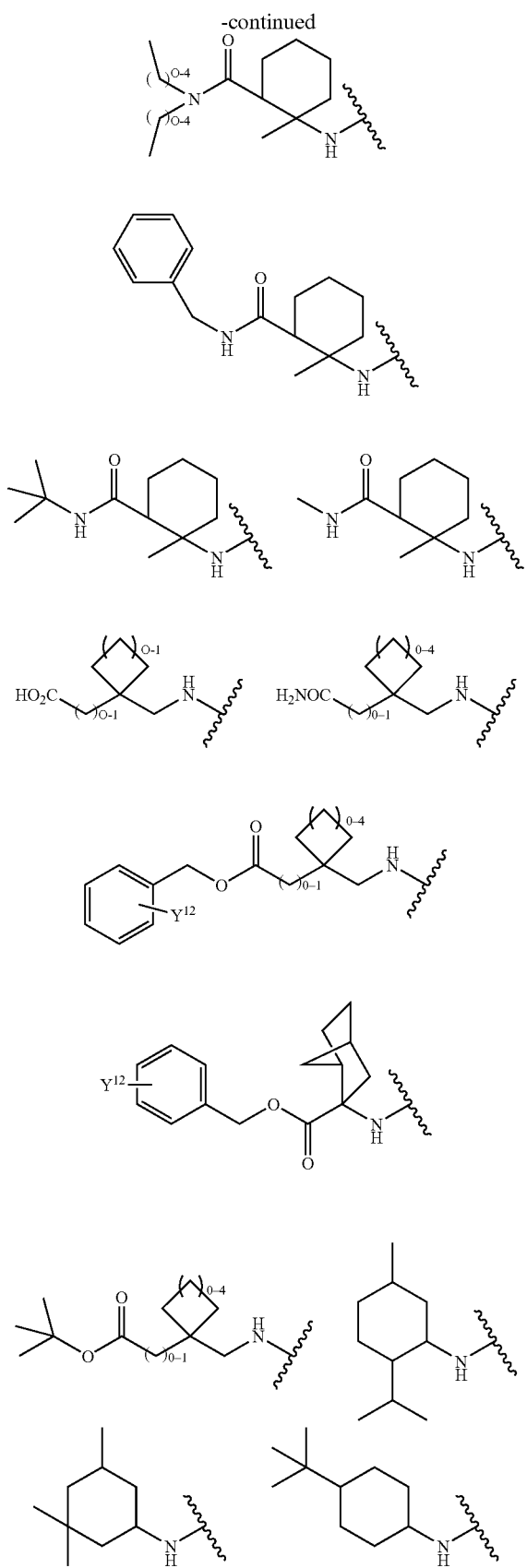
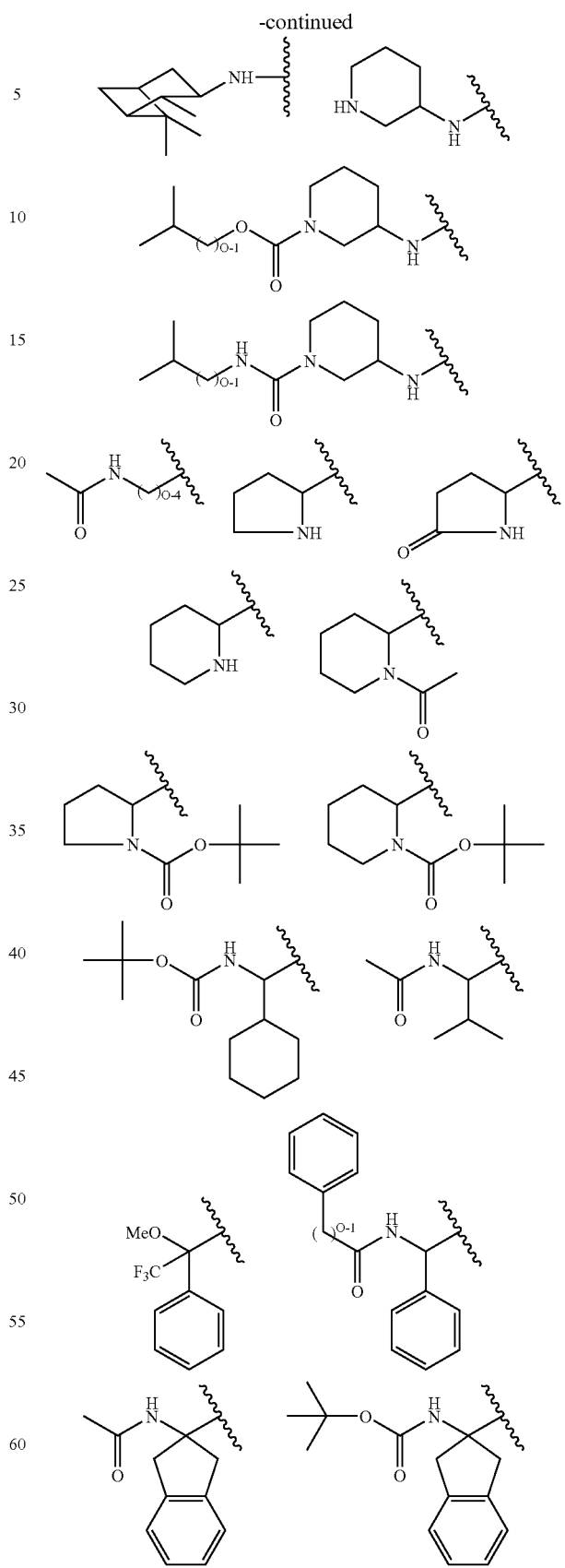

-continued

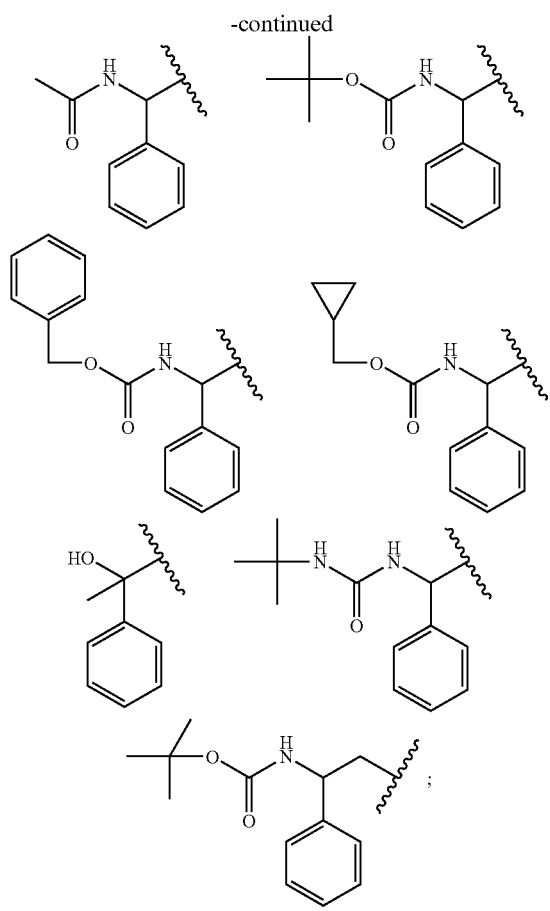

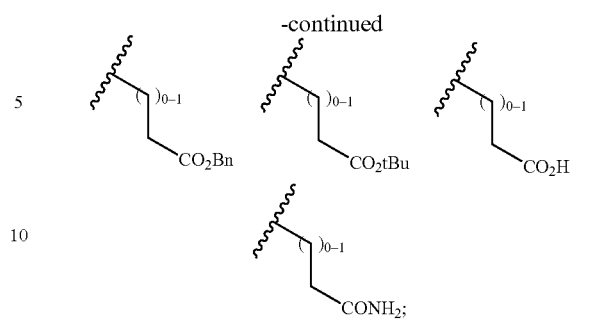

$Y^{14}$ is MeSO$_2$, Ac, Boc, iBoc, Cbz, or Alloc;

$Y^{15}$ and $Y^{16}$ are independently selected from the group consisting of: alkyl, aryl, heteroalkyl and heteroaryl;

$Y^{17}$ is CF$_3$, NO$_2$, CONH$_2$, OH, COOCH$_3$, OCH$_3$, OC$_6$H$_5$, C$_6$H$_5$, COC$_6$H$_5$, NH$_2$ or COOH; and $Y^{18}$ is COOCH$_3$, NO$_2$, N(CH$_3$)$_2$, F, OCH$_3$, CH$_2$COOH, COOH, SO$_2$NH$_2$, or NHCOCH$_3$.

In another class of embodiments of the present invention, Cap is selected from the group consisting of the following structures:

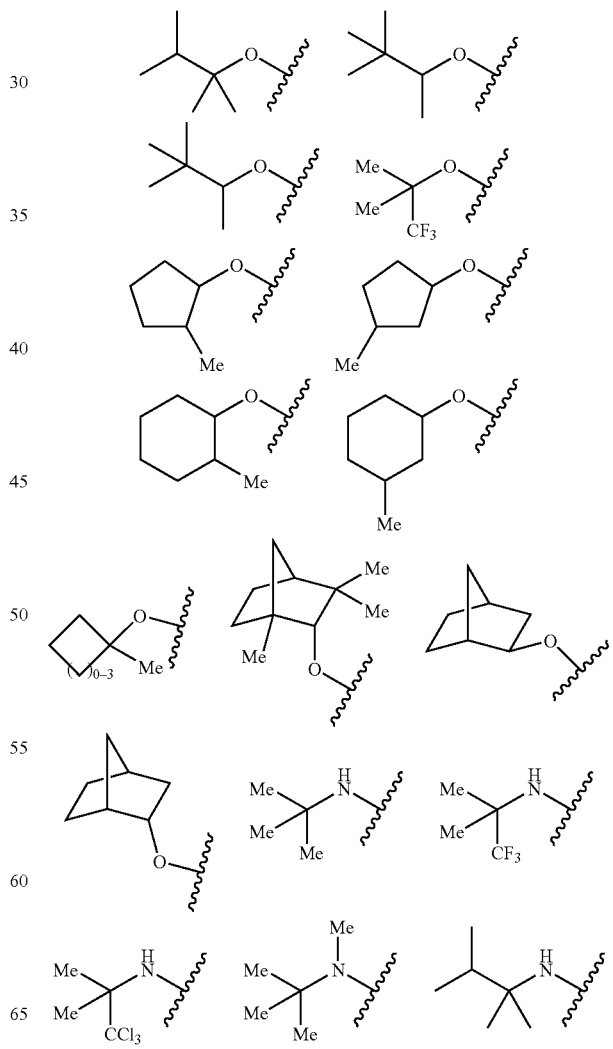

$Y^{11}$ is H, COOH, COOEt, OMe, Ph, OPh, NHMe, NHAc, NHPh, CH(Me)$_2$, 1-triazolyl, 1-imidazolyl or NHCH$_2$COOH;

$Y^{12}$ is H, COOH, COOMe, OMe, F, Cl, Br, NH$_2$, NHSO$_2$CH$_3$, NHCOCH$_3$, NO$_2$, SO$_2$NH$_2$, CF$_3$, Me, OH or CONH$_2$;

$Y^{13}$ is selected from the following:

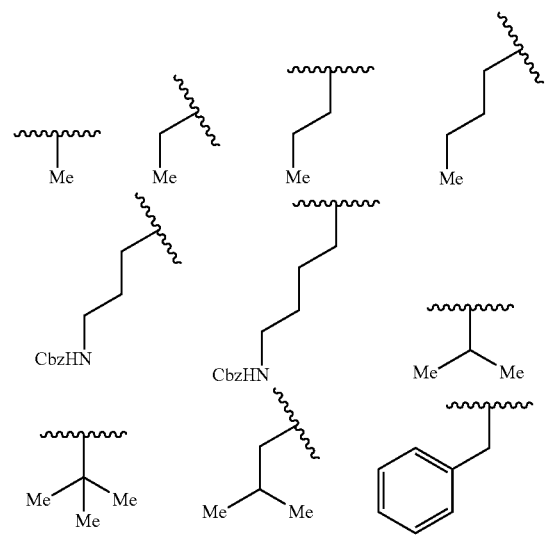

-continued
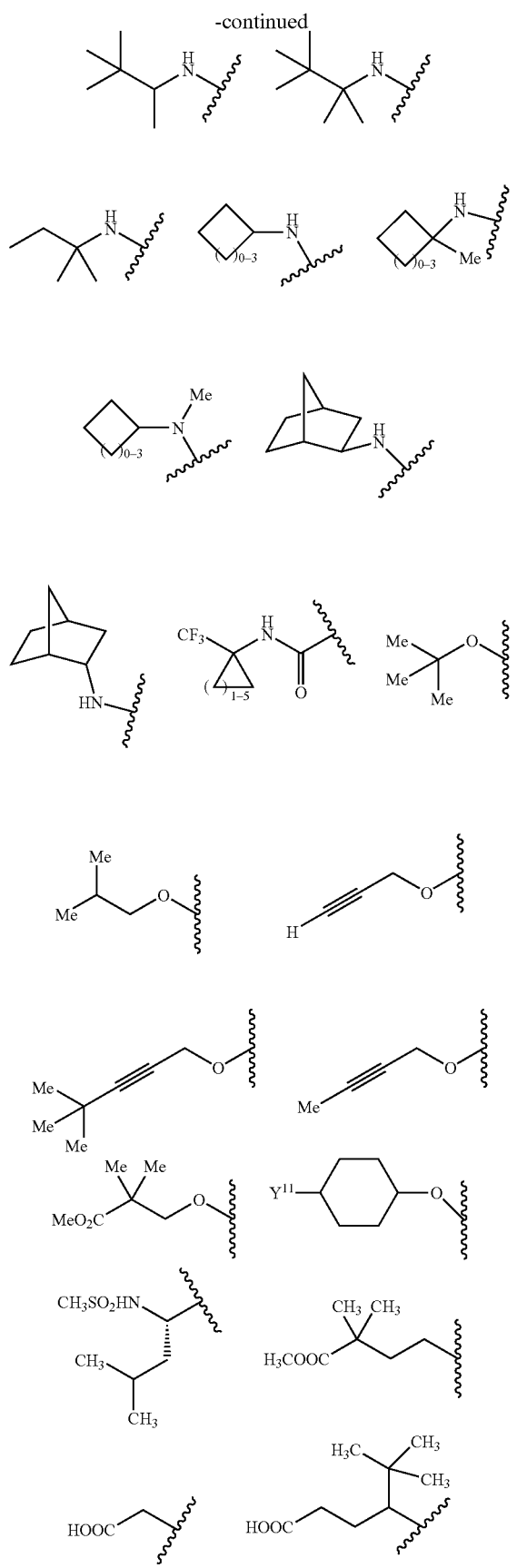
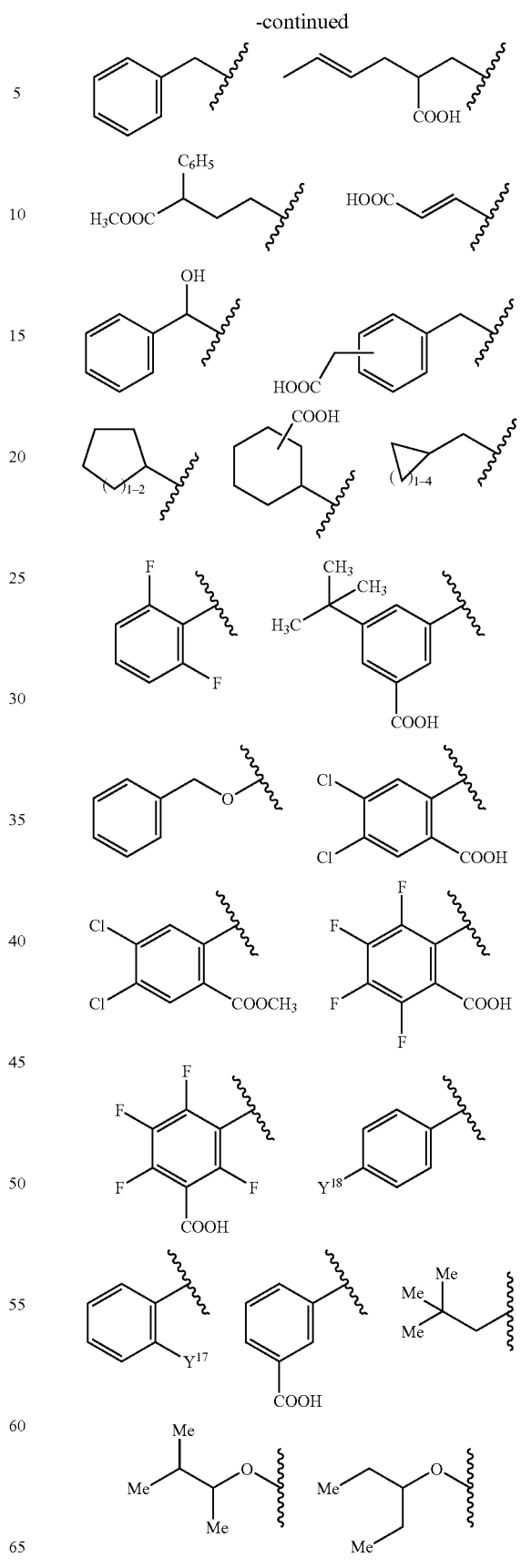

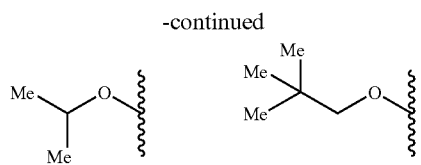
$Y^{17}$ is $CF_3$, $NO_2$, $CONH_2$, OH, $NH_2$ or COOH; and
$Y^{18}$ is F or COOH.
In still another class of embodiments of the present invention, Cap is selected from the group consisting of the following structures:
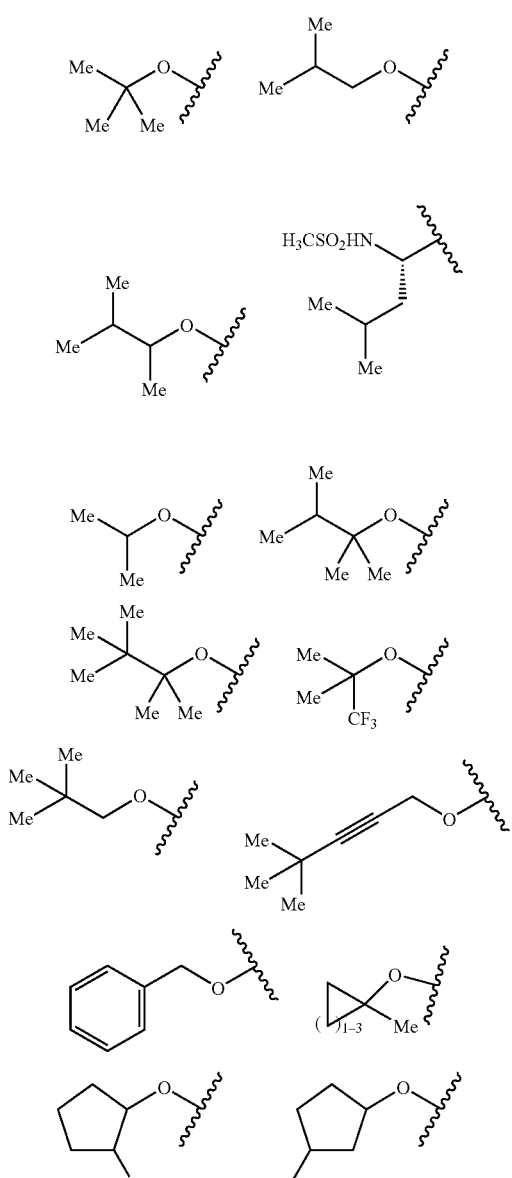
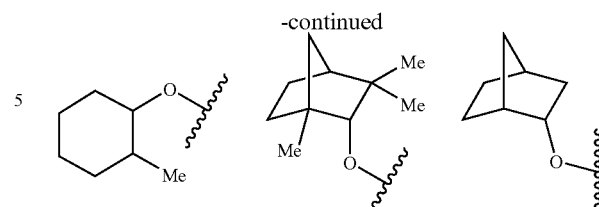
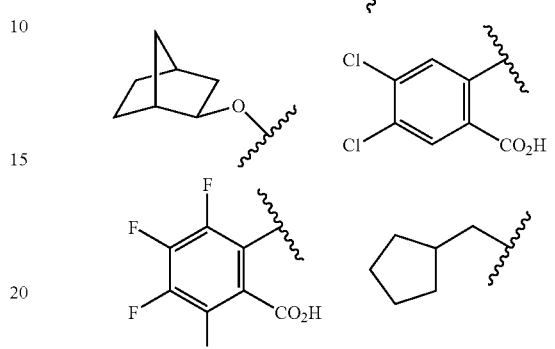
In an aspect of the present invention, W is C=O;
$R^3$ is selected from the group consisting of the following structures:
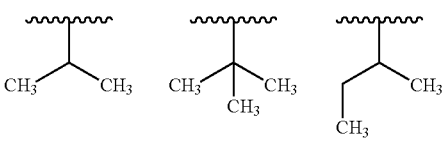

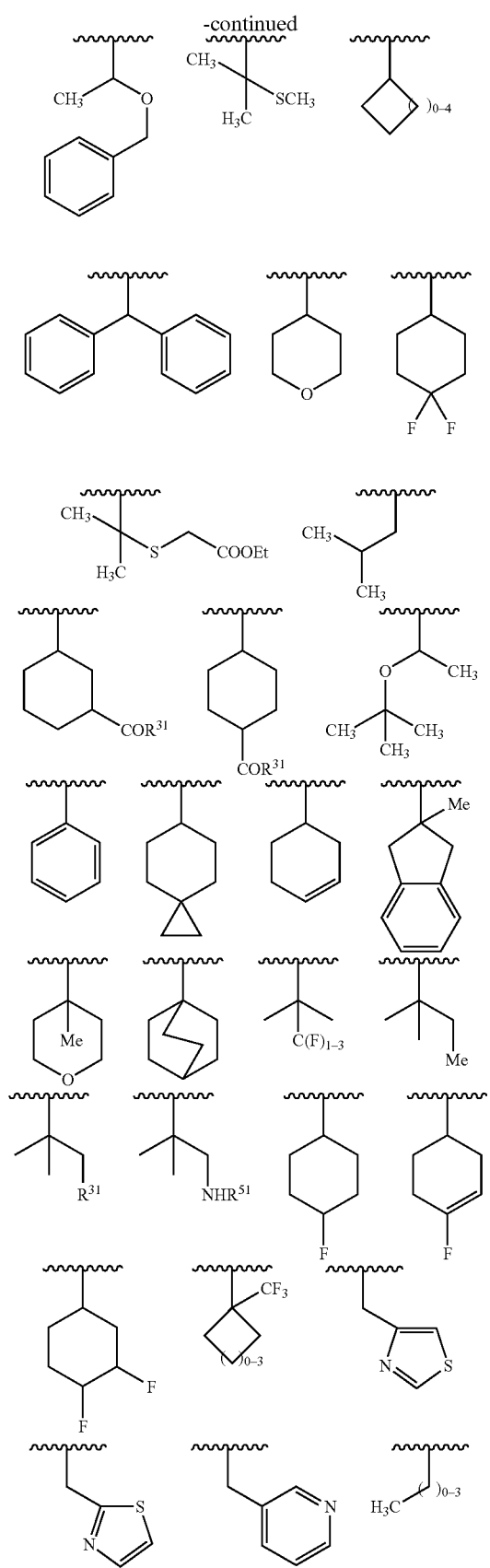
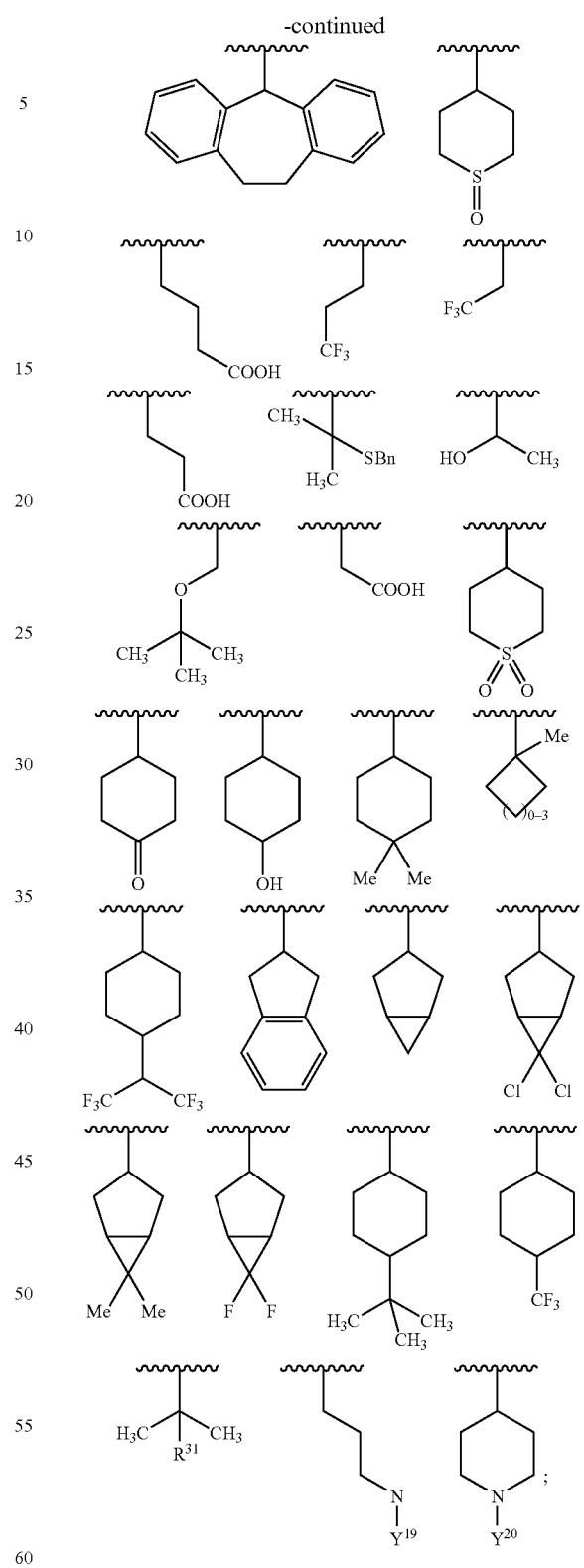
$R^{51}$ is H, COCH$_3$, COOtBu or CONHtBu;
$R^{31}$ is OH or O-alkyl;
$Y^{19}$ is selected from the group consisting of the following structures:

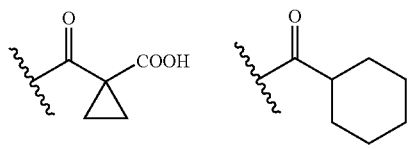
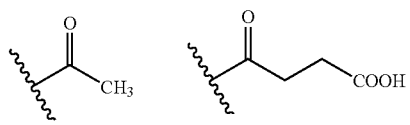
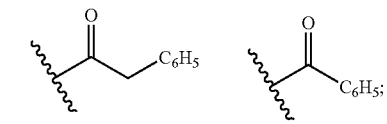
and Y$^{20}$ is selected from the group consisting of the following structures:
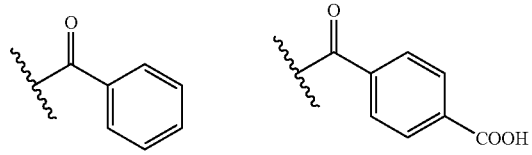
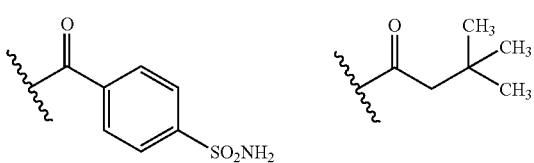
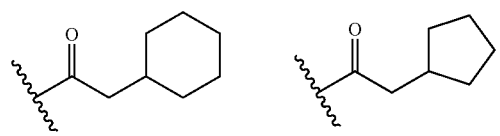
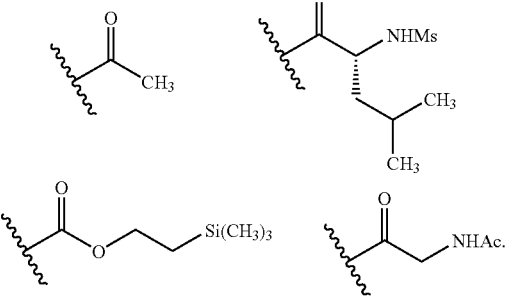
In another aspect of the present invention, R$^3$ is selected from the group consisting of the following structures:
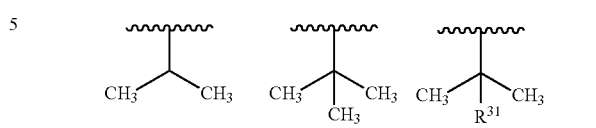
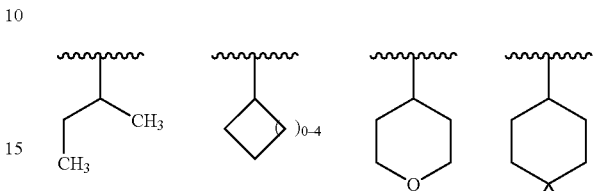
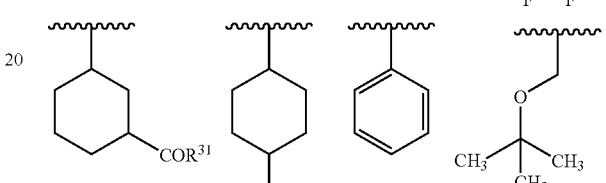
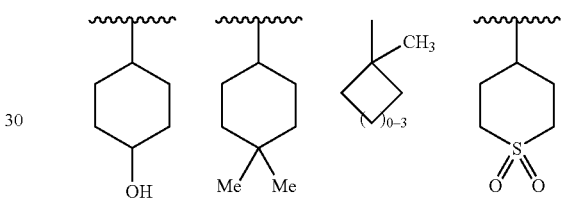
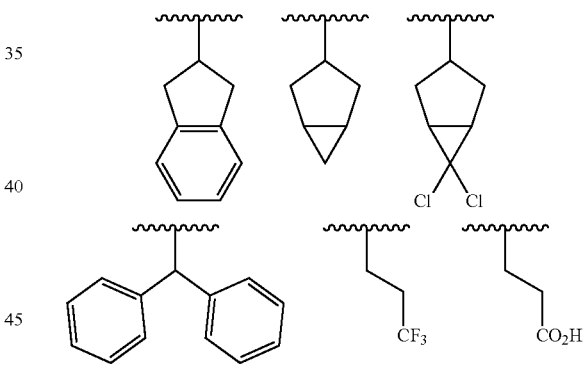
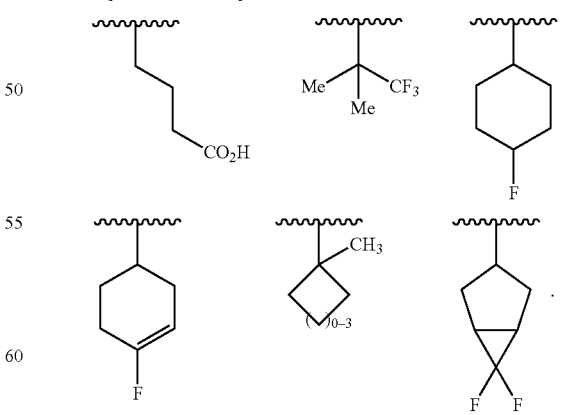
In another aspect of the present invention, R$^3$ is selected from the group consisting of the following structures:

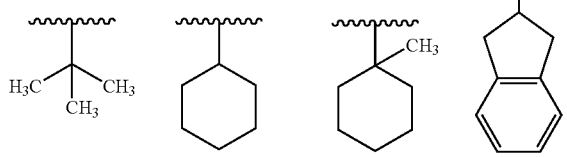

In another aspect of the present invention, W is C=O;
P' is selected from the group consisting of the following structures:

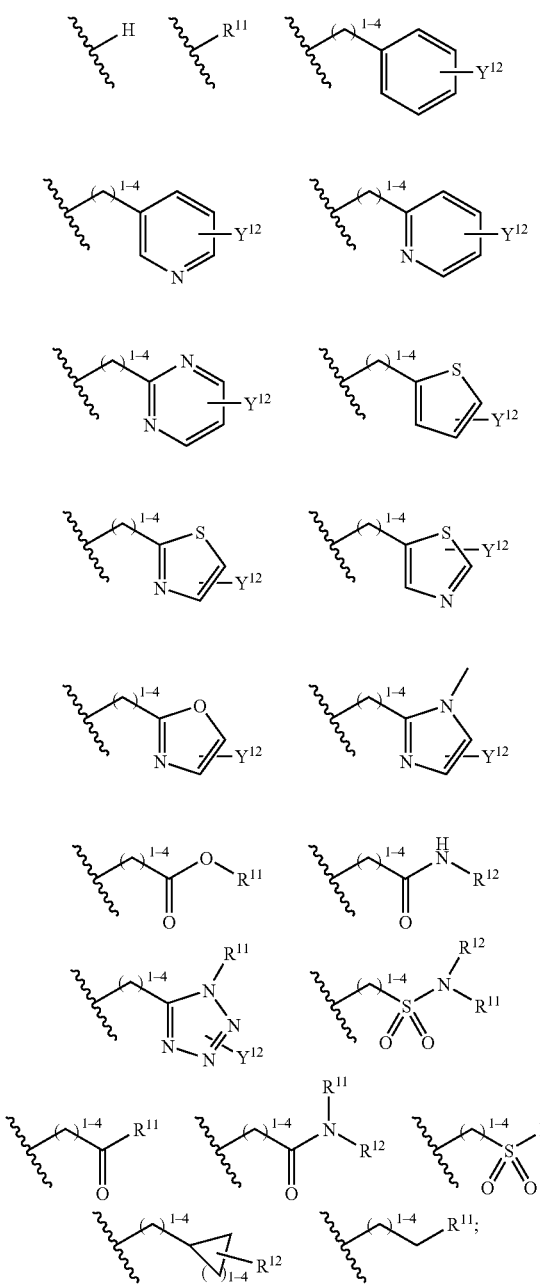

$R^{11}$ and $R^{12}$ is independently selected from the group consisting of: H, methyl, ethyl, propyl, propargyl, allyl, isopropyl, isobutyl, tert-butyl, benzyl, phenyl, 2-pyridyl, 3-pyridyl, 2-thiaphenyl, α-methylbenzyl, α,α-dimethylbenzyl, 1-methylcyclopropyl, 1-methylcyclopentyl and

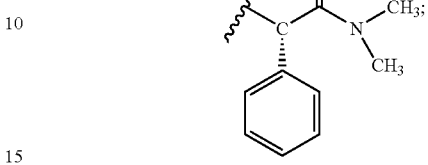

and $Y^{12}$ is one or more substituents independently selected from H, COOH, COOMe, OMe, F, Cl, Br, $NH_2$, $NHSO_2CH_3$, $CON(CH_3)_2$, $NHCOCH_3$, COOtBu, $NO_2$, $SO_2NH_2$, $CF_3$, Me, Et, OH, $OCF_3$, $CONH_2$. In another aspect of the present invention, P' is selected from the group consisting of the following structures:

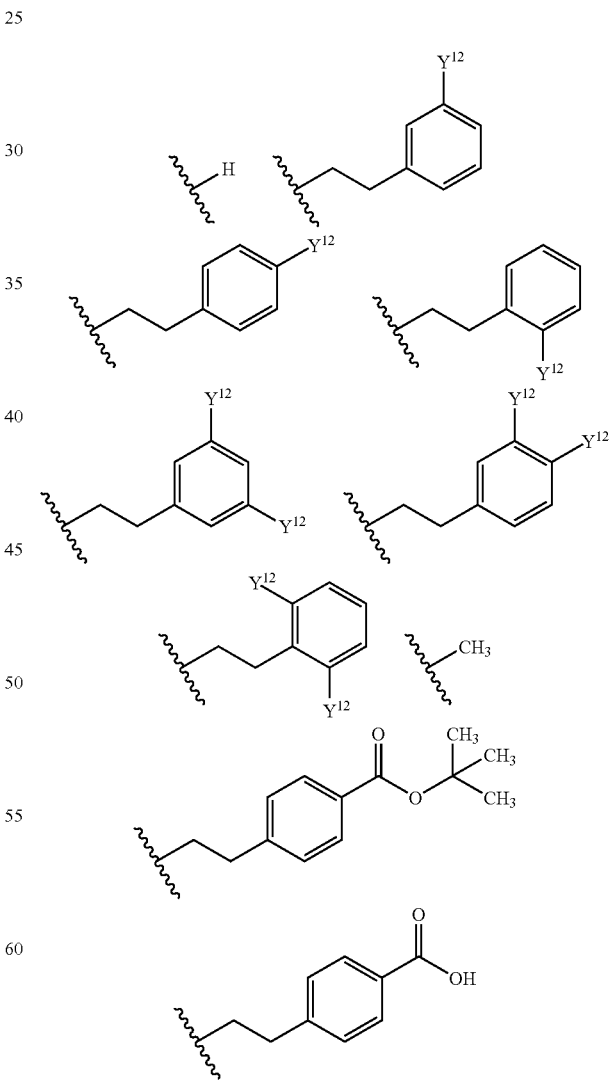

-continued
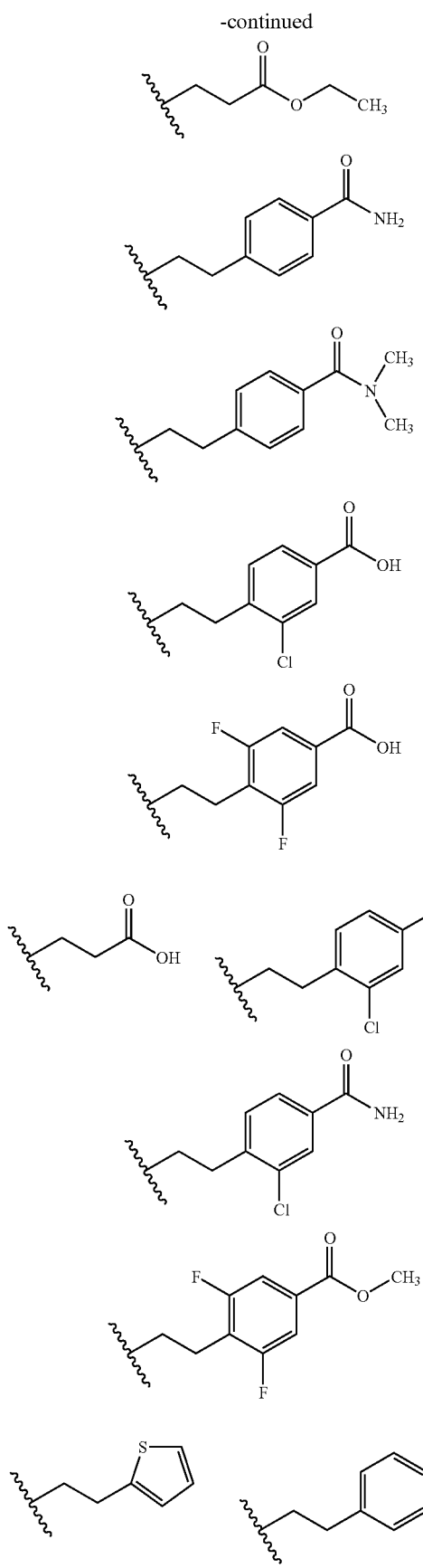
-continued
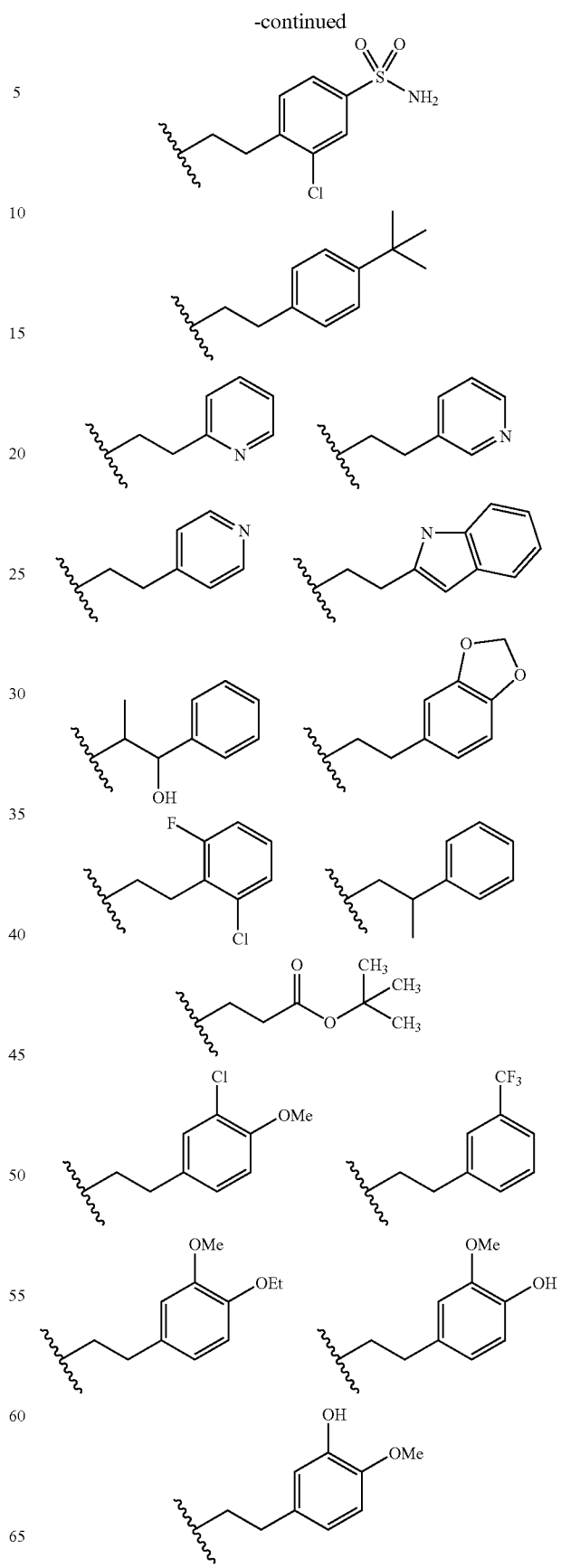

-continued
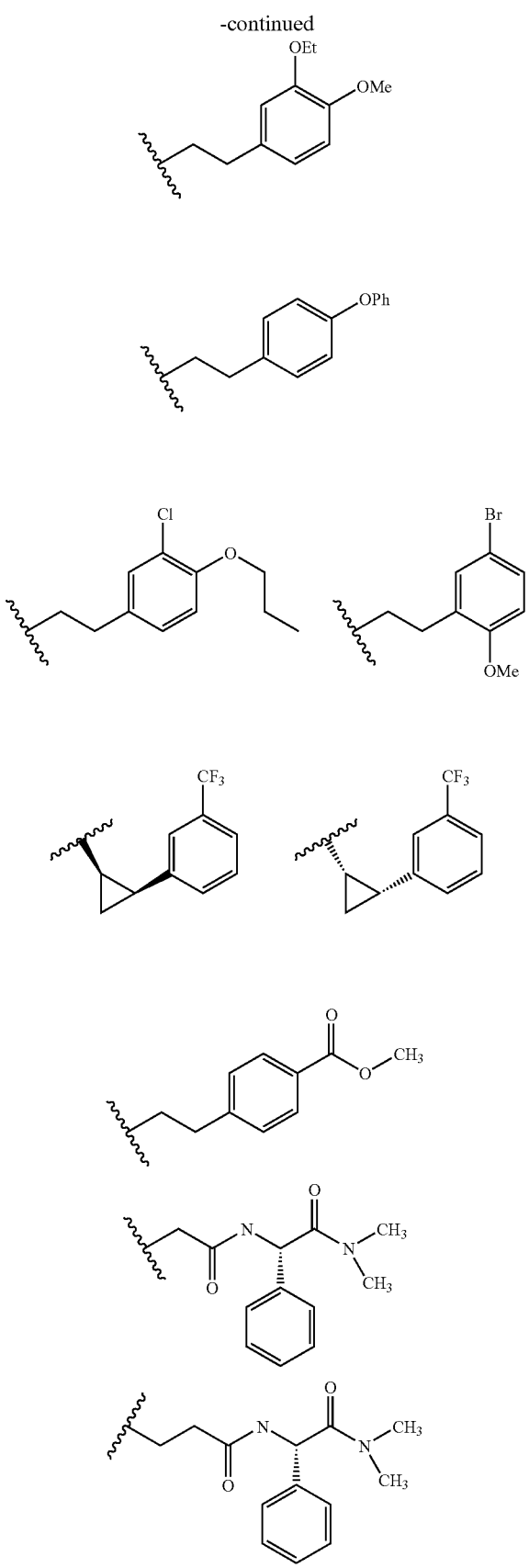
-continued
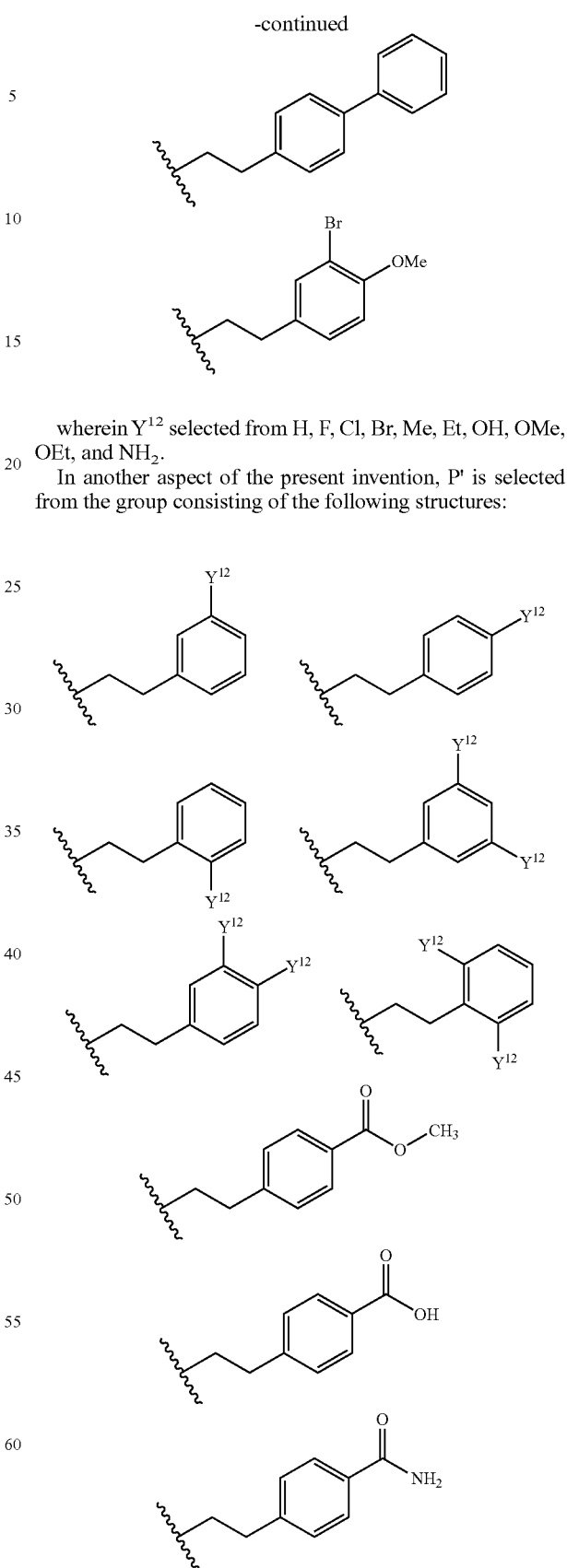
wherein $Y^{12}$ selected from H, F, Cl, Br, Me, Et, OH, OMe, OEt, and $NH_2$.
In another aspect of the present invention, P' is selected from the group consisting of the following structures:

-continued
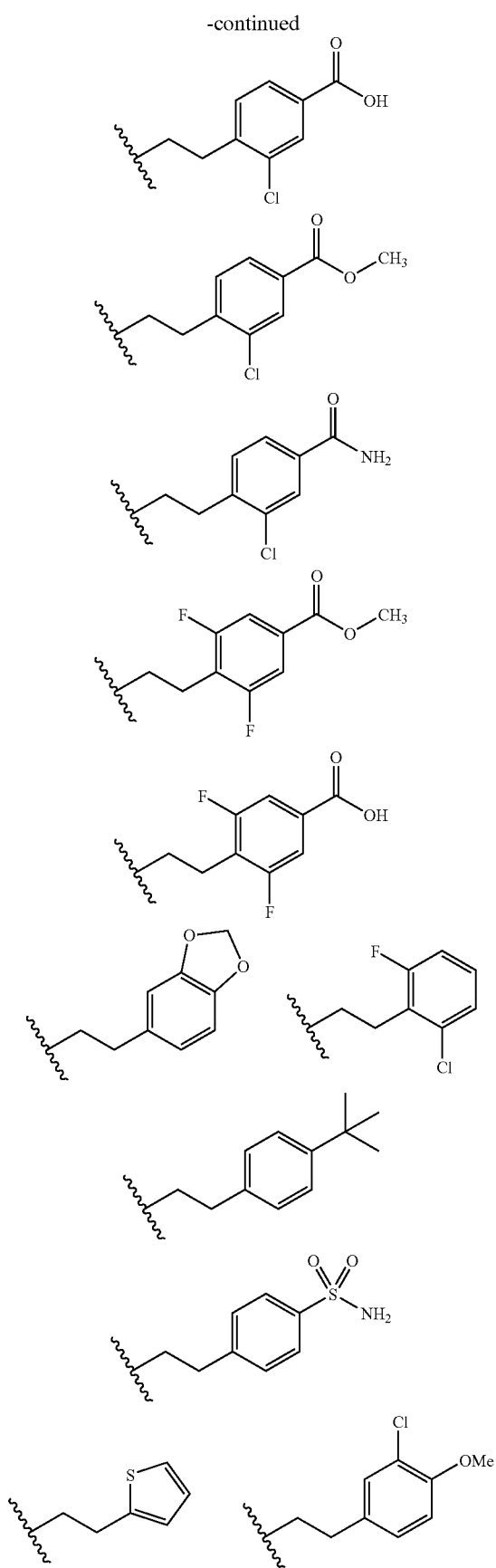
-continued
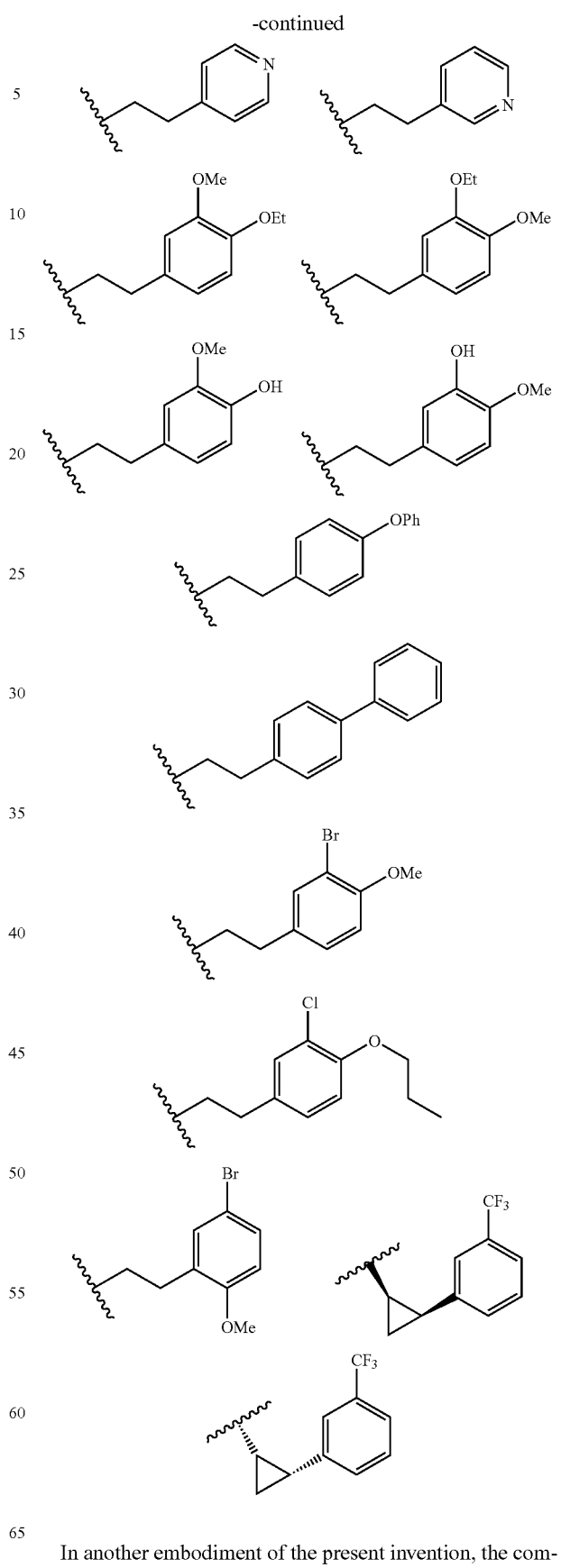
In another embodiment of the present invention, the compounds are represented by structural Formula 7:

Formula 7
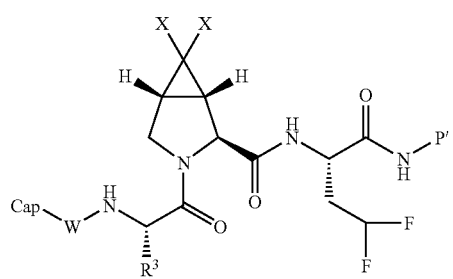
wherein X is CH$_3$, F, Cl or Br, and the other moieties are as defined before.
In another embodiment of the present invention, in for Formula 7, Cap is selected from the group consisting of the following structures:
-continued
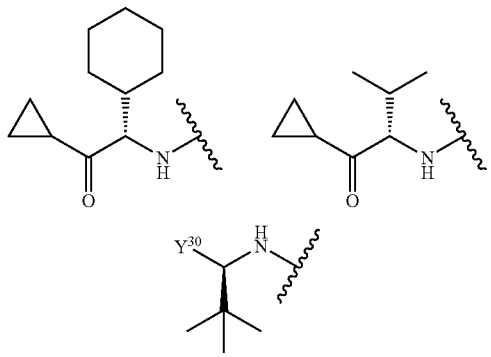
wherein Y$^{30}$ is selected from the group consisting of the following structures:
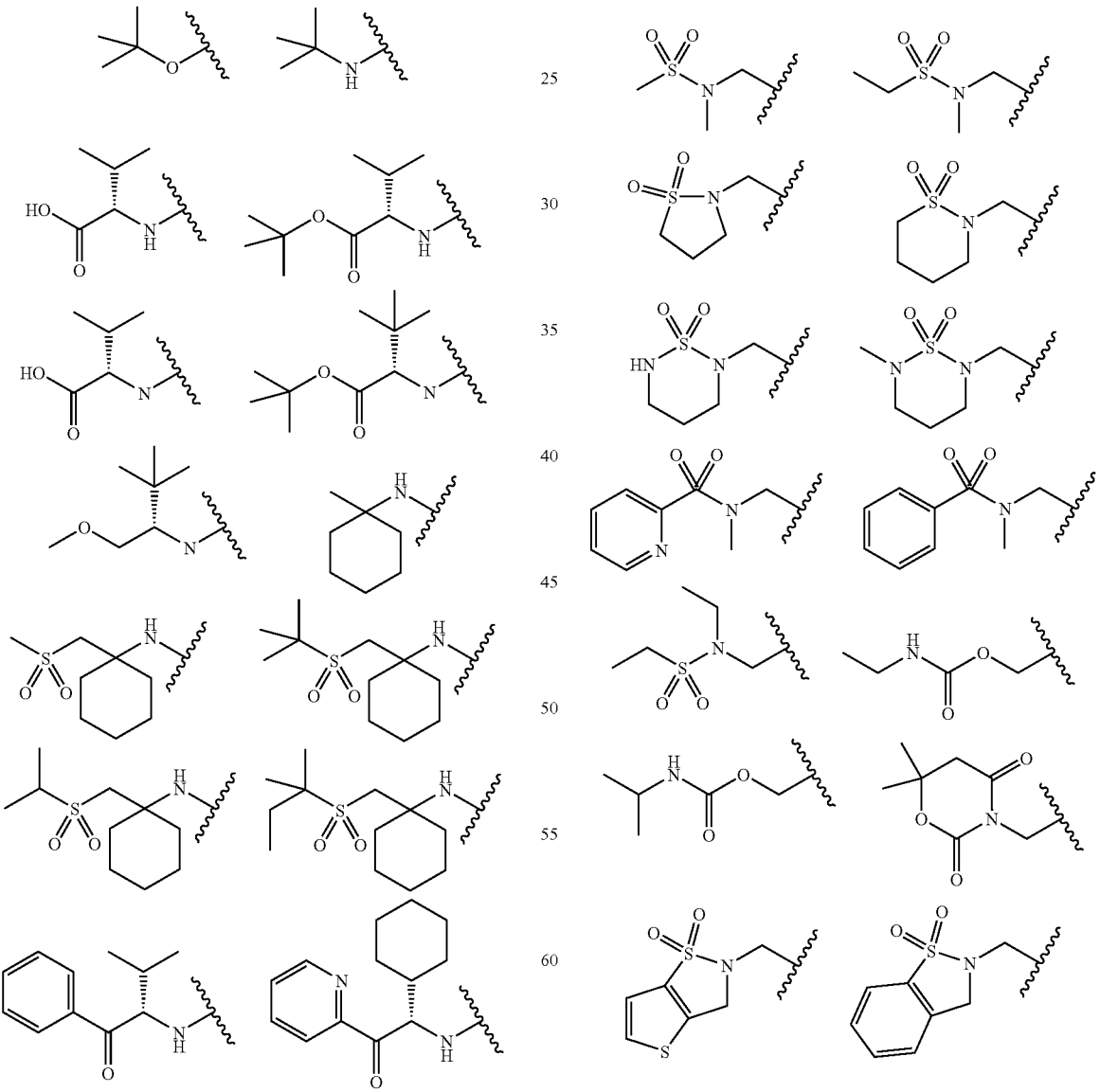

-continued
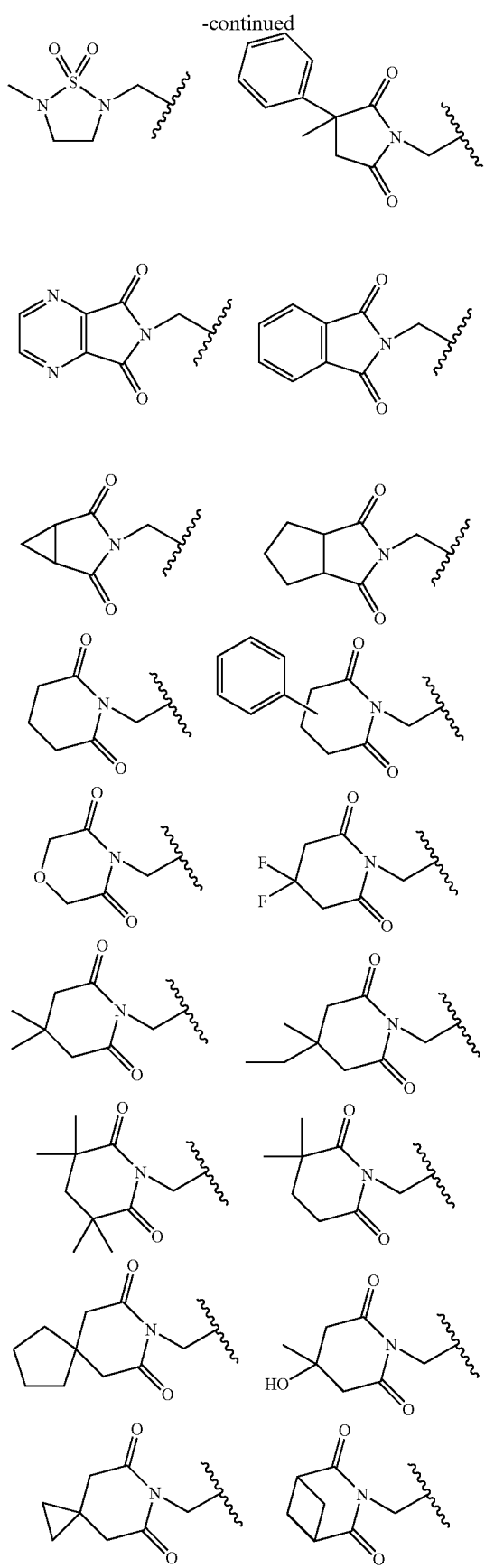
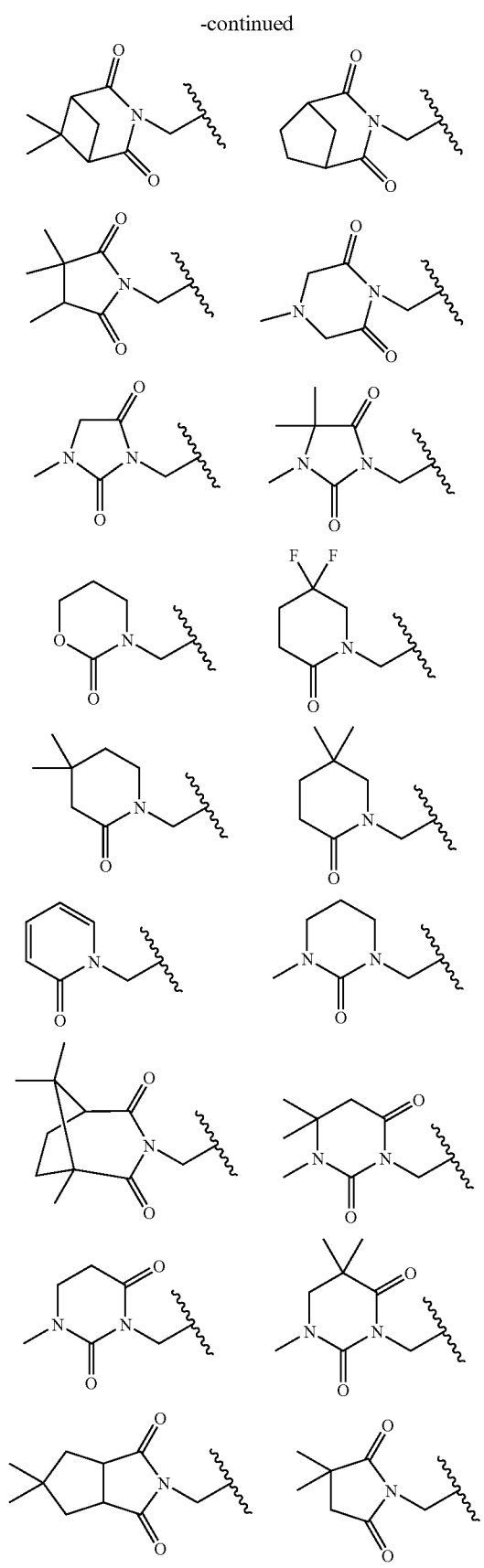

-continued
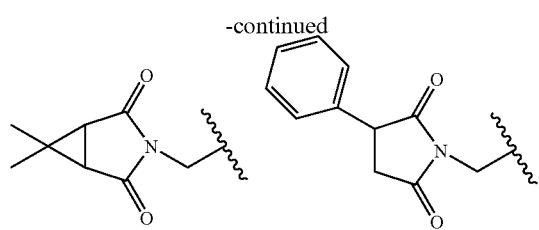
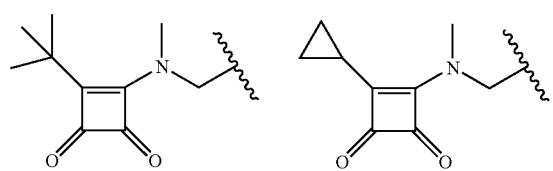
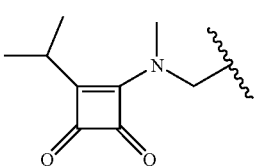
In another embodiment of the present invention, in Formula 7, Cap is selected from the group consisting of the following structures:
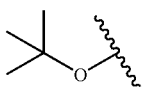
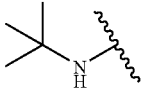
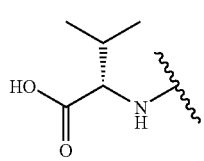
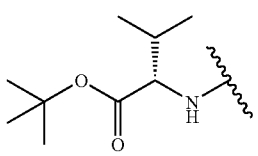
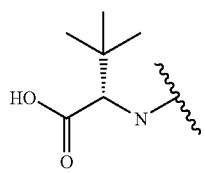
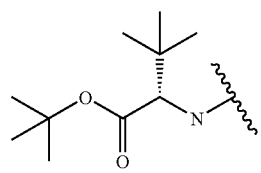
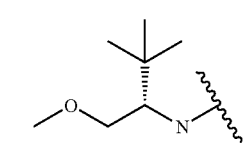
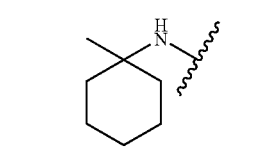
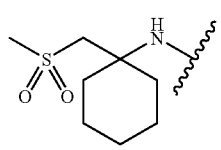
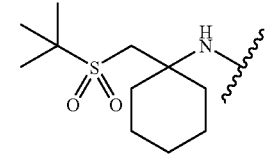
-continued
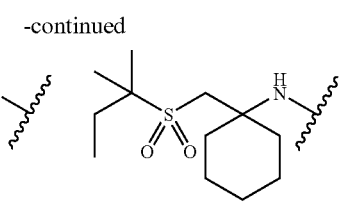
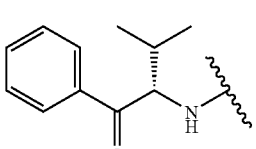
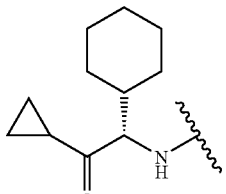
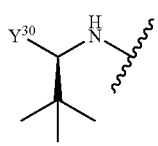
wherein $Y^{30}$ is selected from the group consisting of the following structures:
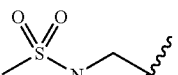
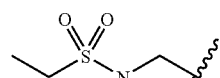
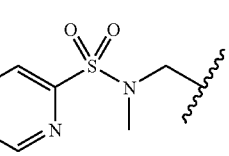
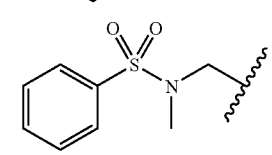
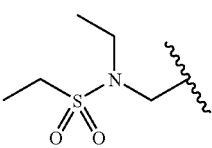
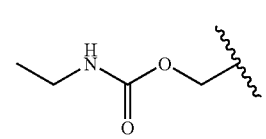

-continued
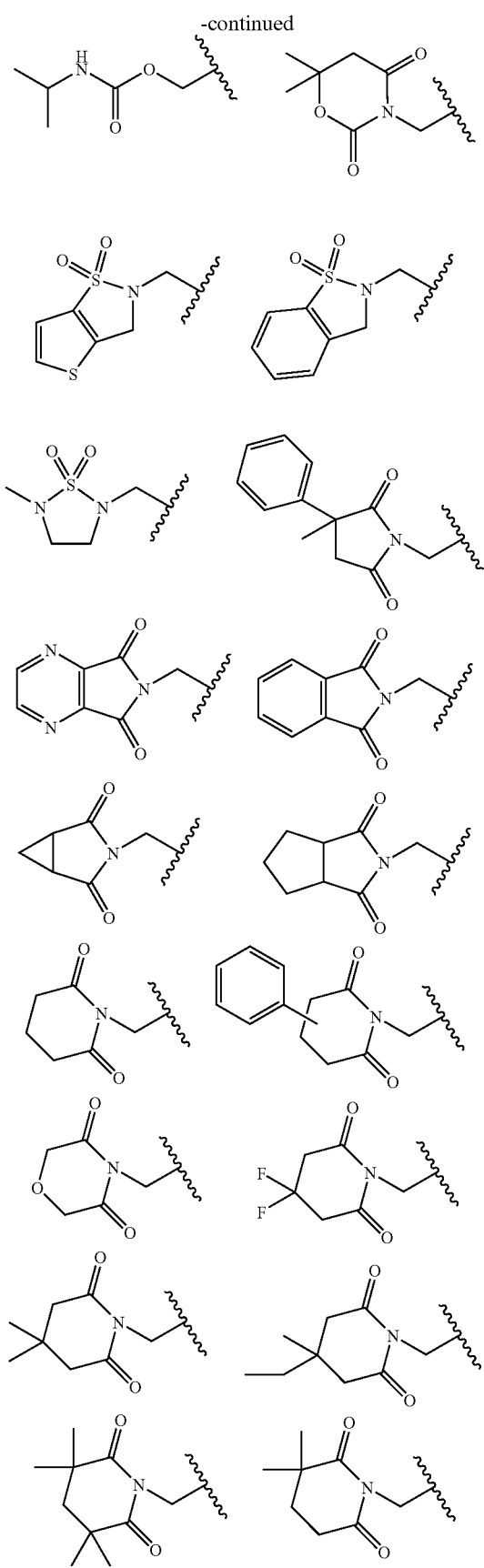
-continued
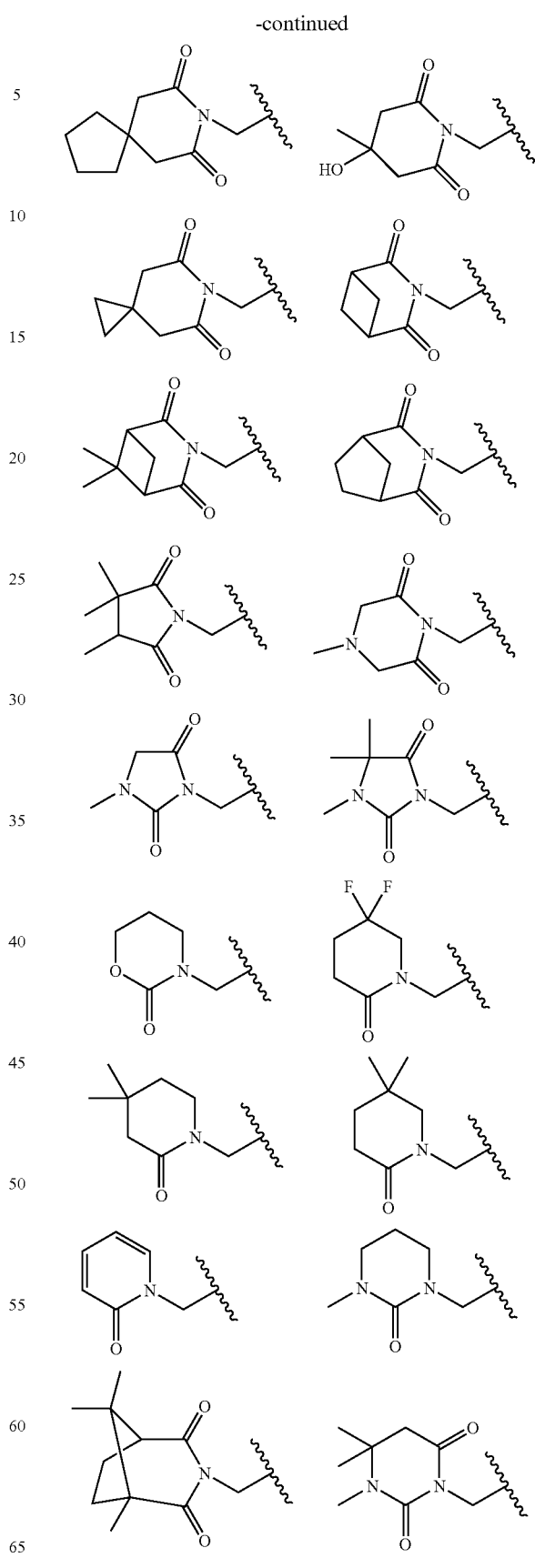

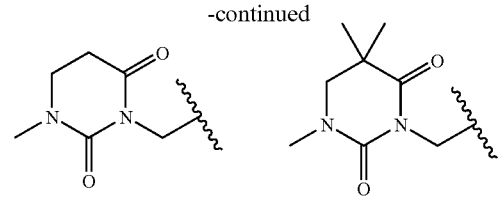
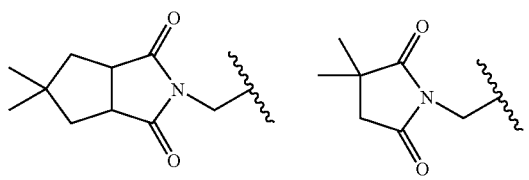
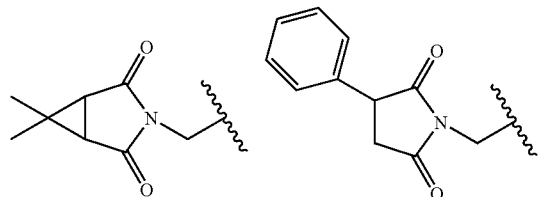
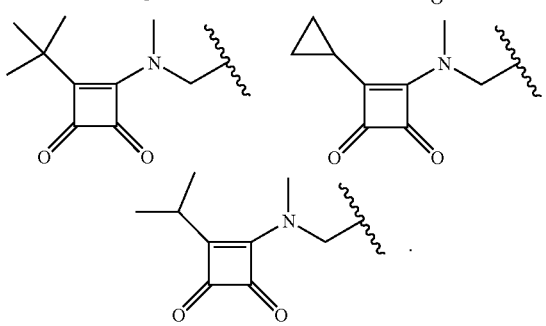
In another aspect of the present invention, in Formula 7, P' is selected from the group consisting of the following structures:
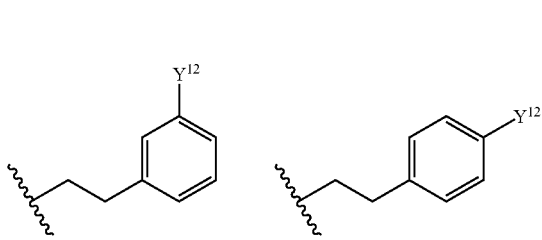
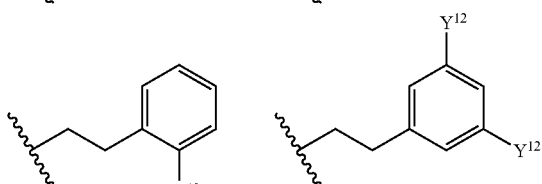
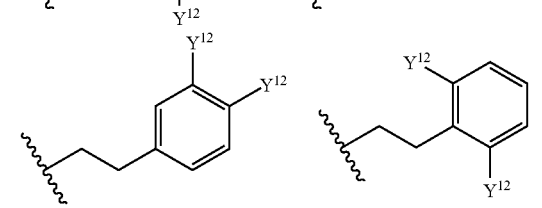
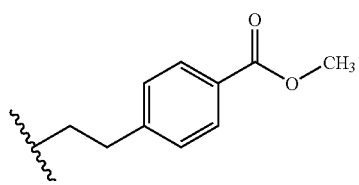
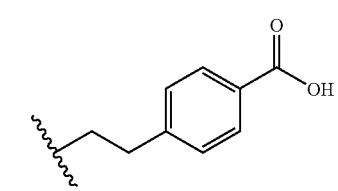
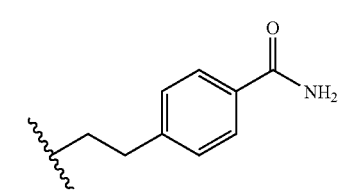
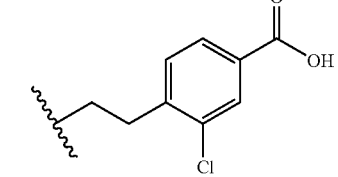
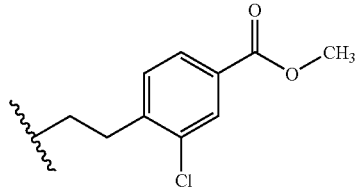
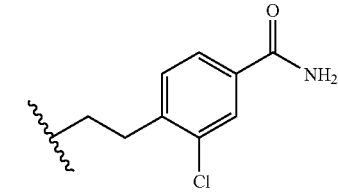
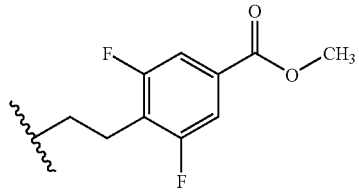
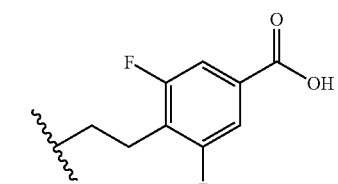

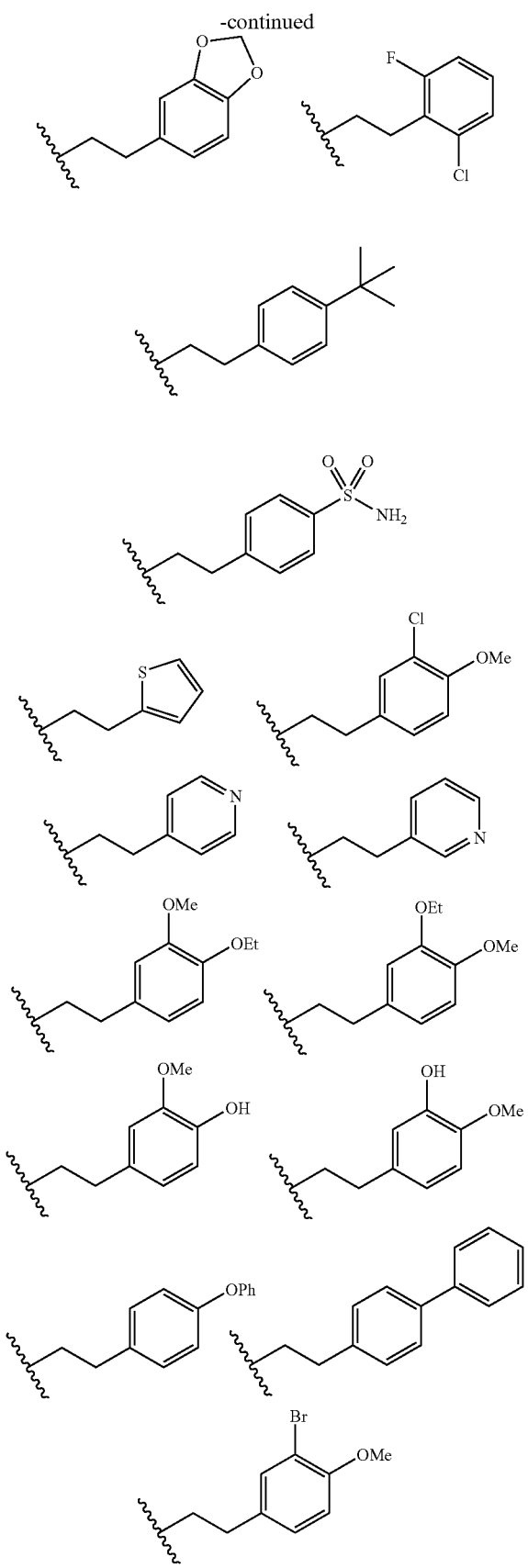
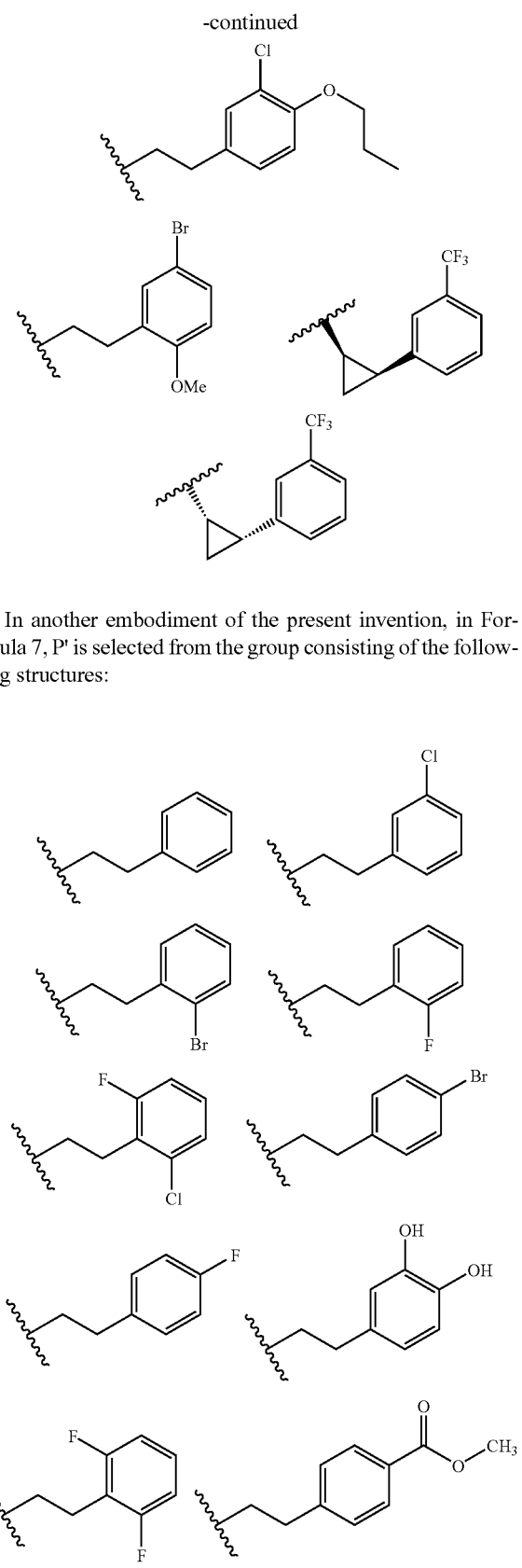
In another embodiment of the present invention, in Formula 7, P' is selected from the group consisting of the following structures:

-continued

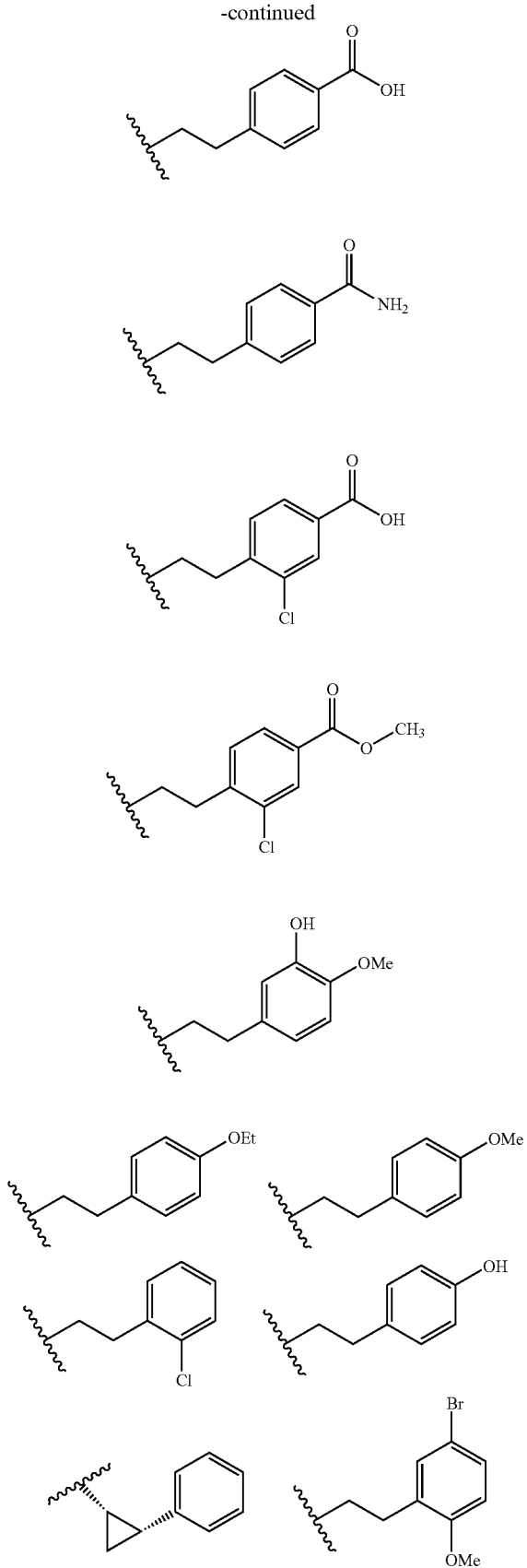

In another aspect of the present invention, W is C=O.

In still another aspect of the present invention, $R_3$ is selected from the group consisting of the following structures:

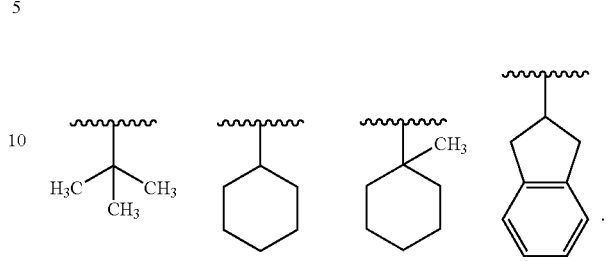

In another embodiment of the present invention, in Formula 7, Cap is selected from the group consisting of the following structures:

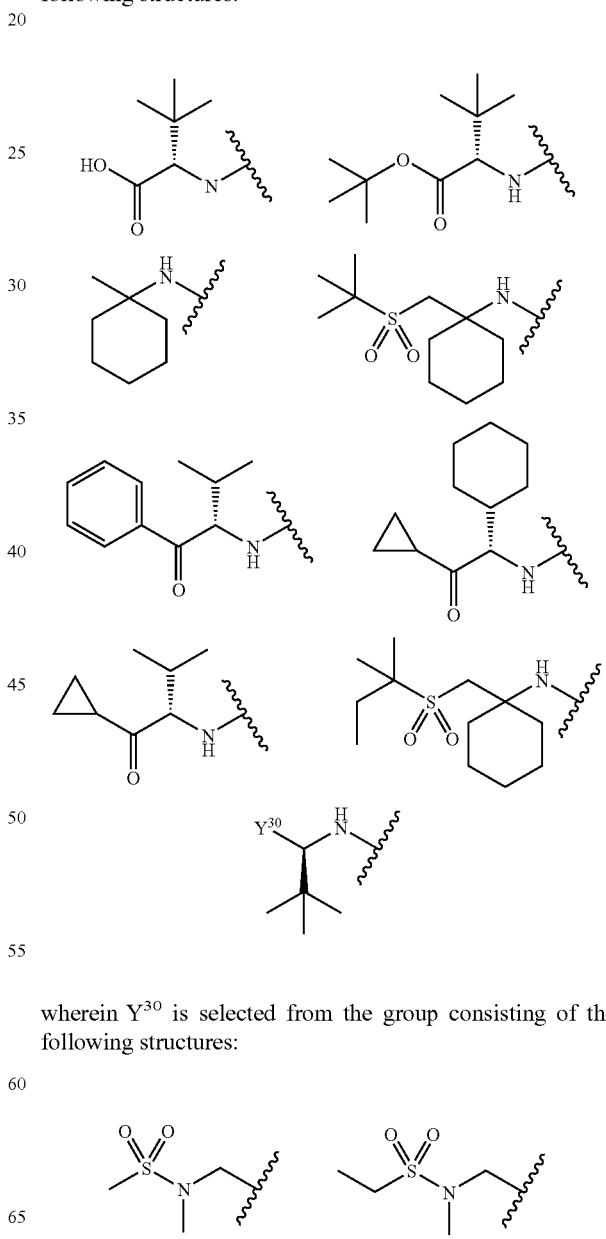

wherein $Y^{30}$ is selected from the group consisting of the following structures:

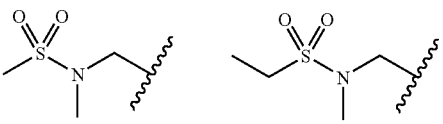

-continued
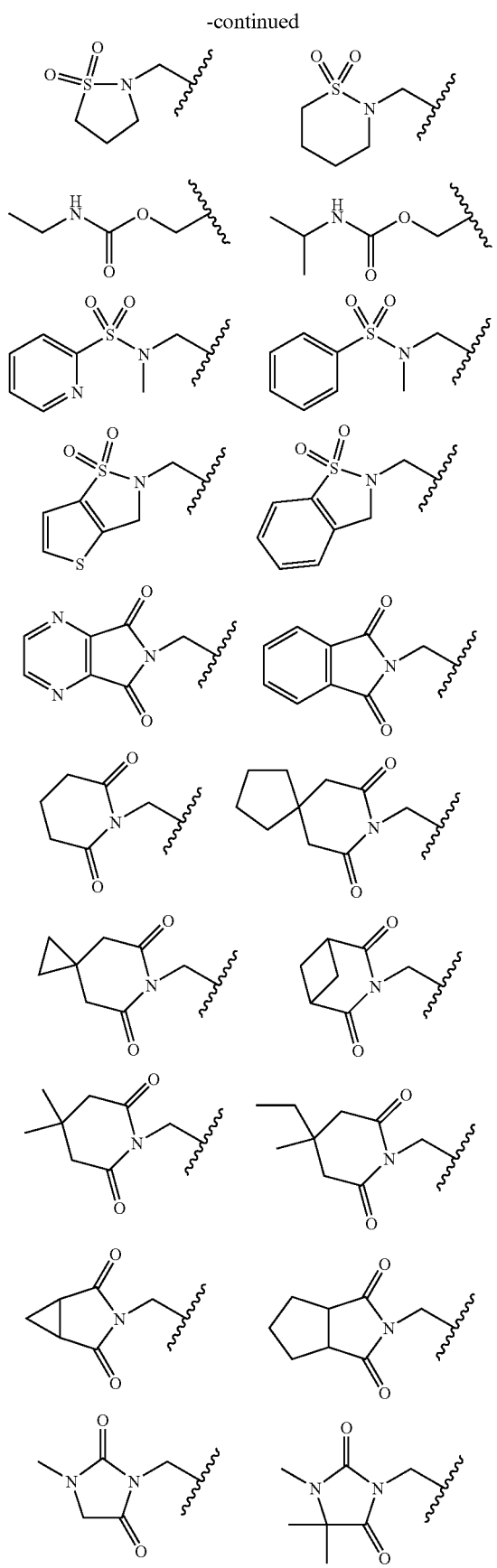
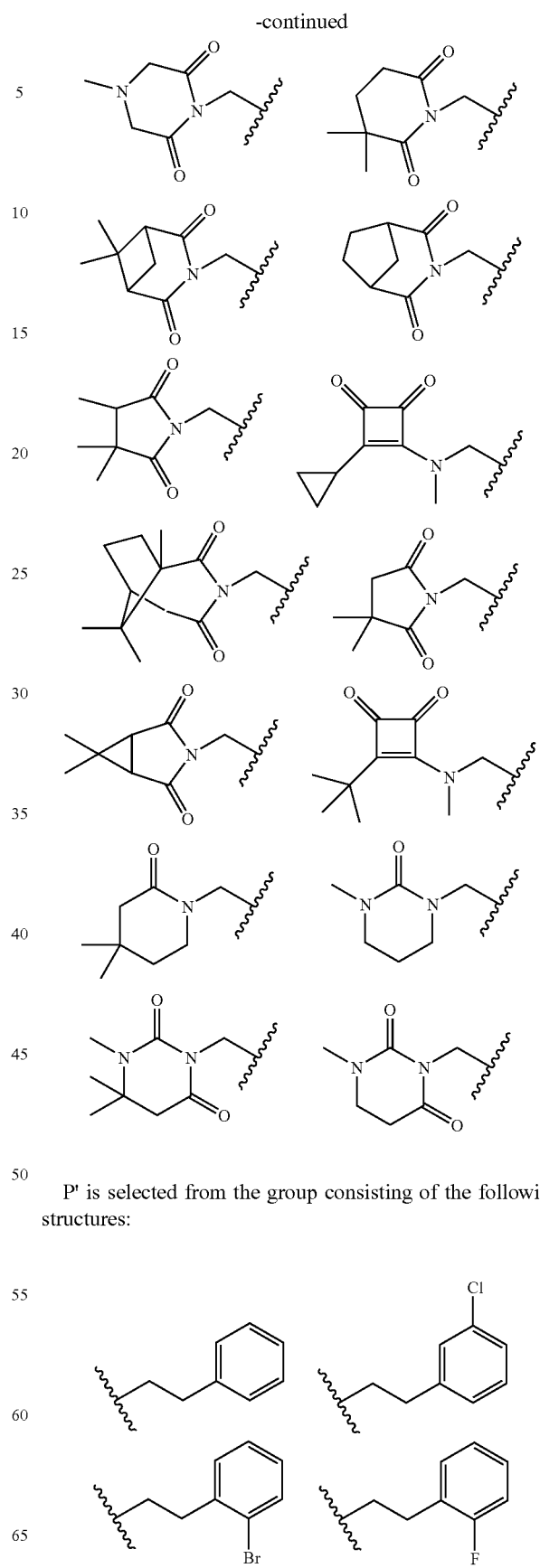
P' is selected from the group consisting of the following structures:
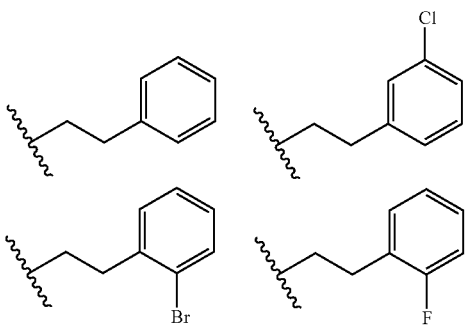

-continued

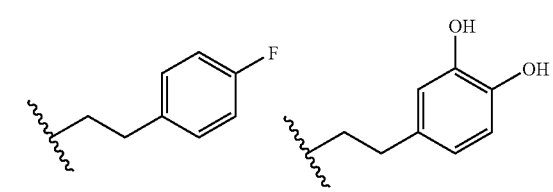
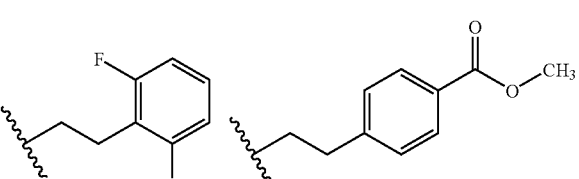
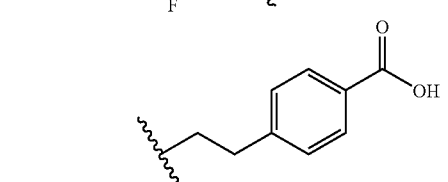
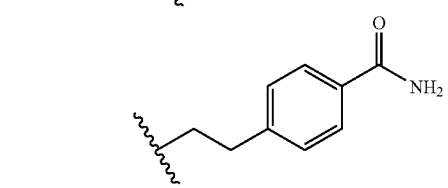
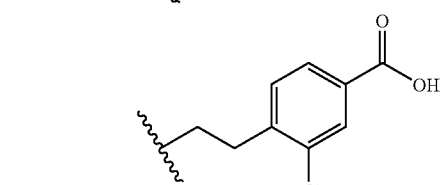
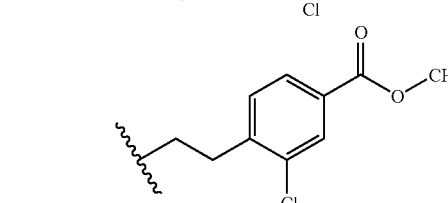
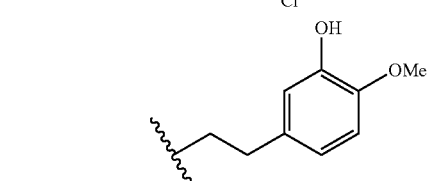
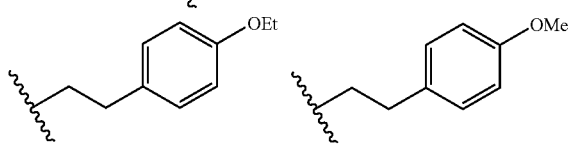
-continued
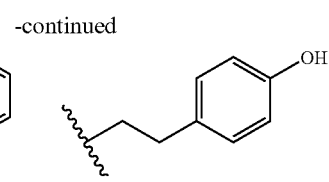
R is 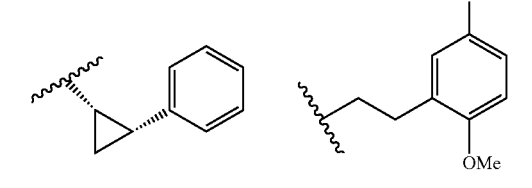
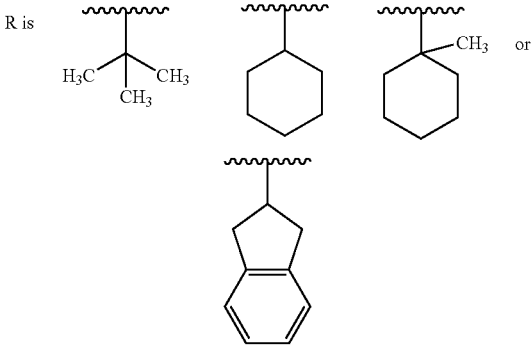
and W is C=O.
In another embodiment of the present invention, Cap is selected from the group consisting of the following structures:
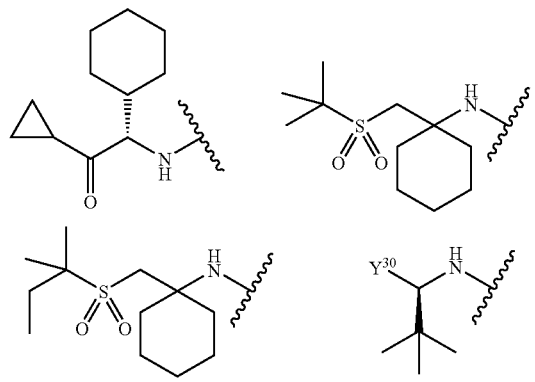
wherein $Y^{30}$ is selected from the group consisting of the following structures:
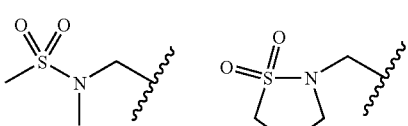

-continued
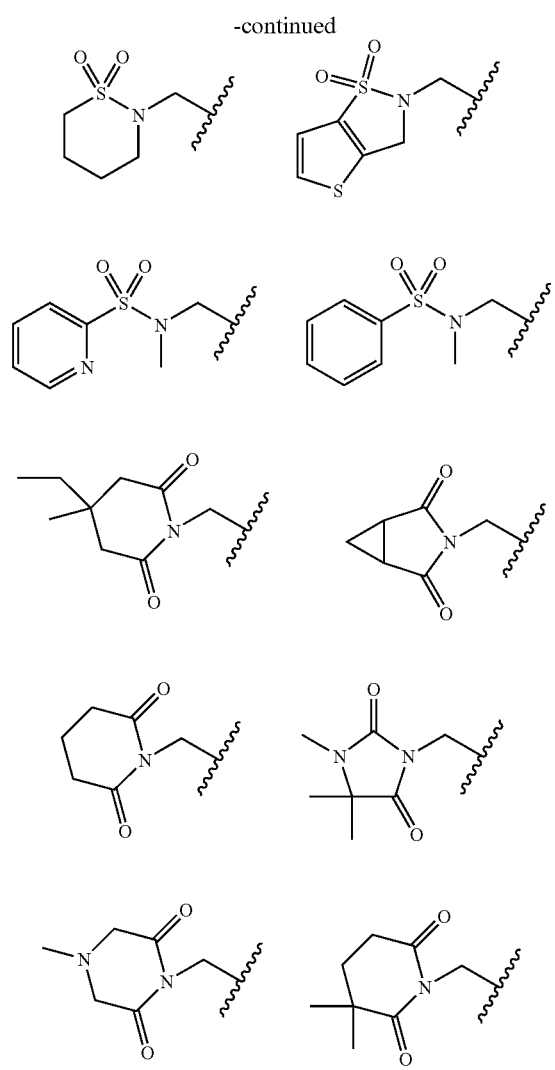
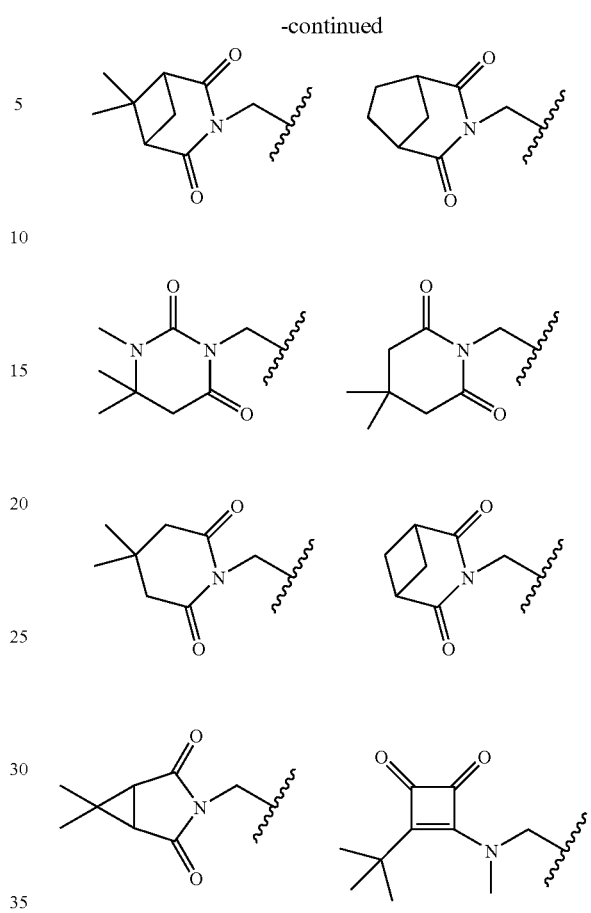
In still another embodiment of the present invention is a compound selected from the following structures in Table 1 below (or a pharmaceutically acceptable salt, solvate or ester thereof) which are shown along with their Ki values which are given in micromoles.
TABLE 1
| Example No | Structure | Ki (μM) |
|---|---|---|
| 101 | 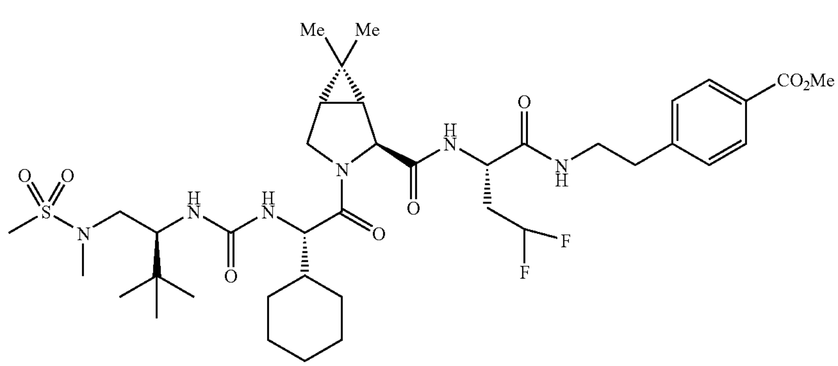 | 0.011 |

TABLE 1-continued

| Example No | Structure | Ki (μM) |
|---|---|---|
| 102 | 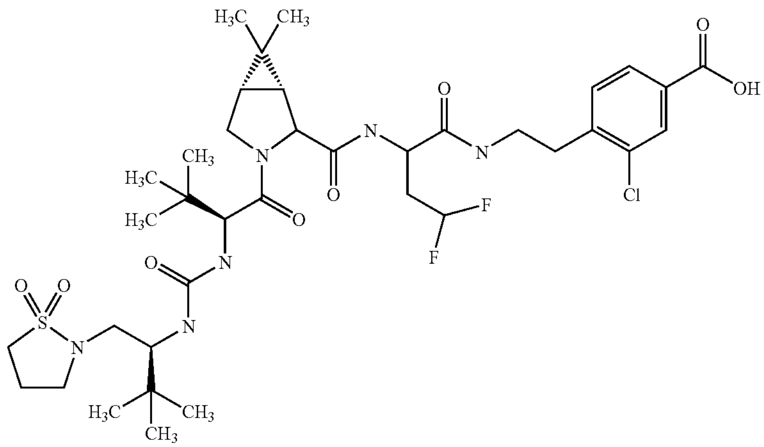 | 0.021 |
| 103 | 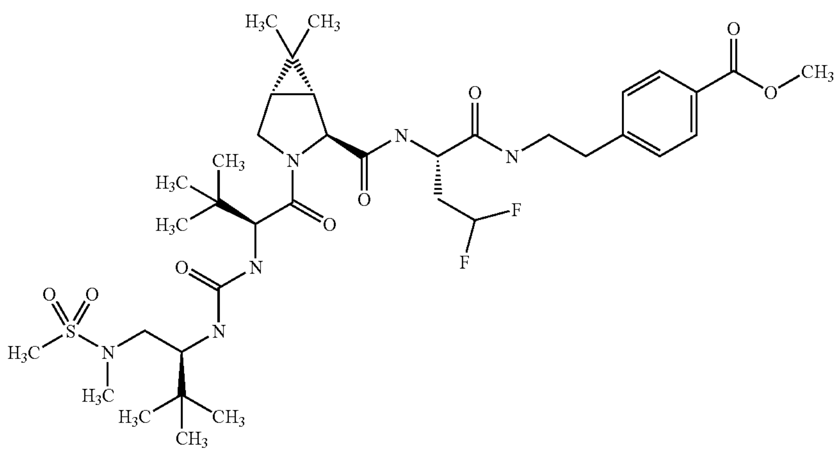 | 0.022 |
| 104 | 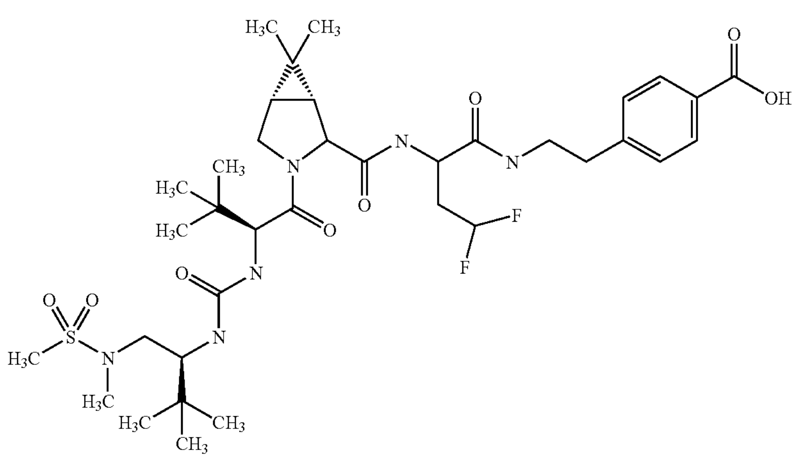 | 0.024 |

TABLE 1-continued
| Example No | Structure | Ki (μM) |
|---|---|---|
| 105 | 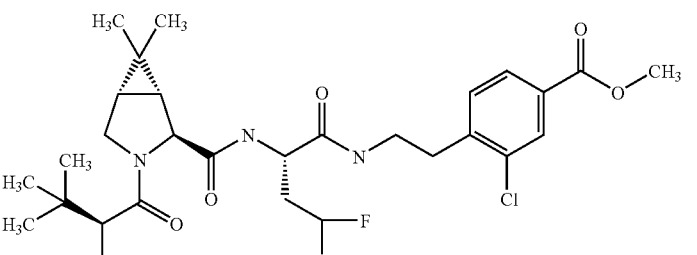 | 0.024 |
| 106 | 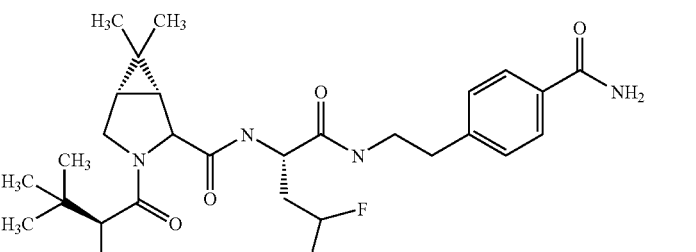 | 0.027 |
| 107 | 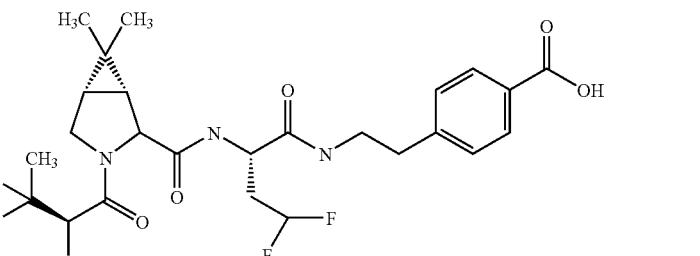 | 0.029 |

TABLE 1-continued

| Example No | Structure | Ki (μM) |
|---|---|---|
| 108 | 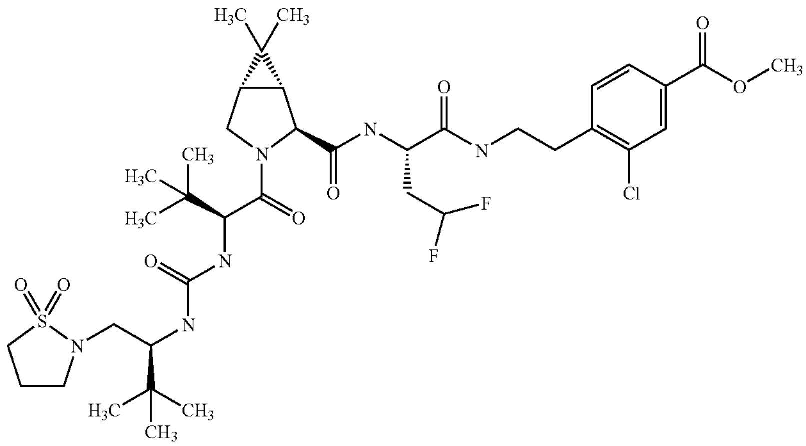 | 0.03 |
| 109 | 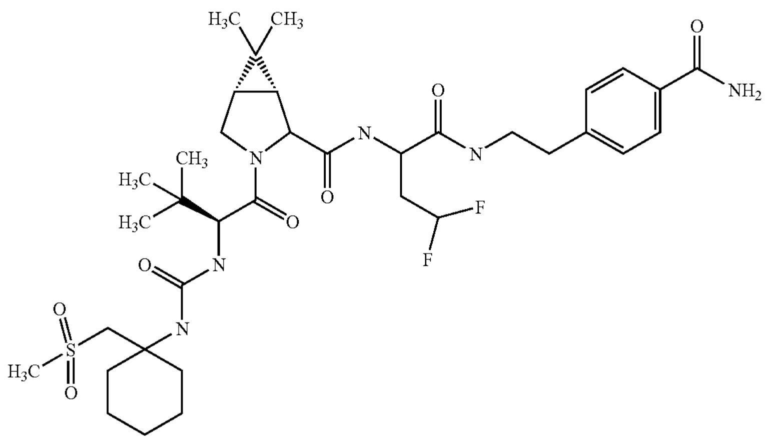 | 0.038 |
| 110 | 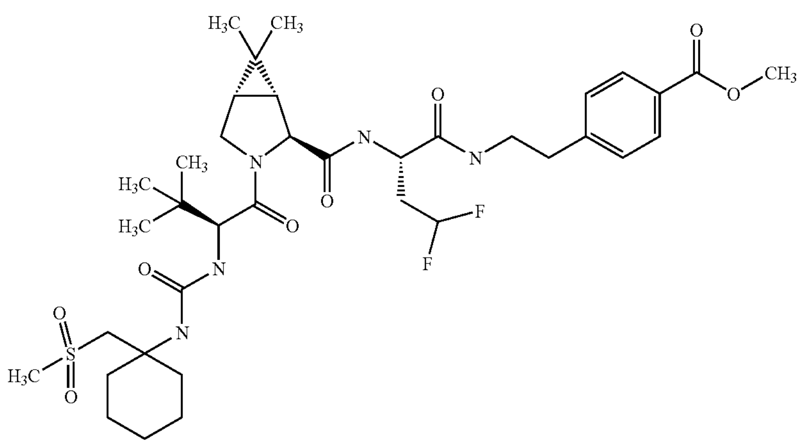 | 0.04 |

TABLE 1-continued
| Example No | Structure | Ki (μM) |
|---|---|---|
| 111 | 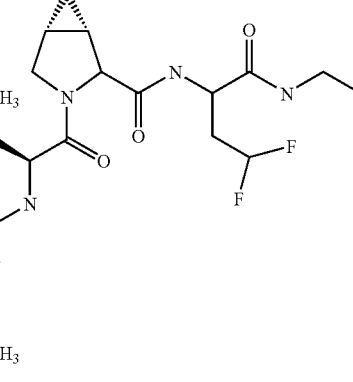 | 0.042 |
| 112 | 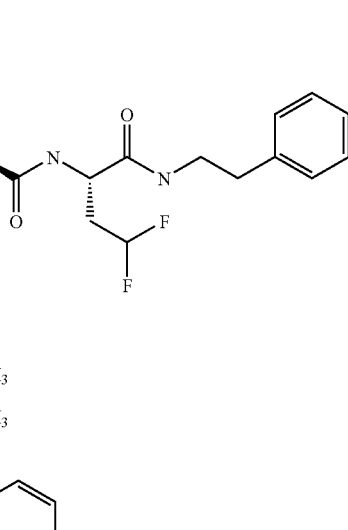 | 0.05 |
| 113 | 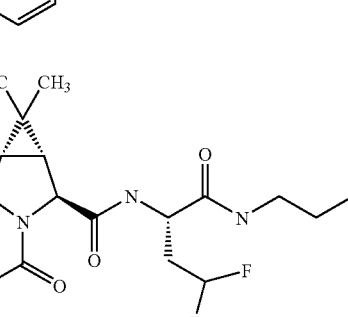 | 0.09 |

TABLE 1-continued

| Example No | Structure | Ki (μM) |
|---|---|---|
| 114 | 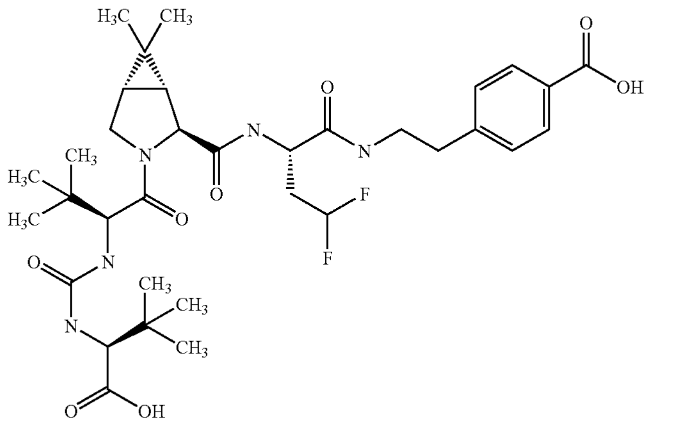 | 0.09 |
| 115 | 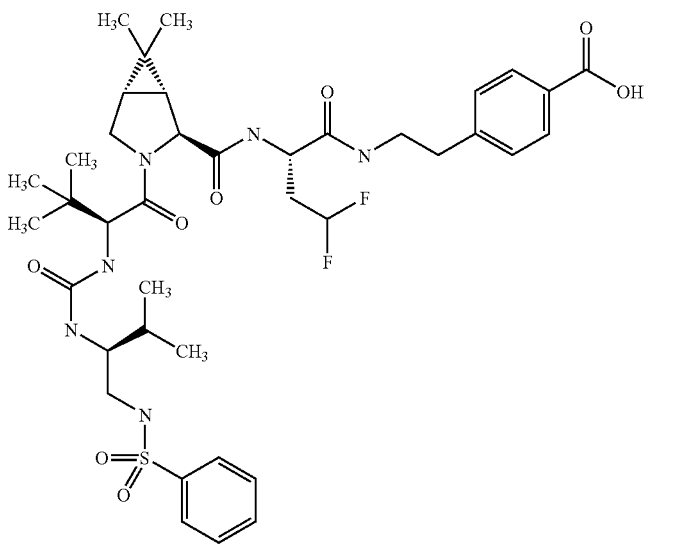 | 0.09 |
| 116 | 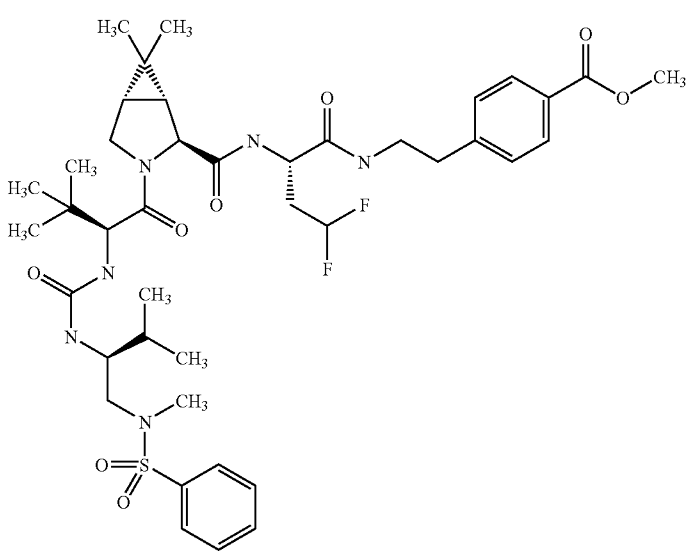 | 0.1 |

As discussed above, the hepatitis C virus (HCV) proteases, like the NS3 or NS4a protease, can be modulated by the inventive compounds. To that end, a pharmaceutical composition is disclosed comprising as an active ingredient a compound represented by Formula 1 and many times also comprising a pharmaceutically acceptable carrier as well. In other embodiments, the present invention is directed to a pharmaceutical composition comprising a compound represented by Formula 1 and an antiviral agent such as ribavirin or a pegylated interferon such as α-interferon. Also disclosed is a method of treatment of a hepatitis C virus associated disorder, comprising administering an effective amount of one or more of the inventive compounds.

Also disclosed is a method of modulating the activity of hepatitis C virus (HCV) protease, comprising contacting HCV protease with one or more inventive compounds.

Also disclosed is a method of treating, preventing, or ameliorating one or more symptoms of hepatitis C, comprising administering an effective amount of one or more of the inventive compounds.

Additional representative compounds of the invention which exhibit excellent HCV protease inhibitory activity are listed below in Tables 2 and 3. The Ki values for each compound are rated, "A" for Ki values less than or equal to 0.1 micromoles, "B" for Ki values greater than 0.1 micromoles to less than 0.5 micromoles, and "C" for Ki values greater than or equal to 0.5 micromoles.

TABLE 2

| Example No | Structure | Ki Rating |
|---|---|---|
| 117 | 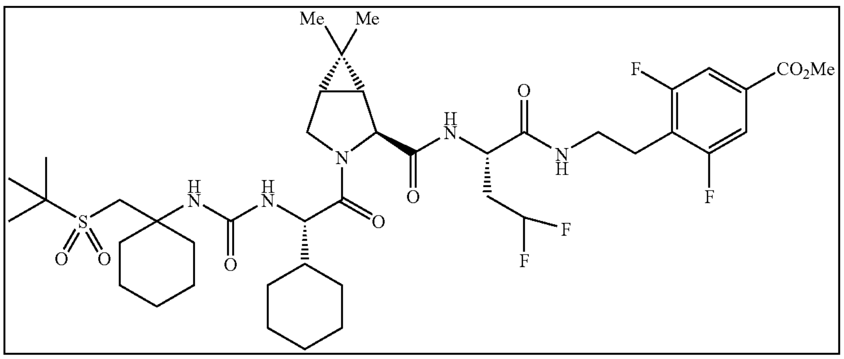 | |
| 118 | 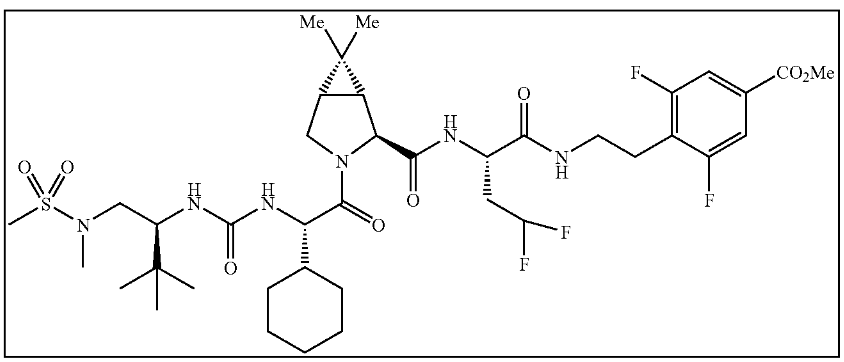 | |
| 119 | 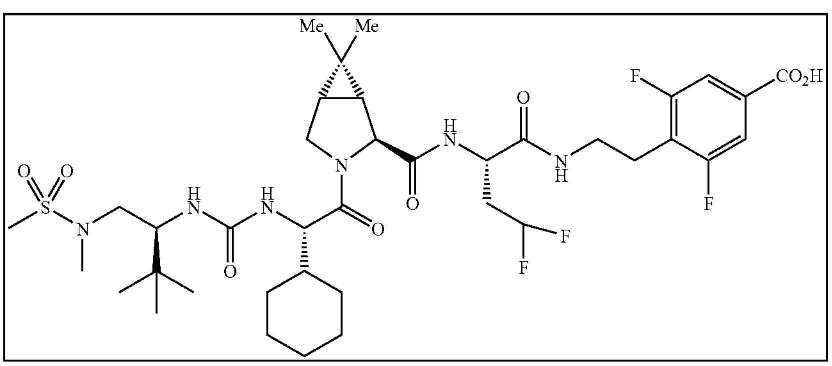 | |

TABLE 2-continued

| Example No | Structure | Ki Rating |
|---|---|---|
| 120 | 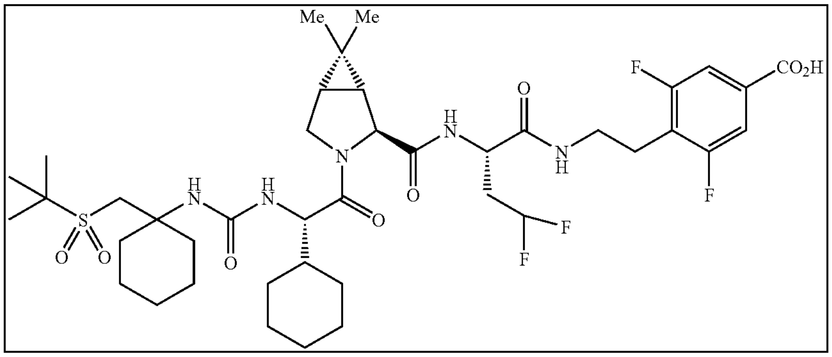 | |
| 121 | 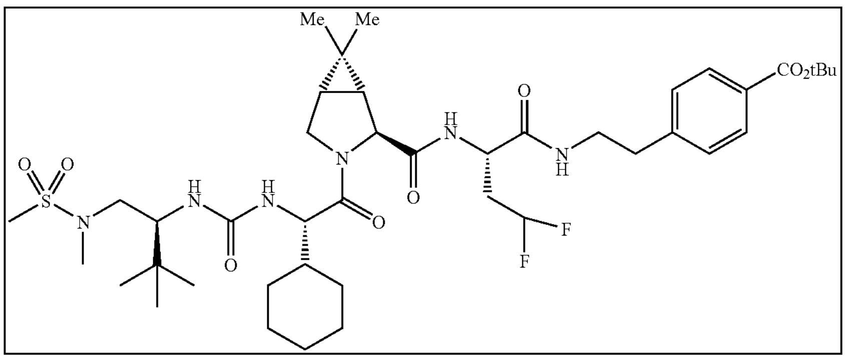 | |
| 122 | 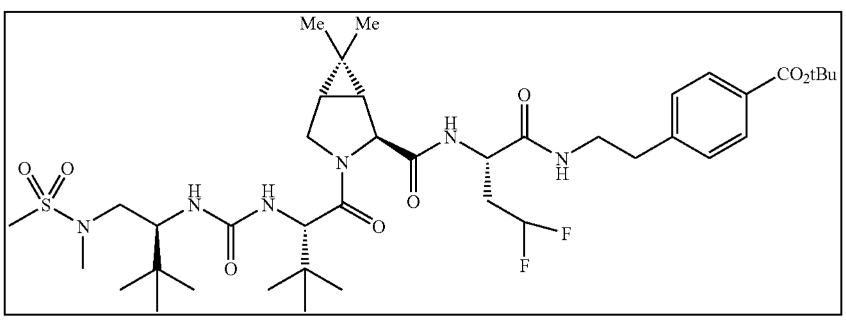 | |
| 123 | 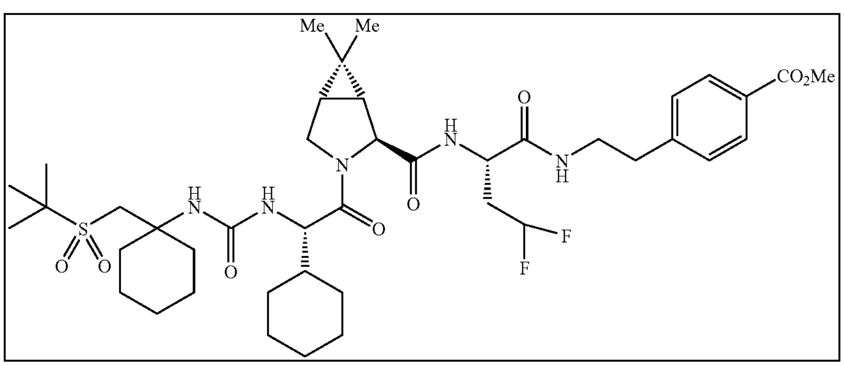 | |

TABLE 2-continued
| Example No | Structure | Ki Rating |
|---|---|---|
| 124 | 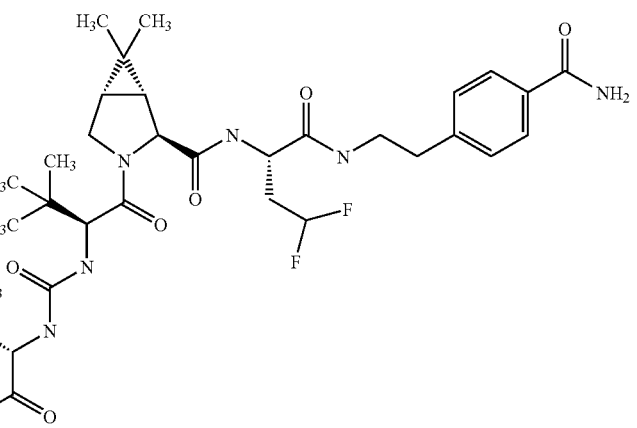 | B |
| 125 | 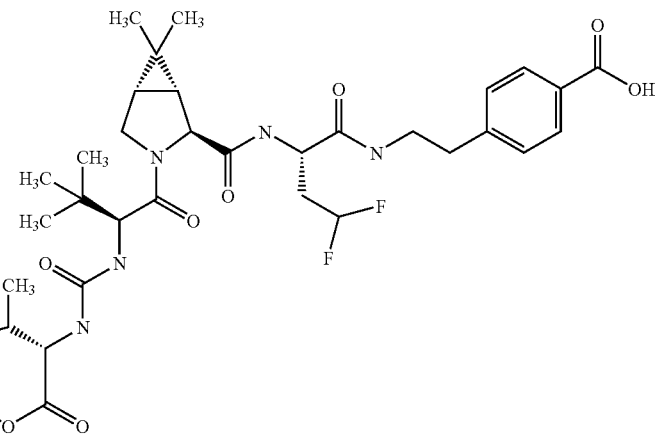 | B |
| 126 | 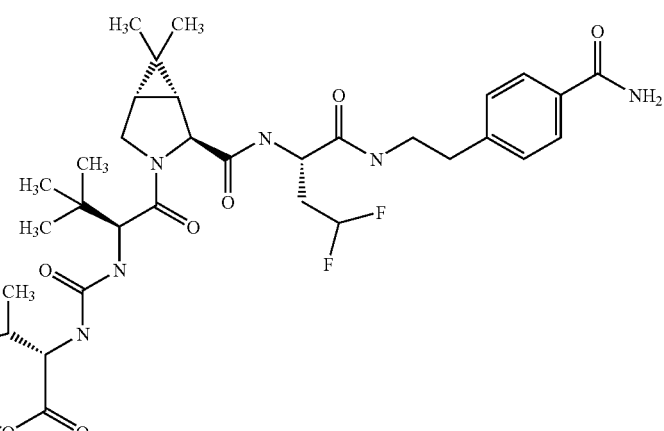 | B |

TABLE 2-continued

| Example No | Structure | Ki Rating |
|---|---|---|
| 127 | 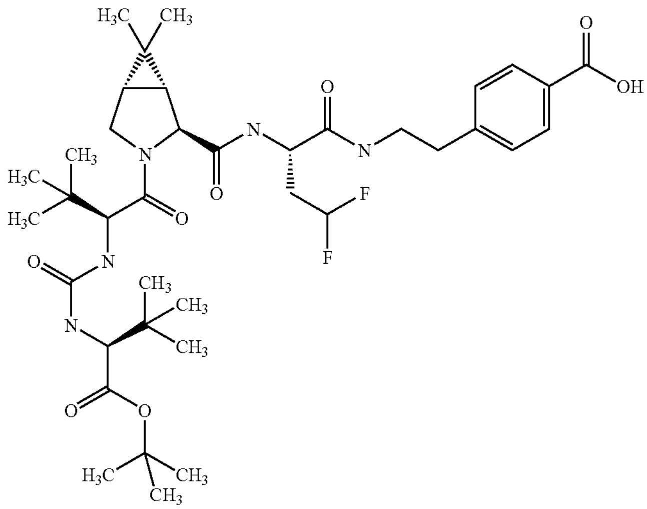 | B |
| 128 | 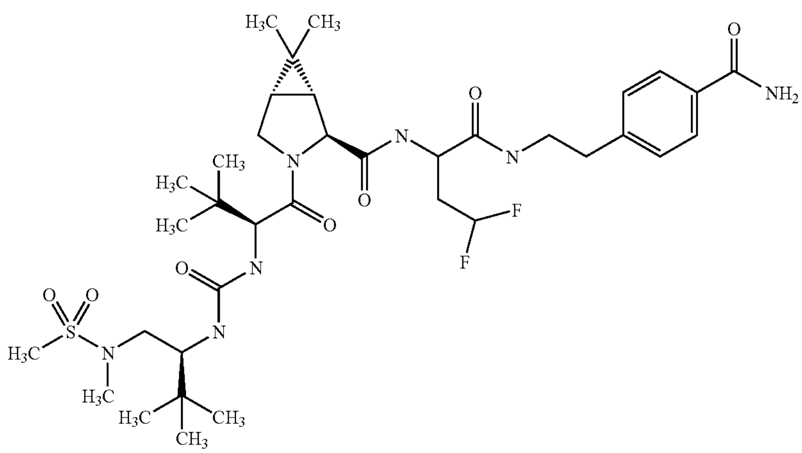 | B |
| 129 | 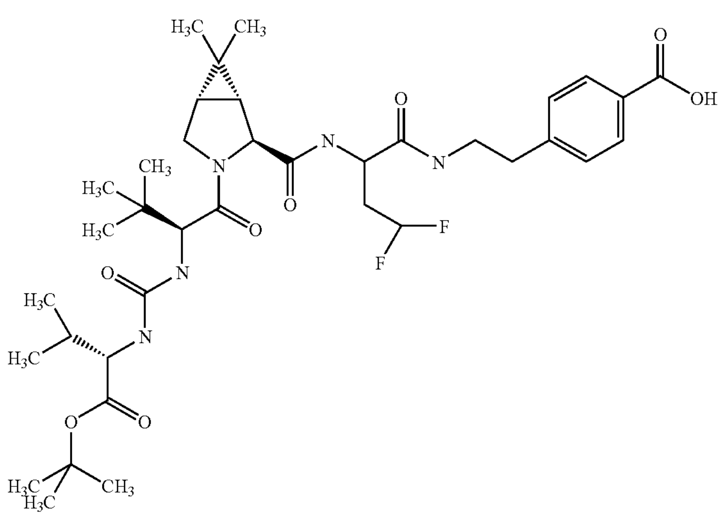 | B |

TABLE 2-continued

| Example No | Structure | Ki Rating |
|---|---|---|
| 130 | 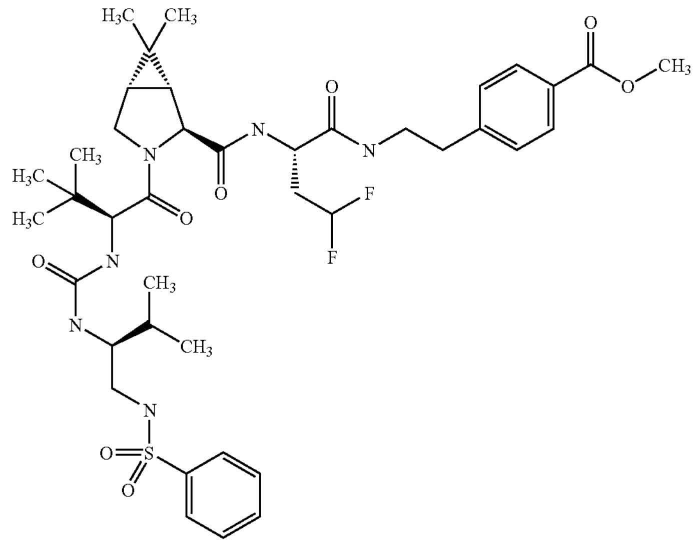 | B |
| 131 | 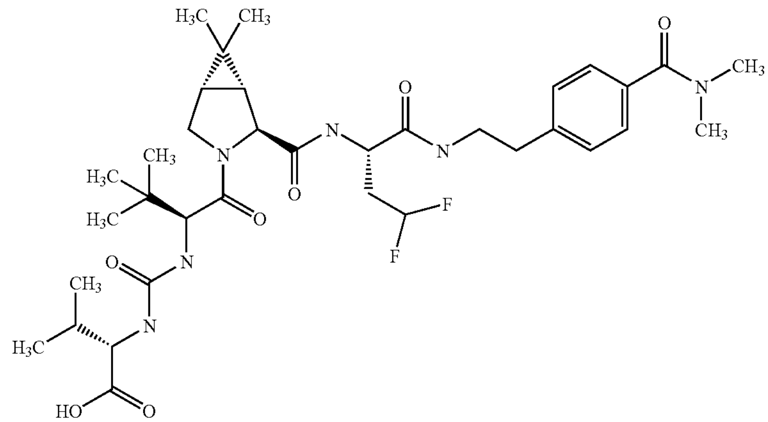 | B |
| 132 | 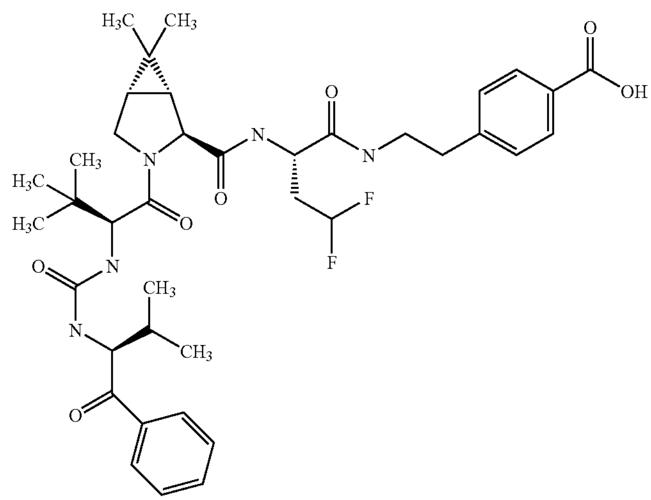 | B |

TABLE 2-continued

| Example No | Structure | Ki Rating |
|---|---|---|
| 133 | 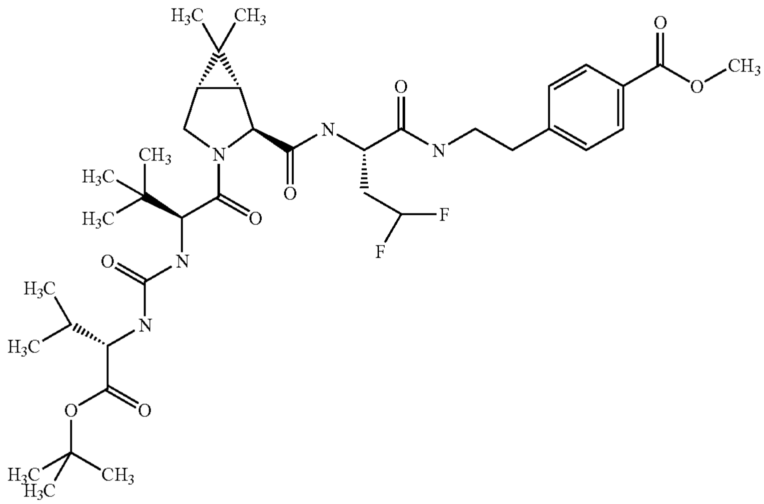 | B |
| 134 | 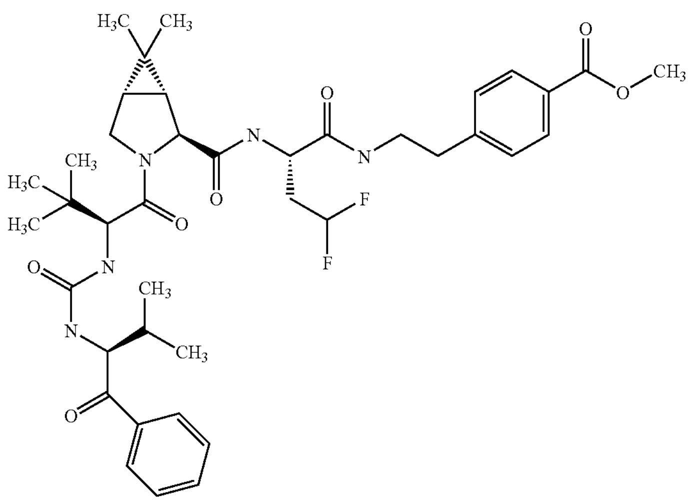 | B |
| 135 | 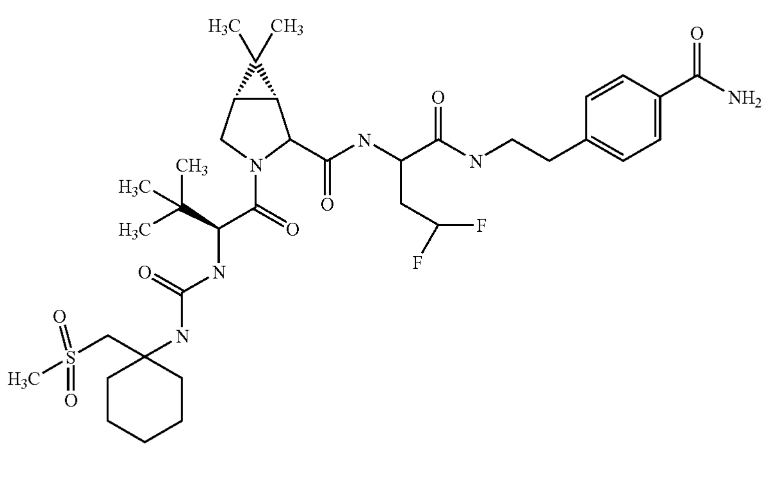 | B |

TABLE 2-continued

| Example No | Structure | Ki Rating |
|---|---|---|
| 136 | 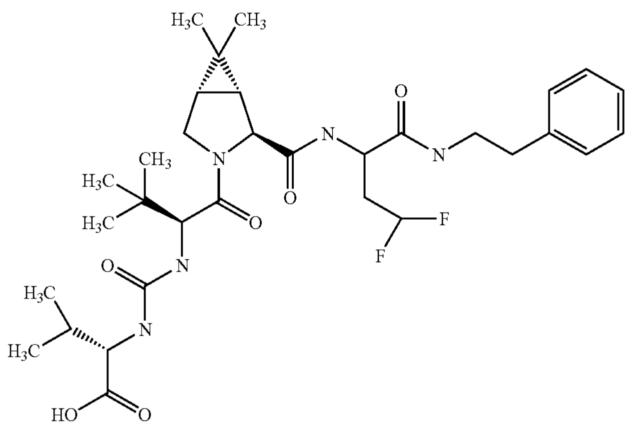 | B |
| 137 | 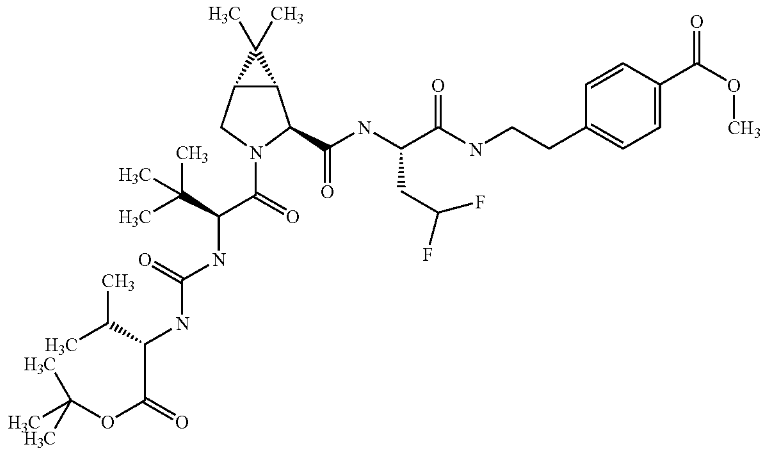 | B |
| 138 | 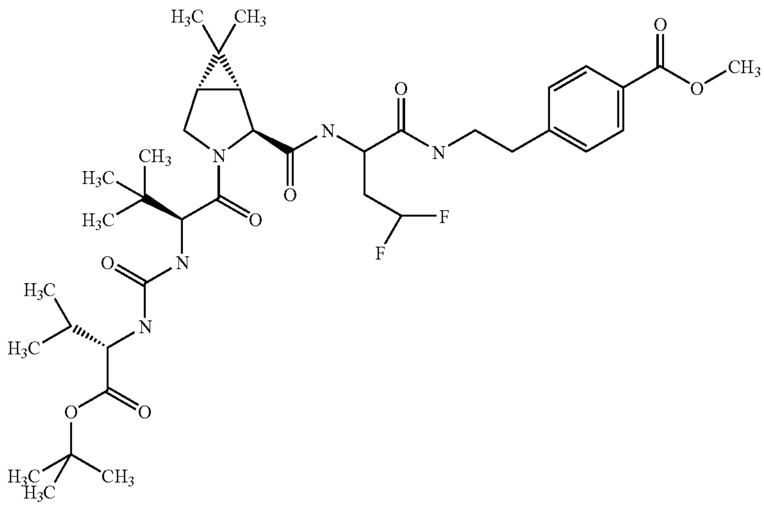 | B |

TABLE 2-continued

| Example No | Structure | Ki Rating |
|---|---|---|
| 139 | 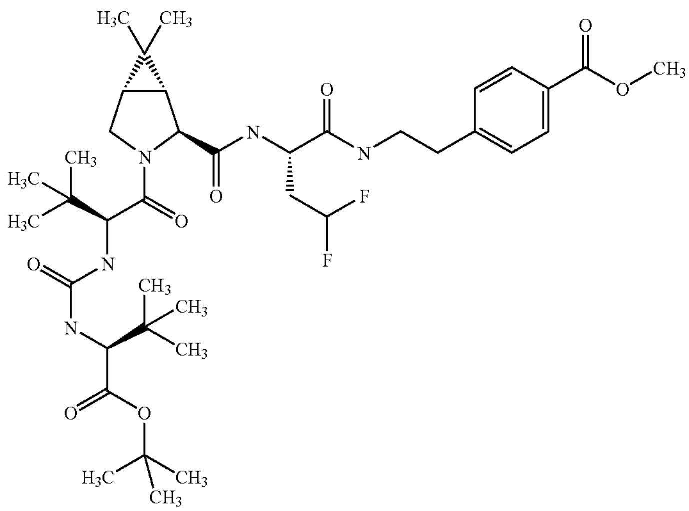 | B |
| 140 | 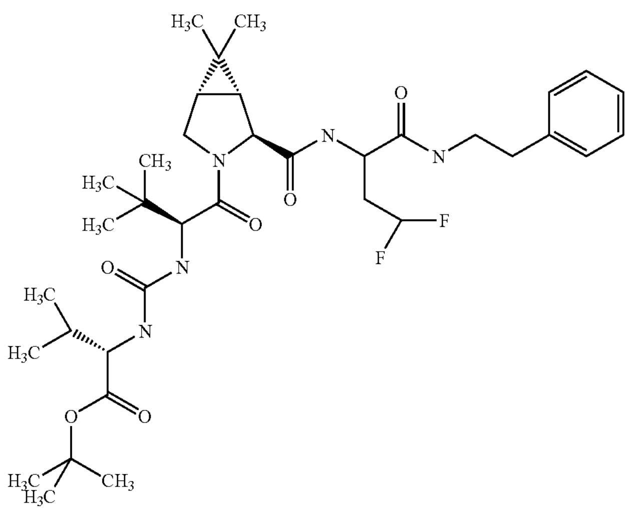 | B |
| 141 | 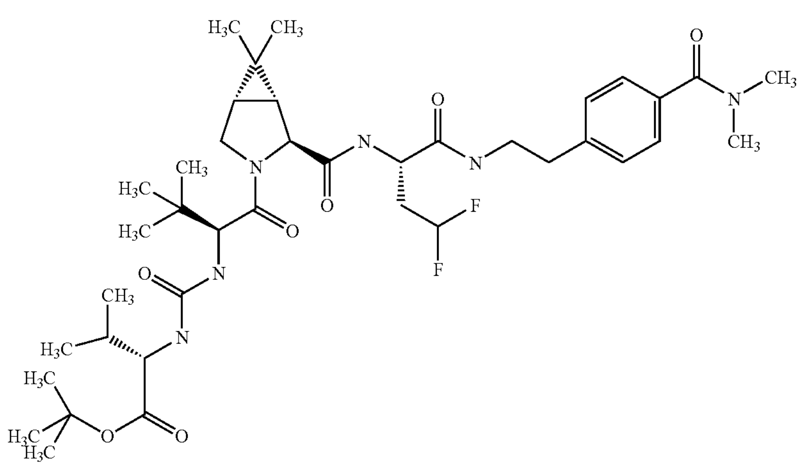 | B |

TABLE 2-continued
| Example No | Structure | Ki Rating |
|---|---|---|
| 142 | 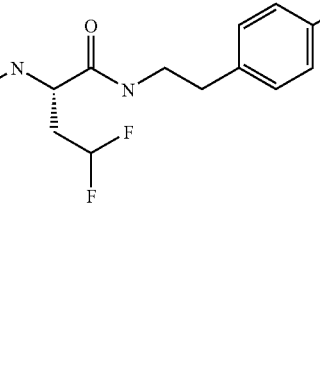 | B |
| 143 | 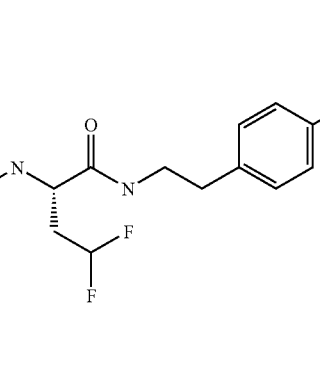 | B |
| 144 | 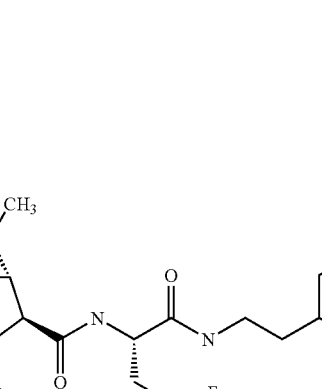 | B |

TABLE 2-continued

| Example No | Structure | Ki Rating |
|---|---|---|
| 145 | 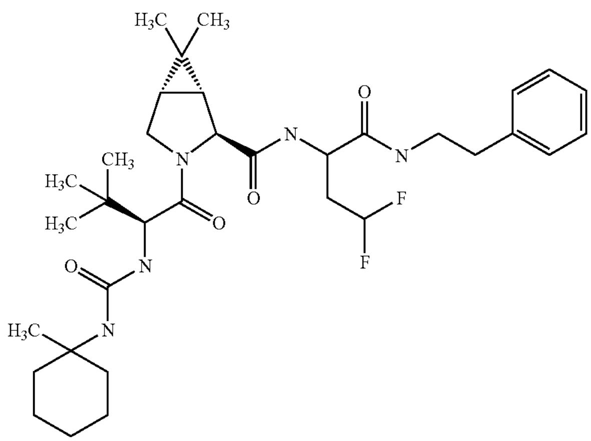 | C |
| 146 | 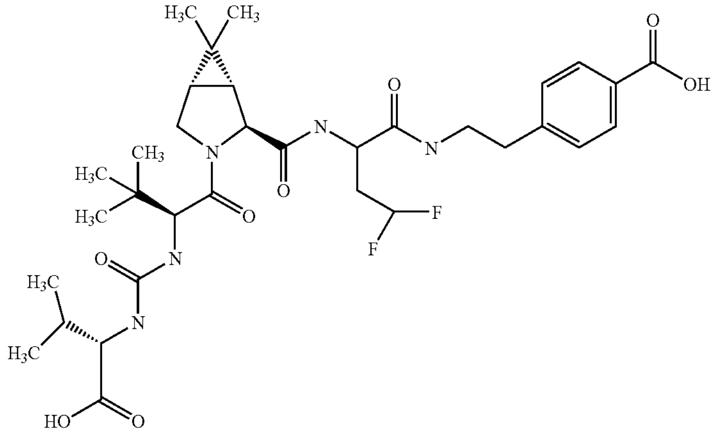 | C |
| 147 | 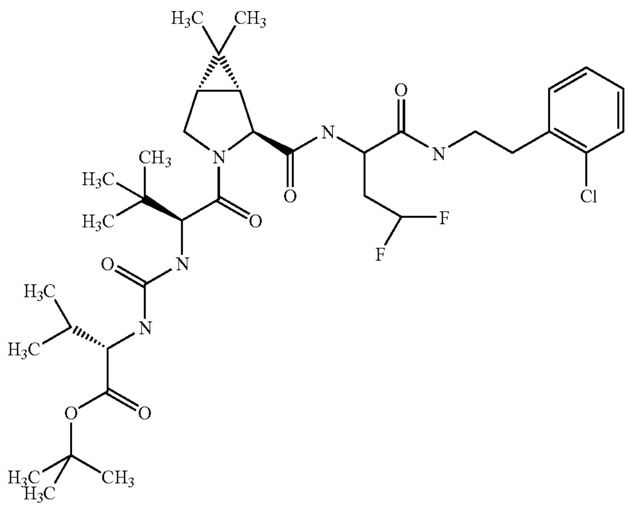 | C |

TABLE 2-continued

| Example No | Structure | Ki Rating |
|---|---|---|
| 148 | 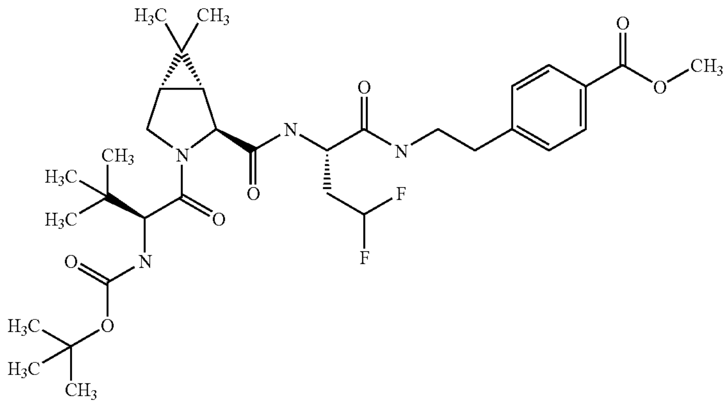 | C |
| 149 | 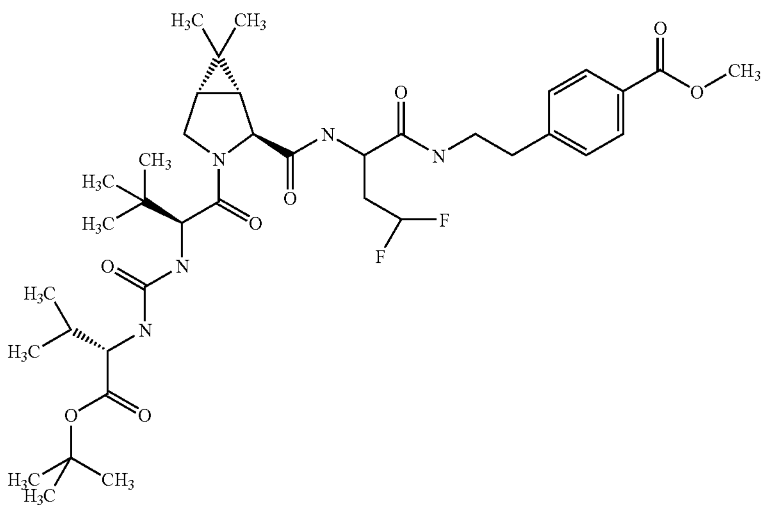 | C |
| 150 | 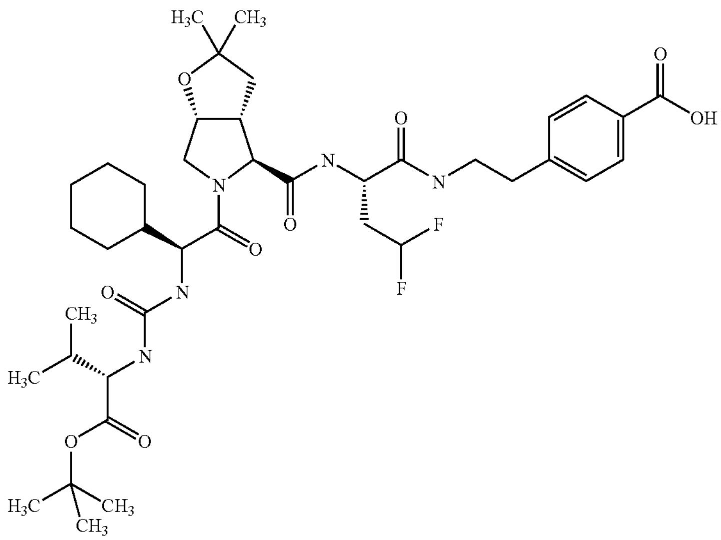 | C |

TABLE 2-continued

| Example No | Structure | Ki Rating |
|---|---|---|
| 151 | 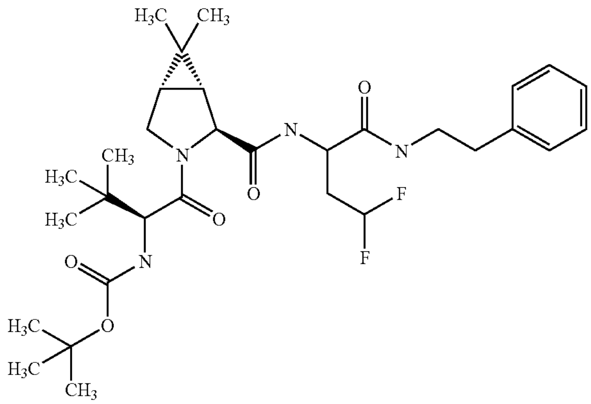 | C |
| 152 | 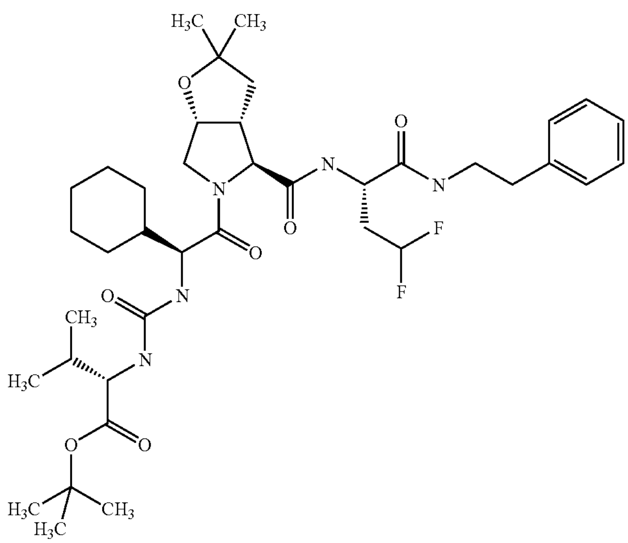 | C |
| 153 | 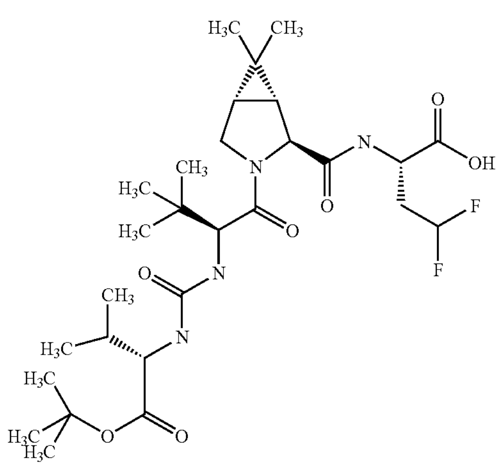 | C |

TABLE 2-continued

| Example No | Structure | Ki Rating |
|---|---|---|
| 154 | 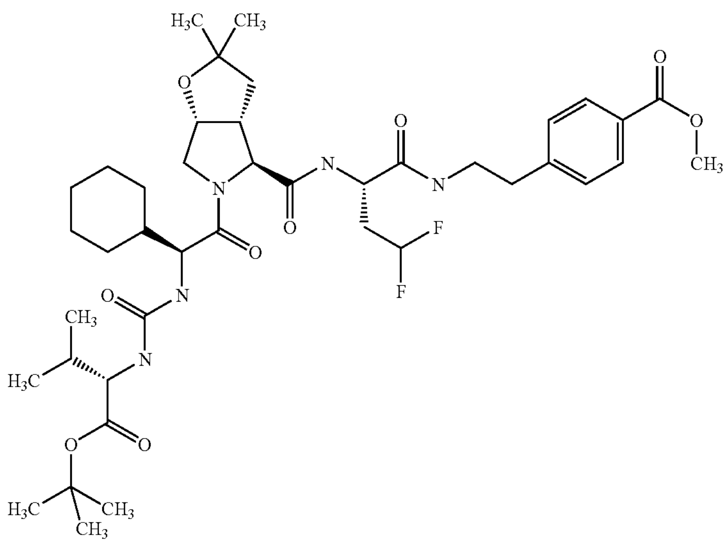 | C |
| 155 | 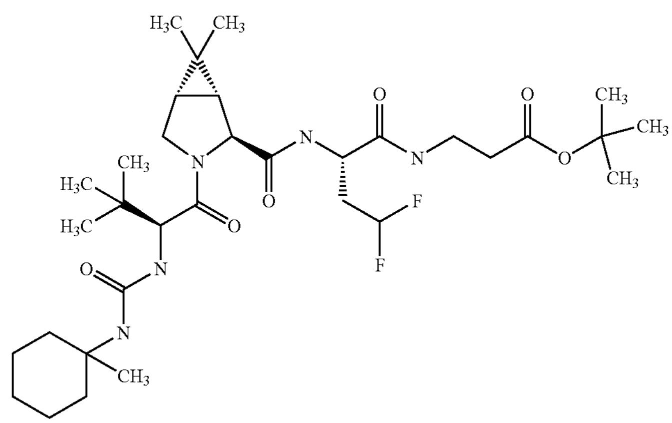 | C |
| 156 | 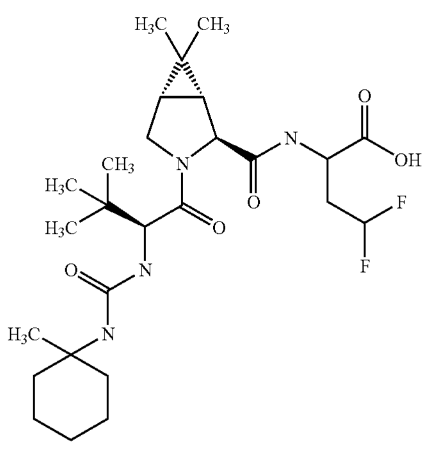 | C |

TABLE 2-continued

| Example No | Structure | Ki Rating |
|---|---|---|
| 157 | 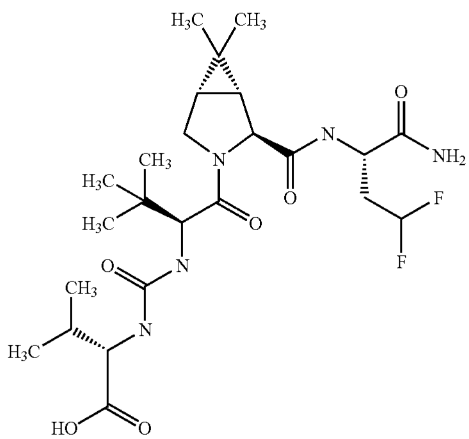 | C |
| 158 | 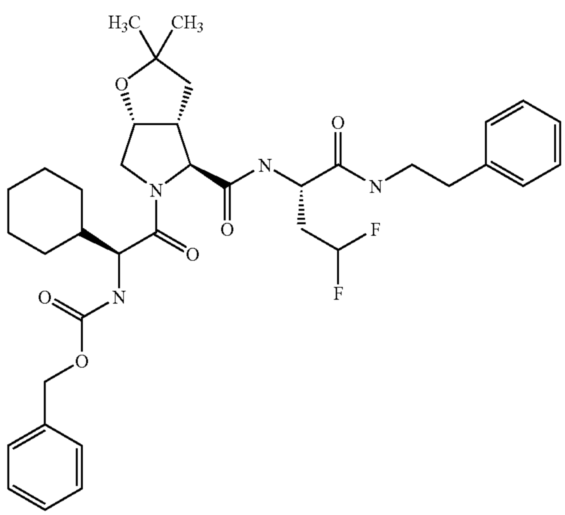 | C |
| 159 | 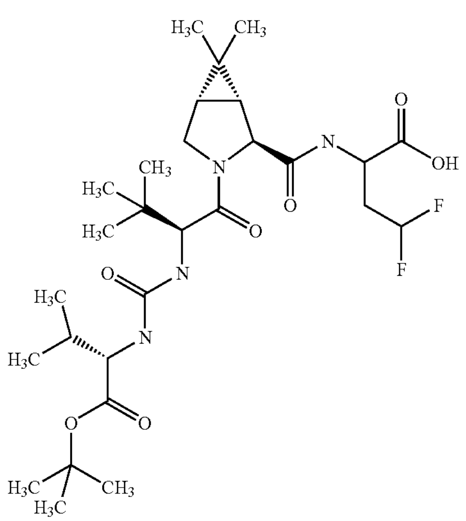 | C |

TABLE 2-continued

| Example No | Structure | Ki Rating |
|---|---|---|
| 160 | 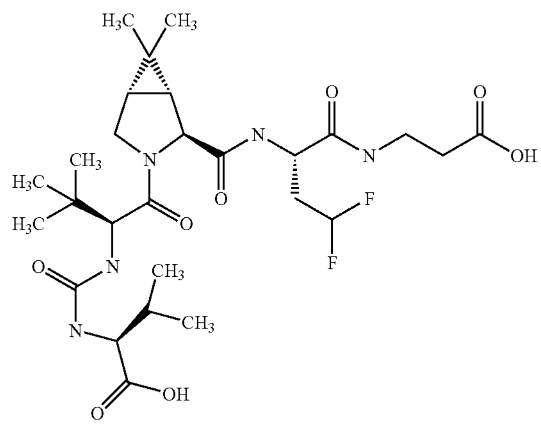 | C |
| 161 | 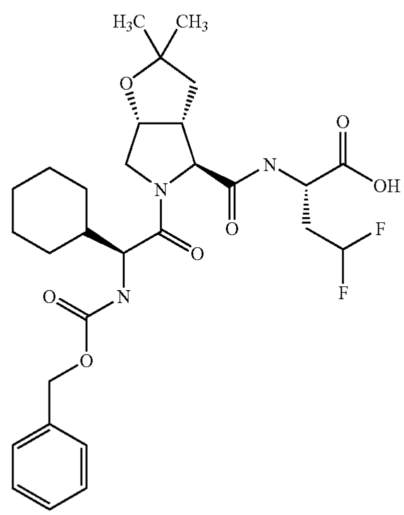 | C |
| 162 | 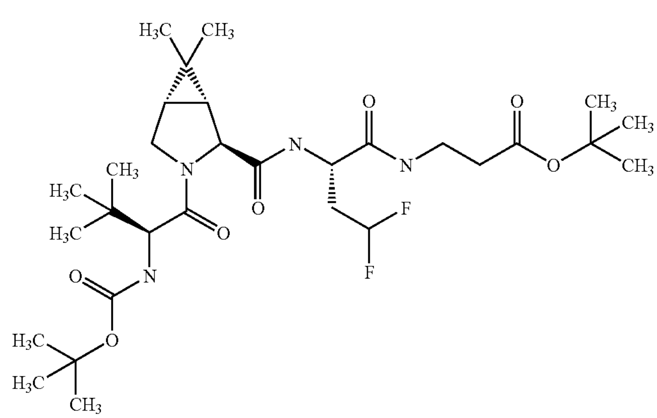 | C |

TABLE 2-continued

| Example No | Structure | Ki Rating |
|---|---|---|
| 163 | 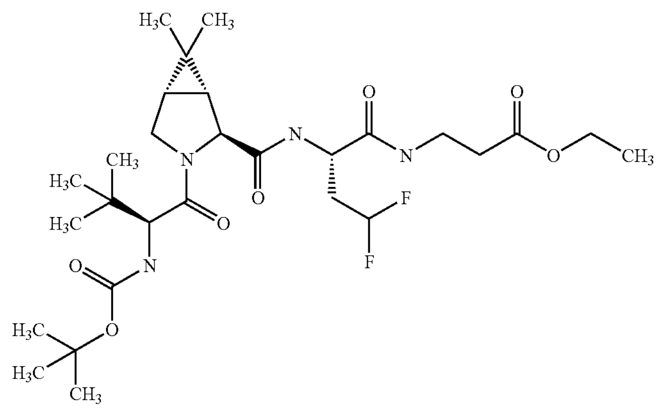 | C |
| 164 | 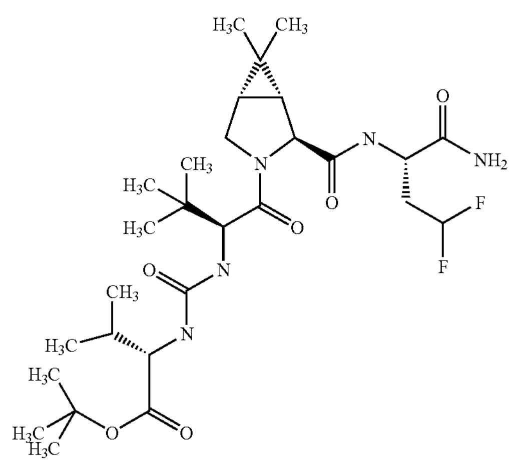 | C |
| 165 | 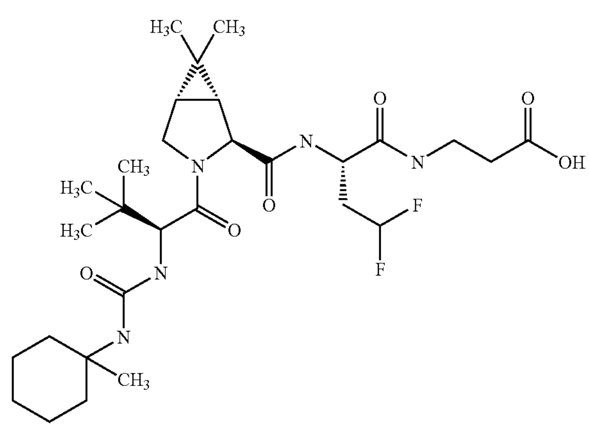 | C |

TABLE 2-continued

| Example No | Structure | Ki Rating |
|---|---|---|
| 166 | 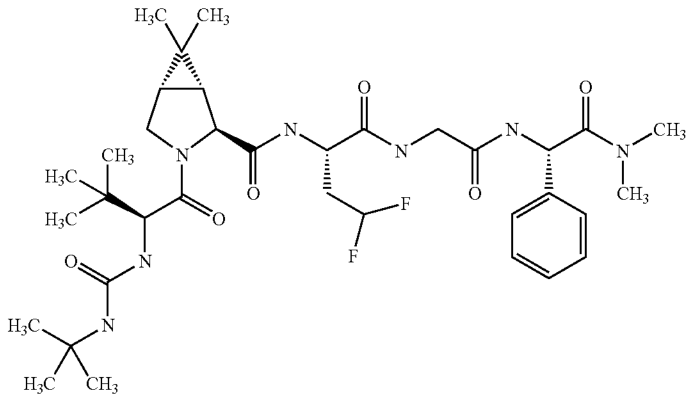 | C |
| 167 | 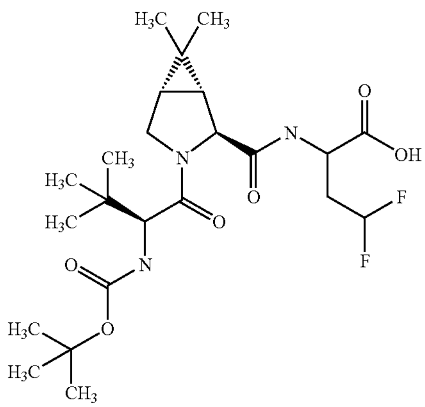 | C |
| 168 | 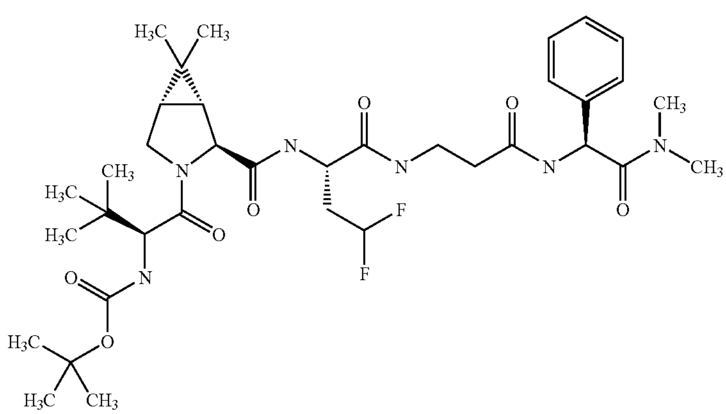 | C |

TABLE 2-continued

| Example No | Structure | Ki Rating |
|---|---|---|
| 169 | 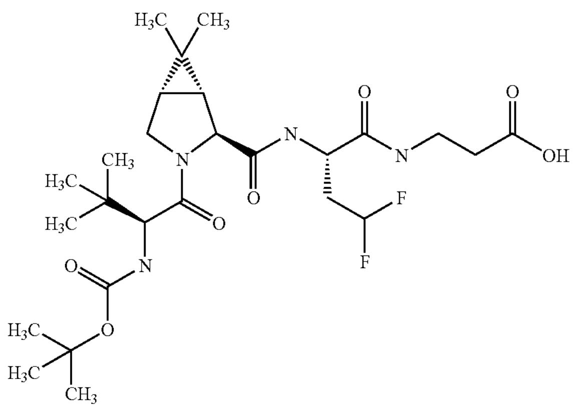 | C |
| 170 | 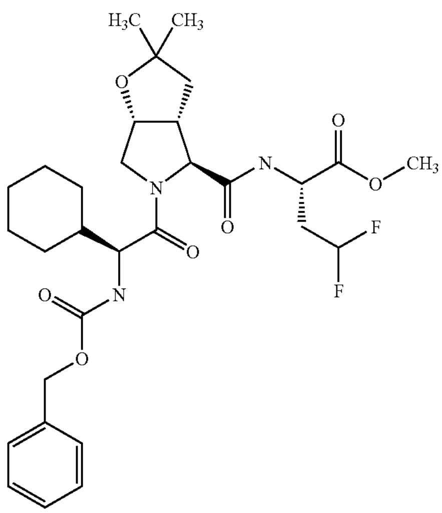 | C |
| 171 | 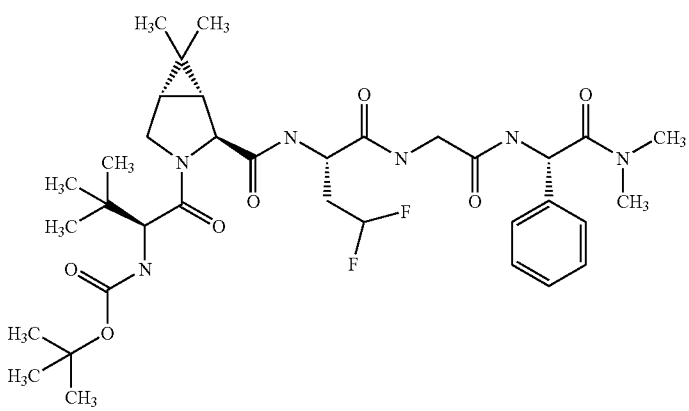 | C |

TABLE 2-continued

| Example No | Structure | Ki Rating |
|---|---|---|
| 172 | 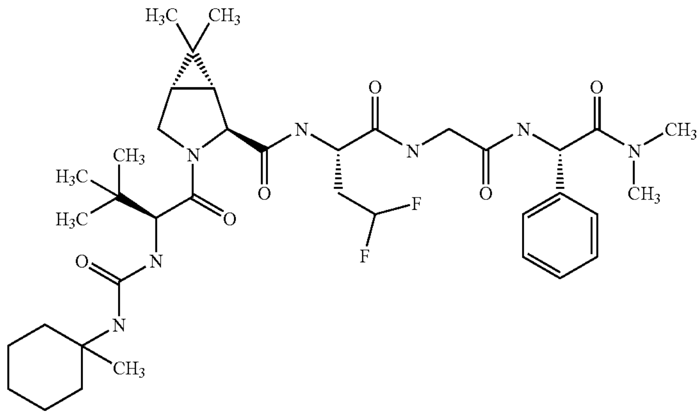 | C |
| 173 | 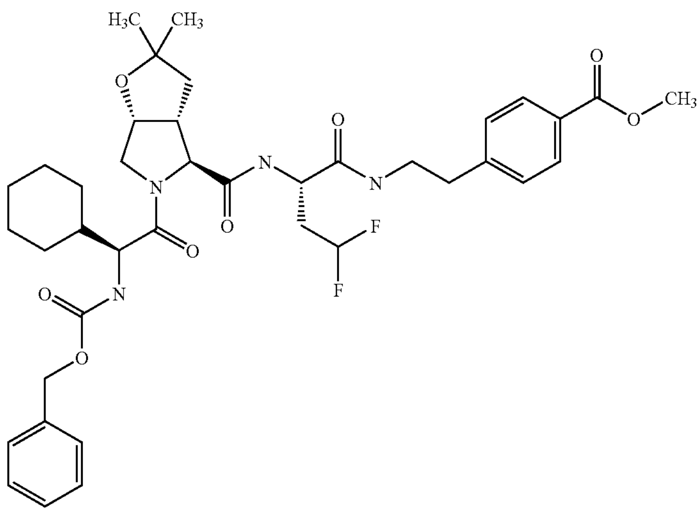 | C |
| 174 | 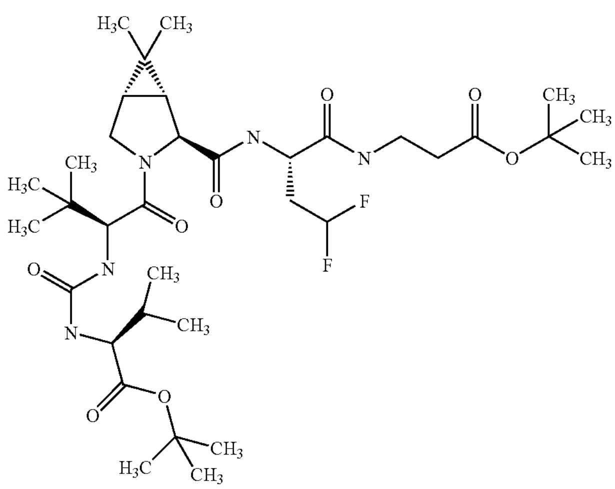 | C |

TABLE 2-continued
| Example No | Structure | Ki Rating |
|---|---|---|
| 175 | 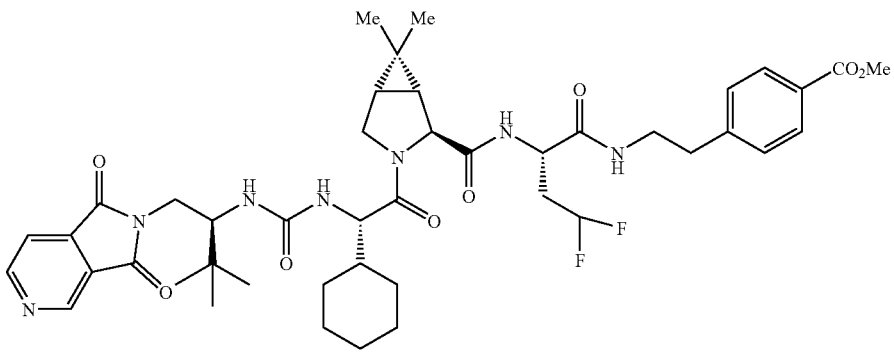 | |
| 176 | 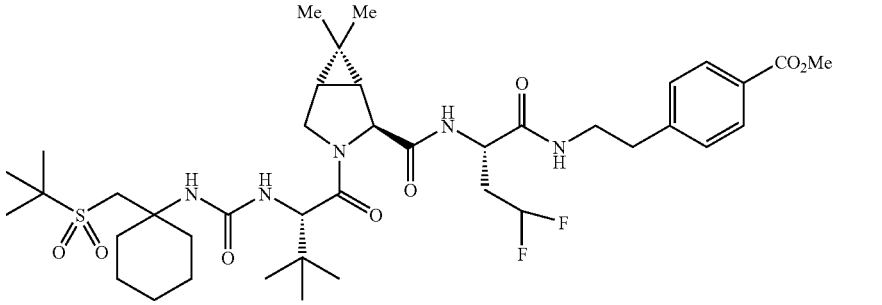 | |
| 177 | 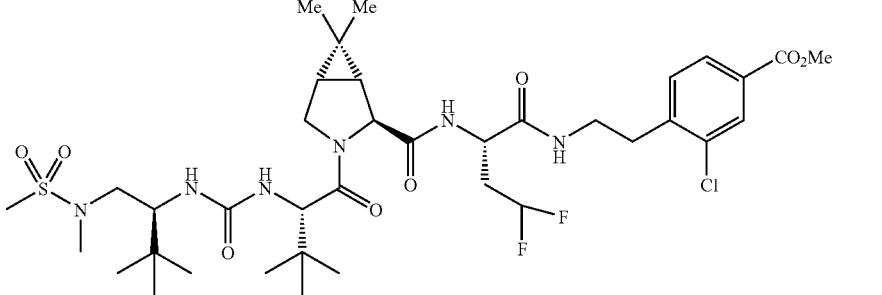 | |
TABLE 3
| Example No | Structure | Ki |
|---|---|---|
| 201 | 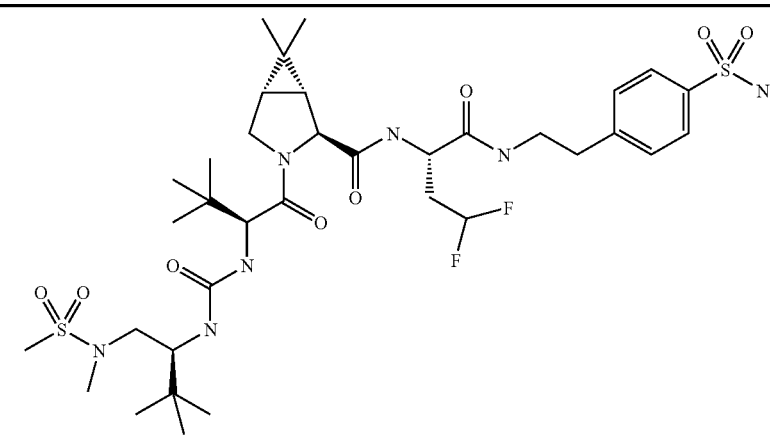 | A |

TABLE 3-continued

| Example No | Structure | Ki |
|---|---|---|
| 202 | 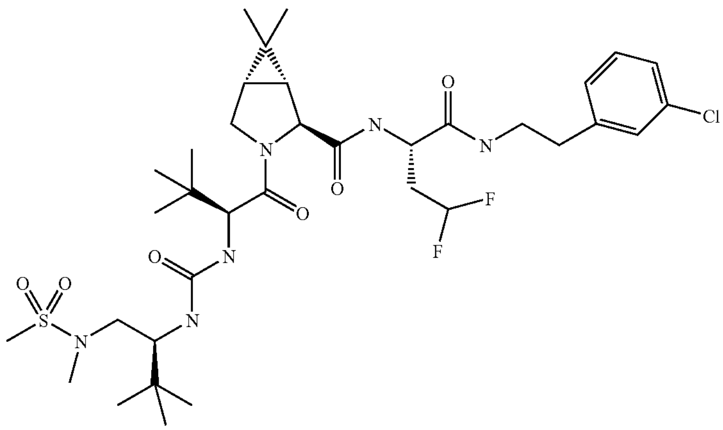 | A |
| 203 | 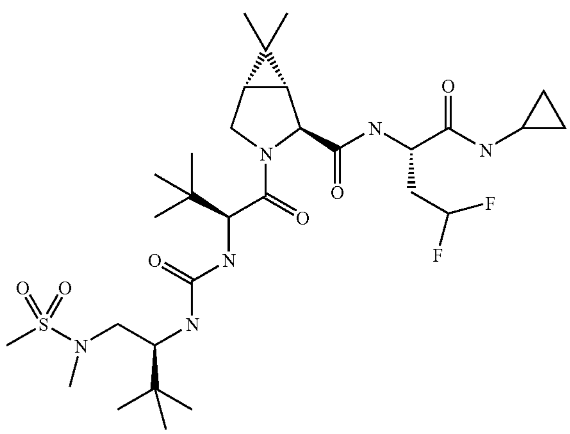 | C |
| 204 | 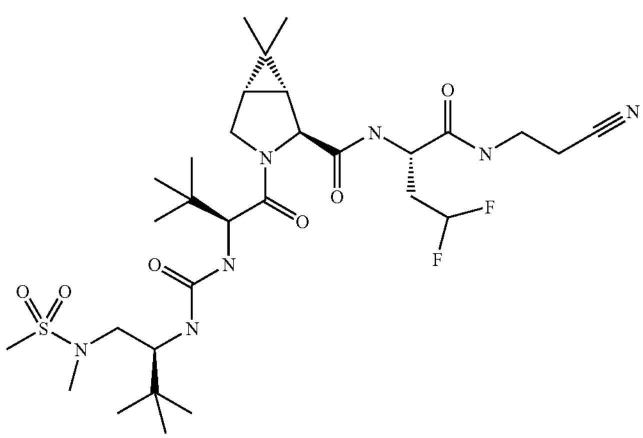 | C |

TABLE 3-continued
| Example No | Structure | Ki |
|---|---|---|
| 205 | 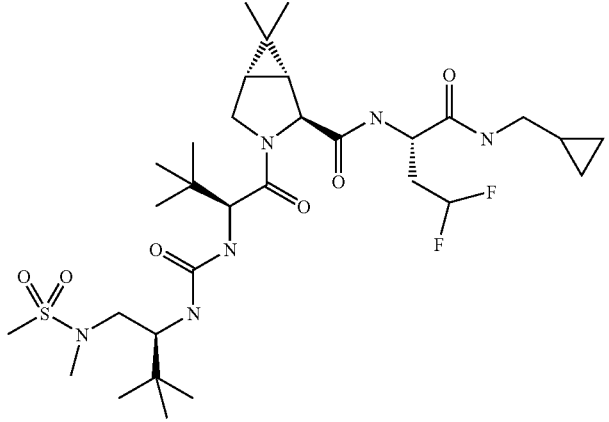 | C |
| 206 | 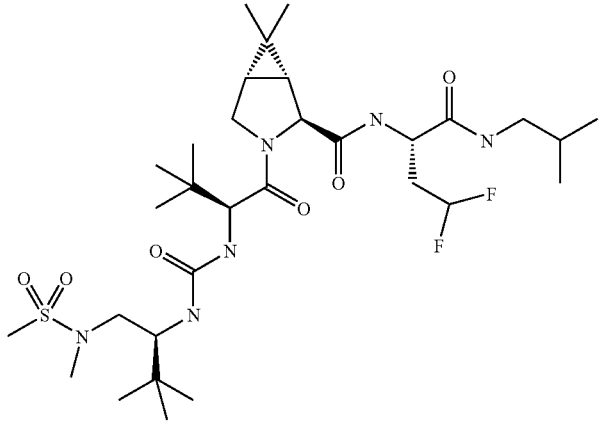 | C |
| 207 | 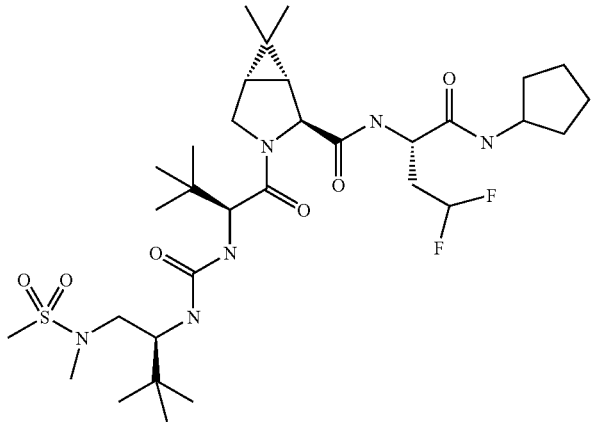 | C |

TABLE 3-continued

| Example No | Structure | Ki |
|---|---|---|
| 208 | 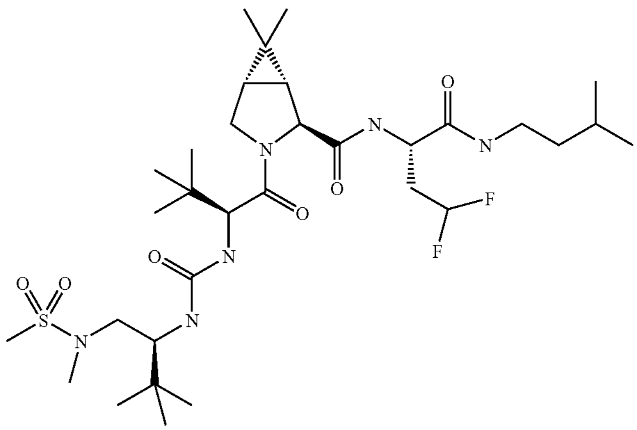 | C |
| 209 | 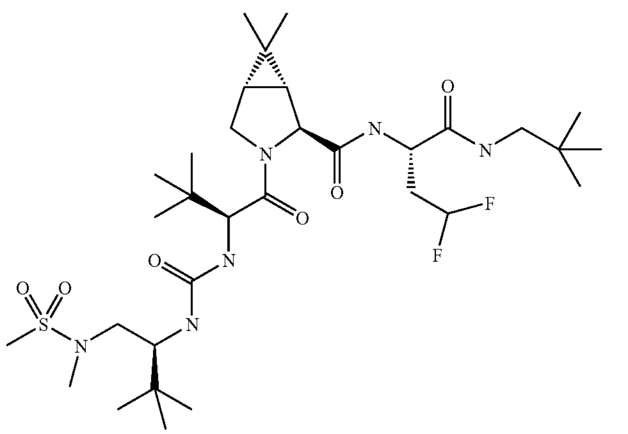 | C |
| 210 | 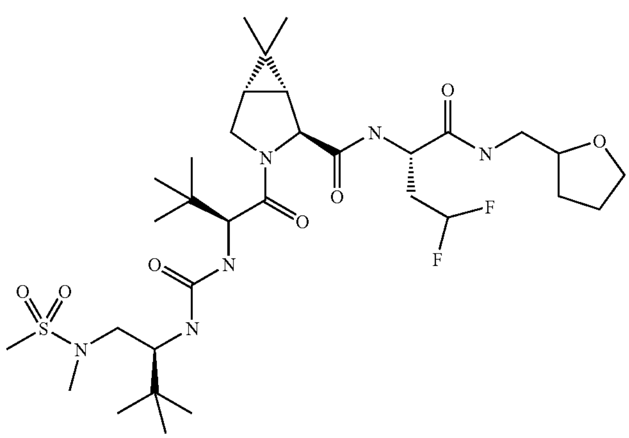 | C |

TABLE 3-continued

| Example No | Structure | Ki |
|---|---|---|
| 211 | 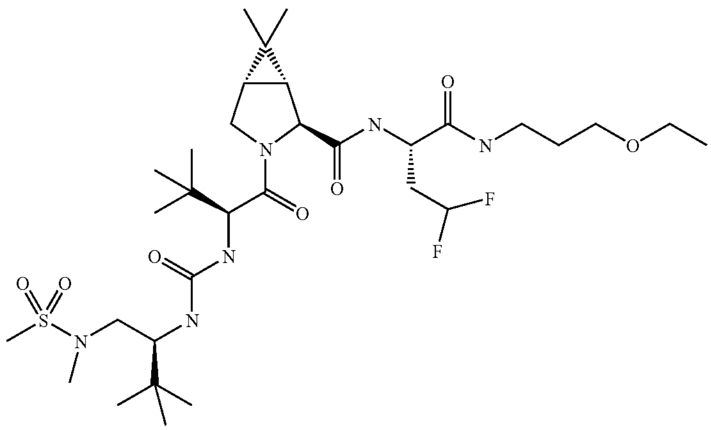 | C |
| 212 | 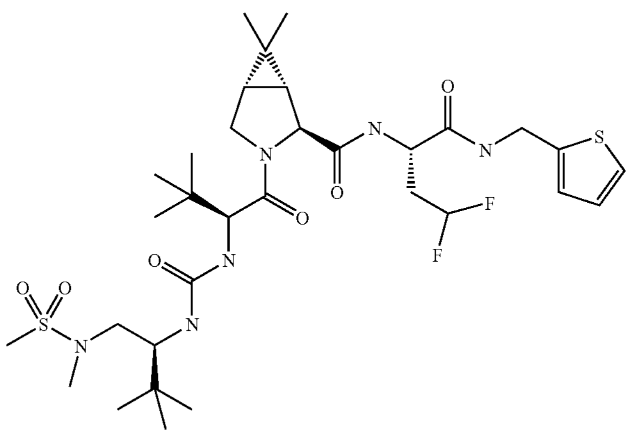 | C |
| 213 | 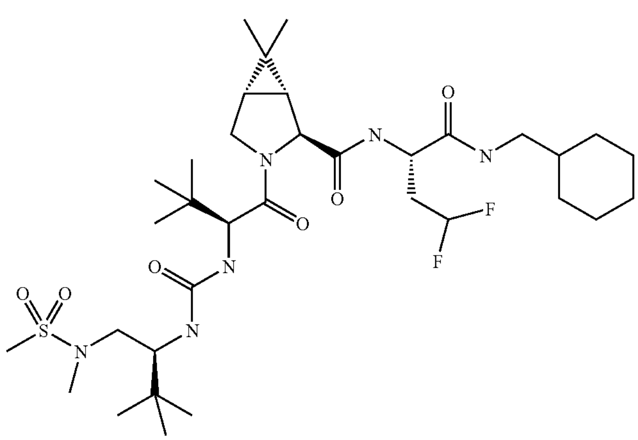 | C |

TABLE 3-continued

| Example No | Structure | Ki |
|---|---|---|
| 214 | 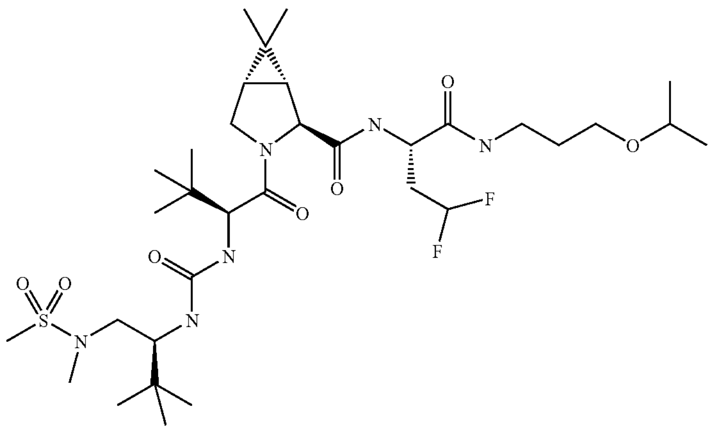 | C |
| 215 | 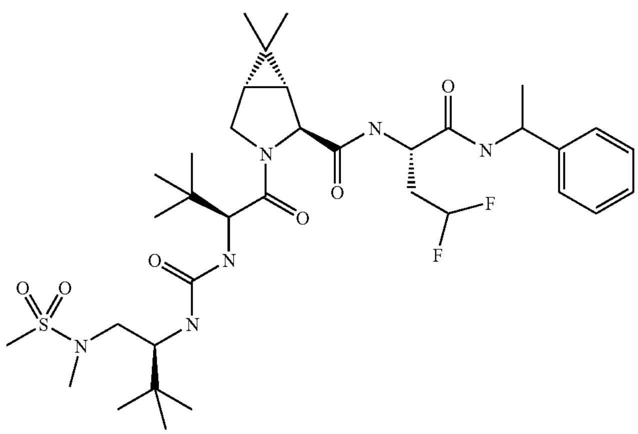 | C |
| 216 | 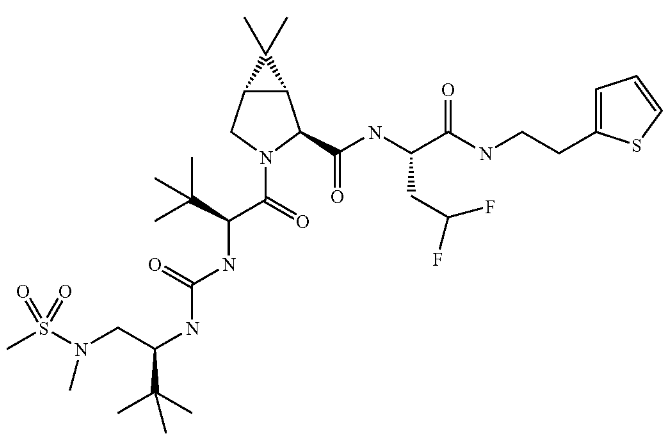 | A |

TABLE 3-continued

| Example No | Structure | Ki |
|---|---|---|
| 217 | 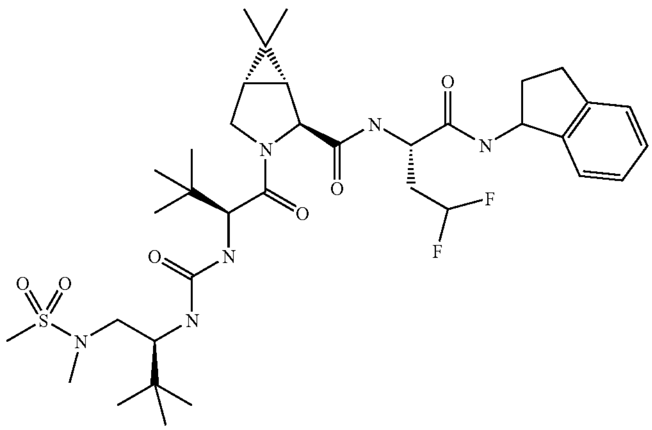 | C |
| 218 | 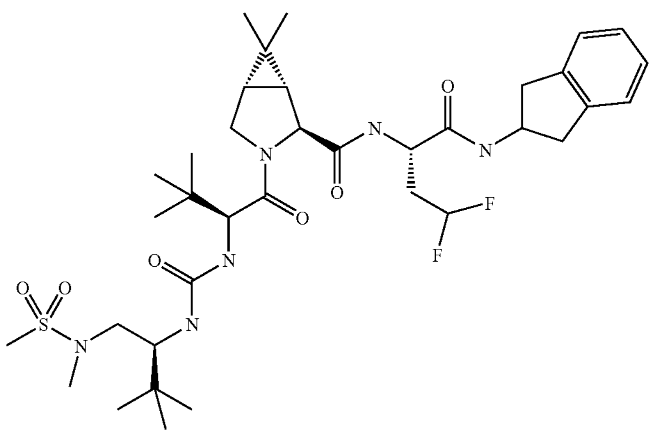 | C |
| 219 | 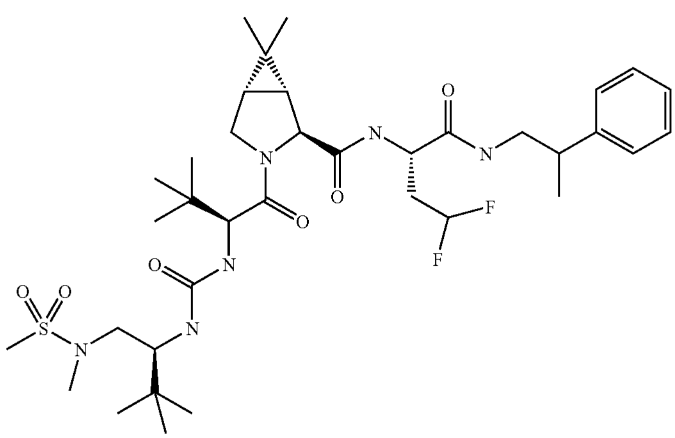 | A |

TABLE 3-continued
| Example No | Structure | Ki |
|---|---|---|
| 220 | 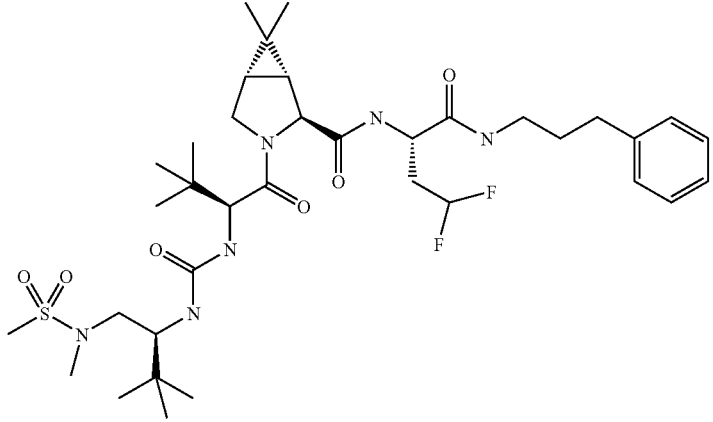 | C |
| 221 | 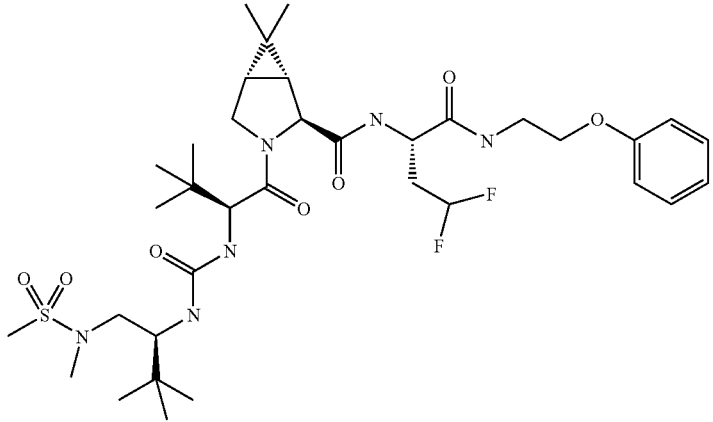 | C |
| 222 | 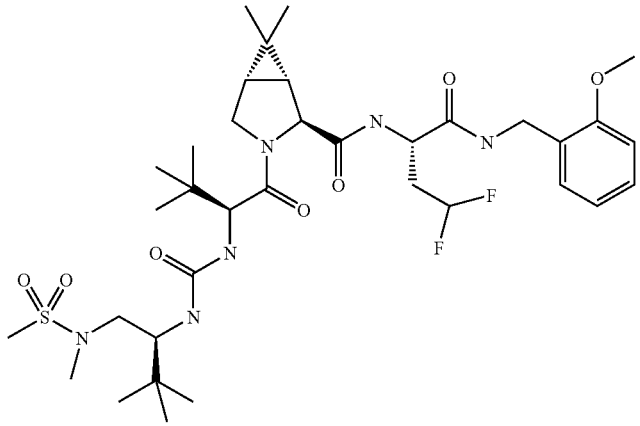 | C |

TABLE 3-continued

| Example No | Structure | Ki |
|---|---|---|
| 223 | 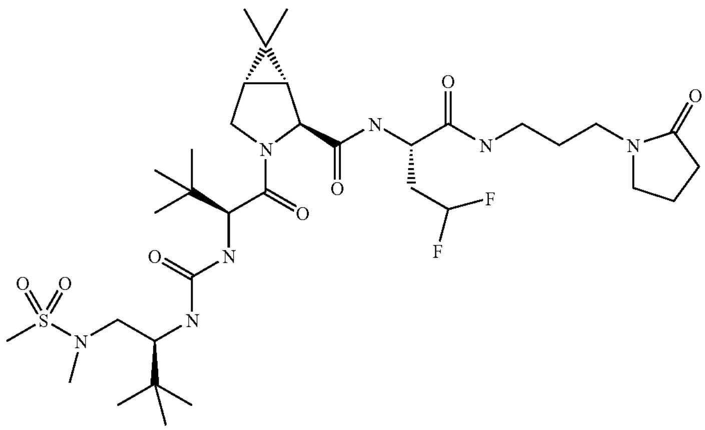 | C |
| 224 | 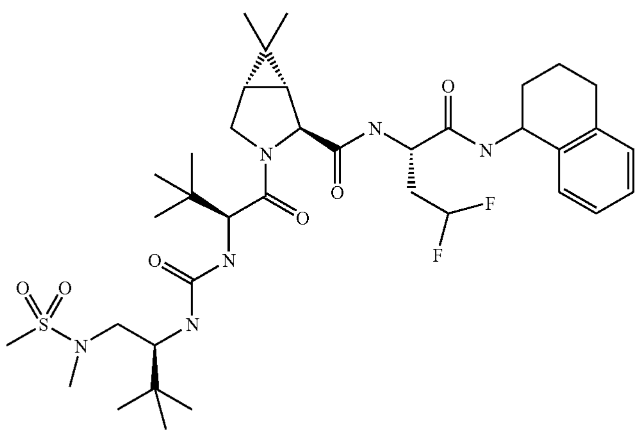 | C |
| 225 | 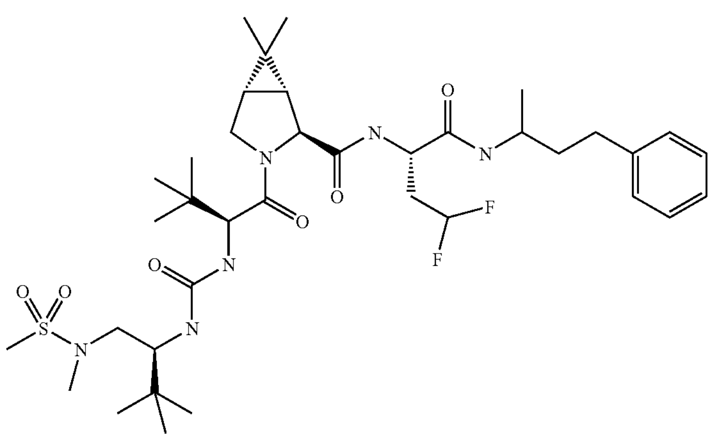 | C |

TABLE 3-continued

| Example No | Structure | Ki |
|---|---|---|
| 226 | 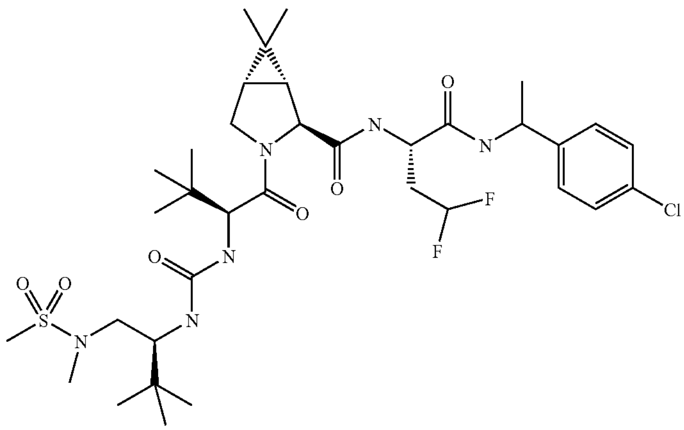 | C |
| 227 | 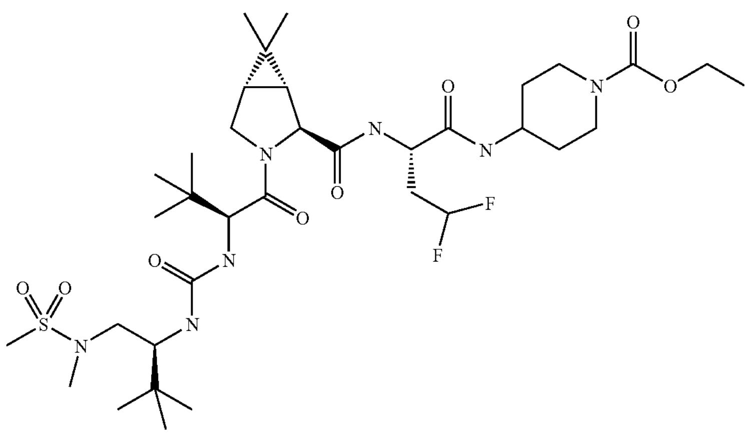 | C |
| 228 | 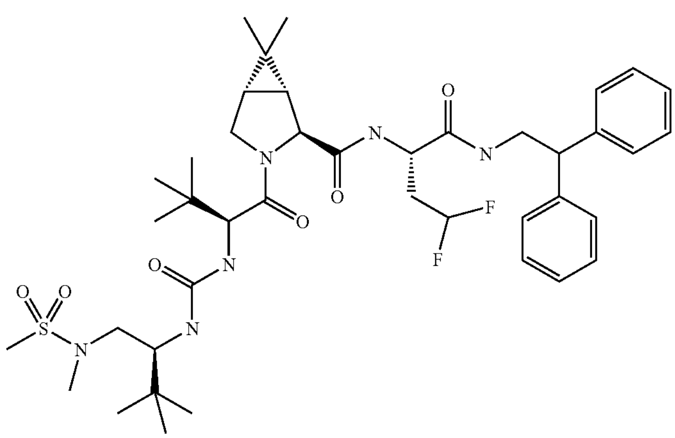 | C |

TABLE 3-continued
| Example No | Structure | Ki |
|---|---|---|
| 229 | 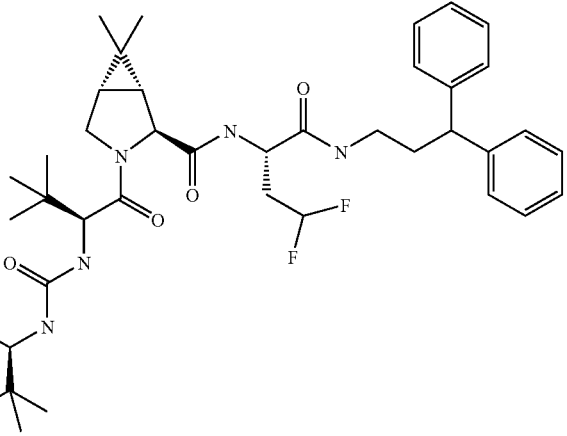 | C |
| 230 | 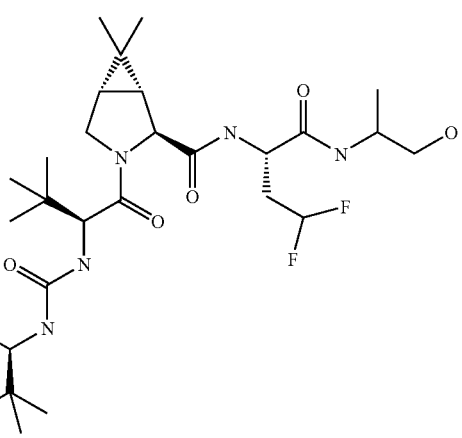 | C |
| 231 | 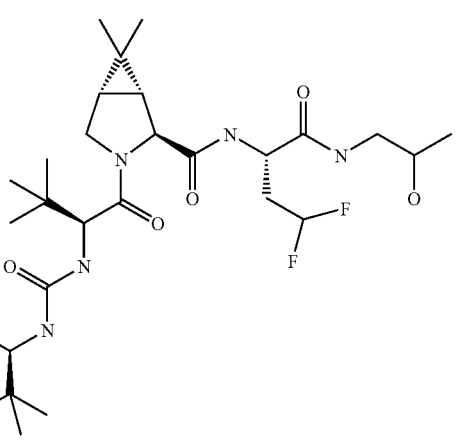 | C |

TABLE 3-continued
| Example No | Structure | Ki |
|---|---|---|
| 232 | 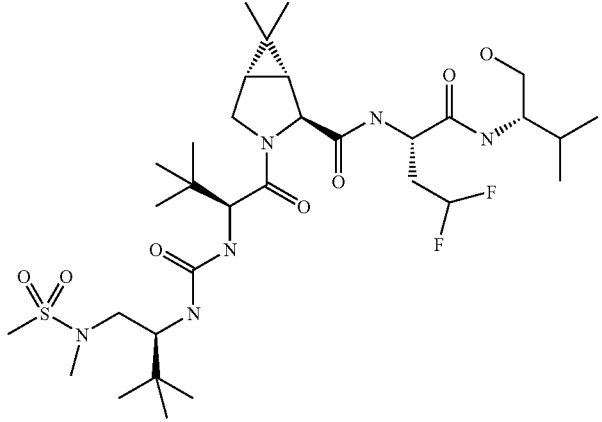 | C |
| 233 | 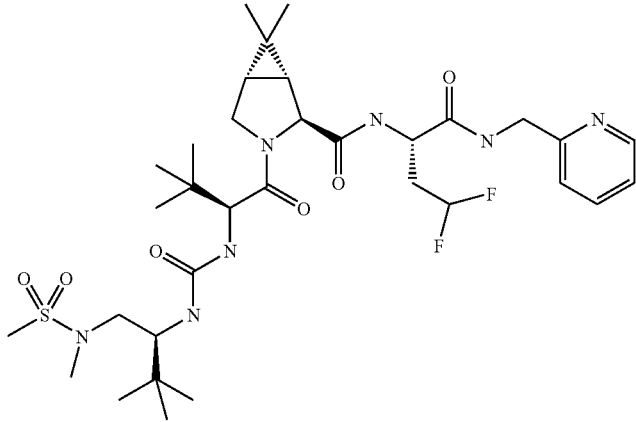 | C |
| 234 | 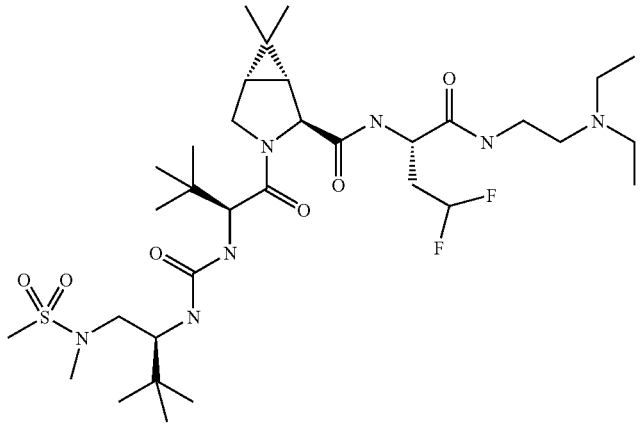 | C |

TABLE 3-continued

| Example No | Structure | Ki |
|---|---|---|
| 235 | 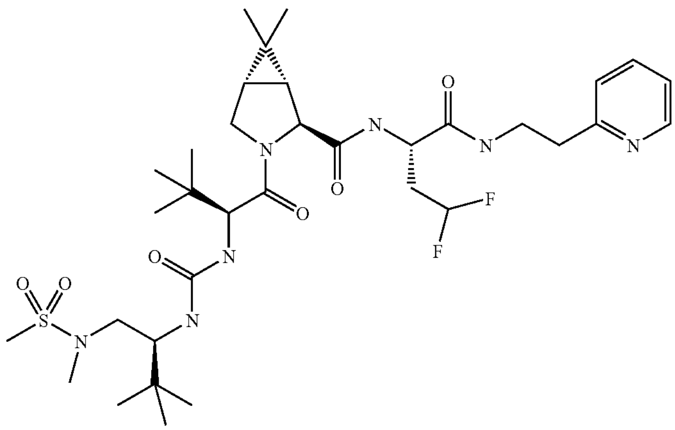 | B |
| 236 | 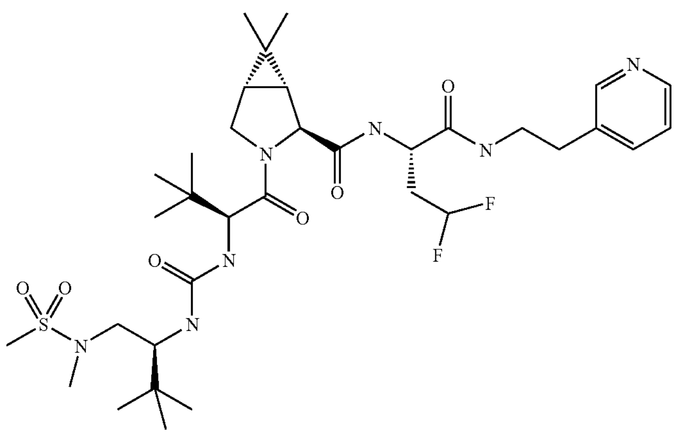 | A |
| 237 | 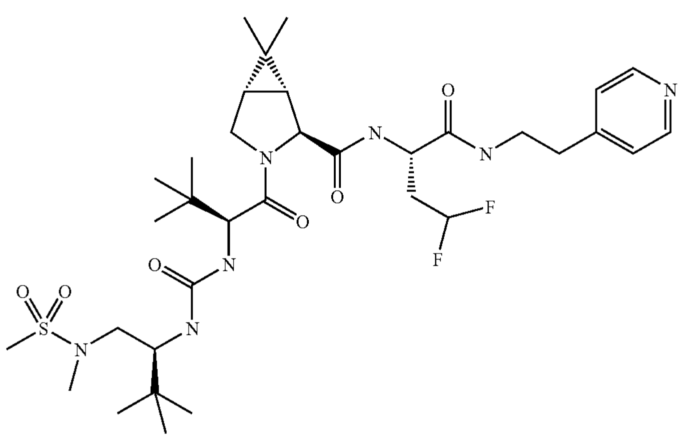 | A |

TABLE 3-continued

| Example No | Structure | Ki |
|---|---|---|
| 238 | 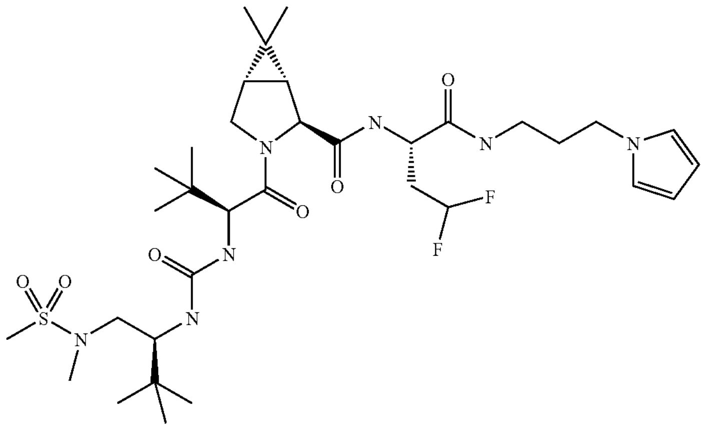 | C |
| 239 | 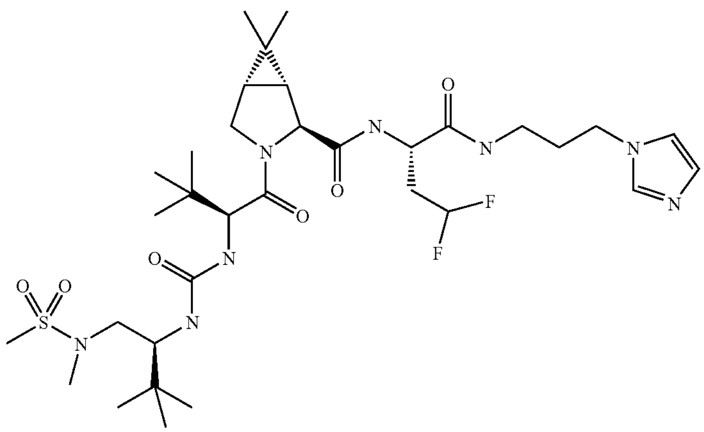 | C |
| 240 | 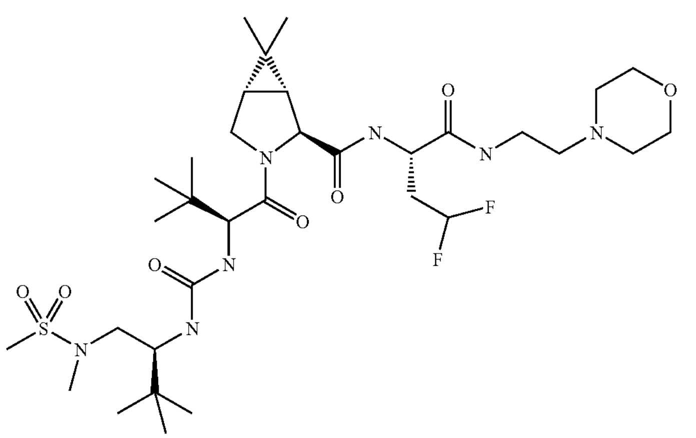 | C |

TABLE 3-continued

| Example No | Structure | Ki |
|---|---|---|
| 241 | 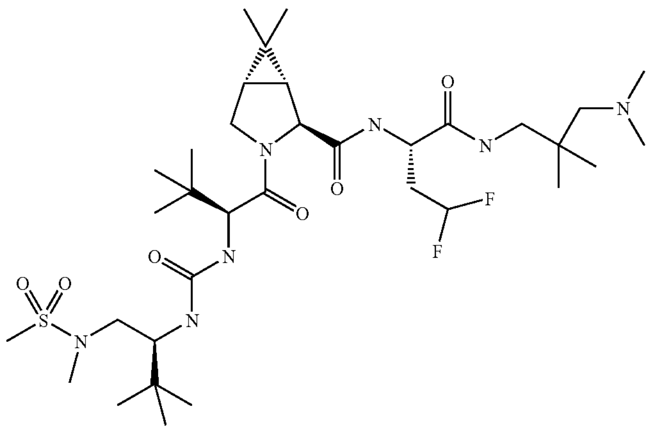 | C |
| 242 | 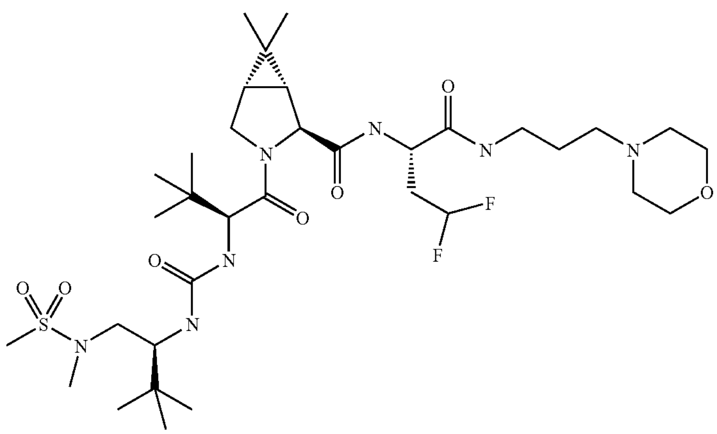 | C |
| 243 | 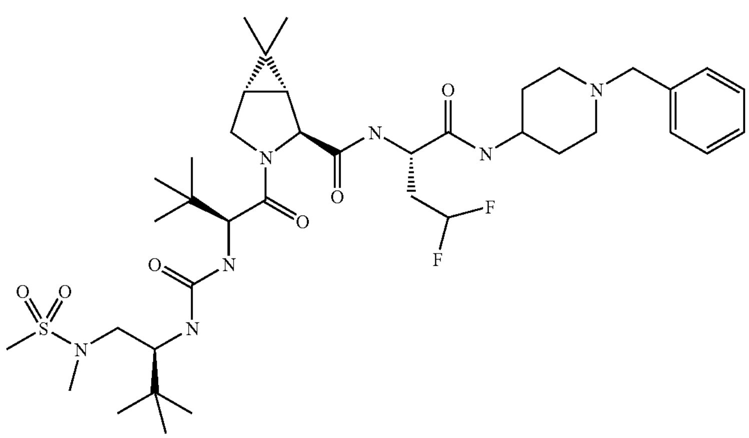 | C |

TABLE 3-continued
| Example No | Structure | Ki |
|---|---|---|
| 244 | 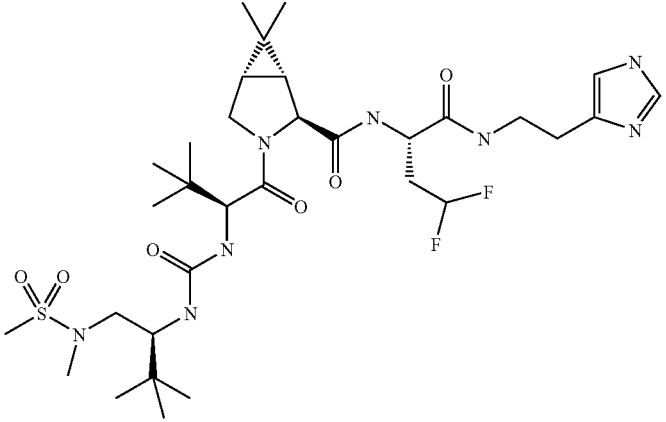 | C |
| 245 | 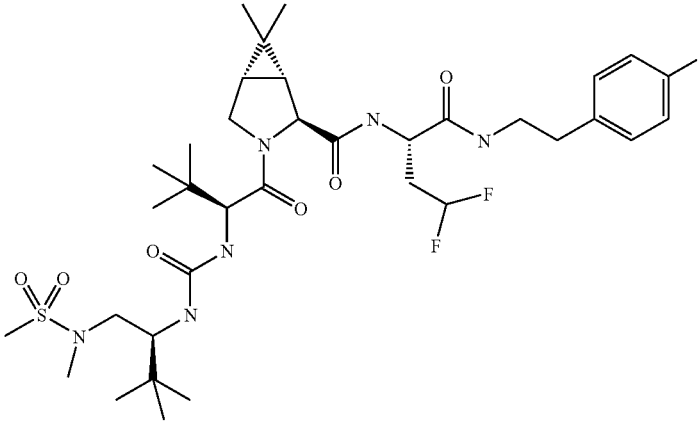 | A |
| 246 | 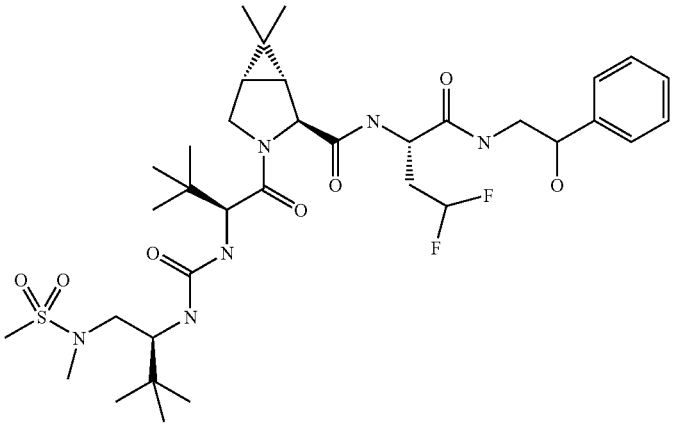 | B |

TABLE 3-continued

| Example No | Structure | Ki |
|---|---|---|
| 247 | 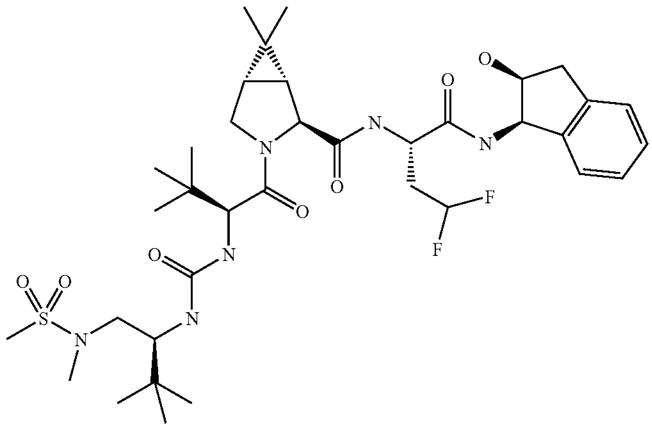 | C |
| 248 | 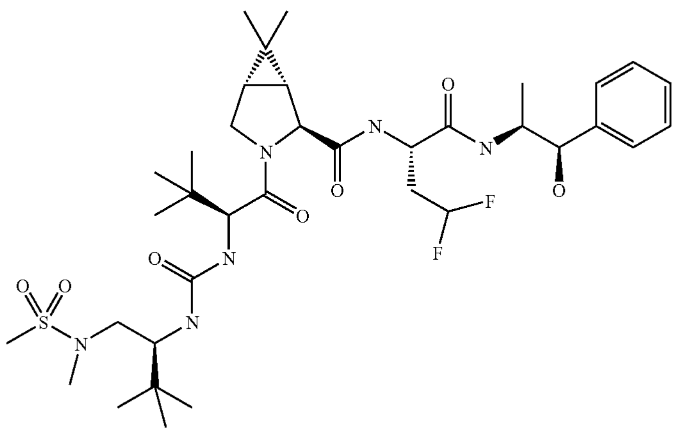 | A |
| 249 | 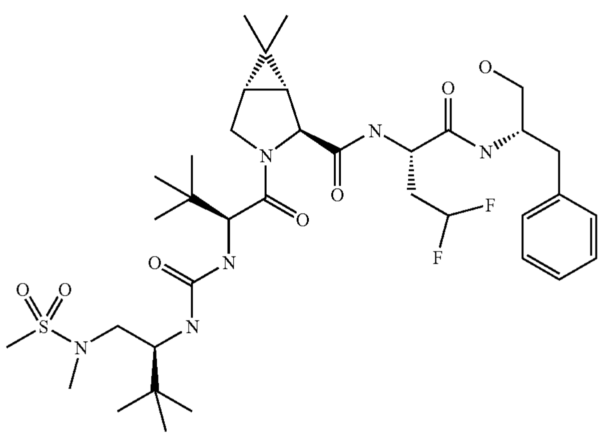 | C |

TABLE 3-continued

| Example No | Structure | Ki |
|---|---|---|
| 250 | 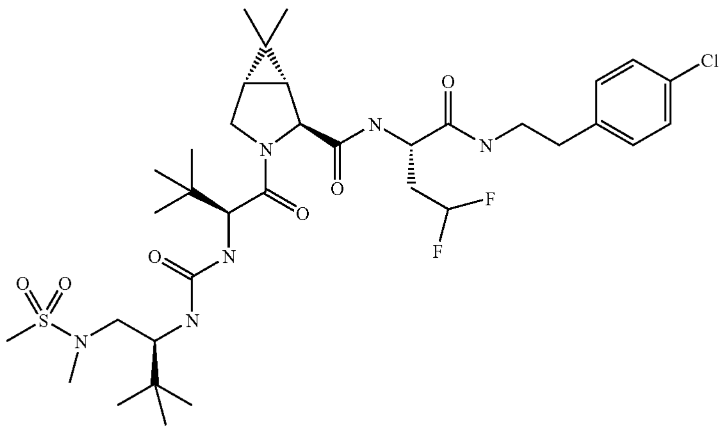 | A |
| 251 | 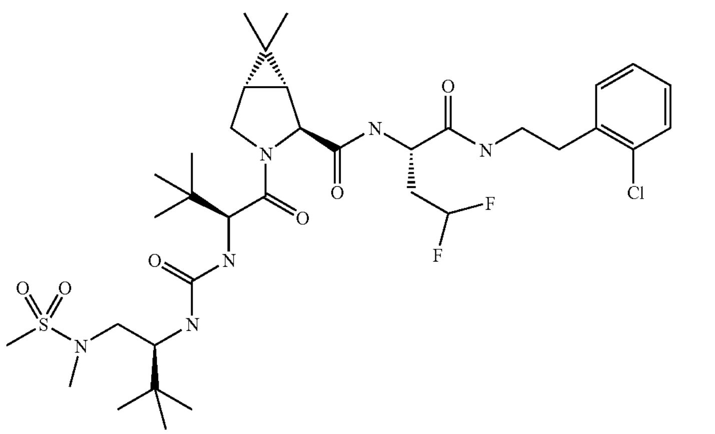 | A |
| 252 | 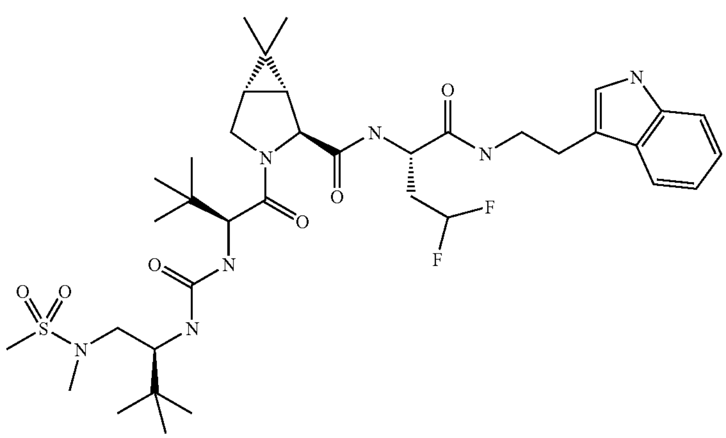 | A |

TABLE 3-continued

| Example No | Structure | Ki |
|---|---|---|
| 253 | 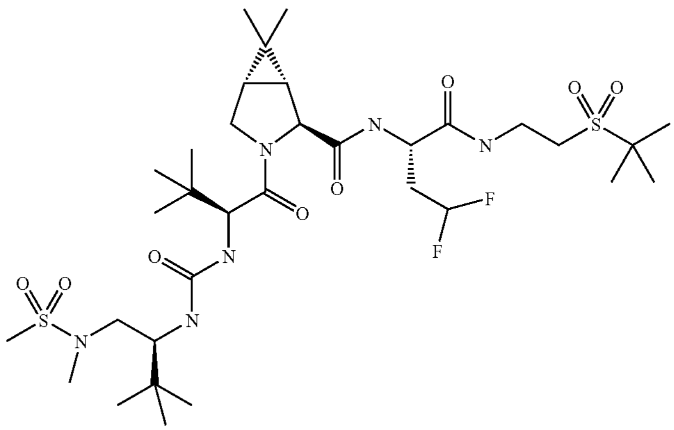 | C |
| 254 | 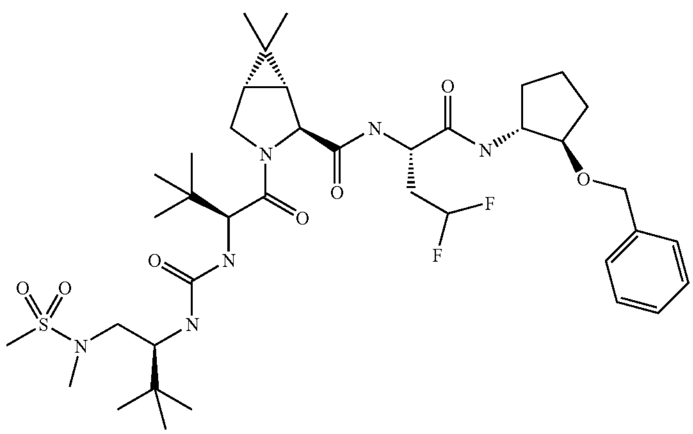 | C |
| 255 | 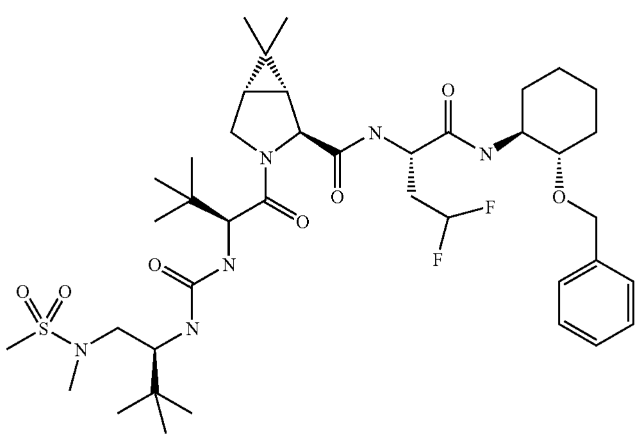 | C |

TABLE 3-continued

| Example No | Structure | Ki |
|---|---|---|
| 256 | 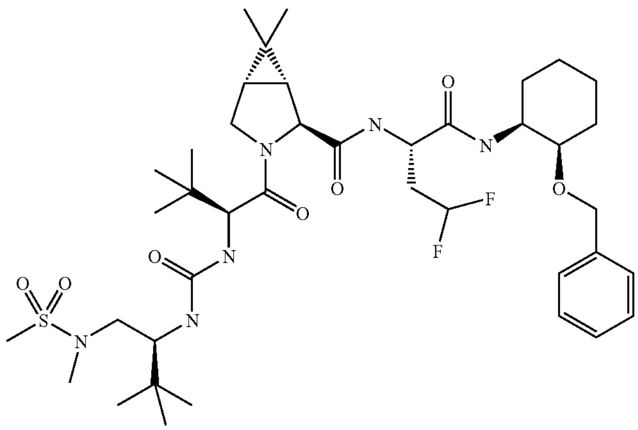 | C |
| 257 | 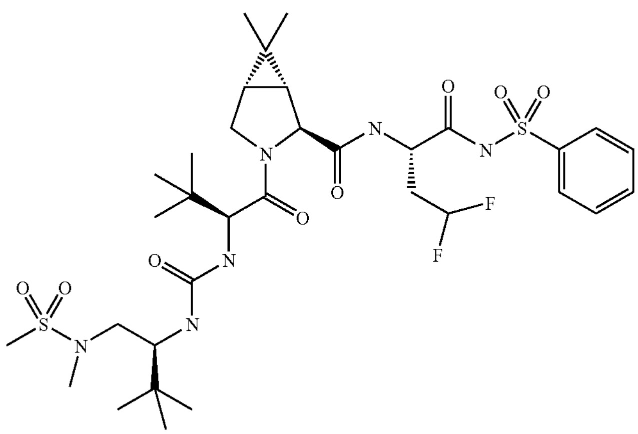 | C |
| 258 | 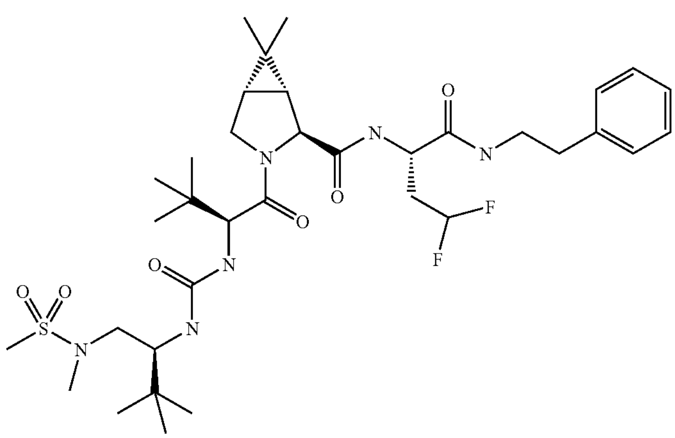 | A |

TABLE 3-continued

| Example No | Structure | Ki |
|---|---|---|
| 259 | 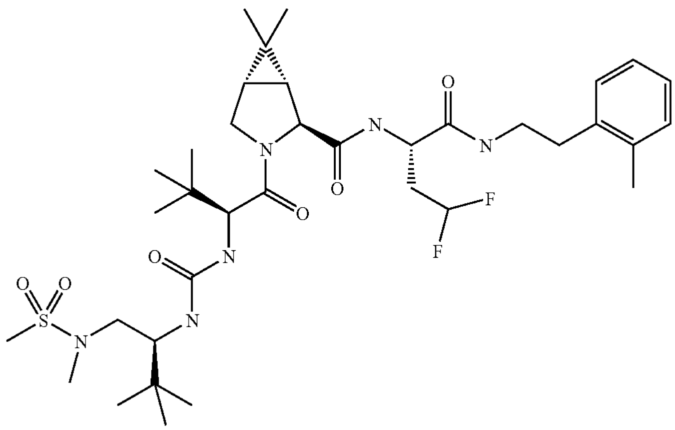 | A |
| 260 | 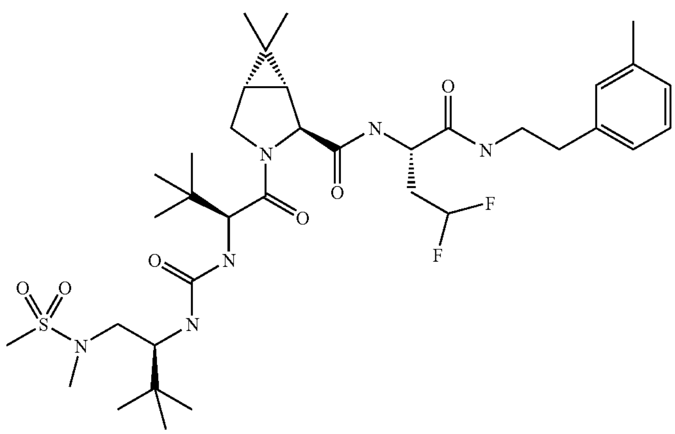 | A |
| 261 | 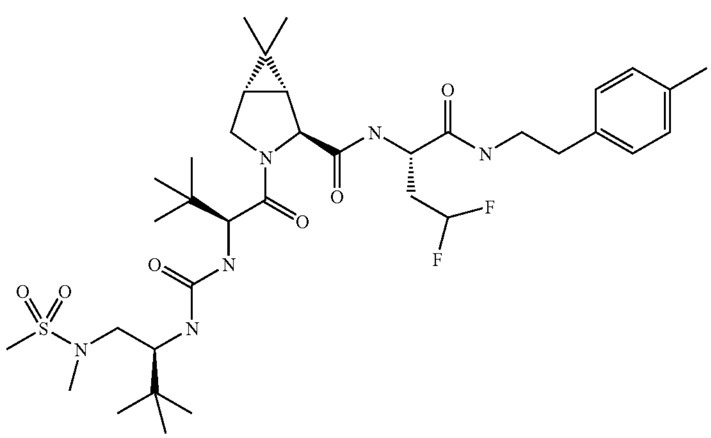 | A |

TABLE 3-continued

| Example No | Structure | Ki |
|---|---|---|
| 262 | 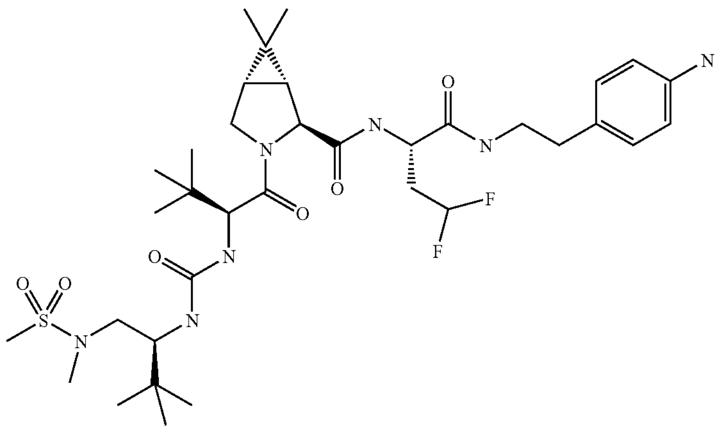 | A |
| 263 | 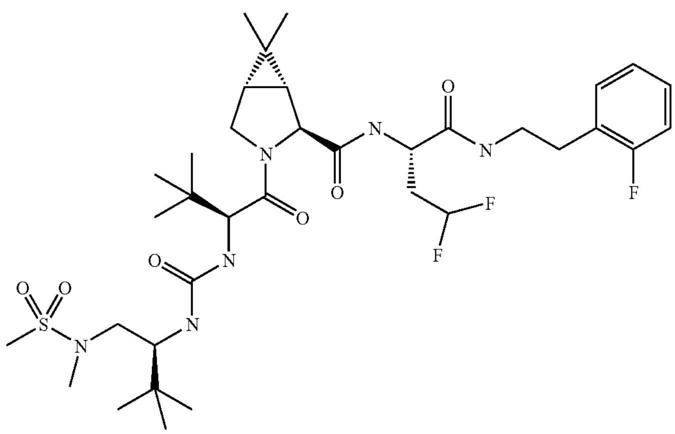 | A |
| 264 | 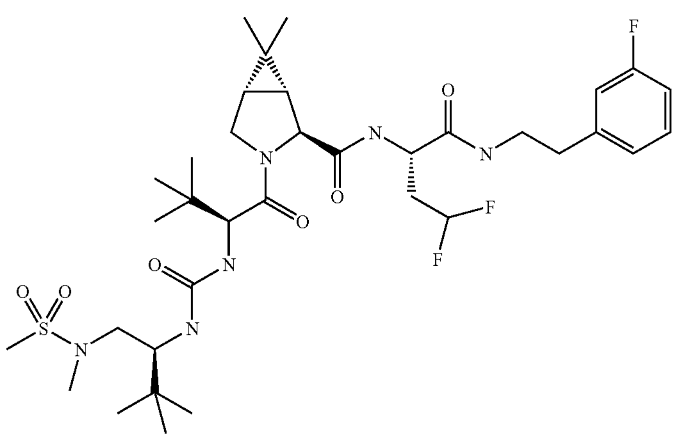 | A |

TABLE 3-continued

| Example No | Structure | Ki |
|---|---|---|
| 265 | 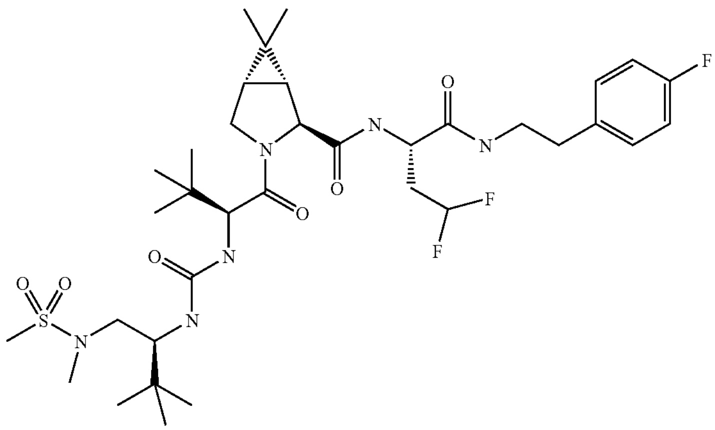 | A |
| 266 | 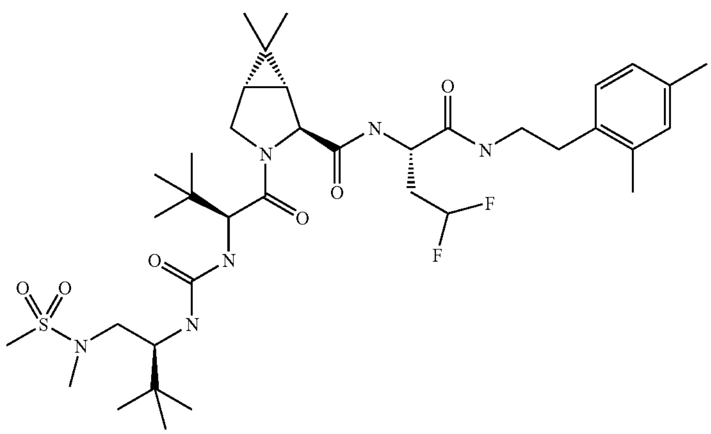 | A |
| 267 | 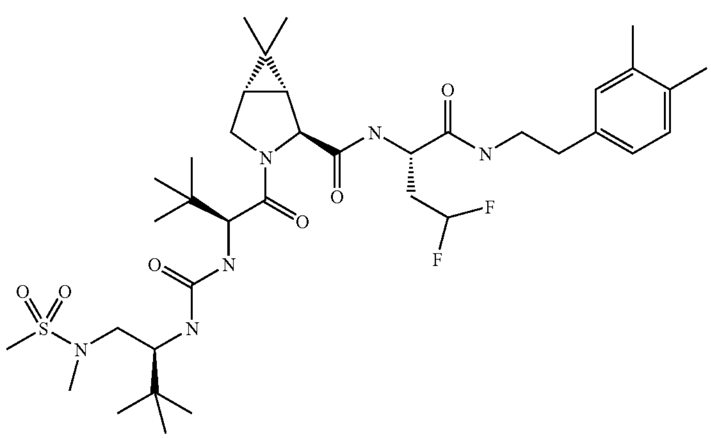 | A |

TABLE 3-continued

| Example No | Structure | Ki |
|---|---|---|
| 268 | 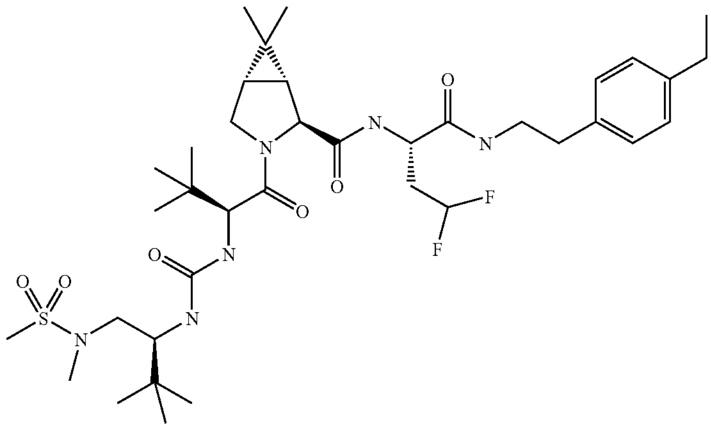 | A |
| 269 | 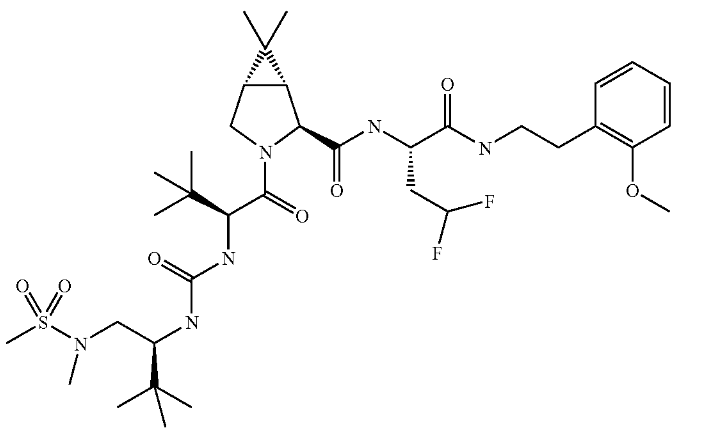 | A |
| 270 | 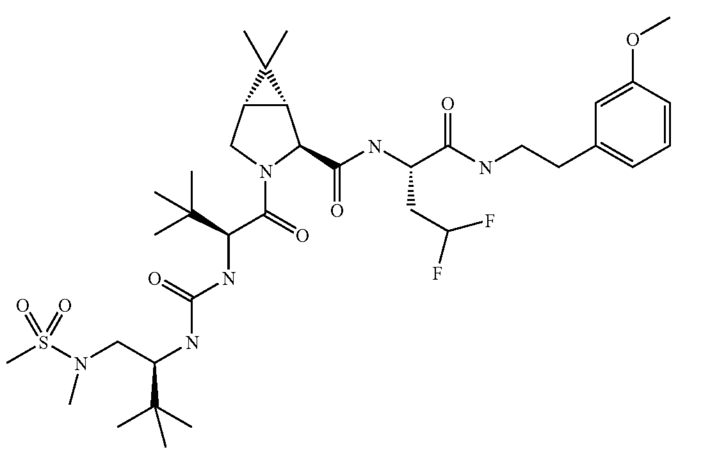 | A |

TABLE 3-continued

| Example No | Structure | Ki |
|---|---|---|
| 271 | 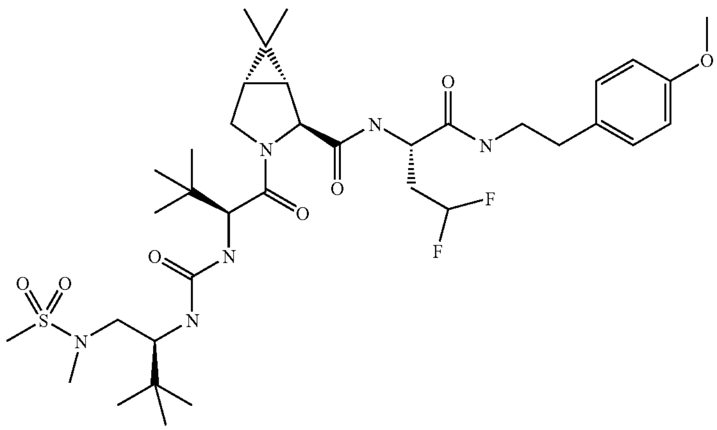 | A |
| 272 | 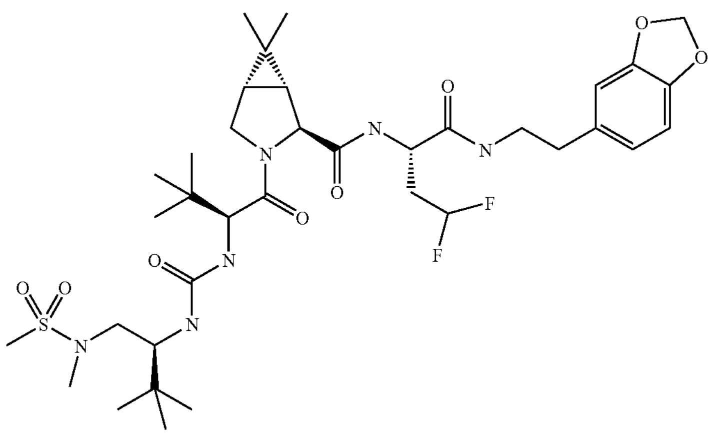 | A |
| 273 | 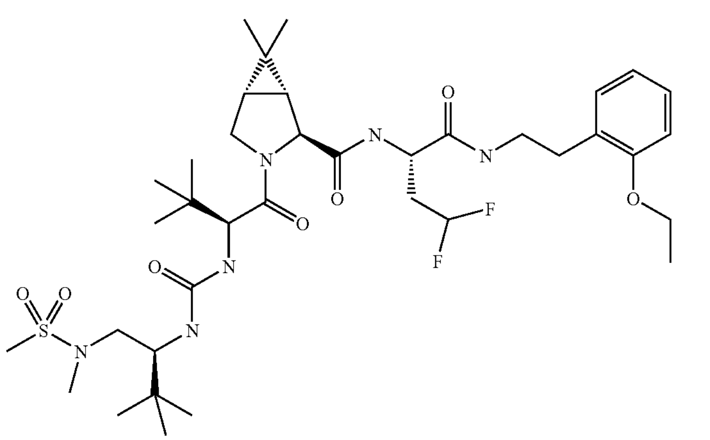 | A |

TABLE 3-continued

| Example No | Structure | Ki |
|---|---|---|
| 274 | 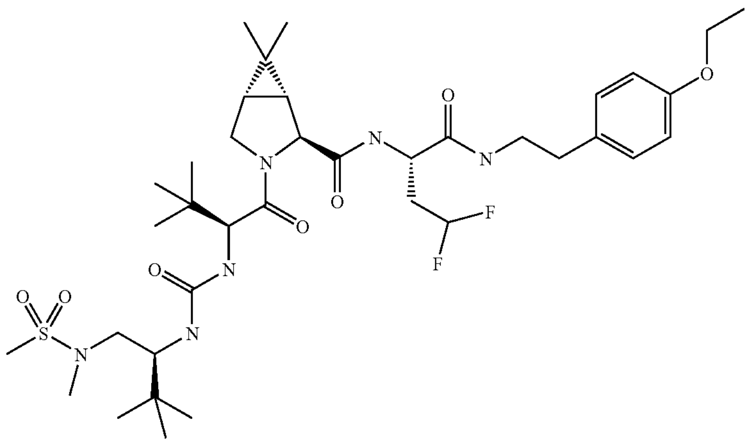 | A |
| 275 | 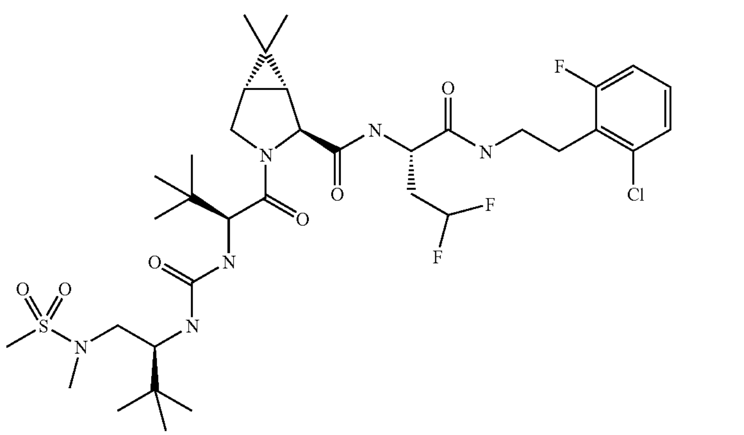 | A |
| 276 | 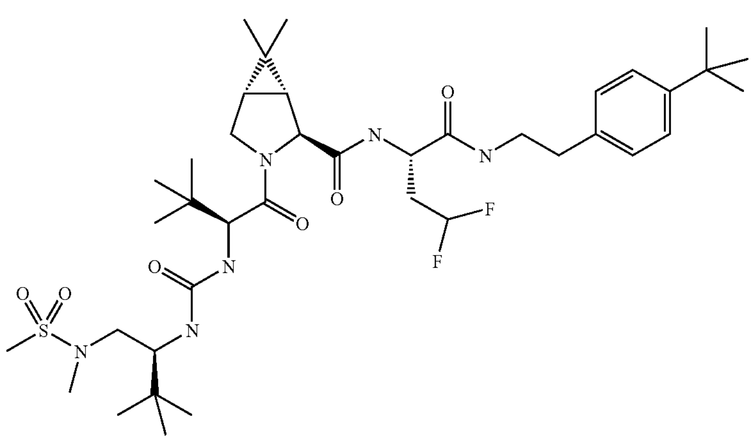 | A |

TABLE 3-continued

| Example No | Structure | Ki |
|---|---|---|
| 277 | 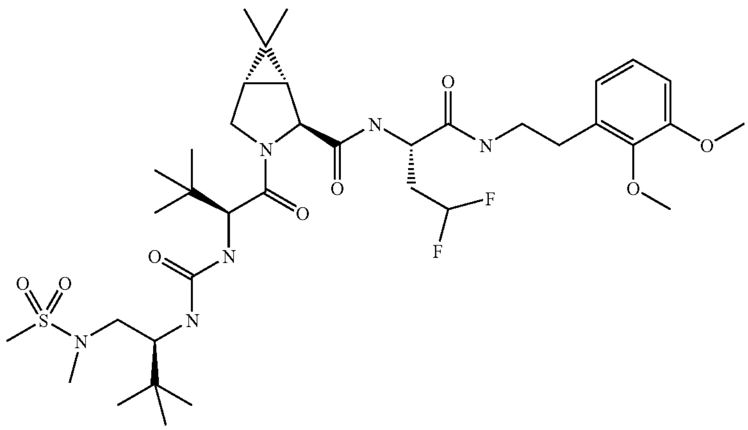 | B |
| 278 | 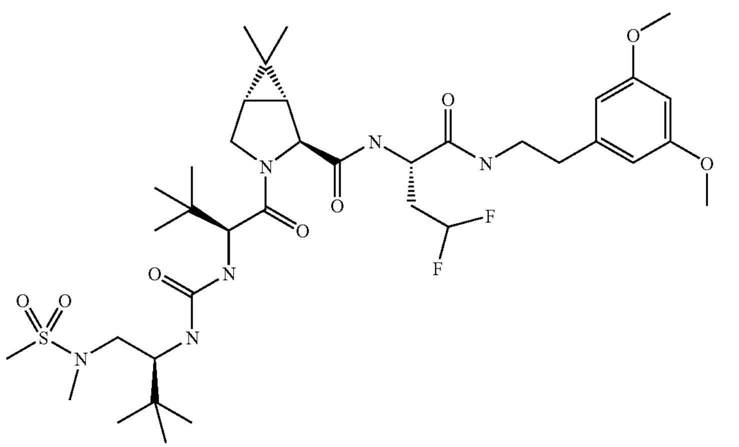 | B |
| 279 | 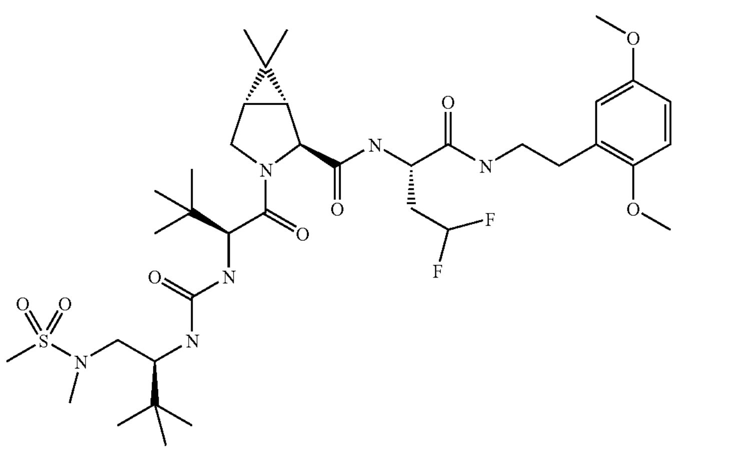 | B |

TABLE 3-continued

| Example No | Structure | Ki |
|---|---|---|
| 280 | 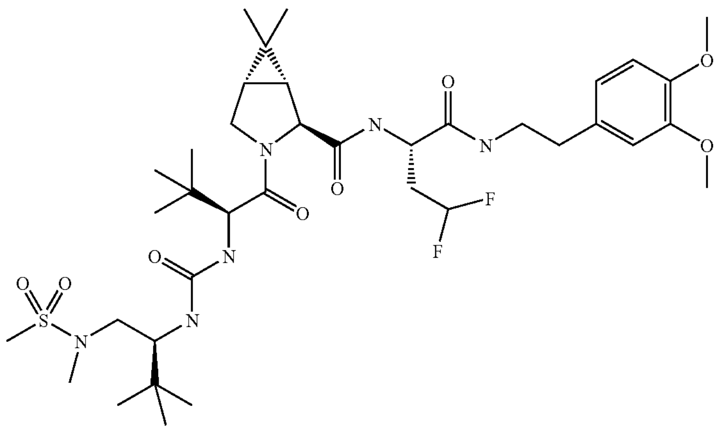 | A |
| 281 | 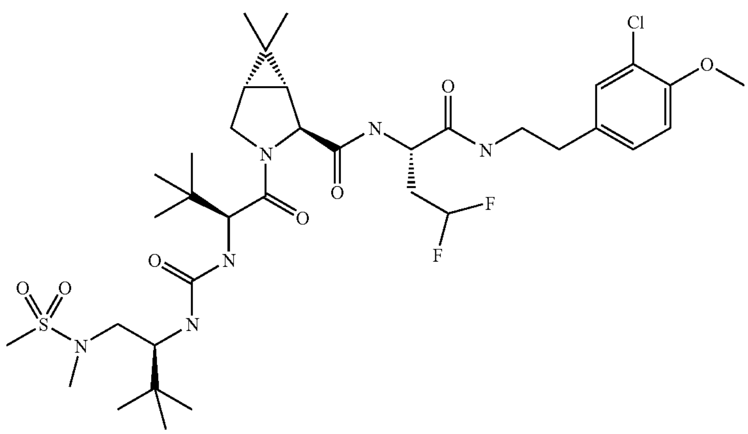 | A |
| 282 | 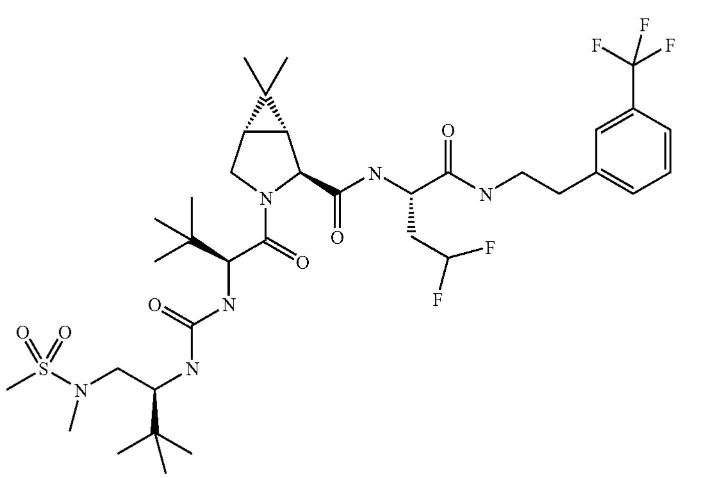 | A |

TABLE 3-continued

| Example No | Structure | Ki |
|---|---|---|
| 283 | 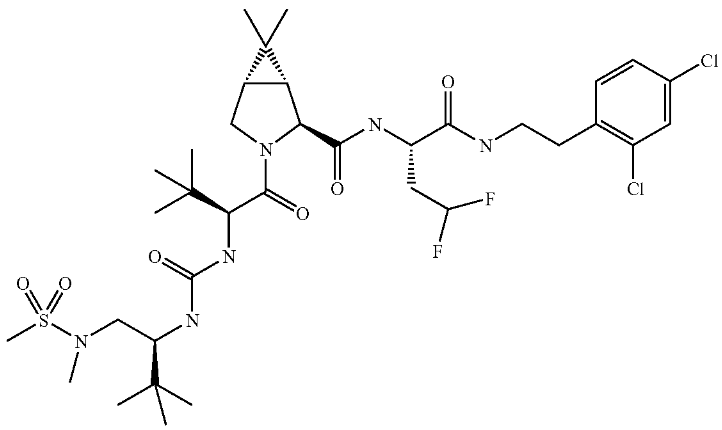 | A |
| 284 | 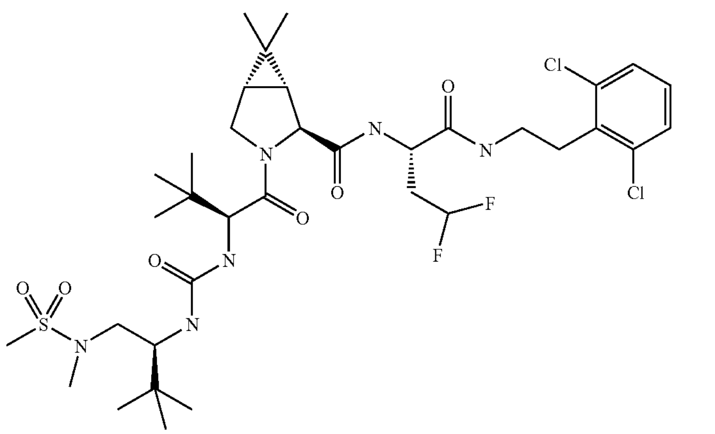 | A |
| 285 | 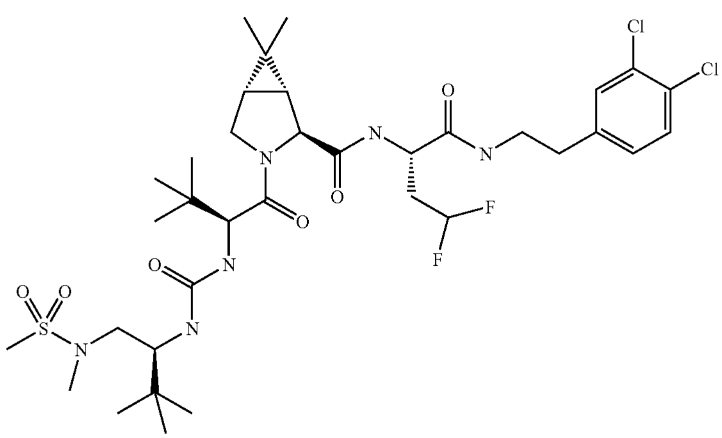 | A |

TABLE 3-continued
| Example No | Structure | Ki |
|---|---|---|
| 286 | 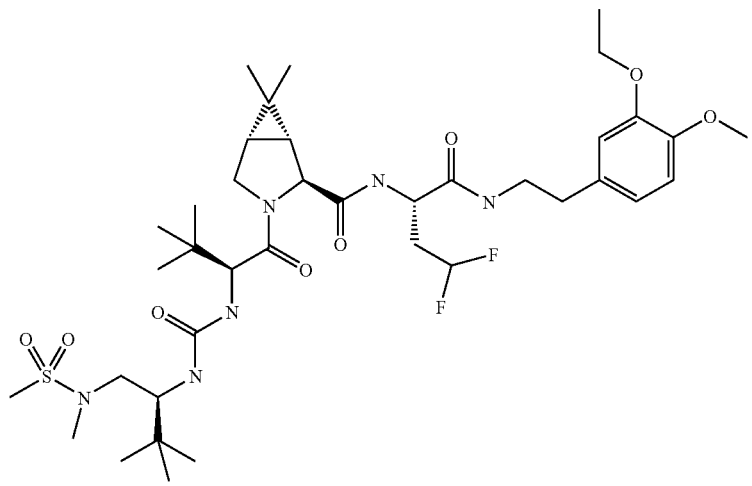 | A |
| 287 | 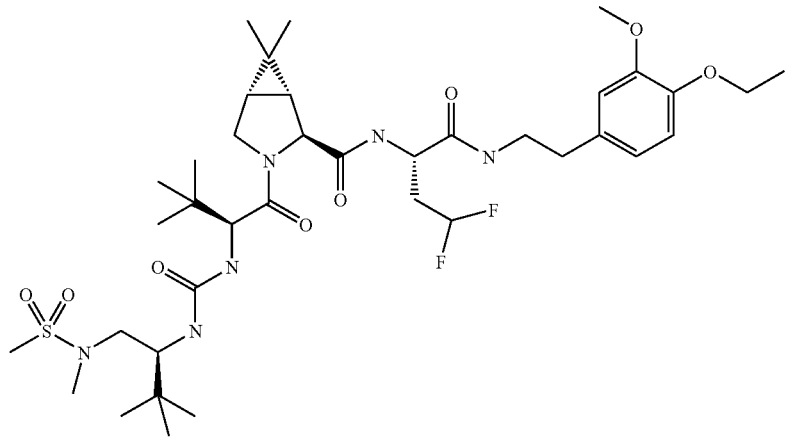 | A |
| 288 | 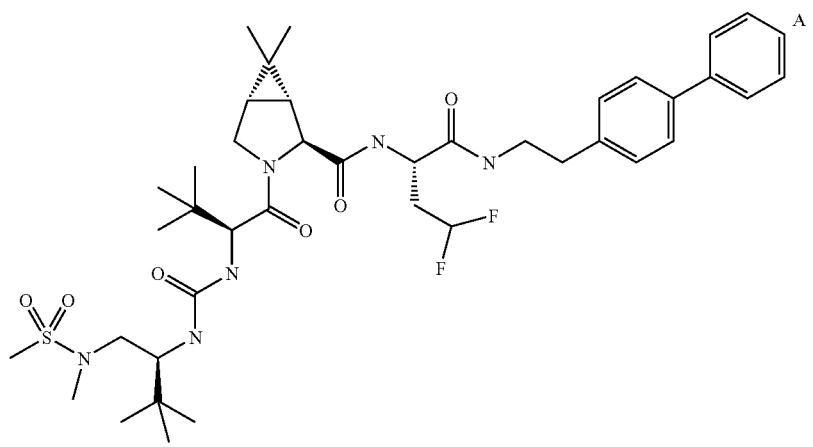 | A |

US 7,449,447 B2
TABLE 3-continued
| Example No | Structure | Ki |
|---|---|---|
| 289 | 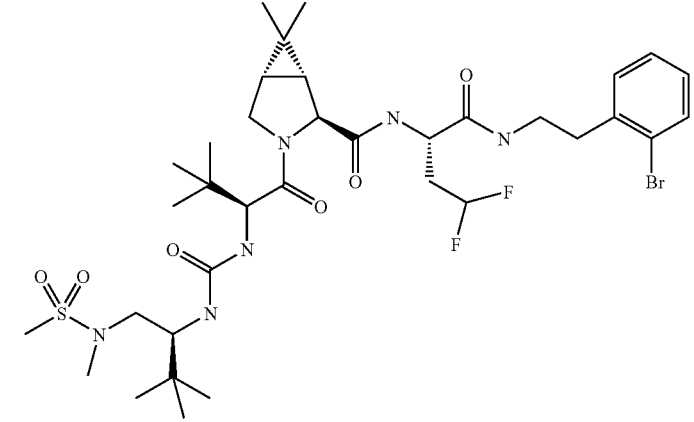 | A |
| 290 | 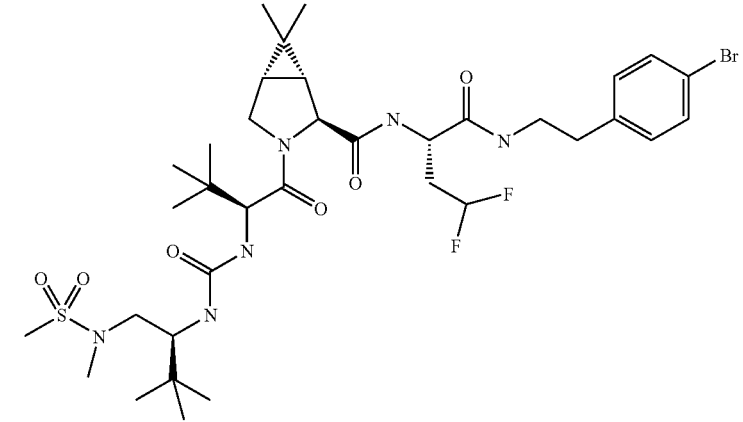 | A |
| 291 | 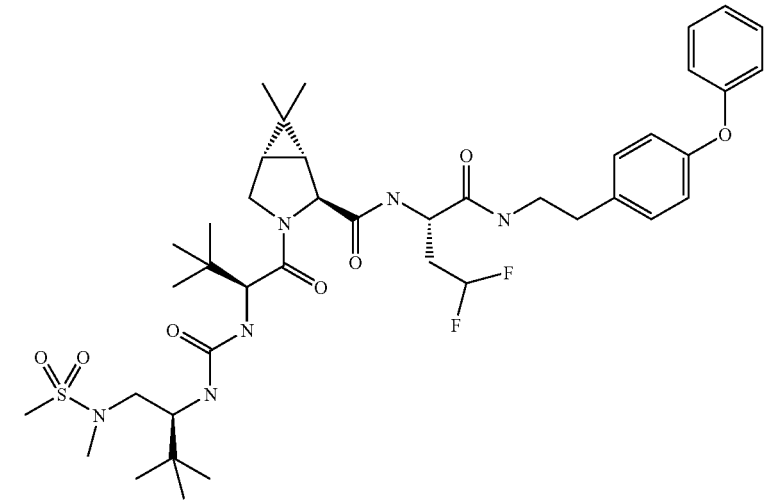 | A |

TABLE 3-continued

| Example No | Structure | Ki |
|---|---|---|
| 292 | 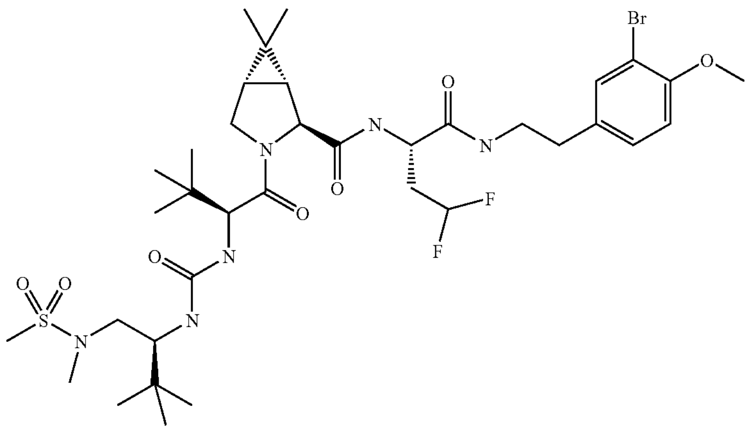 | A |
| 293 | 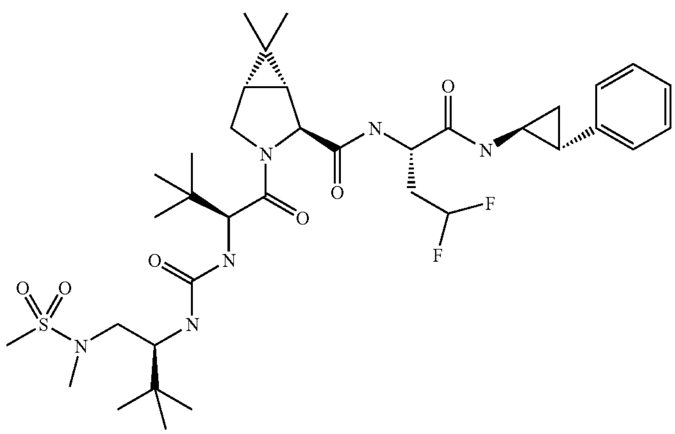 | C |
| 294 | 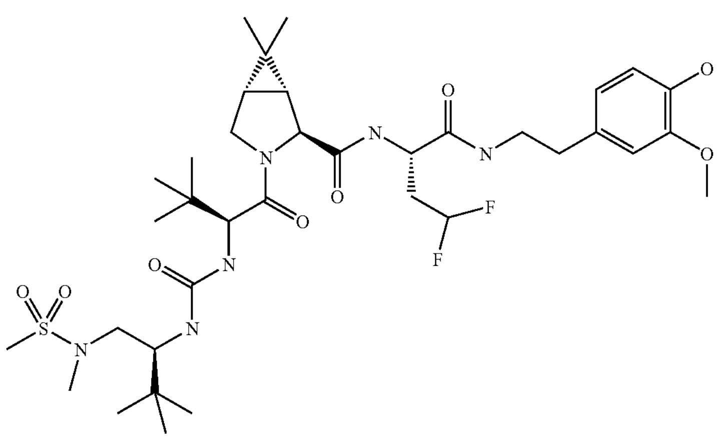 | A |

TABLE 3-continued

| Example No | Structure | Ki |
|---|---|---|
| 295 | 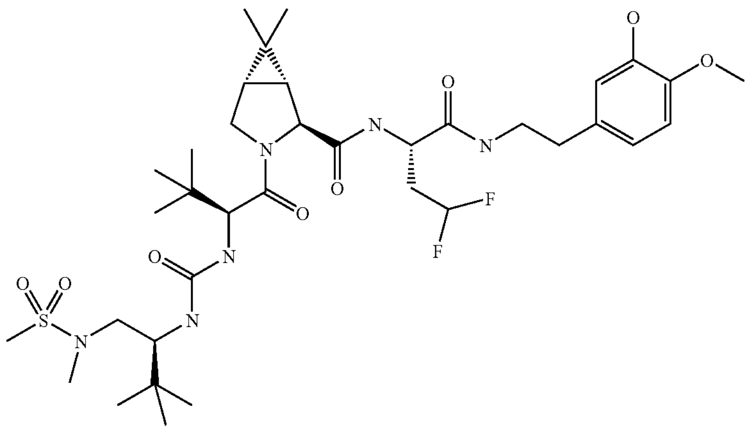 | A |
| 296 | 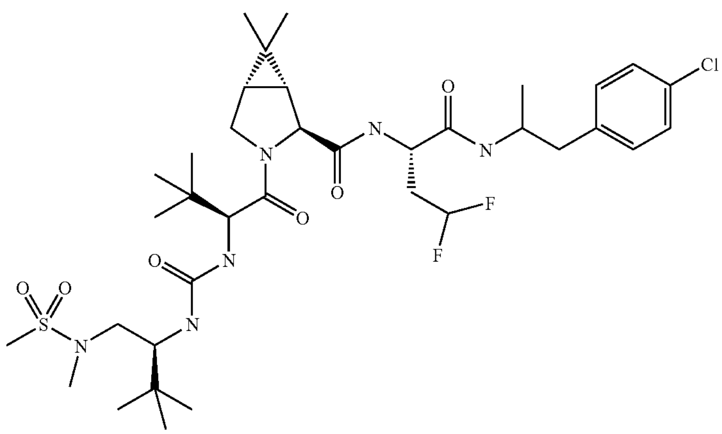 | B |
| 297 | 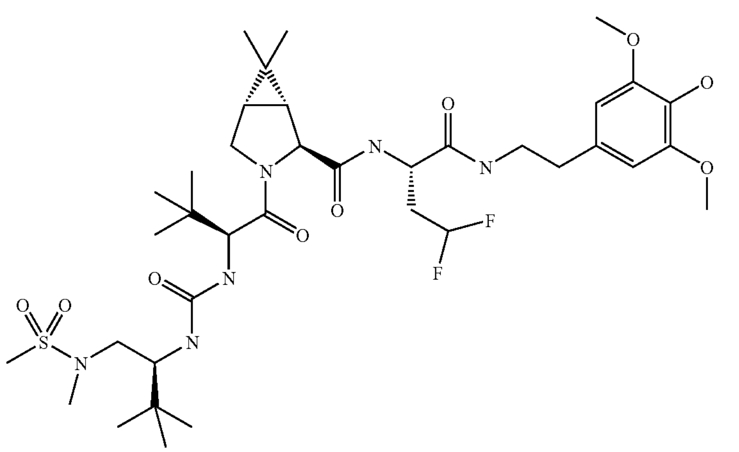 | B |

TABLE 3-continued

| Example No | Structure | Ki |
|---|---|---|
| 298 | 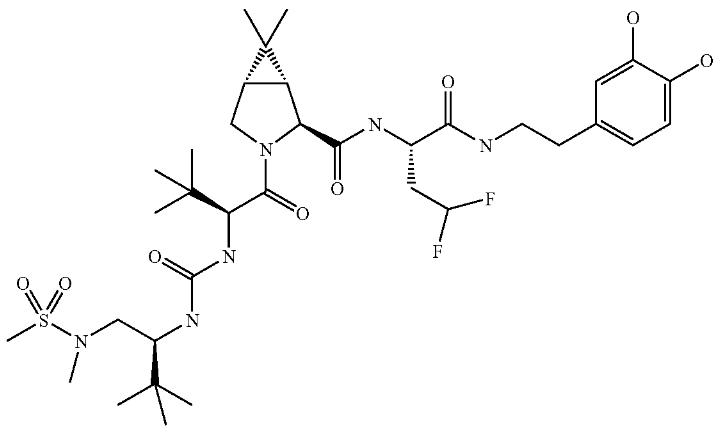 | A |
| 299 | 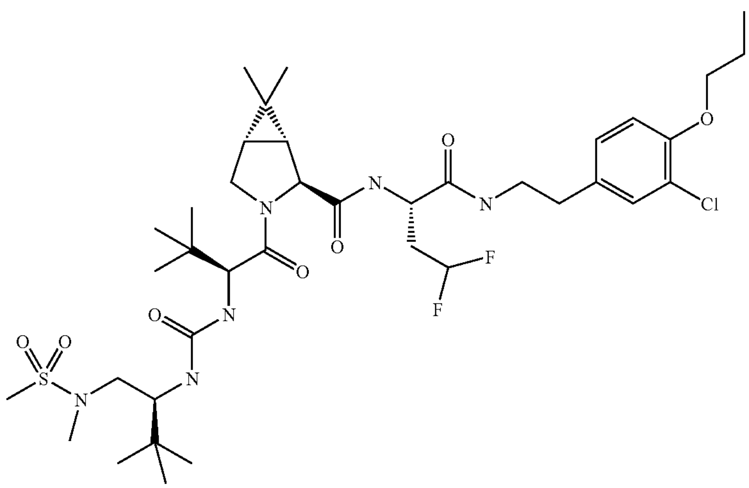 | A |
| 300 | 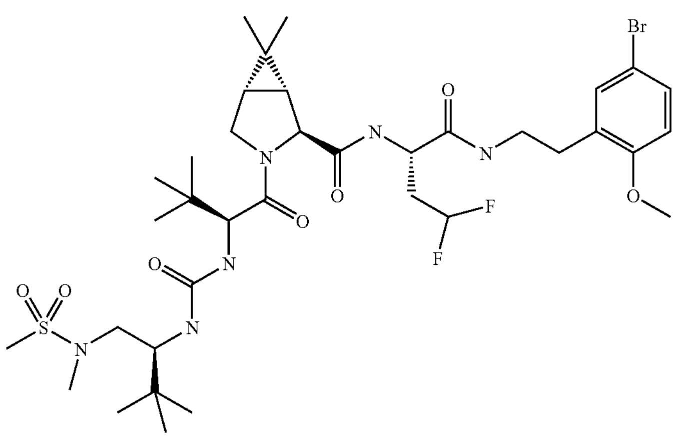 | A |

TABLE 3-continued
| Example No | Structure | Ki |
|---|---|---|
| 301 | 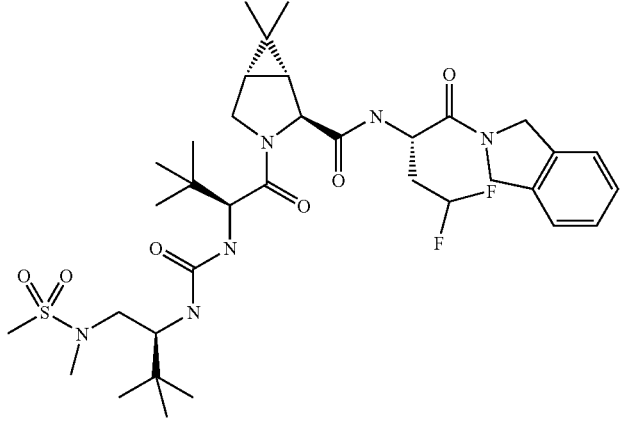 | C |
| 302 | 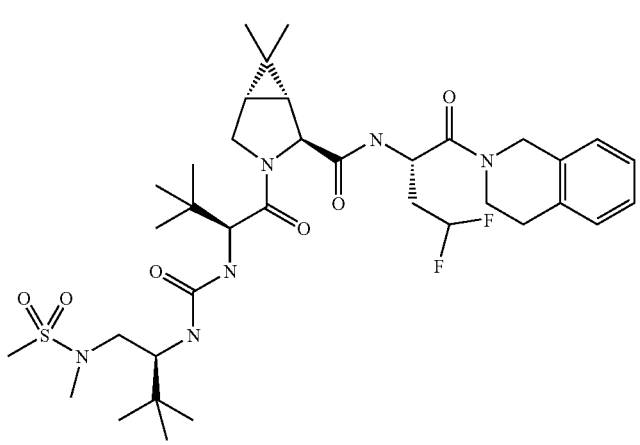 | C |
| 303 | 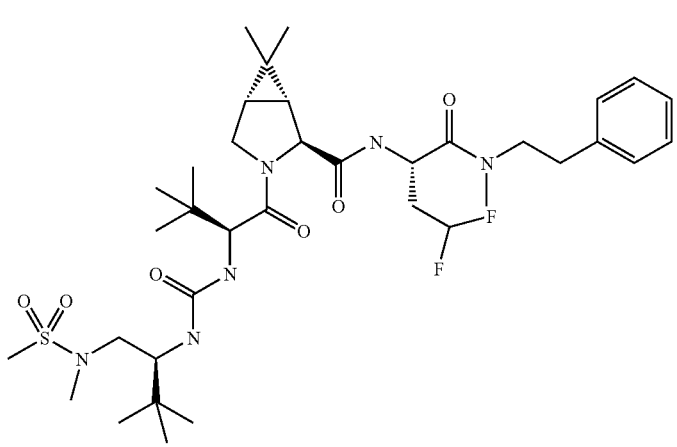 | C |

TABLE 3-continued
| Example No | Structure | Ki |
|---|---|---|
| 304 | 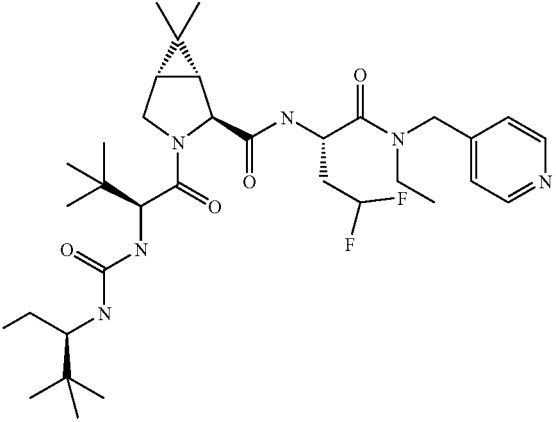 | C |
| 305 | 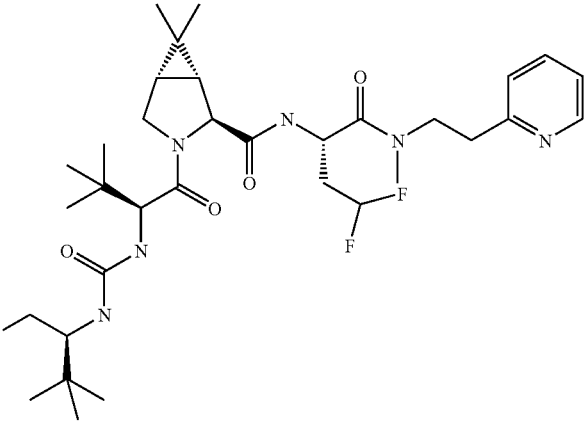 | C |
| 306 | 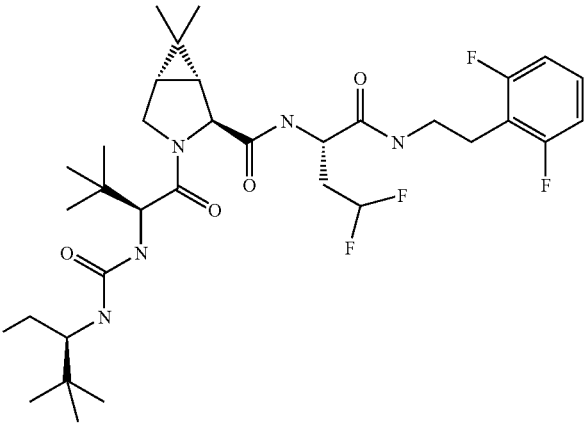 | A |

TABLE 3-continued

| Example No | Structure | Ki |
|---|---|---|
| 307 | 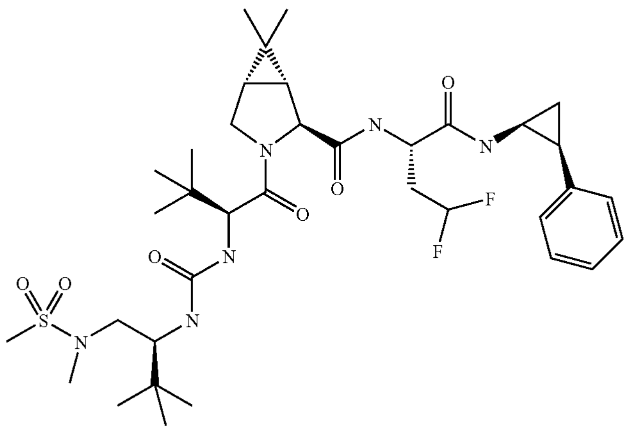 | A |
| 308 | 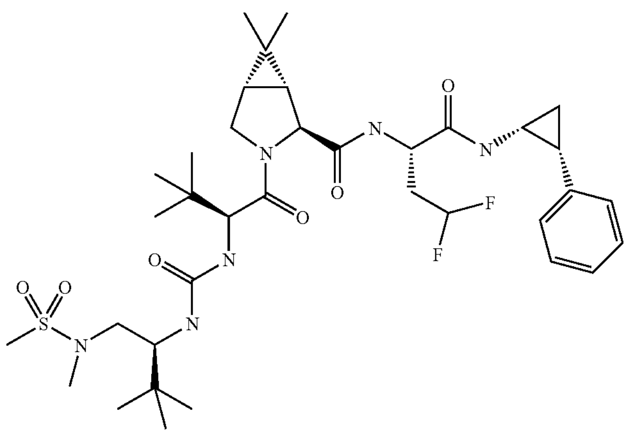 | A |
| 309 | 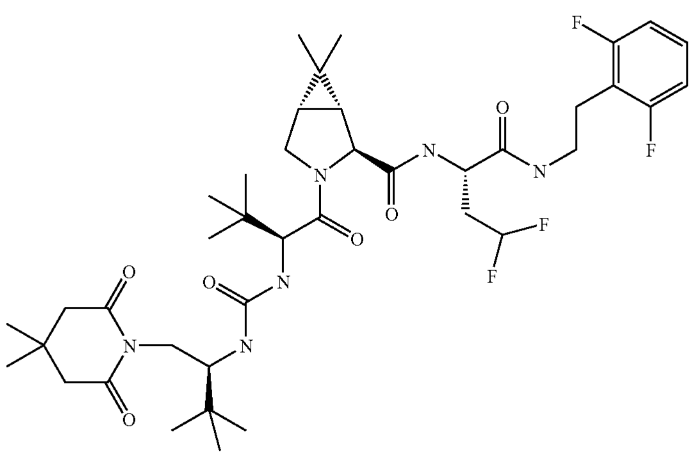 | A |

One inventive group of compounds of Formula 1 is where $R^1$ is NH or O with proviso that when $R^1$ is O, P is not H.

In another embodiment, this invention provides pharmaceutical compositions comprising the inventive compounds as an active ingredient. The pharmaceutical compositions generally additionally comprise a pharmaceutically acceptable carrier diluent, excipient or carrier (collectively referred to herein as carrier materials). Because of their HCV inhibitory activity, such pharmaceutical compositions possess utility in treating hepatitis C and related disorders.

In yet another embodiment, the present invention discloses methods for preparing pharmaceutical compositions comprising the inventive compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally, intravenously or subcutaneously.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gel—refers to the active ingredients dispersed or solubilized in a hydrophillic semi-solid matrix.

Powder for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrant—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binder—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'1-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glident—material that prevents caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses the use of the pharmaceutical compositions disclosed above for treatment of diseases such as, for example, hepatitis C and the like. The method comprises administering a therapeutically effective amount of the inventive pharmaceutical composition to a patient having such a disease or diseases and in need of such a treatment.

In yet another embodiment, the compounds of the invention may be used for the treatment of HCV in humans in monotherapy mode or in a combination therapy (e.g., dual combination, triple combination etc.) mode such as, for example, in combination with antiviral and/or immunomodulatory agents. Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406• (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As stated earlier, the invention includes tautomers, rotamers, enantiomers and other stereoisomers of the inventive compounds also. Thus, as one skilled in the art appreciates, some of the inventive compounds may exist in suitable isomeric forms. Such variations are contemplated to be within the scope of the invention.

Another embodiment of the invention discloses a method of making the compounds disclosed herein. The compounds may be prepared by several techniques known in the art. Representative illustrative procedures are outlined in the following reaction schemes. The invention disclosed herein is then further exemplified by preparative examples which should not be construed to limit the scope of the invention which is defined in the appended claims. Alternative mechanistic pathways and analogous structures will be apparent to those skilled in the art.

It is to be understood that while the following illustrative schemes describe the preparation of a few representative inventive compounds, suitable substitution of any of both the natural and unnatural amino acids will result in the formation of the desired compounds based on such substitution. Such variations are contemplated to be within the scope of the invention.

For the procedures described below, the following abbreviations are used:

Ac: Acetyl;
AcOH: Acetic acid;
ADDP: 1,1'-(Azodicarbobyl)dipiperidine
Alloc: Allyloxy Carbonyl
Boc: tert-Butyloxycarbonyl;
$^tBu$ or $Bu^t$: tert-Butyl;
Cbz: Benzyloxycarbonyl;
DCM means diclhloromethane;
DCC: 1,3-Dicyclohexylcarbodiimide;
DMF means N,N-dimethylformamide;
DMSO means dimethyl sulfoxide;
DTT: DL-Dithiothreitol
EDCI: 1-(3-dimethylaminopropyl)-3-ethylcarbodiimide hydrochloride;
Et: Ethyl;
EtOAc means ethyl acetate;
EtOH: Ethanol;
$Et_2O$: Diethyl ether;
Fmoc means 9-fluorenylmethyloxycarbonyl;
HOOBt: 3-Hydroxy-1,2,3-benzotriazin-4(3H)-one;
HOBt: N-Hydroxybenzotriazole;
HPLC: High Performance Liquid Chromatography
iBoc: isobutoxycarbonyl;
iPr: isopropyl;
Me: Methyl;
MeOH means methyl alcohol;
MOPS means 3-[N-Morpholino]propanesulfonic acid;
MS means mass spectrum;

NMM means N-methyl morpholine;
NMR means nuclear magnetic resonance;
OD means optical density;
PAP means phenylazophenol;
Ph: Phenyl;
Pd/C means palladium on charcoal catalyst;
rt means room temperature;
THF means tetrahydrofuran;
TLC: Thin Layer Chromatography;
Ts: p-toluenesulfonyl.

General Preparative Schemes:

The following schemes describe the methods of synthesis of intermediate building blocks:

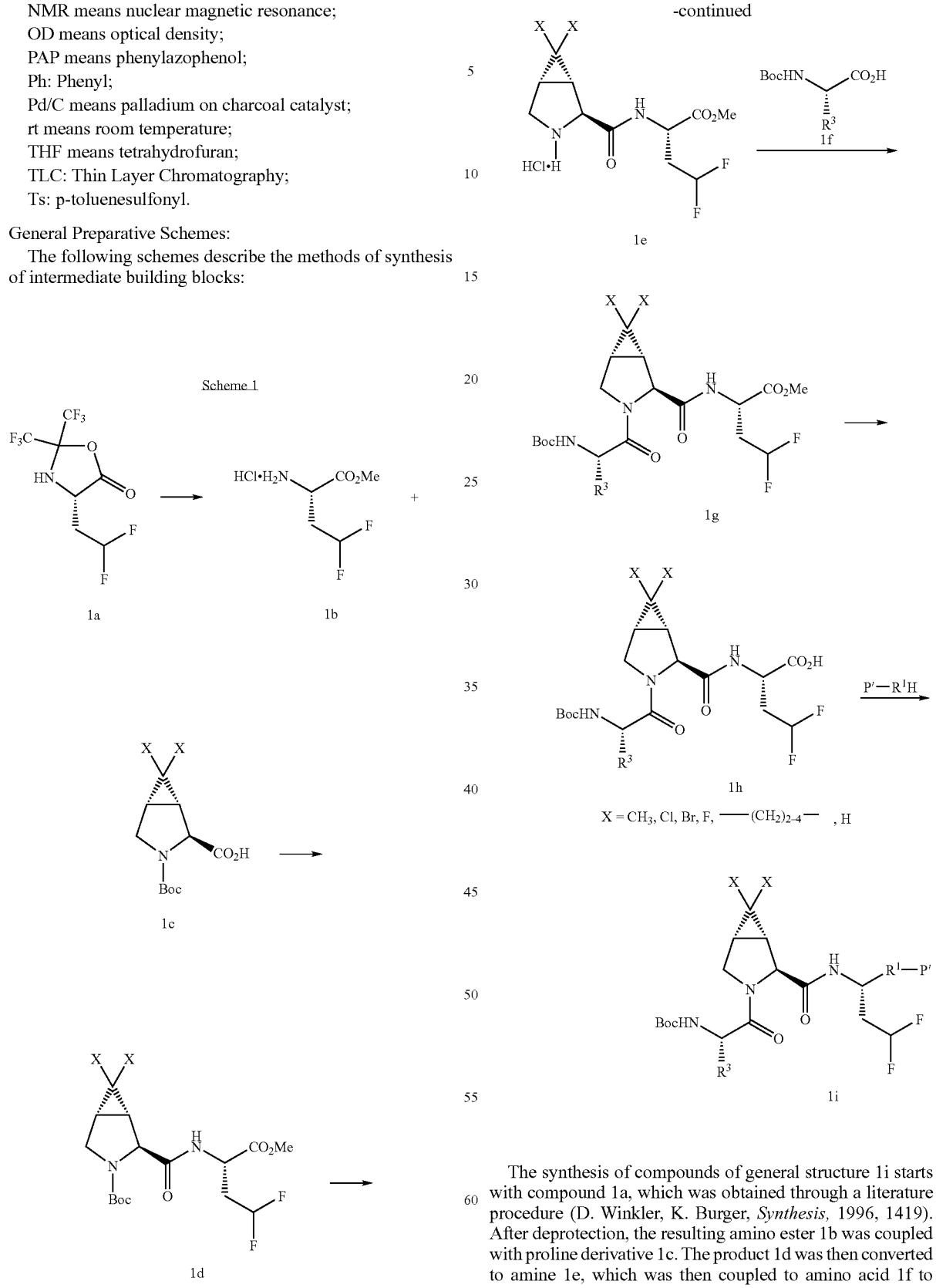

The synthesis of compounds of general structure 1i starts with compound 1a, which was obtained through a literature procedure (D. Winkler, K. Burger, *Synthesis*, 1996, 1419). After deprotection, the resulting amino ester 1b was coupled with proline derivative 1c. The product 1d was then converted to amine 1e, which was then coupled to amino acid 1f to afford tri-peptide 1g. The ester was hydrolyzed to acid 1h, which was coupled to an appropriate amine to give compound 1i.

Scheme 2

On the other hand, compound 1g was converted to amine hydrochloride 2a. An appropriate capping group was then introduced into 5 the amine to give product 2b. The acid 2c could be obtained through hydrolysis of 2b. And, finally, coupling of 2c with an amine afford compound 2d.

Scheme 3

Alternatively, tri-peptide 1i could be treated with 4 N HCl in dioxane to give amine 3a, upon which an appropriate capping group was put to provide target compounds of type 2d.

Preparation of Intermediates

Intermediate A:

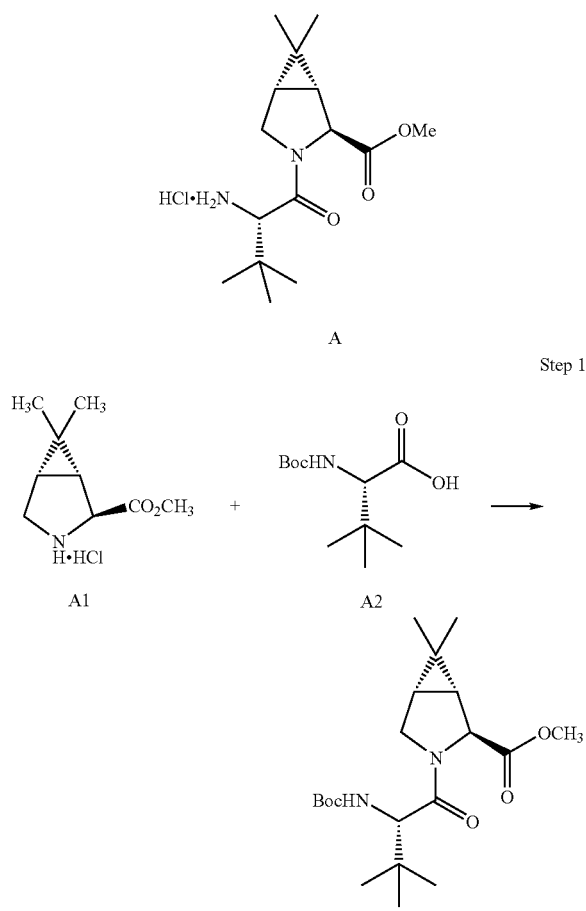

The amino ester A1 was prepared following the method of R. Zhang and J. S. Madalengoitia (*J. Org. Chem.* 1999, 64, 330), with the exception that the Boc group was cleaved by the reaction of the Boc-protected amino acid with methanolic HCl (4M HCl in dioxane was also employed for the deprotection).

(Note: In a variation of the reported synthesis, the sulfonium ylide was replaced with the corresponding phosphonium ylide).

A solution of Boc-tert-Leu A2 (Fluka, 5.0 g, 21.6 mmol) in dry $CH_2Cl_2$/DMF (50 mL, 1:1 ) was cooled to 0° C. and treated with the amine hydrochloride A1 (5.3 g, 25.7 mmol), NMM (6.5 g, 64.8 mmol) and BOP reagent (11.6 g, 25.7 mmol). The reaction was stirred at rt. for 24 h, diluted with aqueous HCl (1 M) and extracted with $CH_2Cl_2$. The combined organic layers were washed with aqueous 1M HCl, sat'd. $NaHCO_3$, brine, dried ($MgSO_4$), filtered and concentrated in vacuo and purified by chromatography ($SiO_2$, Acetone/Hexane 1:5) to yield A3 as a colorless solid.

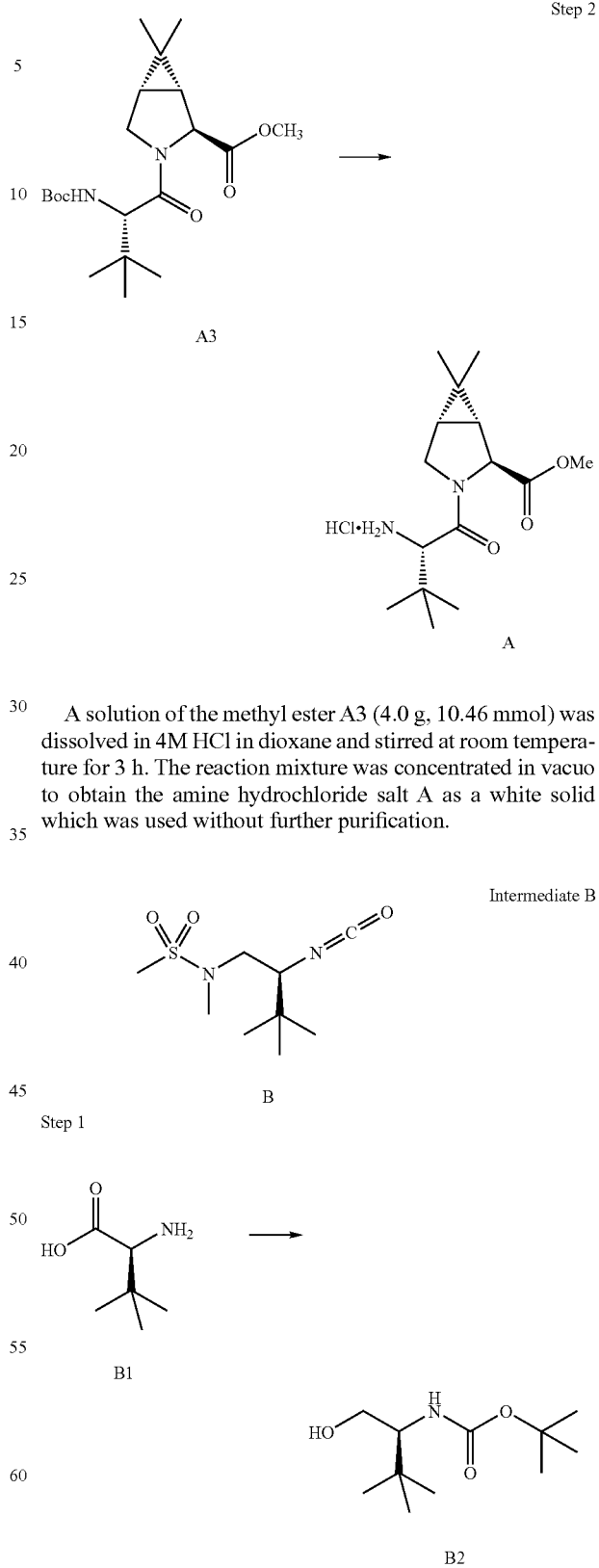

A solution of the methyl ester A3 (4.0 g, 10.46 mmol) was dissolved in 4M HCl in dioxane and stirred at room temperature for 3 h. The reaction mixture was concentrated in vacuo to obtain the amine hydrochloride salt A as a white solid which was used without further purification.

L-tert-Leucine (1 eq, 10 g) was slowly added to a suspension of lithium aluminum hydride (150 mmol, 1M solution in THF). The reaction mixture was refluxed for 6 h. The mixture was cooled to 0° C. and quenched by addition of 10 mL of aqueous 10% NaOH and 10 mL of water. The mixture was stirred at room temperature for 10 minutes and then treated with di-tert-butylcarbonate (1.1 eq, 18.22 g) and the mixture was stirred at 60° C. overnight. The reaction mixture was filtered through magnesium sulfate. The filtrate was concentrated and the residue was chromatographed on silica gel to give the product B2 in 62% yield.

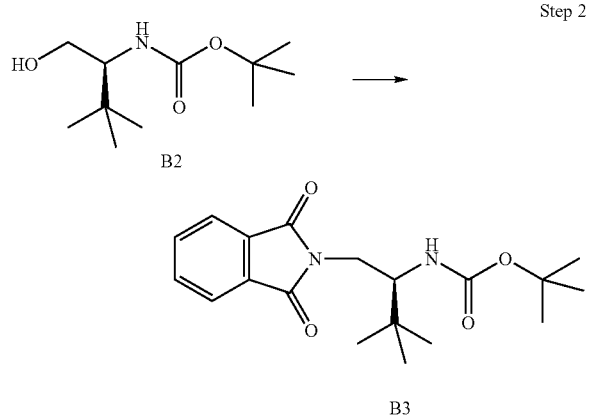

Step 2

B2

B3

To a solution of phthalimide (1.01 g) in 50 mL of dry THF was added triphenylphosphine (3 eq) and alcohol B2 (1 eq). The mixture was cooled in an ice-water bath and diisopropyl azodicarboxylate (2.5 eq) was added dropwise. The resulting mixture was stirred at 0° C. for 10 min and warmed to room temp and stirred for approximately 2.5 h until no more starting material was detected by TLC (ethyl acetate/hexanes; 3:7). The mixture was concentrated under reduced pressure. The residue was resuspended in 80 mL of dichloromethane. The solids were filtered off. The filtrate was concentrated to half its volume and hexanes (30 mL) were added. The solids were filtered off. The filtrate was concentrated under reduced pressure and the residue was chromatographed on silica gel (gradient: ethyl acetate/hexanes; 1:9 to 4:6) to give the product B3.

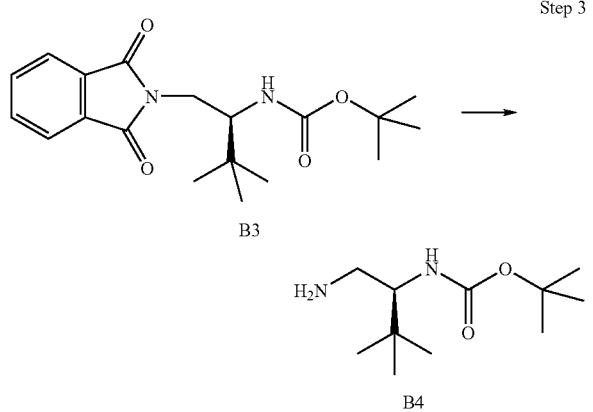

Step 3

B3

B4

To a solution of the phthalimide B3 (7 g) in 100 mL of MeOH was added hydrazine (0.9 mL, 28.68 mmol, 1.4 eq) and the mixture was refluxed (under N2) for 6 h. TLC showed some starting material present and more hydrazine was added (0.45 mL) and stirring was continued at room temperature overnight. A white precipitate was formed. The solids were filtered off and the filtrate was concentrated to yield the product B4 (4.48 g) as a white solid.

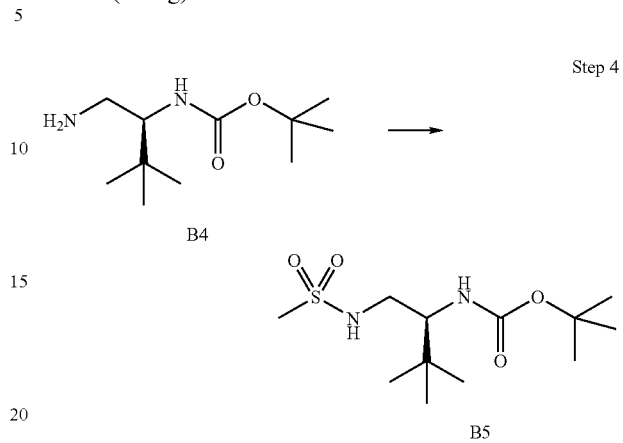

Step 4

B4

B5

A solution of amine B4 (2.16 g, 10 mmol) in 100 mL of dichloromethane was cooled to 0° C. and treated with triethylamine (2 eq, 2.8 mL). Methanesulfonyl chloride (1.2 eq, 0.93 mL) was added dropwise. The heterogeneous mixture was stirred overnight (temp 0 to 25° C.). The solids were filtered off and the filtrate was washed with aqueous saturated ammonium chloride solution (100 mL), and brine (100 mL). The organic layer was dried over sodium sulfate, filtered and concentrated. The residue was taken in minimum amount of dichloromethane/ethyl acetate (approx 10 mL) and the insoluble white solid was filtered off. The filtrate was purified by column chromatography on silica gel to give the product B5 (2.7 g) as a thick semisolid.

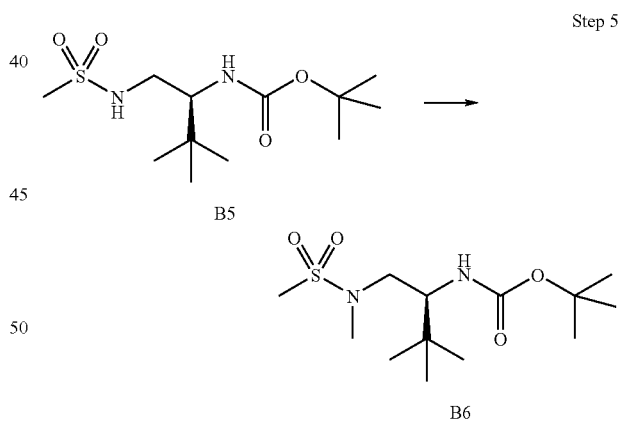

Step 5

B5

B6

A solution of sulfonamide B5 (2.2 g, 7.5 mmol) in 50 mL of dry DMF was cooled to 0° C. and treated with cesium carbonate (3 eq, 7.34 g). Iodomethane (5 eq, 2.34 mL) was added dropwise and the mixture was stirred for 45 min. The cooling bath was removed and the mixture was stirred for further 4 h. The reaction was quenched by addition of aqueous saturated ammonium chloride solution (100 mL) and extracted with ethyl acetate (2×100 mL). The combined organic layers were washed with water (200 mL), brine (200 mL) and dried over sodium sulfate. The organic layer was filtered and concentrated. The residue was chromatographed on silica gel to afford the product B6 (2.16 g).

Step 6

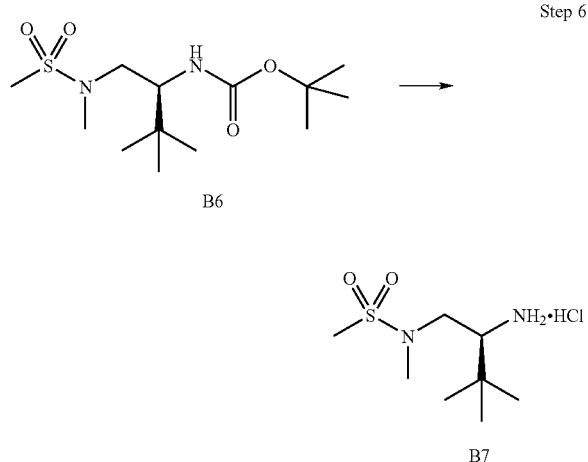

The N-Boc protected amine 2f (2.1 g, 6.82 mmol) was dissolved in 20 mL of 4M HCl in dioxane at room temperature. The reaction mixture was stirred for 1 h and then all the volatiles were removed under reduced pressure to afford the product 2g in quantitative yield.

Step 7

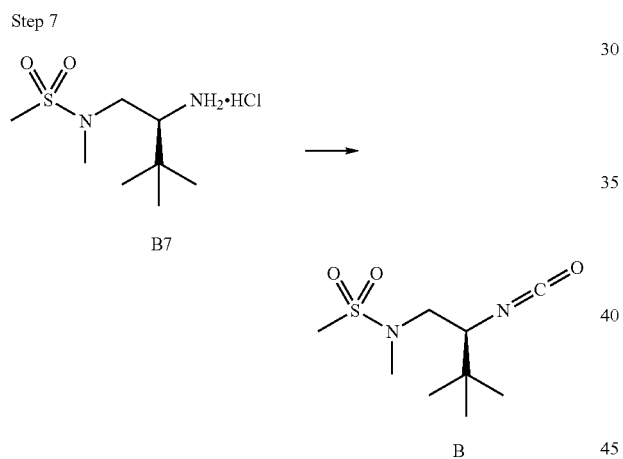

A mixture of amine hydrochloride B7 in dichloromethane and aqueous saturated sodium bicarbonate solution at 0° C. was treated with phosgene (15% solution in toluene) and stirred for 2 h. The reaction mixture was diluted with dichloromethane and washed with cold aqueous saturated sodium bicarbonate solution. The organic layer was dried over magnesium sulfate, filtered, and further diluted with toluene. The mixture was concentrated and the product B was adjusted and kept as a 0.2M solution in toluene.

Intermediate C

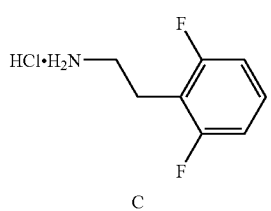

-continued

Step 1

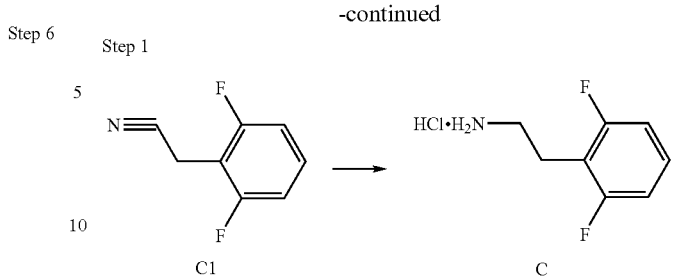

The difluorophenylacetonitrile C1 (Aldrich, 300 mg) was dissolved in 20 mL of methanol and treated with cobalt(II) chloride hexahydrate (2 eq, 950 mg). The resulting solution was cooled to 0° C. and sodium borohydride (10 eq, 756 mg) was added in small portions. The mixture was stirred for about 45 min and carefully treated with aq 1M HCl until the black precipitate dissolved. The mixture was treated with aqueous 2M NaOH until it became basic. The mixture was extracted with dichloromethane (3×50 mL). The combined organic layers were dried over magnesium sulfate, and filtered. The filtrate was treated with 4M HCl in dioxane (4 mL) and concentrated in vacuo to afford the product as a white solid which was used without further purification.

Step 2

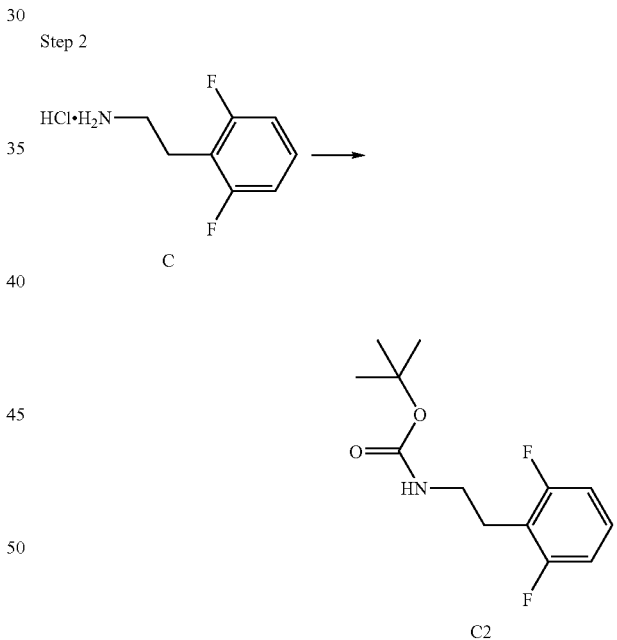

A solution of the amine hydrochloride C (2 mmol) in 20 mL of dry dichloromethane was cooled to 0° C. and treated with N-methylmorpholine (5 eq, 1.1 mL, d 0.920). Di-tert-butyldicarbonate (1.2 eq, 523 mg) in 5 mL of dichloromethane was added dropwise. Reaction mixture was stirred for 1 h. The mixture was diluted with 100 mL of ether and washed with 50 mL of aqueous 1M HCl. The organic layer was dried over magnesium sulfate, filtered and concentrated. The residue was chromatographed on silica gel (gradient: ethyl acetate/hexanes; 0:10 to 1:9) to afford the product C2 (270 mg, 53% for two steps) as a white solid.

Step 3

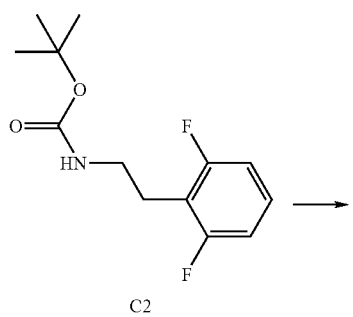

C2

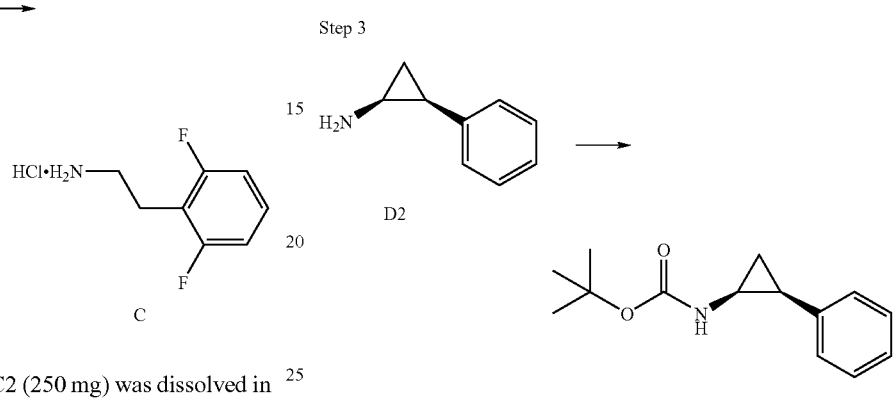

The N-Boc protected amine C2 (250 mg) was dissolved in 10 mL of 4M HCl in dioxane. The resulting solution was stirred for about 2 h and monitored by TLC (acetone/hexanes; 1:9) for disappearance of starting material. After all the starting material had been consumed, the volatiles were removed under vacuum to afford the product C (187 mg, 98%) as a white solid.

Intermediate D

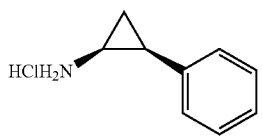

(+/−)-D

Step 1

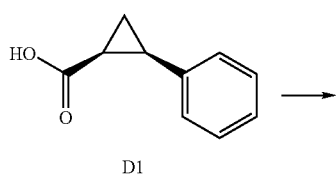

The cyclopropane carboxylic acid D1 (Rare Chemicals, 300 mg) was dissolved in 15 mL of acetonitrile and treated with triethylamine (1 eq, 0.26 mL, d 0.726). Diphenylphosphoryl azide (1 eq, 0.40 mL, d 1.270) was also added and the resulting mixture was heated at 50° C. for 2 h. After cooling to room temperature, aqueous 1N HCl (15 mL) was added and the reaction mixture was refluxed overnight. The acetonitrile was evaporated under reduced pressure and the pH of the aqueous layer was brought to 14 with aqueous 1N NaOH. The aqueous layer was extracted with dichloromethane (3×50 mL). The combined organic layers were dried over magnesium sulfate, filtered and concentrated under reduced pressure. The product D2 was used without further purification.

Step 3

A solution of the amine D2 (1.85 mmol) in 20 mL of dry dichloromethane was cooled to 0° C. and treated with N-methylmorpholine (5 eq, 1.0 mL, d 0.920). Di-tert-butylcarbonate (1.2 eq, 483 mg) in 10 mL of dichloromethane was added dropwise. Reaction mixture was stirred for 1 h. The mixture was diluted with 100 mL of ether and washed with 50 mL of aqueous 1M HCl. The organic layer was dried over magnesium sulfate, filtered and concentrated. The residue was chromatographed on silica gel (gradient: acetone/hexanes; 0:10 to 2:8) to afford the product D3 (250 mg, 58% for two steps) as a white solid.

Step 3

The N-Boc protected amine D3 (220 mg) was dissolved in 10 mL of 4M HCl solution in dioxane. The mixture was stirred for 1.5 h at room temperature. All the volatiles were removed under reduced pressure to give the product (±)-D (160 mg, 98%) as a white solid.

PREPARATIVE EXAMPLES

Example 1

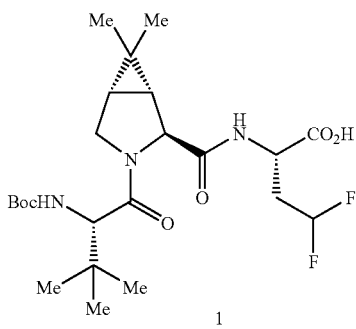

1

Step 1:

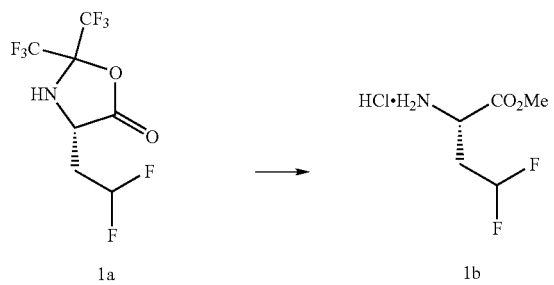

To a stirred solution of 1a (4.7 g, 16.4 mmol) in methanol (80 mL) at room temperature was added concentrated hydrochloric acid (4 mL, 48 mmol). The resulting solution was brought to reflux and stirred overnight. The solution was concentrated in vacuo to give the desired product 1b (4.6 g, quant.), which was used without further purification.

Step 2:

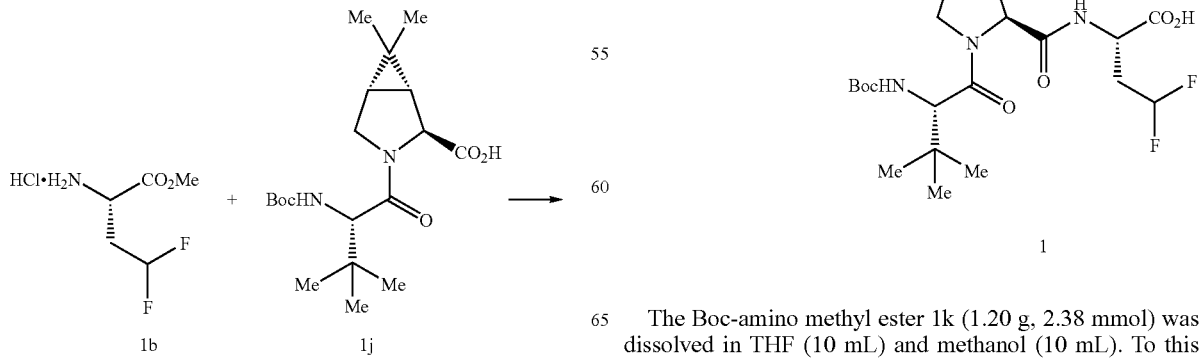

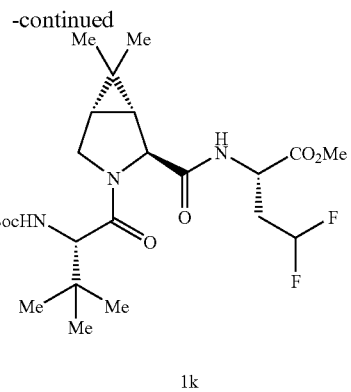

1k

To a solution of the amine 1b (0.809 g, 4.27 mmol), dipeptide acid 1j (1.39 g, 3.77 mmol), HOOBt (0.67 g, 4.11 mmol) and EDCI (0.87 g, 4.54 mmol) in DMF (50 mL) and $CH_2Cl_2$ (50 mL) at −20° C., was added NMM (1.70 mL, 15.5 mmol). After being stirred at this temperature for 30 min, the reaction mixture was kept in a freezer overnight (18 h). It was then stirred in air and allowed to warm to room temperature in 1 h. EtOAc (200 mL), brine (50 mL) and 5% $H_3PO_4$ (50 mL) were added. The layers were separated and the organic solution was washed with 5% $H_3PO_4$ (150 mL), saturated aqueous sodium bicarbonate solution (2×150 mL) and water (150 mL). It was then dried with magnesium sulfate, filtered and concentrated in vacuo. Flash chromatography with 10-20% EtOAc/$CH_2Cl_2$ afforded 1.20 g (63%) as a white solid.

Step 3:

The Boc-amino methyl ester 1k (1.20 g, 2.38 mmol) was dissolved in THF (10 mL) and methanol (10 mL). To this solution was added a solution of lithium hydroxide (0.143 g, 5.96 mmol) in water (10 mL). The resulting solution was stirred at room temperature two and half hours. The progress of the reaction was monitored by TLC. The solution was then concentrated in vacuo and to the residue was added EtOAc (200 mL) and water (100 mL). The aqueous layer was saturated with sodium chloride. After the layers were separated, the aqueous layer was extracted with EtOAc (2×100 mL). The combined organic solution was dried (MgSO$_4$), filtered and concentrated in vacuo to give a white solid which was used without further purification.

Example 2

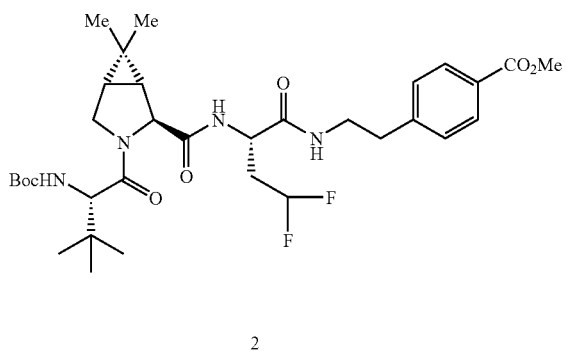

2

Step 1:

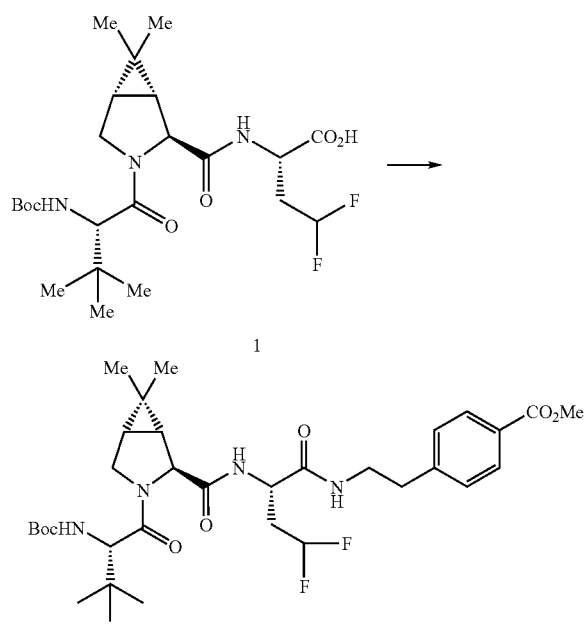

To a solution of (p-methoxycarbonyl)phenyl ethyl amine (0.265 g, 1.23 mmol), acid 1 (0.403 g, 0.82 mmol), HOOBt (0.201 g, 1.23 mmol) and EDCI (0.220 g, 1.15 mmol) in DMF (20 mL) and CH$_2$Cl$_2$ (20 mL) at −20° C., was added NMM (0.23 mL, 2.9 mmol). After being stirred at this temperature for 30 min, the reaction mixture was kept in a freezer overnight (18 h). It was then stirred in air and allowed to warm to room temperature in 1 h. EtOAc (100 mL), brine (30 mL) and 5% H$_3$PO$_4$ (30 mL) were added. The layers were separated and the organic solution was washed with 5% H$_3$PO$_4$ (80 mL), saturated aqueous sodium bicarbonate solution (2×80 mL) and water (80 mL). It was then dried with magnesium sulfate, filtered and concentrated in vacuo. Flash chromatography with 5-20% acetone/hexanes afforded 0.33 g (62%) as a white solid.

Example 3

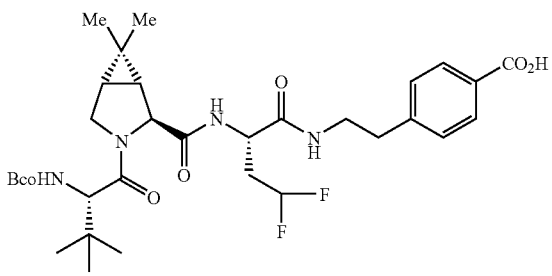

3

Step 1

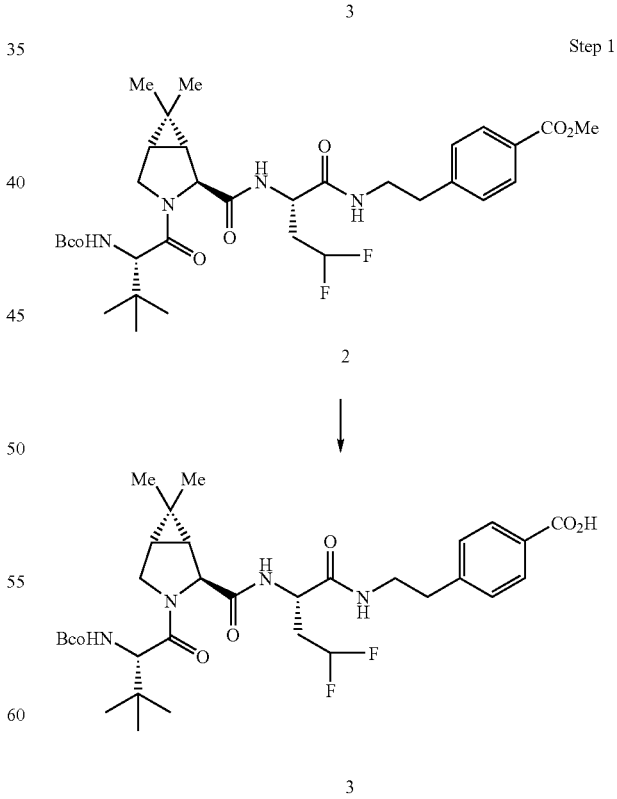

Compound 3 was prepared from compound 2 according to procedures described in Example 1, Step 3.

Example 4
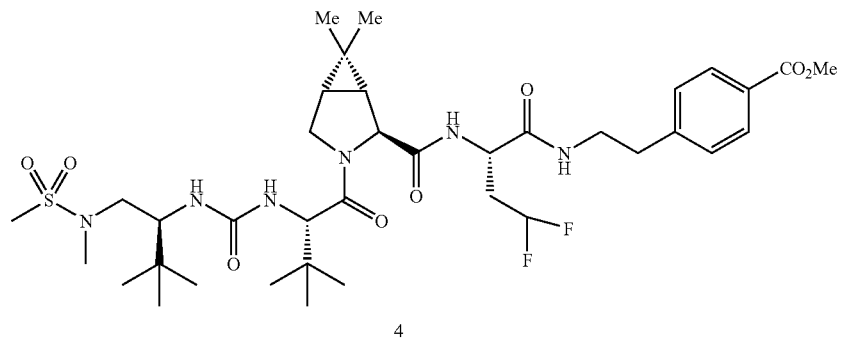
4
Step 1:
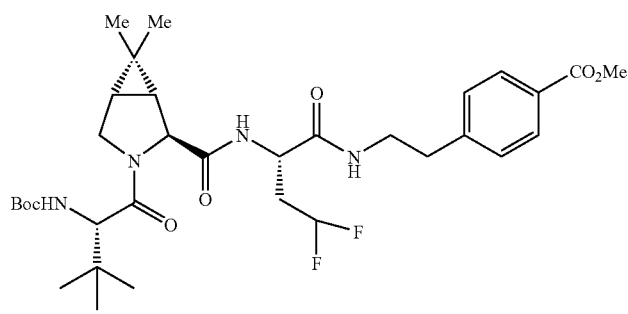
2
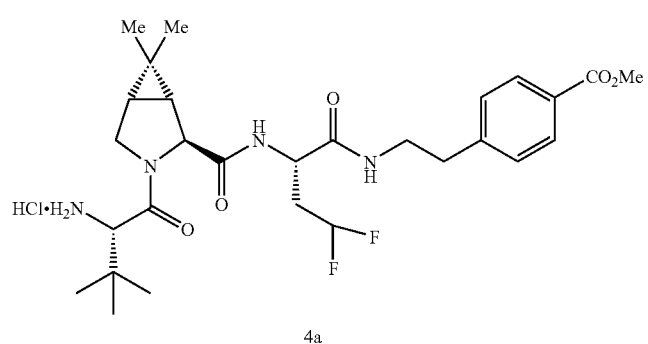
4a
A solution of compound 2 (0.314 g, 0.48 mmol) in 4 N HCl in dioxane was stirred at room temperature for 4 h before it was concentrated in vacuo and used without further purification.

Step 2:

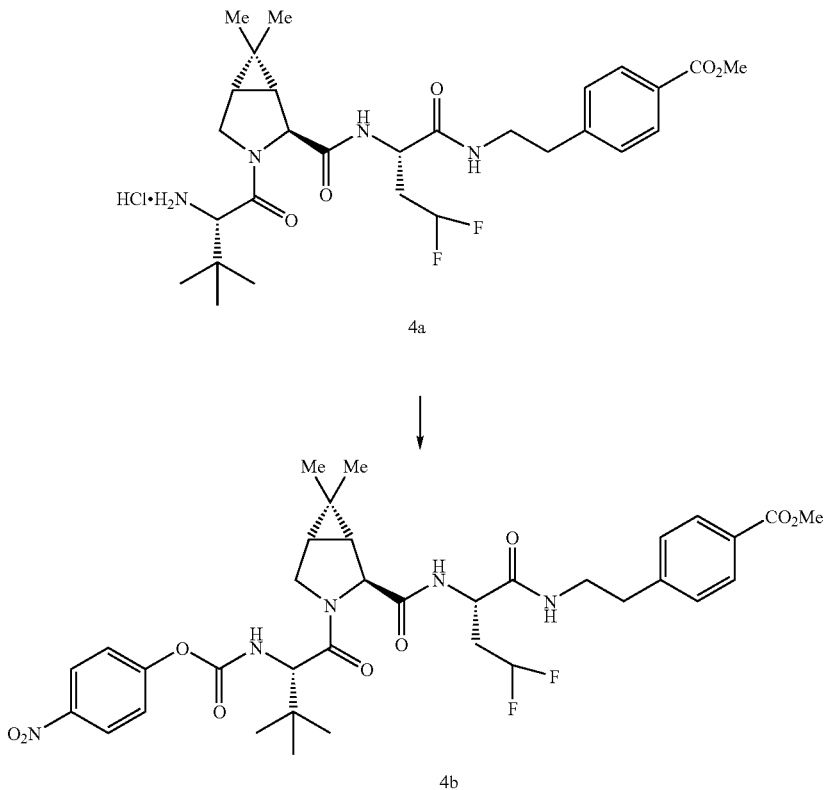

The solution of amine 4a (0.101 g, 0.17 mmol), p-nitrophenyl chloroformate (0.042 g, 0.21 mmol) and diisopropylethyl amine (0.060 mL, 0.34 mmol) in THF/CH$_3$CN (7:1) was stirred at room temperature for 18 h. After it was concentrated, the residue was dissolved in EtOAc (100 mL) and the solution was washed with 5% H$_3$PO$_4$ solution (80 mL), saturated sodium bicarbonate solution (80 mL) and brine (80 mL). It was then dried with magnesium sulfate, filtered and concentrated in vacuo. Flash chromatography with 5-18% acetone/hexanes afforded 0.081 g (67%).

Step 3:

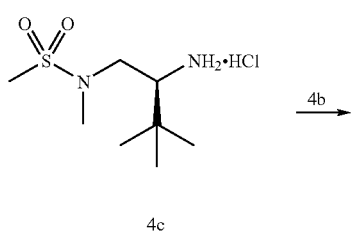

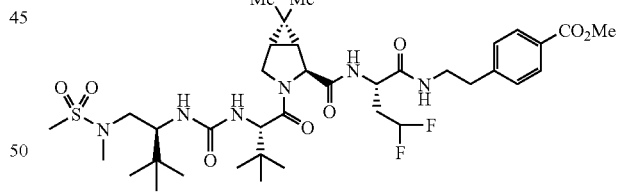

To a solution of the amine 4c (50 mg, 0.24 mmol) and compound 4b (86 mg, 0.12 mmol) in CH$_2$Cl$_2$ (8 mL) at room temperature was added diisopropylethylamine (0.050 mL, 0.30 mmol). The solution was then stirred at room temperature for 18 h. EtOAc (100 mL) was added, and solution was washed with saturated sodium bicarbonate solution (80 mL) and brine (80 mL). The organic solution was then dried with magnesium sulfate, filtered and concentrated in vacuo. Flash chromatography with 15-40% acetone/hexanes afforded 0.038 g (40%) product 4.

Example 5
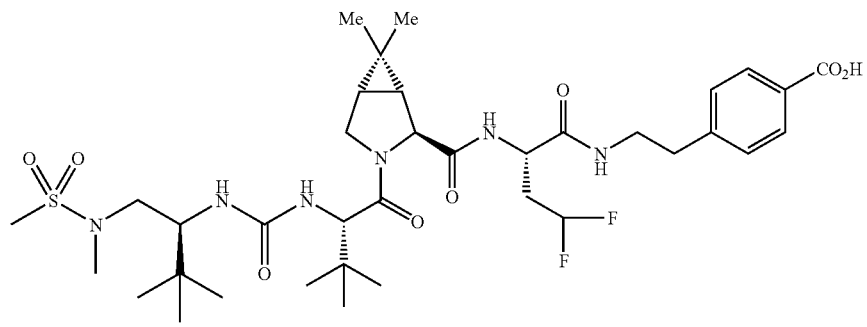
5
Step 1:
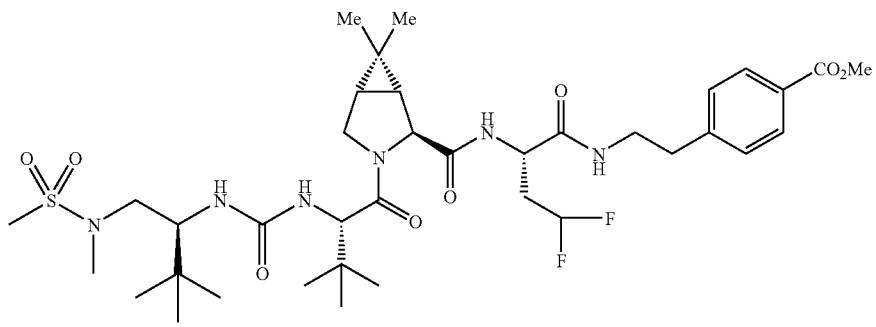
4
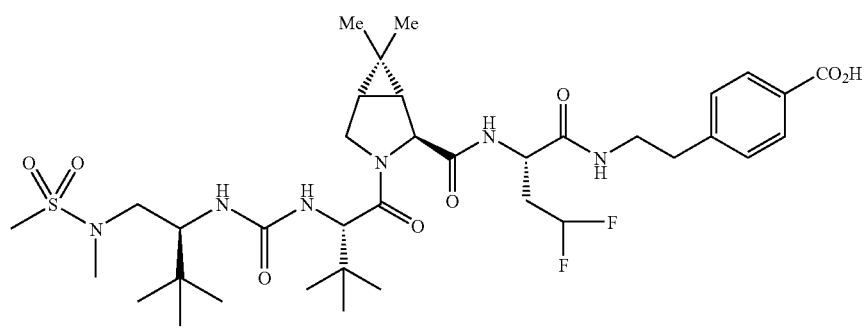
5
Compound 5 was prepared from Compound 4 according to the procedures described in Example 1, Step 3.

Example 6

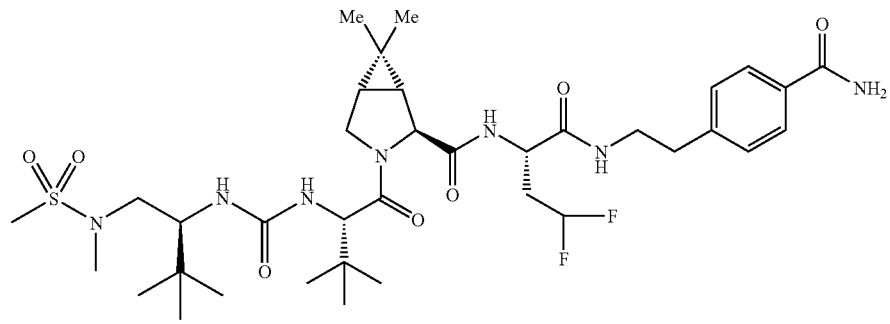

6

Step 1:

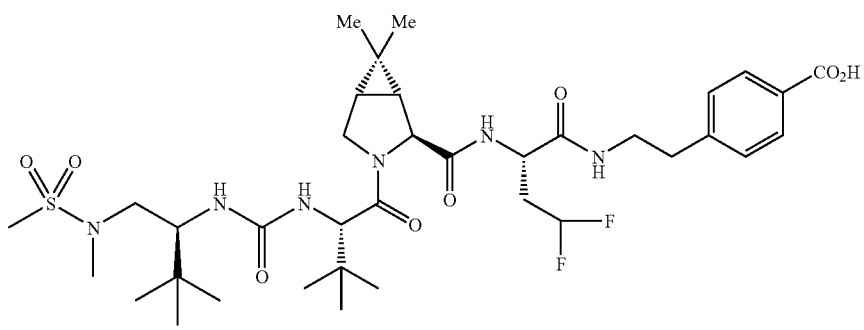

5

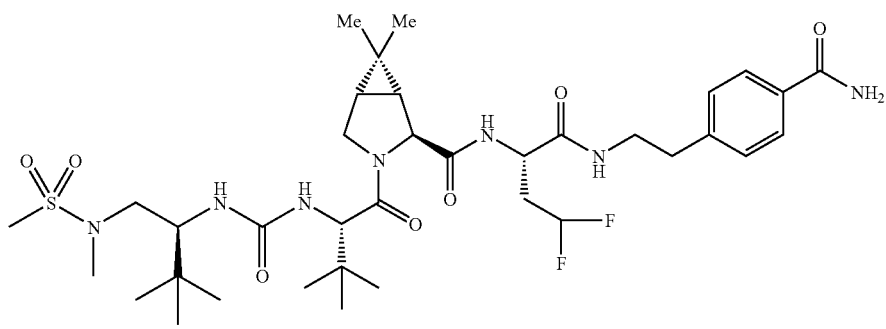

6

To the solution of carboxylic acid 5 (0.018 g, 0.023 mmol) in DMF (5.0 mL) at −20° C. were added ammonium chloride (6.5 mg, 0.12 mmol), HOOBt (7.5 mg, 0.046 mmol), EDCI (9 mg, 0.046 mmol) and NMM (0.01 mL). The yellow suspension was stirred and allowed to warm to room temperature along with dry ice/acetone bath overnight. EtOAc (80 mL), brine (30 mL) and 5% $H_3PO_4$ (30 mL) were added. The layers were separated and the organic solution was washed with 5% $H_3PO_4$ 50 mL), saturated aqueous sodium bicarbonate solution (2×50 mL) and water (50 mL). It was then dried with magnesium sulfate, filtered and concentrated in vacuo. Flash chromatography with 25-45% acetone/hexanes gave two products, the amounts of which are 2.5 mg and 6.8 mg.

Example 7

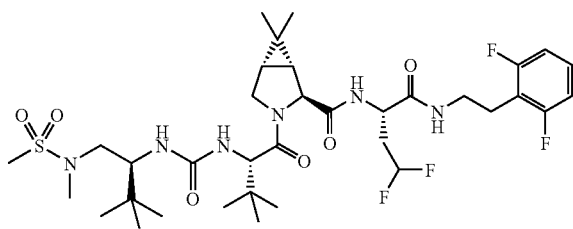

7

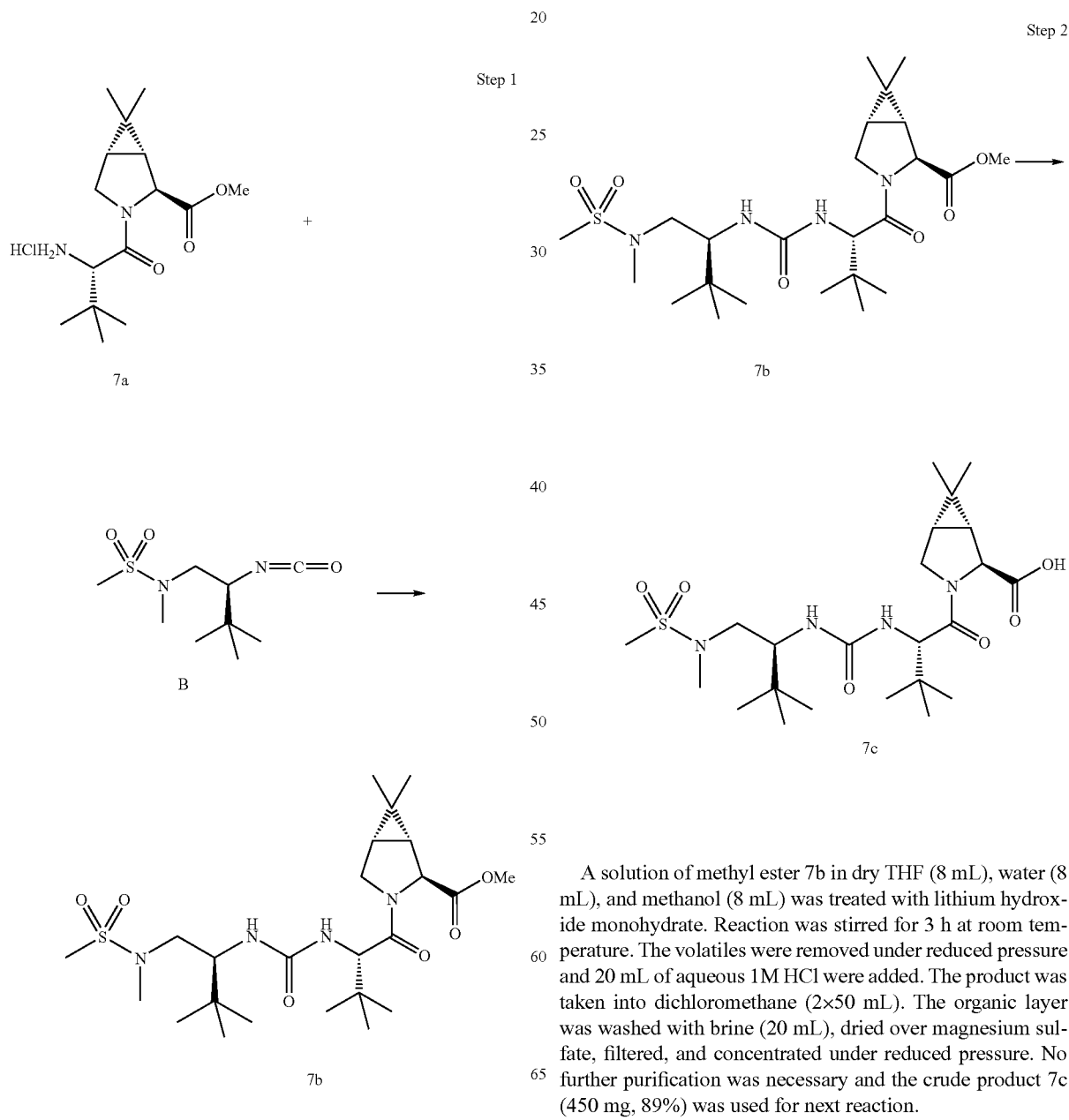

To a solution of the hydrochloric salt 7a in 10 mL of dry dichloromethane was added N-methylmorpholine. The resulting solution was cooled in an ice-water bath and a solution of isocyanate B in toluene was slowly added. The mixture was stirred overnight (temp 0 to 25° C.). The reaction mixture was diluted with 50 mL of dichloromethane and washed with 30 mL of aqueous 1N HCl. Aqueous layer was back extracted with dichloromethane (2×20 mL). The combined organic layers were dried over magnesium sulfate, filtered and concentrated under reduced pressure. TLC (EtOAc/Hexanes; 1:1), MS, and NMR analysis showed data corresponding to the desired product 7b (520 mg, 91%). No further purification was done and crude product was used for next reaction.

A solution of methyl ester 7b in dry THF (8 mL), water (8 mL), and methanol (8 mL) was treated with lithium hydroxide monohydrate. Reaction was stirred for 3 h at room temperature. The volatiles were removed under reduced pressure and 20 mL of aqueous 1M HCl were added. The product was taken into dichloromethane (2×50 mL). The organic layer was washed with brine (20 mL), dried over magnesium sulfate, filtered, and concentrated under reduced pressure. No further purification was necessary and the crude product 7c (450 mg, 89%) was used for next reaction.

Step 3

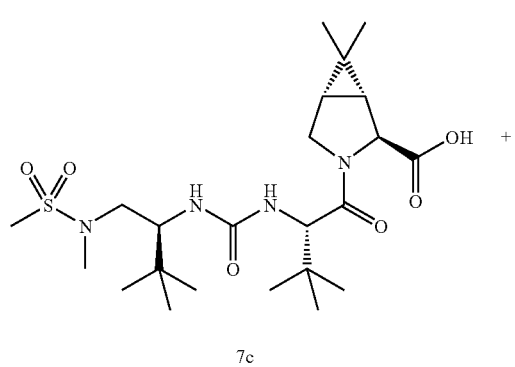

7c

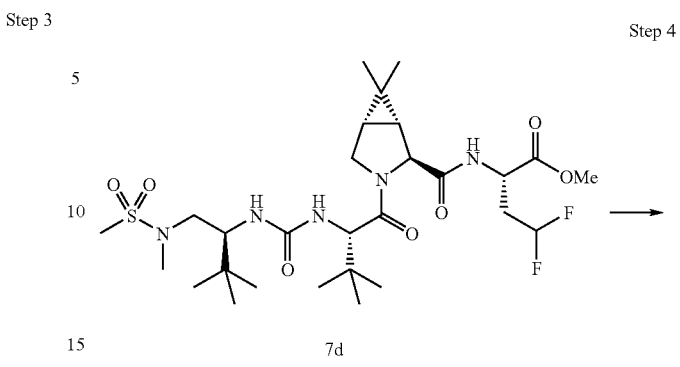

7d

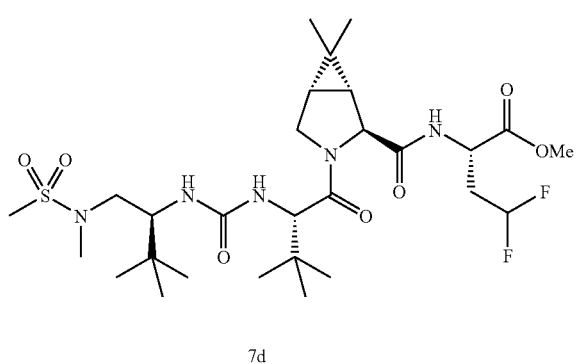

7d

A solution of acid 7c (440 mg) in 15 mL of dry dichloromethane and 15 mL of dry DMF was stirred at 0° C. and treated with HATU (1.4 eq, 380 mg). The amine salt 1b (1.4 eq, 232 mg) was added in 5 mL of dichloromethane followed by addition of N-methylmorpholine (4 eq, 0.38 mL, d 0.920). The reaction mixture was stirred at 0° C. overnight. All the volatiles were removed under vacuum and the residue was dissolved in 300 mL of ethyl acetate. The organic layer was washed with water (2×80 mL), aqueous 1M HCl (80 mL), aqueous saturated sodium bicarbonate solution (80 mL), and brine (50 mL). The organic layer was dried over magnesium sulfate, filtered and concentrated under reduced pressure. The residue was chromatographed on silica gel (gradient: acetone/hexanes; 2:8 to 6:4) to afford the product 7d (410 mg, 73%).

Step 4

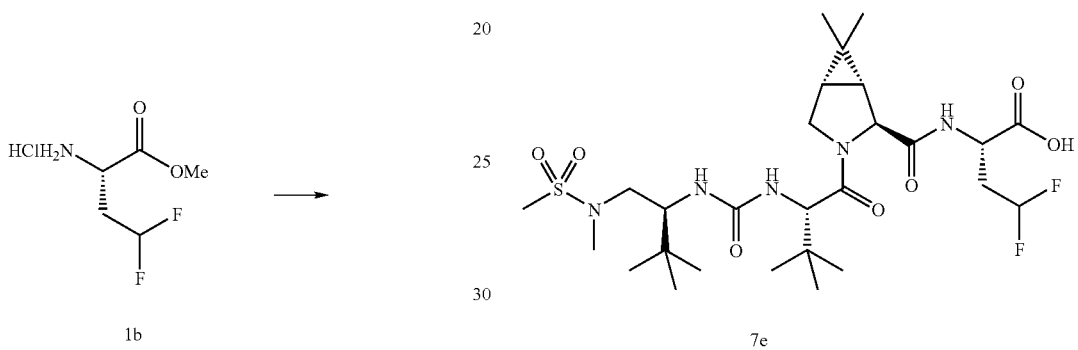

7e

A solution of methyl ester 7d (400 mg) in dry THF (5 mL), water (5 mL), and methanol (5 mL) was treated with lithium hydroxide monohydrate (2.5 eq, 65.7 mg). Reaction was stirred for approximately 3 h at room temperature. The volatiles were removed under reduced pressure and 20 mL of aqueous 1M HCl were added. The product was taken into dichloromethane (2×80 mL). The organic layer was washed with brine (20 mL), dried over magnesium sulfate, filtered, and concentrated under reduced pressure to afford the product 7e (370 mg, 95%).

Step 5

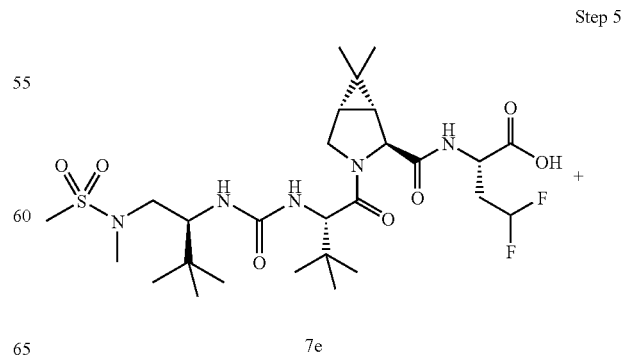

7e

-continued

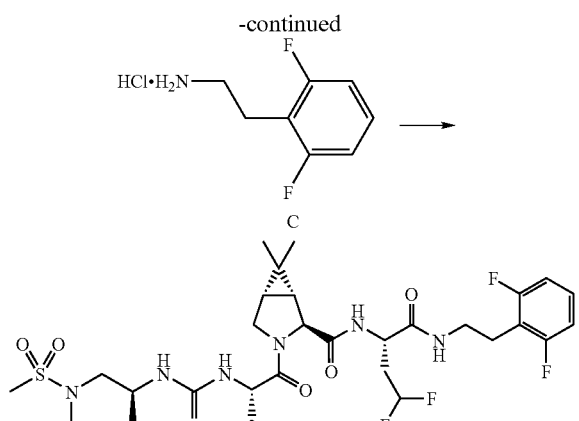

7

A solution of acid 7e (40 mg) in 1 mL of dry dichloromethane and 1 mL of dry DMF was stirred at 0° C. and treated with HATU (1.4 eq, 34 mg). The amine hydrochloride C (1.3 eq, 15.8 mg) was added followed by N-methylmorpholine (4 eq, 0.028 mL, d 0.920). The reaction mixture was stirred at 0° C. overnight. All the volatiles were removed under vacuum and the residue was dissolved in 50 mL of ethyl acetate. The organic layer was washed with water (10 mL), aqueous 1N HCl (10 mL), aqueous saturated sodium bicarbonate solution (10 mL), and brine (10 mL). The organic layer was dried over magnesium sulfate, filtered and concentrated under reduced pressure. The residue was chromatographed on silica gel (gradient: acetone/hexanes; 2:8 to 5:5) to afford the product 7 (40 mg, 82%) as a white solid. HRMS (FAB) calcd for $C_{35}H_{55}F_4N_6O_6S$ [M+H] 763.3840; found 763.3863.

Examples 8 and 9

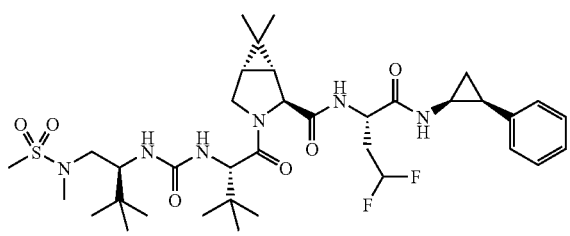

8

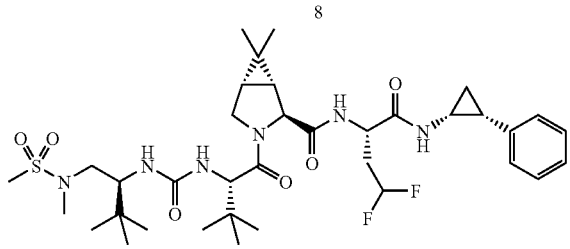

9

-continued

Step 1

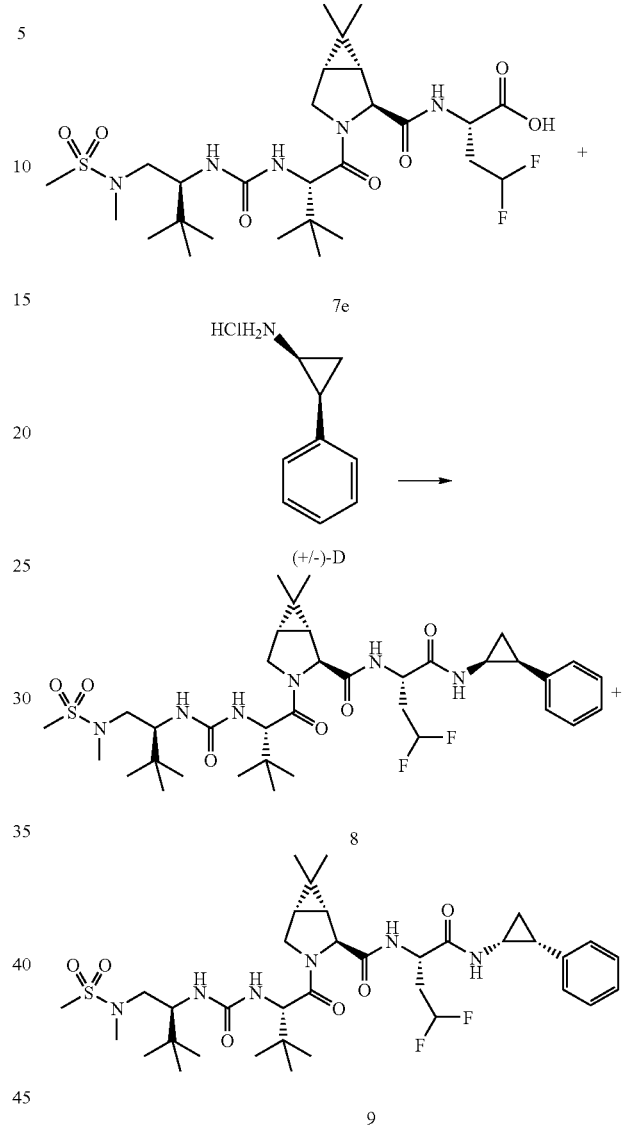

A solution of acid 7e (40 mg) in 1 mL of dry dichloromethane and 1 mL of dry DMF was stirred at 0° C. and treated with HATU (1.4 eq, 17 mg). The amine hydrochloride (±)-D (14 mg) was added in 10 mL of 5 dichloromethane followed by N-methylmorpholine (4 eq, 0.014 mL, d 0.920). The reaction mixture was kept in the freezer (−20° C.) for 48 h. All the volatiles were removed under vacuum and the residue was dissolved in 50 mL of ethyl acetate. The organic layer was washed with water (10 mL), aqueous 1N HCl (10 mL), aqueous saturated sodium bicarbonate solution (10 mL), and brine (10 mL). The organic layer was dried over magnesium sulfate, filtered and concentrated under reduced pressure. The residue was chromatographed on silica gel (gradient: acetone/hexanes; 2:8 to 6:4) to afford the diastereomeric products 8 (20 mg) and 9 (20 mg) as a white solids in 80% combined yield. HRMS (FAB) for 8 calcd for $C_{36}H_{57}F_2N_6O_6S$ [M+H] 739.4028; found 739.4023; HRMS (FAB) for 9 calcd for $C_{36}H_{57}F_2N_6O_6S$ [M+H] 739.4028; found 739.4045.

General Synthetic Procedures Using Parallel Synthesis Method to Prepare Examples of Structure Type 10:

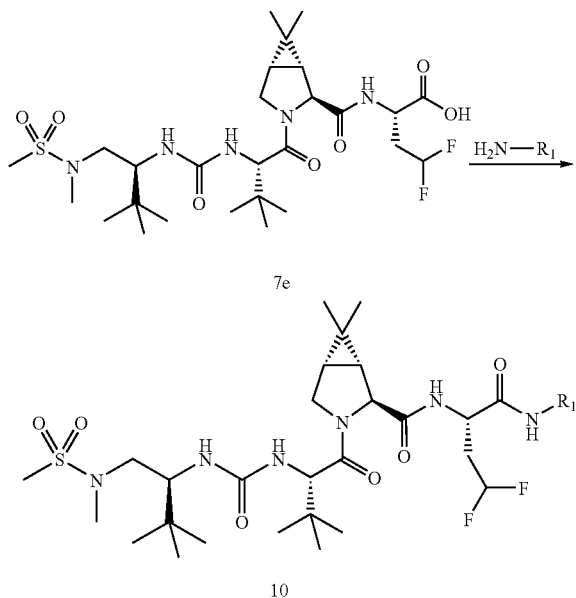

The acid 7e (288 mg) and HOBT (1.5 eq, 96 mg) were dissolved in 50 mL of a 1:1 mixture of acetonitrile/DMF. 48 Wells of an Ex-Block plate were charged with PS-EDC resin (3.0 eq, 19 mg/well). Then, 1 mL of the acid/HOBT solution was added to each well. The amines H$_2$N—R$_1$ were added to their corresponding well (40 µL of a 0.5M solution of amine in dioxane). The Ex-Blok was sealed and shaken overnight. 48 Wells of a second Ex-Block were charged with PS-NCO (6 eq, 40 mg/well) and PS-trisamine (.12 eq, 38 mg/well). The first block was broken into the second block containing the PS-NCO and PS-trisamine resins. The wells of the first block were washed with 500 µL of acetonitrile. The second Ex-Block was sealed and shaken for 6 h and then broken into a collection plate. The wells in the second block were washed with 500 µL of acetonitrile. Aliquots of 100 µL were taken from each well and transferred to an HPLC-plate for LC-MS analysis. The remaining solutions in each well of the collection plate were transferred into bar coded vials. These vials containing the amide products were placed in a speed-vacuum centrifuge and solvent was removed to afford the corresponding products of structure type 10.

Biological Examples

The present invention relates to novel hepatitis C virus ("HCV") protease inhibitors. This utility is manifested in their ability to inhibit the HCV NS3/NS4a serine protease as demonstrated by the following in vitro assays.

Assay for HCV Protease Inhibitory Activity:

Spectrophotometric Assay: Spectrophotometric assays for the HCV serine protease were performed on the inventive compounds by following the procedure described by R. Zhang et al., *Analytical Biochemistry*, 270 (1999) 268-275, the disclosure of which is incorporated herein by reference. The assay based on the proteolysis of chromogenic ester substrates is suitable for the continuous monitoring of HCV NS3 protease activity.

Materials and Methods:

Materials: Chemical reagents for assay related buffers were obtained from Fisher Scientific Company LLC, 3970 Johns Creek Court, Suwanee, GA 30024; Anatrace, Inc. 434 West Dussel Drive, Maumee, Ohio 43537; Sigma Chemical Company (St. Louis, Mo.). Custom peptide synthesis prepared by SynPep Corporation, Dublin, Calif. 94568. 96-well UV plates were obtained from Corning (Corning, N.Y.). The prewarming block was from USA Scientific (Ocala, Fla.) and the 96-well plate vortexer was from Labline Instruments (Melrose Park, Ill.). A Spectramax Plus microtiter plate reader with monochrometer was obtained from Molecular Devices (Sunnyvale, Calif.).

Enzyme Preparation:

HCV NS3 protease (strain 1b) and its NS4A cofactor were constructed as a recombinant single chain protein. The NS4A cofactor domain (amino acid residues 21-32) was fused in frame to the amino terminus of the NS3 protease domain (amino acids 3-181) with a tetrapeptide linker. This NS4A$_{21-32}$-GSGS-NS3$_{3-181}$ construct was then expressed in *E. coli* and purified to >90% homogeneity. Kinetic parameters were determined and found to be the same as that of the full length NS3$_{1-631}$/NS4A$_{1-54}$ protein complex produced in the baculovirus system (D. L. Sali et al, *Biochemistry*, 37 (1998) 3392-340). The details of the cloning, expression, purification and kinetic analysis of the of the single chain recombinant protease have been previously described (S. S. Taremi, et al. Protein Science. 7 (1998) 2143-2149.

Protein concentrations were determined by the Biorad dye method using recombinant HCV protease standards previously quantified by amino acid analysis. Prior to assay initiation, the enzyme storage buffer (50 mM sodium phosphate pH 8.0, 300 mM NaCl, 10% glycerol, 0.05% lauryl maltoside and 10 mM DTT) was exchanged for the assay buffer (25 mM MOPS pH 6.5, 300 mM NaCl, 10% glycerol, 0.05% lauryl maltoside, 5 µM EDTA and 5 µM DTT) utilizing a Biorad Bio-Spin P-6 prepacked column.

Substrate Synthesis and Purification: The synthesis of the substrates was done as reported by R. Zhang et al., (ibid.) and was initiated by anchoring Fmoc-Nva-OH to 2-chlorotrityl chloride resin using a standard protocol (K. Barlos et al., *Int. J. Pept. Protein Res.*, 37 (1991), 513-520). The peptides were subsequently assembled, using Fmoc chemistry, either manually or on an automatic ABI model 431 peptide synthesizer. The N-acetylated and fully protected peptide fragments were cleaved from the resin either by 10% acetic acid (HOAc) and 10% trifluoroethanol (TFE) in dichloromethane (DCM) for 30 min, or by 2% trifluoroacetic acid (TFA) in DCM for 10 min. The combined filtrate and DCM wash was evaporated azeotropically (or repeatedly extracted by aqueous Na$_2$CO$_3$ solution) to remove the acid used in cleavage. The DCM phase was dried over Na$_2$SO$_4$ and evaporated.

The ester substrates were assembled using standard acid-alcohol coupling procedures (K. Holmber et al., *Acta Chem. Scand.*, B33 (1979) 410-412). Peptide fragments were dissolved in anhydrous pyridine (30-60 mg/ml) to which 10 molar equivalents of chromophore and a catalytic amount (0.1 eq.) of para-toluenesulfonic acid (PTSA) were added. Dicyclohexylcarbodiimide (DCC, 3 eq.) was added to initiate the coupling reactions. Product formation was monitored by HPLC and found to be complete following 12-72 hour reaction at room temperature. Pyridine solvent was evaporated under vacuum and further removed by azeotropic evaporation with toluene. The peptide ester was deprotected with 95% TFA in DCM for two hours and extracted three times with anhydrous ethyl ether to remove excess chromophore. The deprotected substrate was purified by reversed phase HPLC on a C3 or C8 column with a 30% to 60% acetonitrile gradient (using six column volumes). The overall yield following HPLC purification was approximately 20-30%. The molecular mass was confirmed by electrospray ionization mass spectroscopy. The substrates were stored in dry powder form under desiccation.

Protease Assay: HCV protease assays were performed at 30° C. using a 200 µl reaction mix in a 96-well microtiter plate. Assay buffer conditions (25 mM MOPS pH 6.5, 300 mM NaCl, 10% glycerol, 0.05% lauryl maltoside, 5 µM EDTA and 5 µM DTT) were optimized for the NS3/NS4A heterodimer (D. L. Sali et al, ibid.)). Typically, 100 µl mixtures of buffer, substrate and inhibitor were placed in wells and allowed to preincubate at 30° C. for approximately 3 minutes. One hundred µls of pre-warmed protease (30° C.) in assay buffer, was then used to initiate the reaction to produce a final concentration of 1.3 nM HCV). The Substrate cleavage by the protease was monitored over 60 minutes by measuring the release of the phenylazophenol (PAP) product at an absorbance of 370 nm with a continuous read every 30 seconds using a SpectraMax Plus microtiter plate reader (Molecular Devices, Sunnyvale, Calif.). Background hydrolysis of the substrate was subtracted. Inhibitors were tested over a range of concentrations (final DMSO concentration 4%)

Evaluation of Inhibitors The inhibition constants ($K_i$) for the competitive inhibitors were determined experimentally at fixed concentrations of enzyme and substrate by plotting $v_o/v_i$ vs. inhibitor concentration ($[I]_o$) according to the rearranged Michaelis-Menten equation for competitive inhibition kinetics: $v_o/v_i = 1 + [I]_o/(K_i(1+[S]_o/K_m))$, where $v_o$ is the uninhibited initial velocity, $v_i$ is the initial velocity in the presence of inhibitor at any given inhibitor concentration ($[I]_o$) and $[S]_o$ is the substrate concentration used. The resulting data were fitted using linear regression and the resulting slope, $1/(K_i(1+[S]_o/K_m))$, was used to calculate the $K_i$ value.

The obtained $K_i$ values for the various compounds of the present invention are given in the afore-mentioned Tables 1, 2 and 3 wherein the compounds have been arranged in the order of ranges of $K_i$ values. From these test results, it would be apparent to the skilled artisan that the compounds of the invention have excellent utility as NS3-serine protease inhibitors.

What is claimed is:

1. A compound, having the general structure shown in Formula 1:

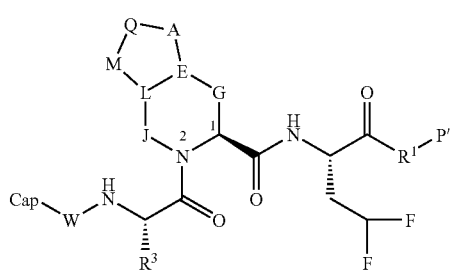

Formula 1 or pharmaceutically acceptable salts of said compounds, wherein:

Cap and P' are independently H, alkyl, alkykaryl, heteroalkyl, heteroaryl, aryl-heteroaryl, alkyl-heteroaryl, cycloalkyl, alkyloxy, alkyl-aryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arlylalkyloxy or heterocyclylamino, wherein each of said alkyl, alkyl-aryl, heteroalkyl, heteroaryl, aryl-heteroaryl, alkyl-heteroaryl, cycloalkyl, alkyloxy, alkyl-aryloxy, aryloxy, heteroaryloxy, heterocyclyloxy, cycloalkyloxy, amino, alkylamino, arylamino, alkyl-arylamino, arylamino, heteroarylamino, cycloalkylamino, carboxyalkylamino, arlylalkyloxy or heterocyclylamino can be unsubstituted or optionally independently substituted with one or two substituents which can be the same or different and are independently selected from $X^1$ and $X^2$;

$X^1$ is alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl, or heteroarylalkyl, and $X^1$ can be unsubstituted or optionally independently substituted with one or more of $X^2$ moieties which can be the same or different and are independently selected;

$X^2$ is hydroxy, alkyl, aryl, alkoxy, aryloxy, thio, alkylthio, arylthio, amino, alkylamino, arylamino, alkylsulfonyl, arylsulfonyl, alkylsulfonamido, arylsulfonamido, carboxy, carbalkoxy, carboxamido, alkoxycarbonylamino, alkoxycarbonyloxy, alkylureido, arylureido, halogen, cyano, keto, ester or nitro, wherein each of said alkyl, alkoxy, and aryl can be unsubstituted or optionally independently substituted with one or more moieties which can be the same or different and are independently selected from alkyl, alkenyl, alkynyl, cycloalkyl, cycloalkyl-alkyl, heterocyclyl, heterocyclylalkyl, aryl, alkylaryl, arylalkyl, arylheteroaryl, heteroaryl, heterocyclylamino, alkylheteroaryl and heteroarylalkyl;

W may be present or absent, and when W is present W is C(=O), C(=S), C(=NH), C(=N—OH), C(=N—CN), S(O) or S(O₂);

Q maybe present or absent, and when Q is present, Q is $(CH_2)_p$, $(CHR)_p$, $(CRR')_p$, $(CHR—CHR')_p$, when Q is absent, M is (i) either directly linked to A when both Q and M are absent, A is directly linked to L;

A is present or absent and if present A is $CH_2$—, $—(CHR)_p$—, $—(CHR—CHR')_p$—, $(CRR')_p$, and when Q is absent, A is —CH(R)(R'); and when A is absent,-Q and E are connected by a bond;

E is present or absent and if present E is CH, C(R);

G may be present or absent, and when G is present, G is $(CH_2)_p$, $(CHR)_p$, or $(CRR')_p$; when G is absent, J is present and E is directly connected to the carbon atom marked position 1;

J may be present or absent, and when J is present, J is $(CH_2)_p$, $(CHR—CHR')_p$, $(CHR)_p$, or $(CRR')_p$; when J is absent and G is present, L is directly linked to the nitrogen atom marked position 2;

L may be present or absent, and when L is present, L is CH, or CR; when L is absent, M is present or absent; if M is present with L being absent, then M is directly and independently linked to E, and J is directly and independently linked to E;

M may be present or absent, and when M is present, M is $(CH_2)_p$, $(CHR)_p$, $(CHR—CHR')_p$, or $(CRR')_p$;

p is a number from 0 to 6;

R, R' and $R^3$ can be the same or different, each being independently selected from the group consisting of: H, $C_1$-$C_{10}$ alkyl, $C_2$-$C_{10}$ alkenyl, $C_3$-$C_8$ cycloalkyl, $C_3$-$C_8$ heterocyclyl, alkoxy, aryloxy, alkyithio, arylthio, amino, amido, arylthioamino, arylcarbonylamino, arylaminocarboxy, alkylaminocarboxy, heteroalkyl, heteroalkenyl, alkenyl, alkynyl, aryl-alkyl, heteroarylalkyl, ester, carboxylic acid, carbamate, urea, ketone, aldehyde, cyano, nitro, halogen, (cycloalkyl)alkyl, aryl, heteroaryl, alkyl-aryl, alkylheteroaryl, alky-heteroaryl and (heterocyclyl)alkyl;

R and R' in (CRR') can be linked together such that the combination forms a cycloalkyl or heterocyclyl moiety; and R¹ is N(R) or O.

2. The compound according to claim 1, wherein W is C=O and

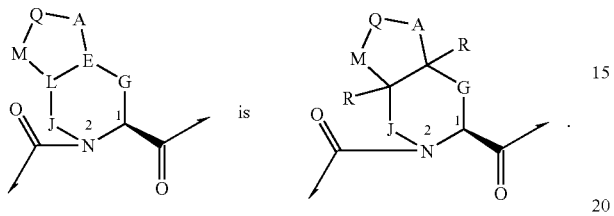

is

3. The compound according to claim 2, wherein

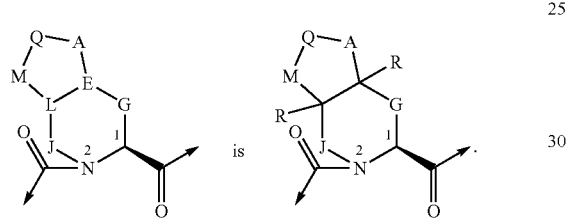

is selected from the group consisting of the following structures:

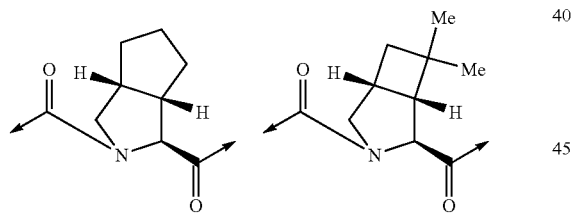

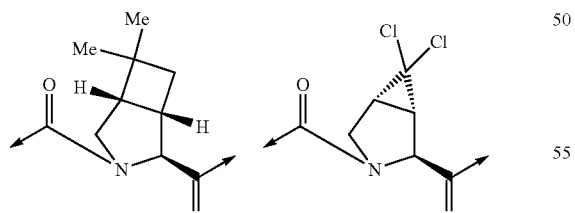

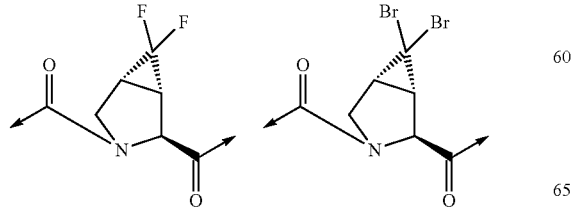

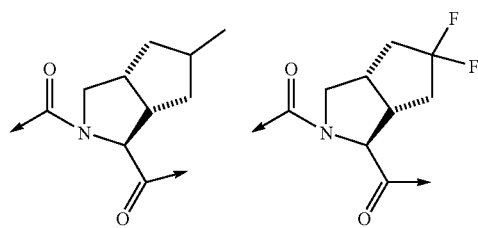

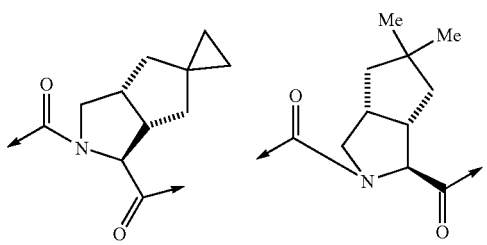

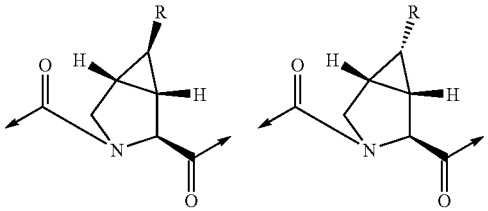

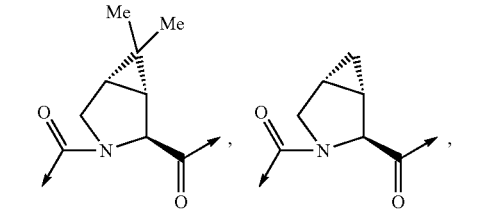

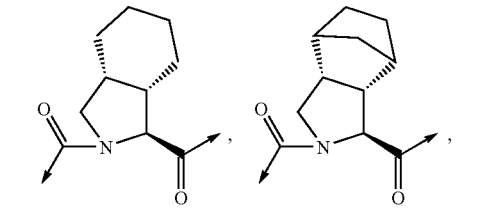

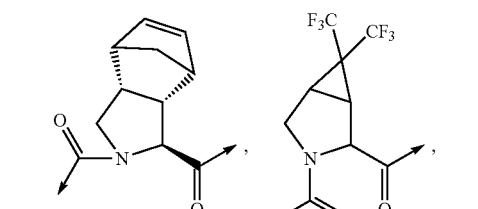

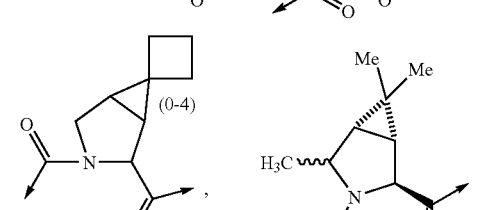

-continued
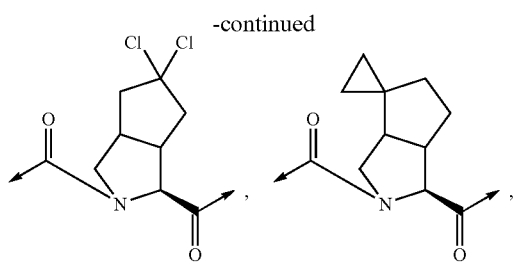
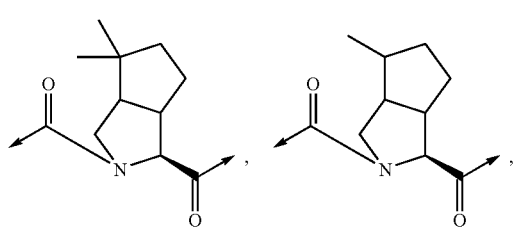
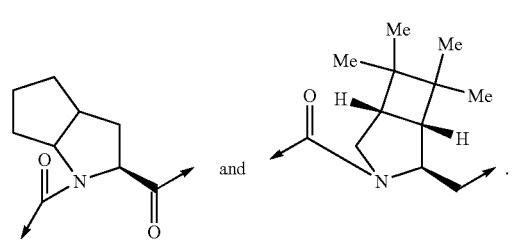
4. The compound according to claim 3, wherein the portion represented by
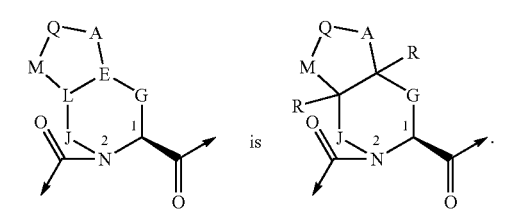
is selected from the group consisting of the following structures:
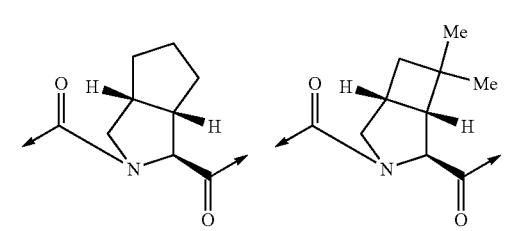
-continued
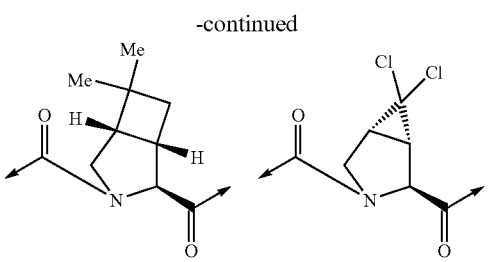
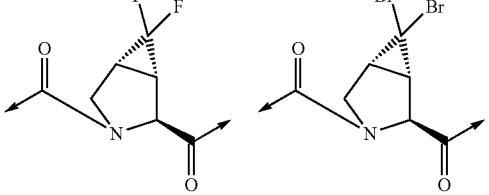
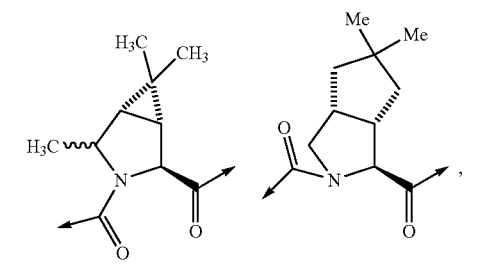
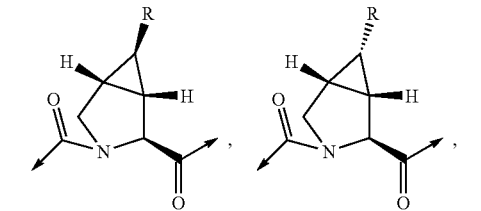
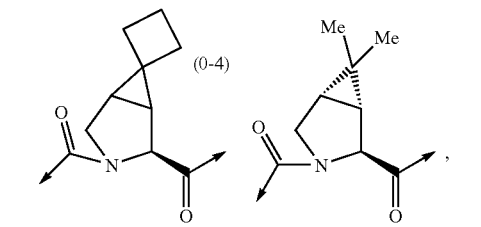
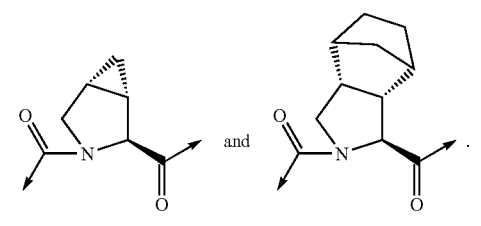

5. The compound according to claim 4, wherein
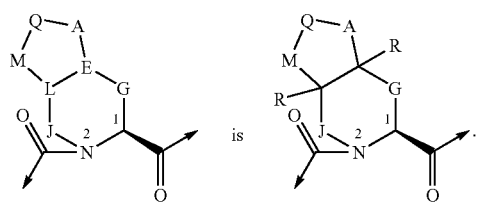
is selected from the group consisting of the following structures:
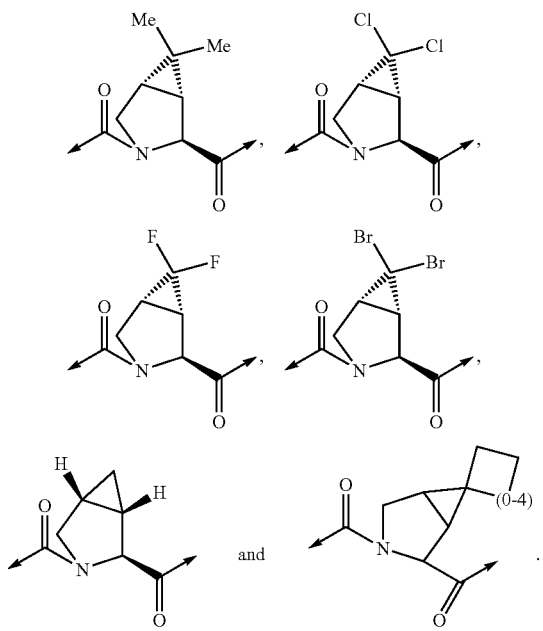
6. The compound according to claim 5, wherein
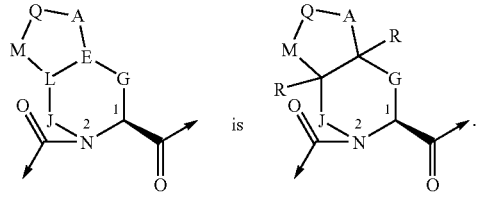
is selected from the group consisting of the following structures:
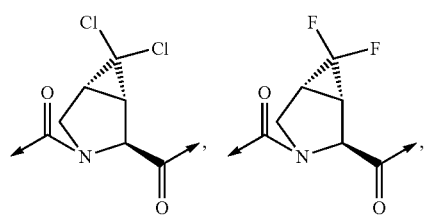
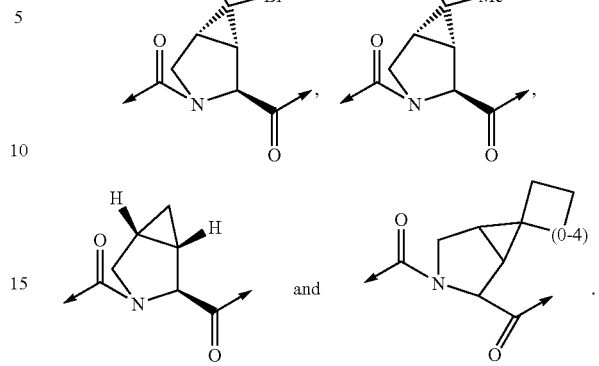
7. The compound according to claim 1, wherein W is C=O; and
Cap is selected from the group consisting of the following structures:
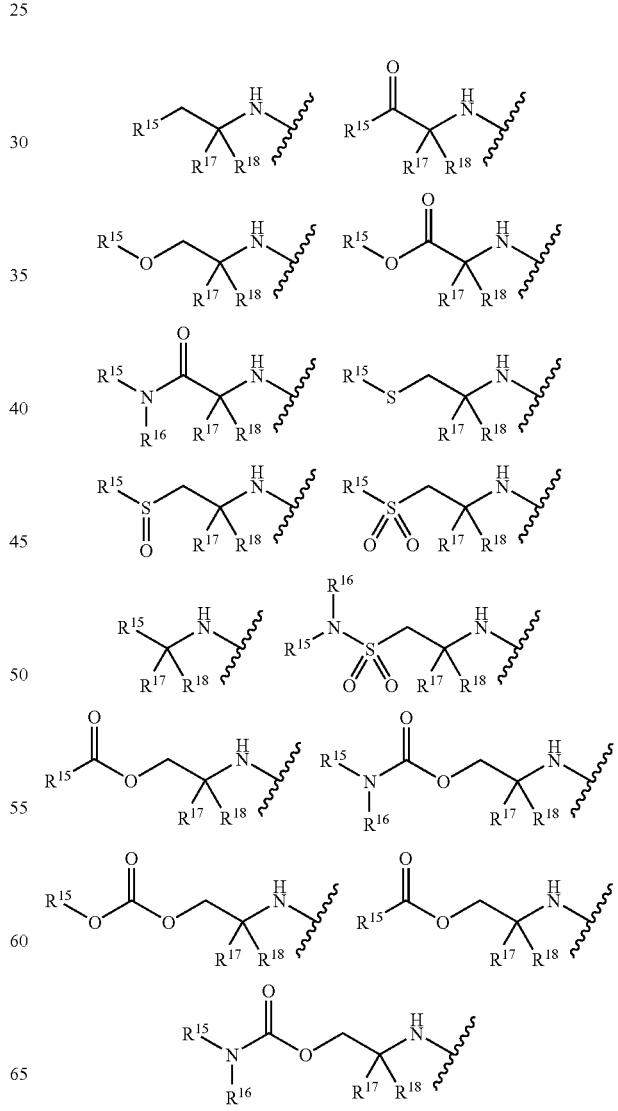

-continued

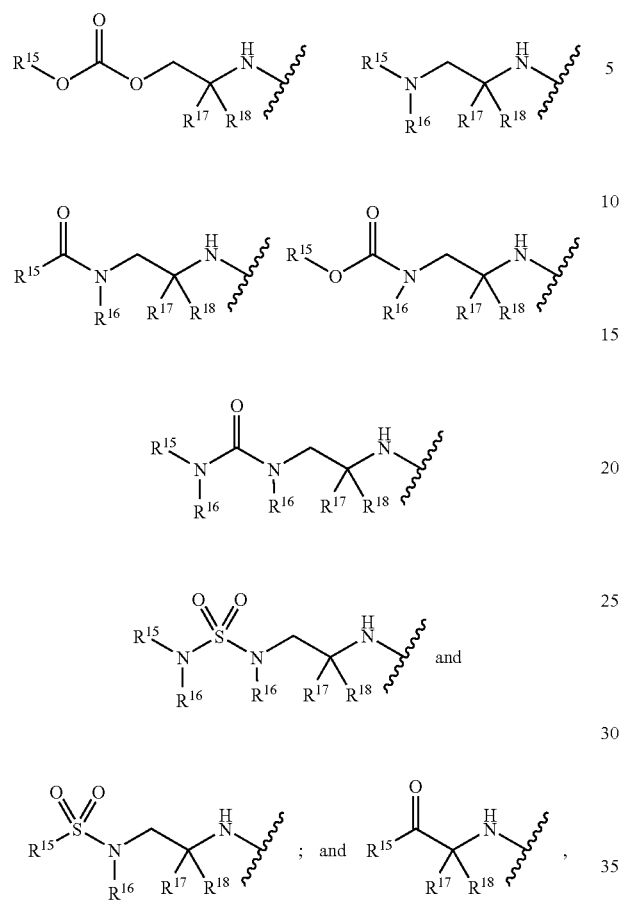

R[15], R[16], R[17] and R[18] are independently selected from the group consisting of: H, $C_1$-$C_{10}$ alkyl, $C_1$-$C_{10}$ heteroalkyl, $C_2$-$C_{10}$ alkenyl, $C_2$-$C_{10}$ heteroalkenyl, $C_2$-$C_{10}$ alkynyl, $C_2$-$C_{10}$ heteroalkynyl, $C_3$-$C_8$ cycloalkyl, $C_3$-$C_8$ heterocyclyl, aryl, heteroaryl, cycloalkylalkyl and haloalkyl;

R[15] may be linked together with R[16] such that the combination is a three to eight-membered cyclic structure; and R[17] may be linked to R[18] such that the combination is a four to eight-membered cyclic structure.

8. The compound of claim 7, wherein Cap is selected from the group consisting of the following structures:

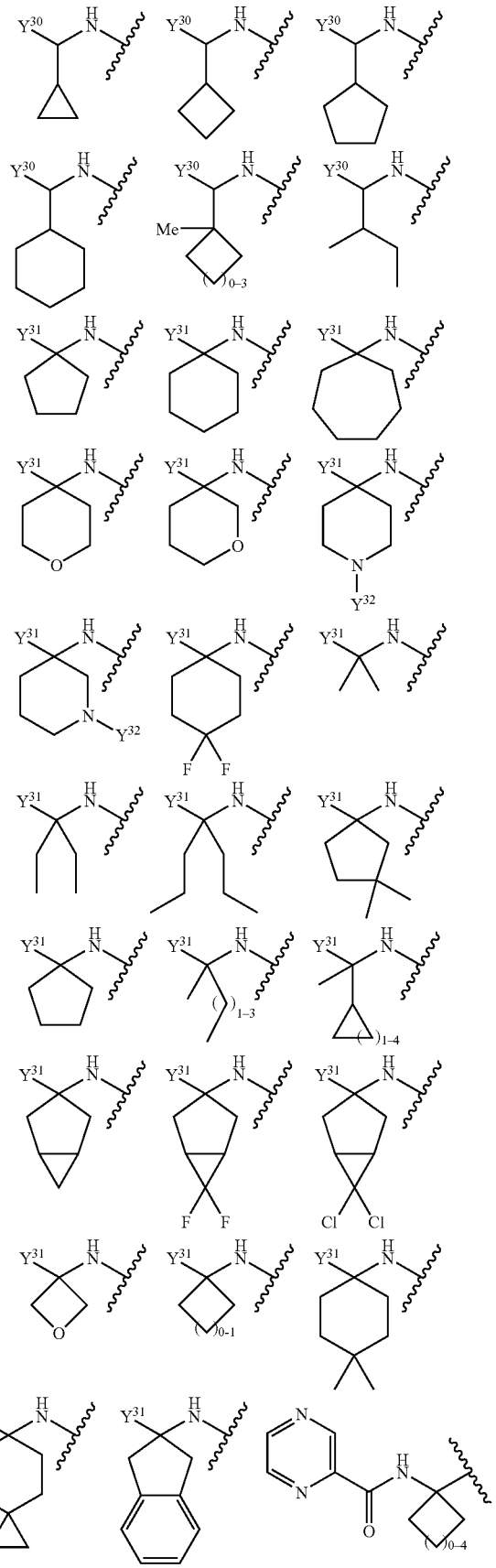

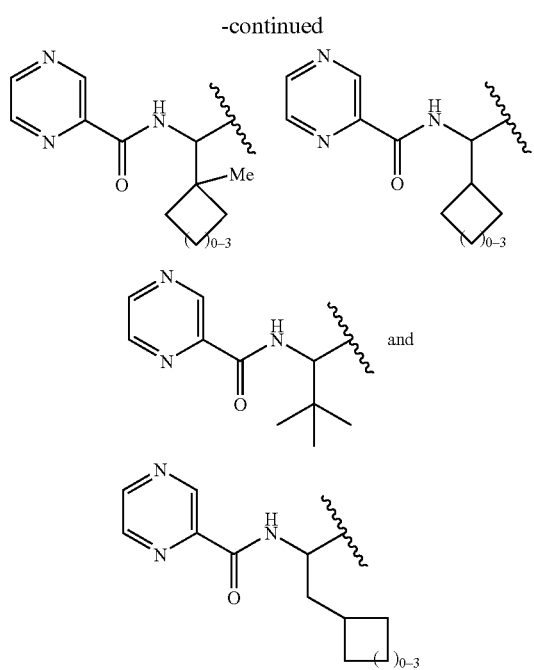
Y30 is selected from the group consisting of the following structures:
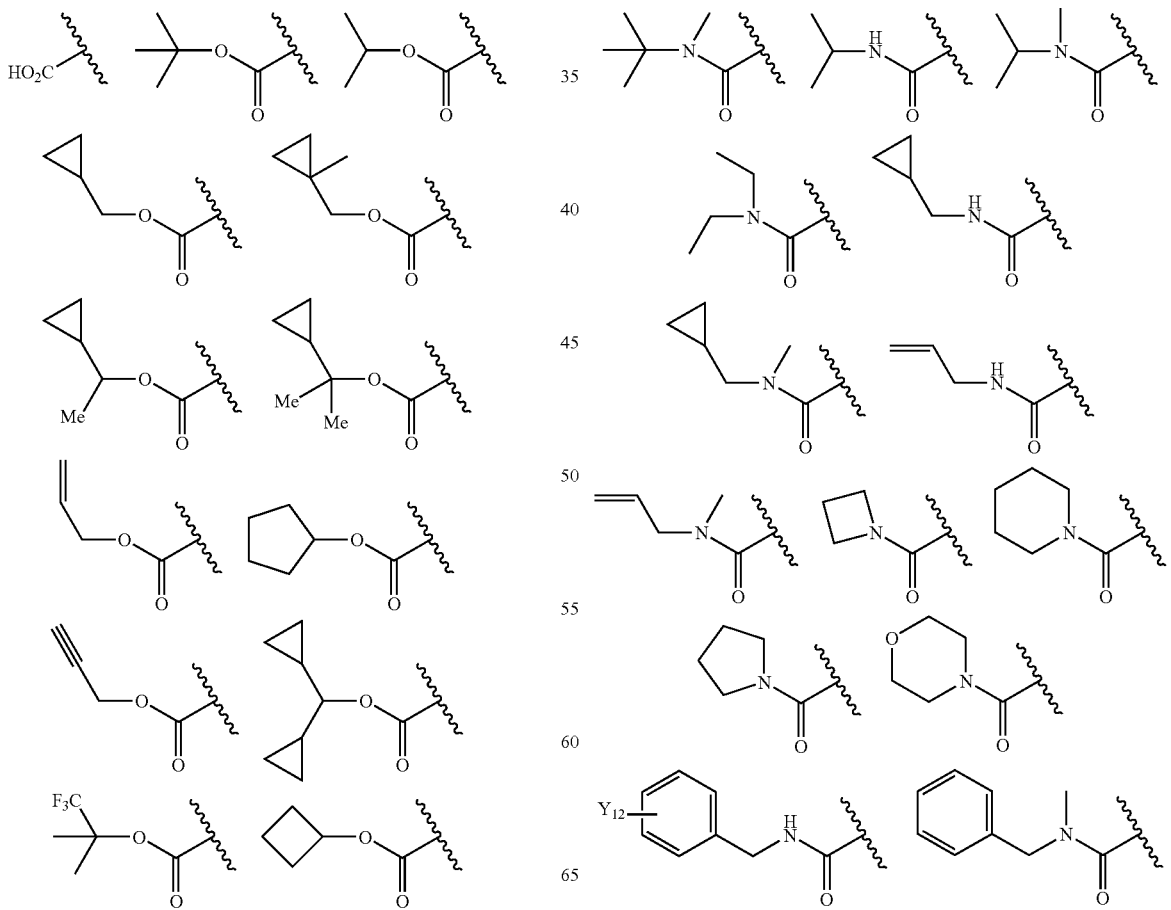

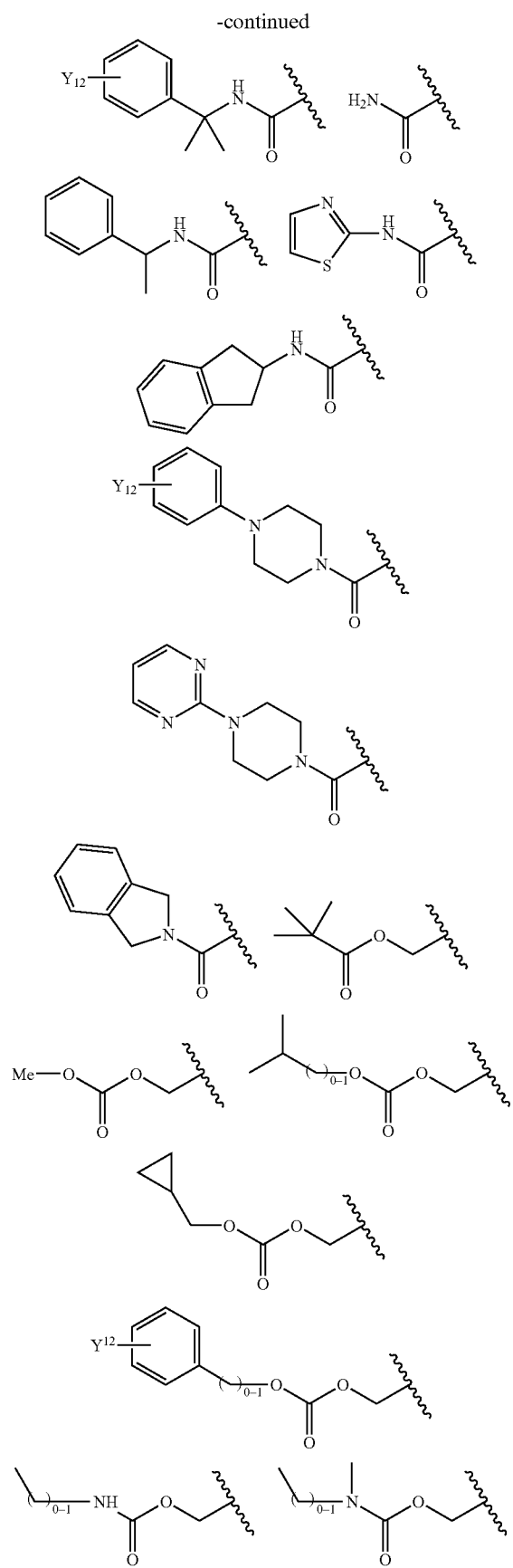
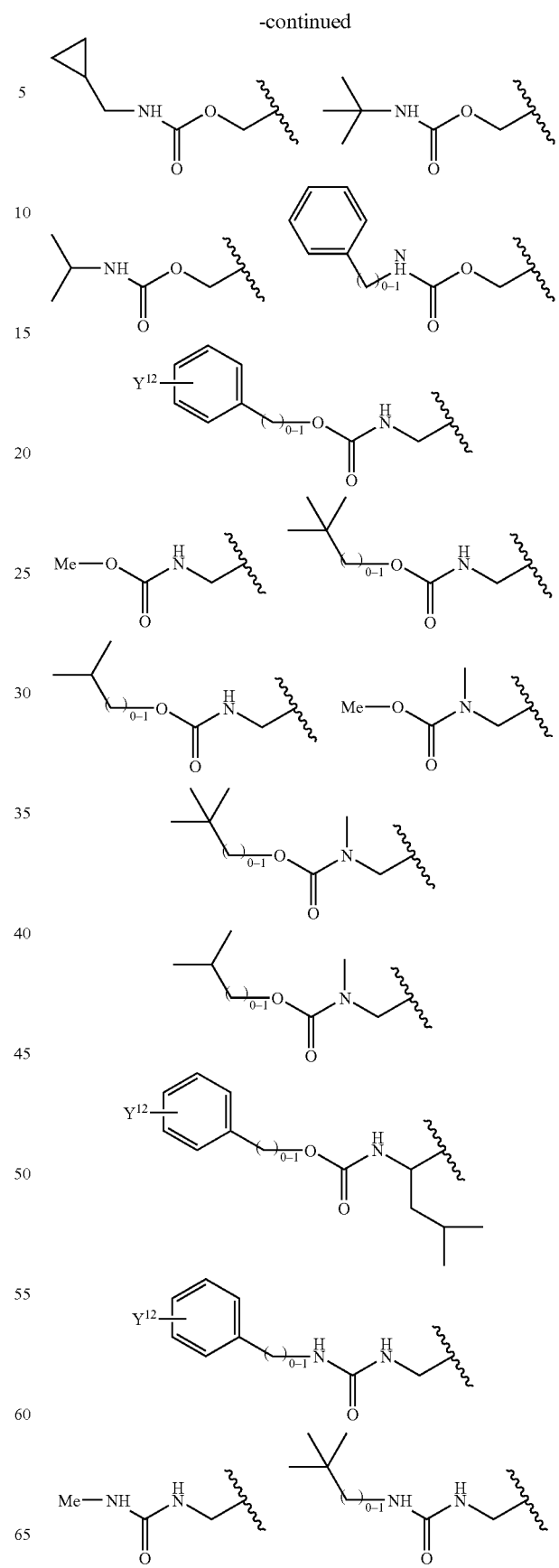

-continued
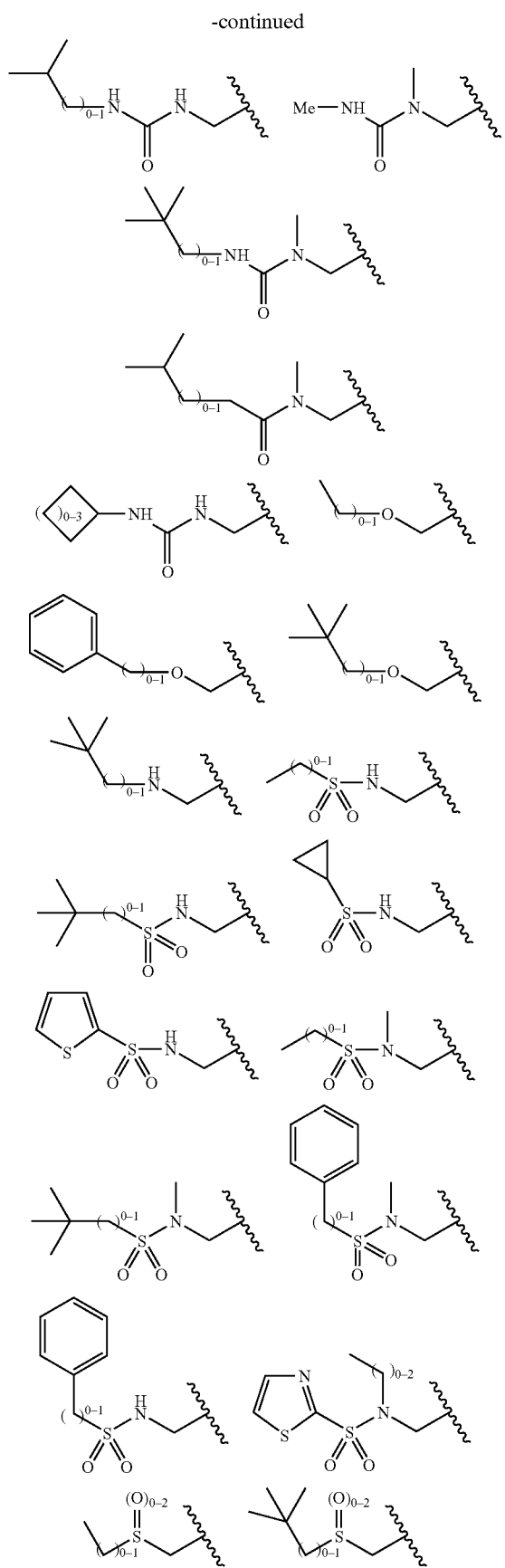
-continued
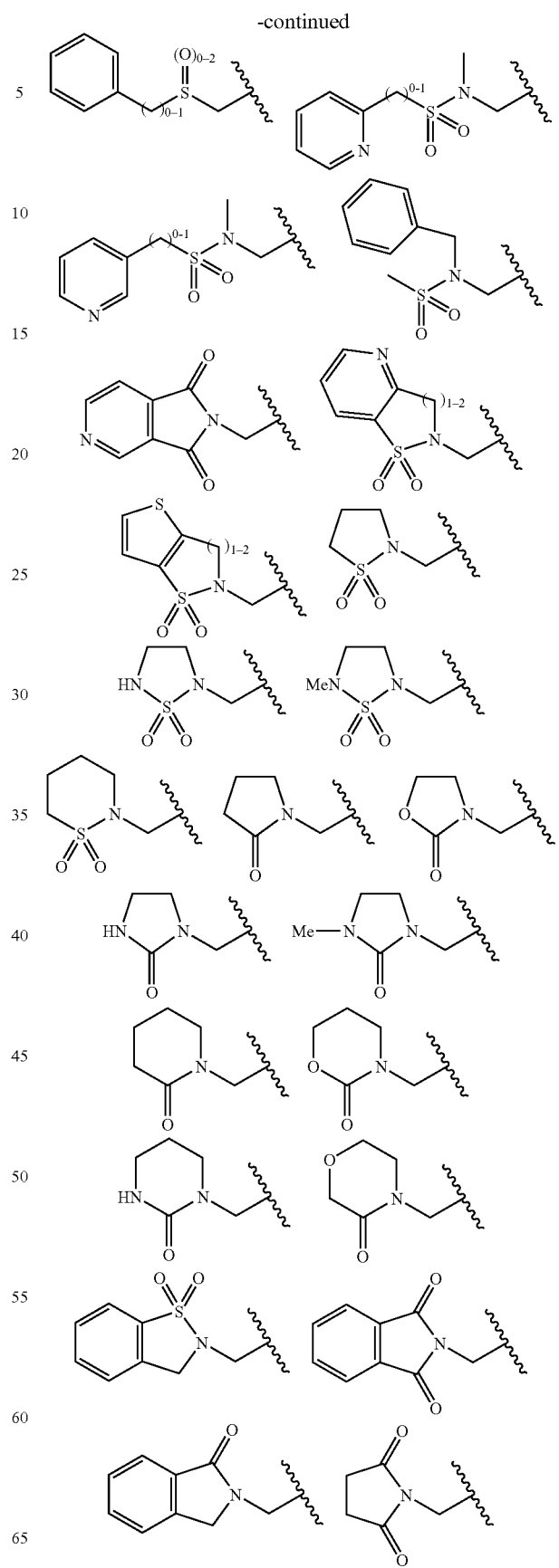

-continued
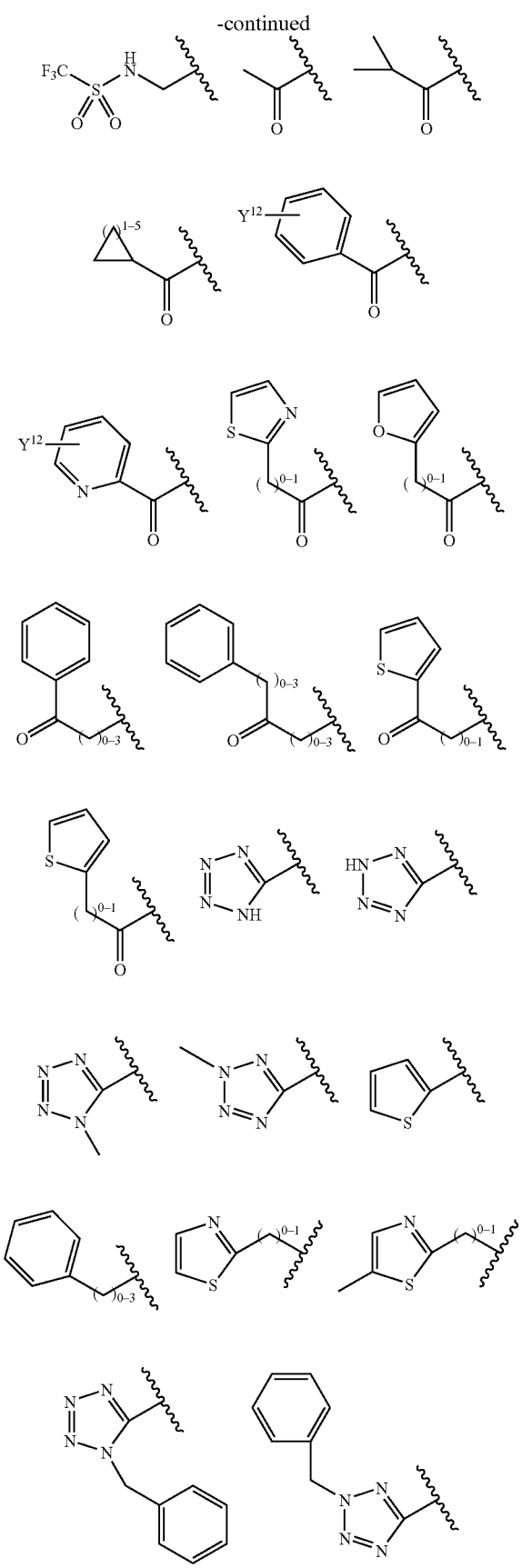
-continued
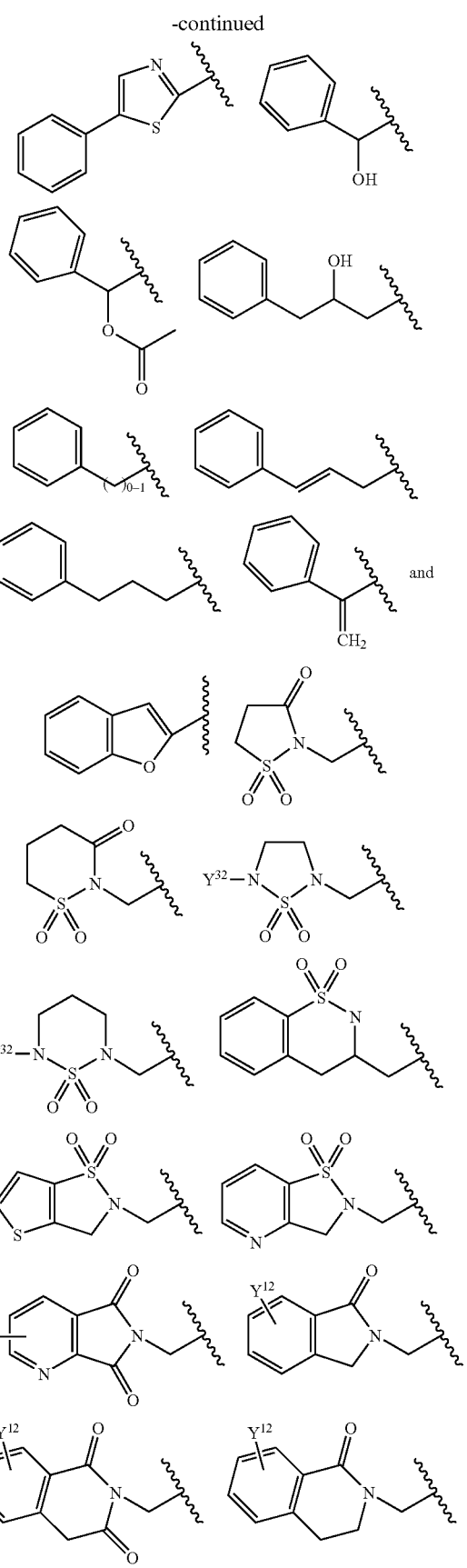

-continued
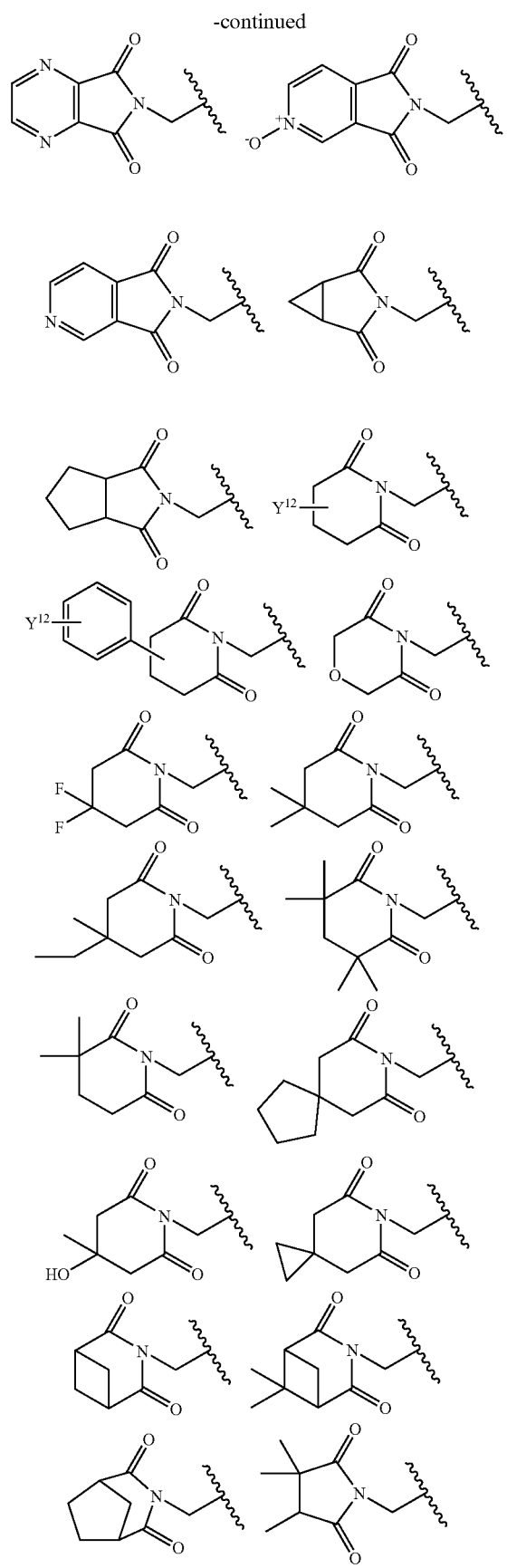
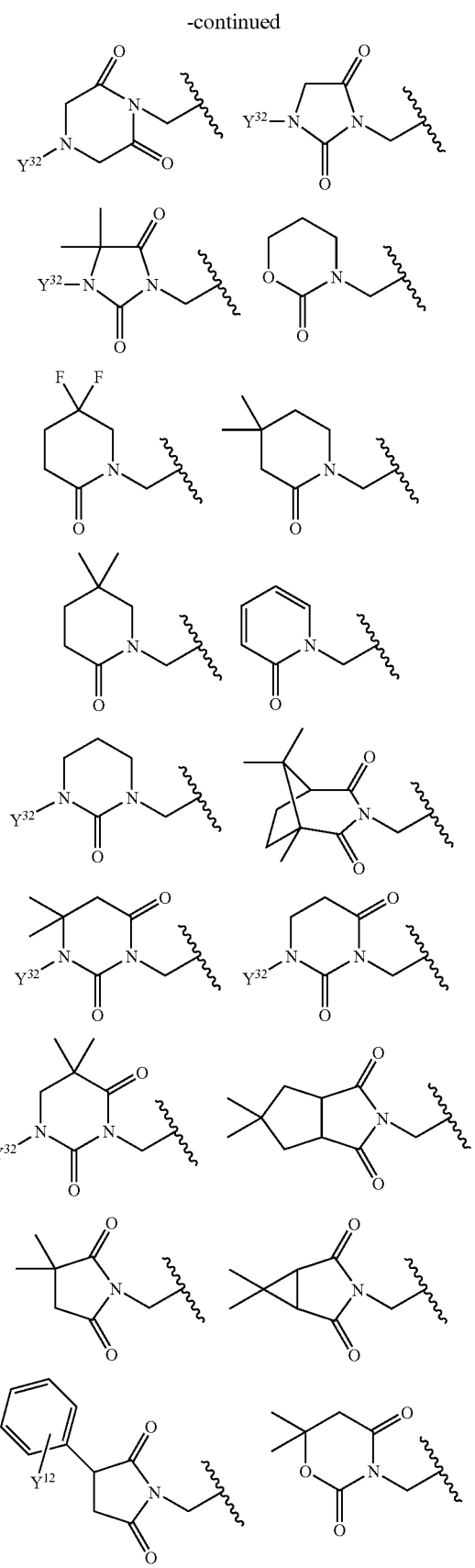

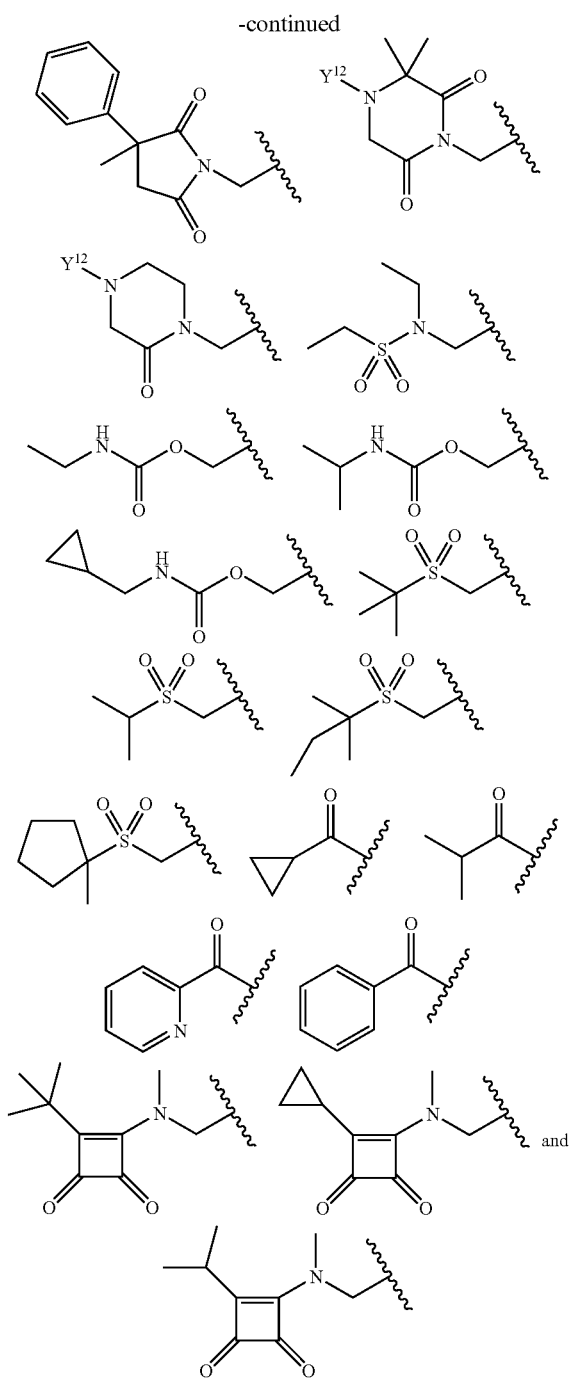
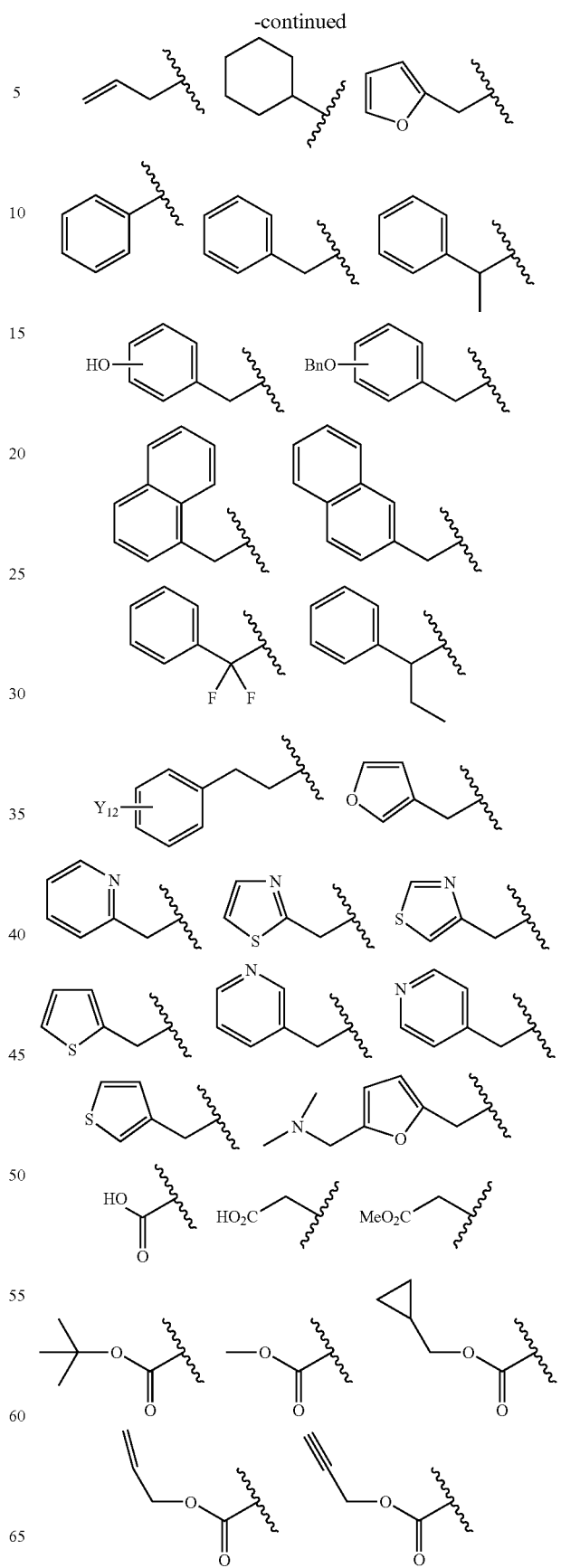
$Y^{31}$ is selected from the group consisting of the following structures:
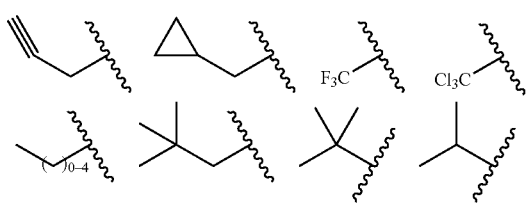

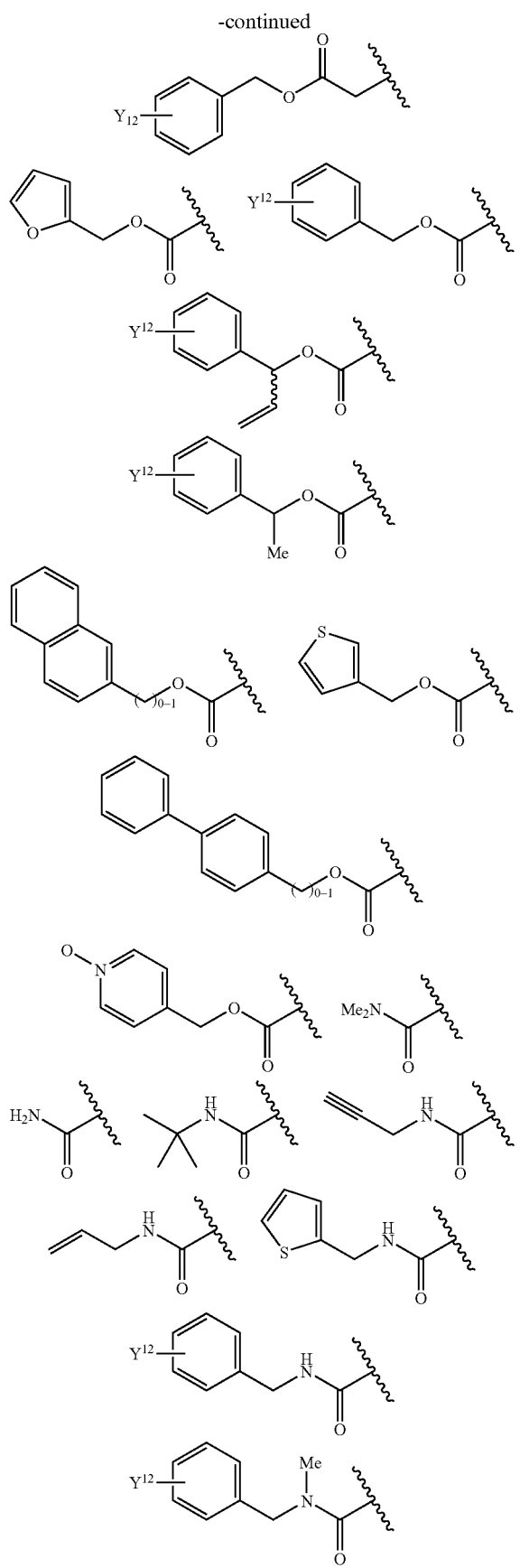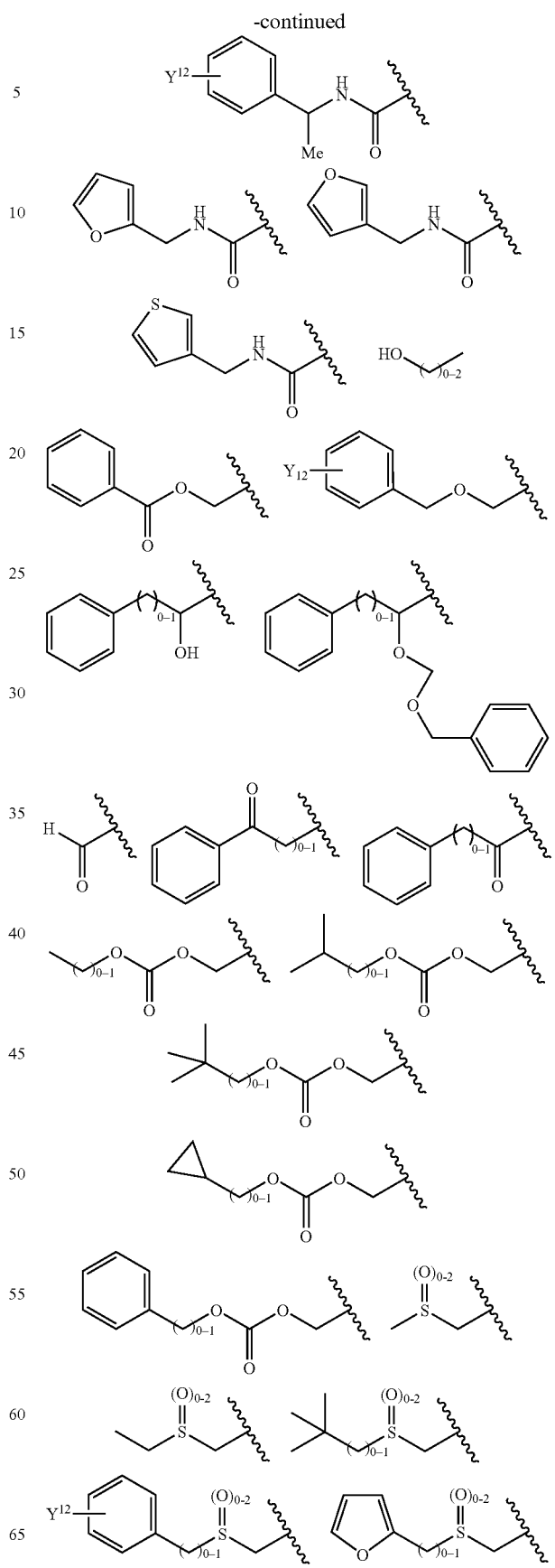

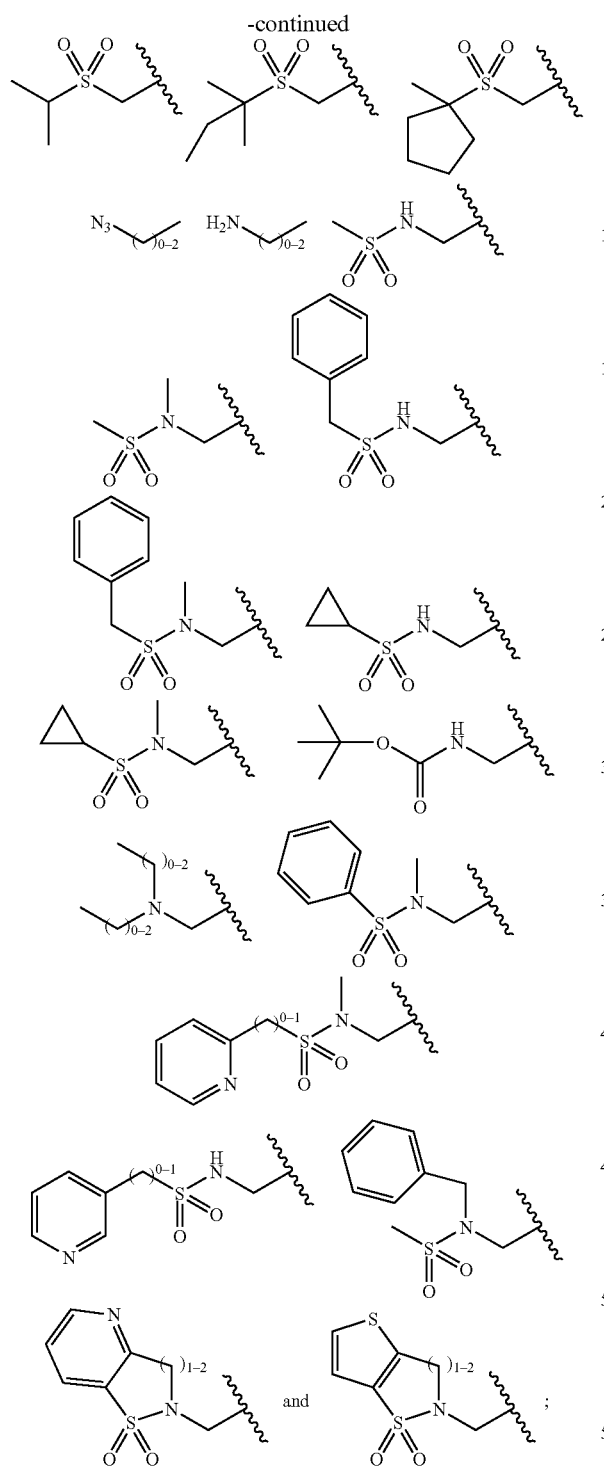

$Y^{32}$ is selected from the group consisting of the following structures:

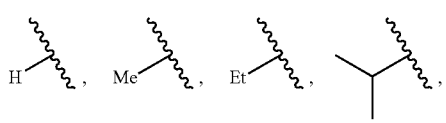

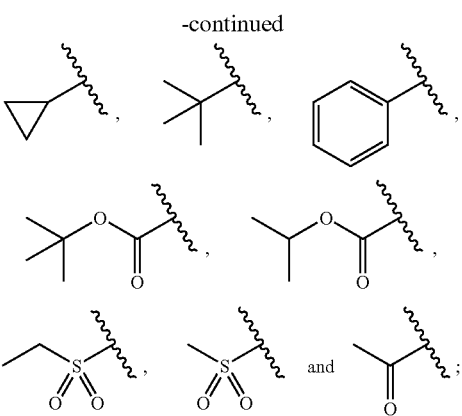

and $Y^{12}$ is selected from H, COOH, COOMe, OMe, F, Cl, Br, $NH_2$, $NHSO_2CH_3$, $NHCOCH_3$, $NO_2$, $SO_2NH_2$, $CF_3$, OH, $OCF_3$, $CONH_2$, Me, Et, isopropyl, cyclopropyl or tert-butyl.

9. The compound according to claim 8, wherein Cap is selected from the group consisting of the following structures:

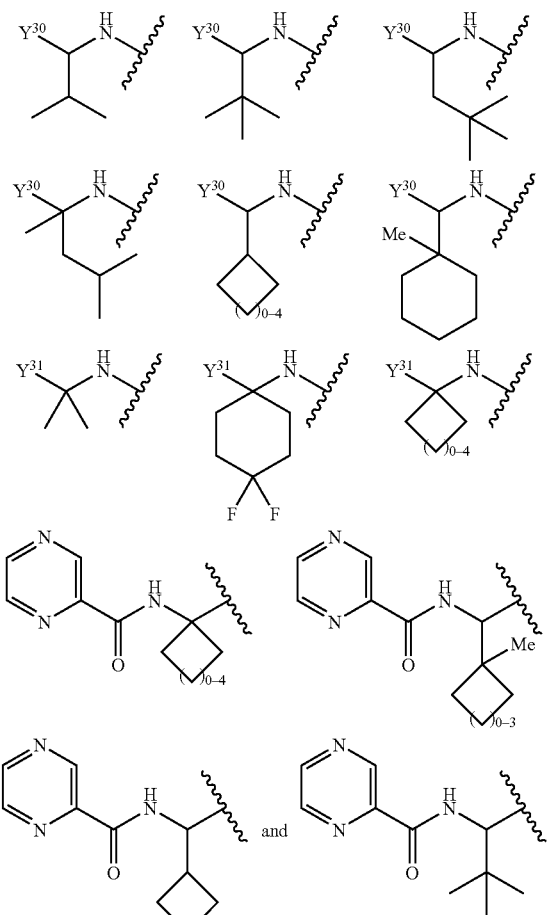

$Y^{30}$ is selected from the group consisting of the following structures:

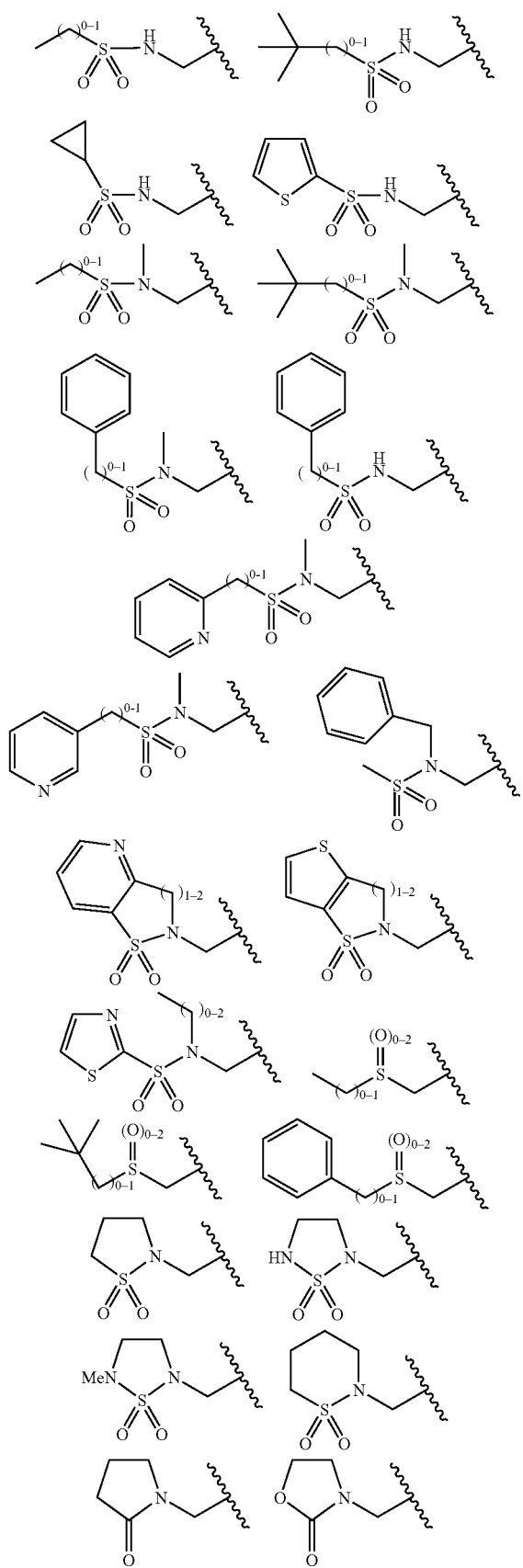
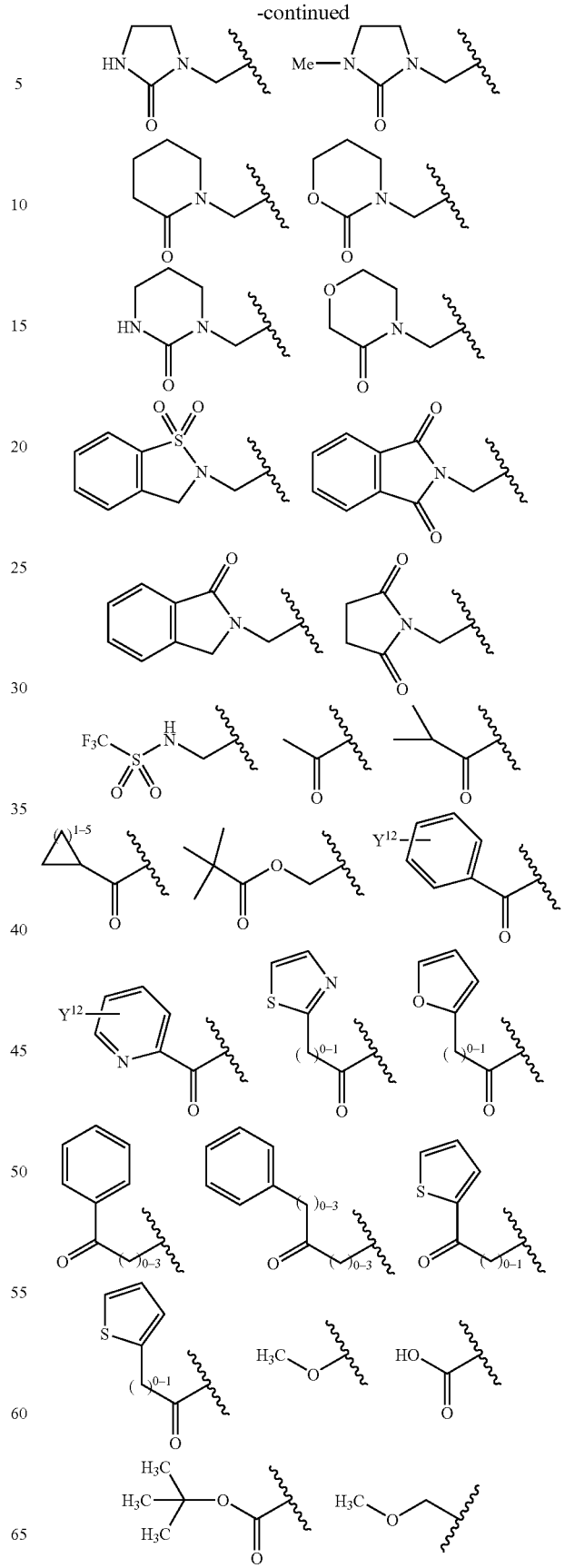
-continued

-continued
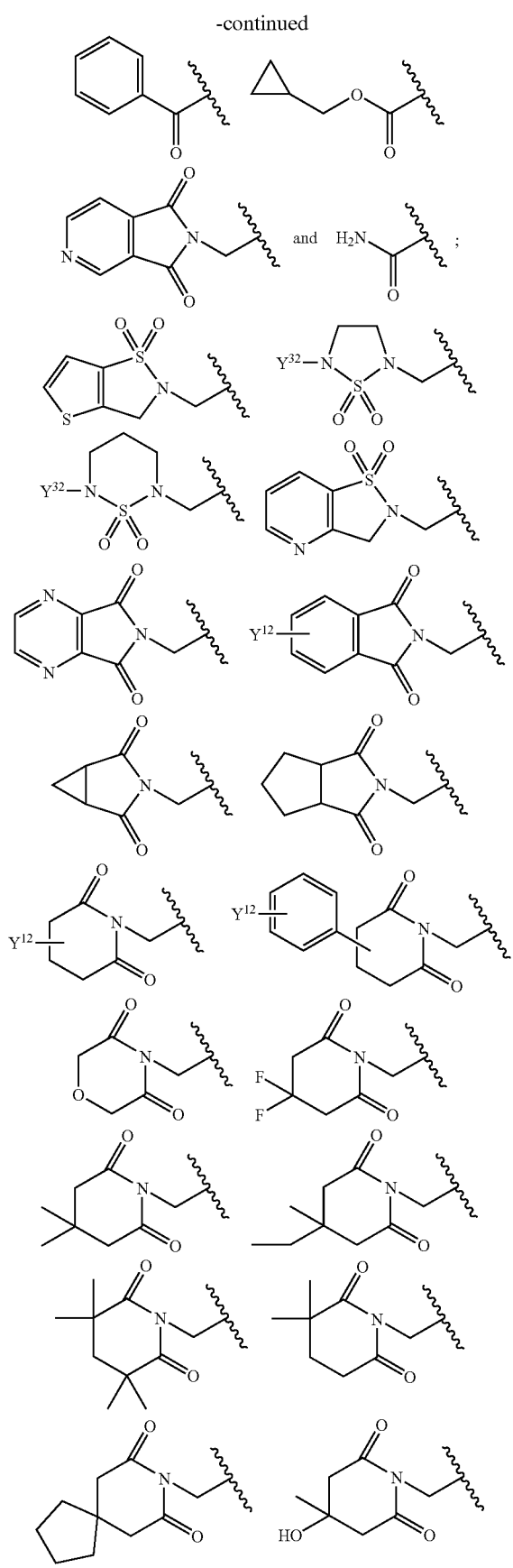
and
-continued
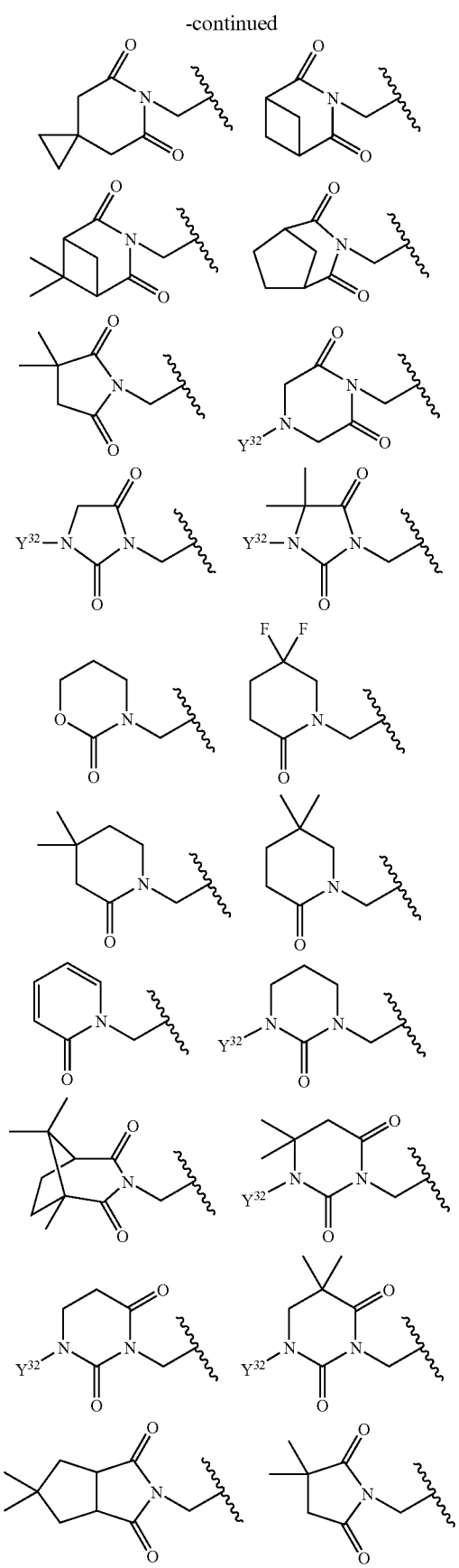

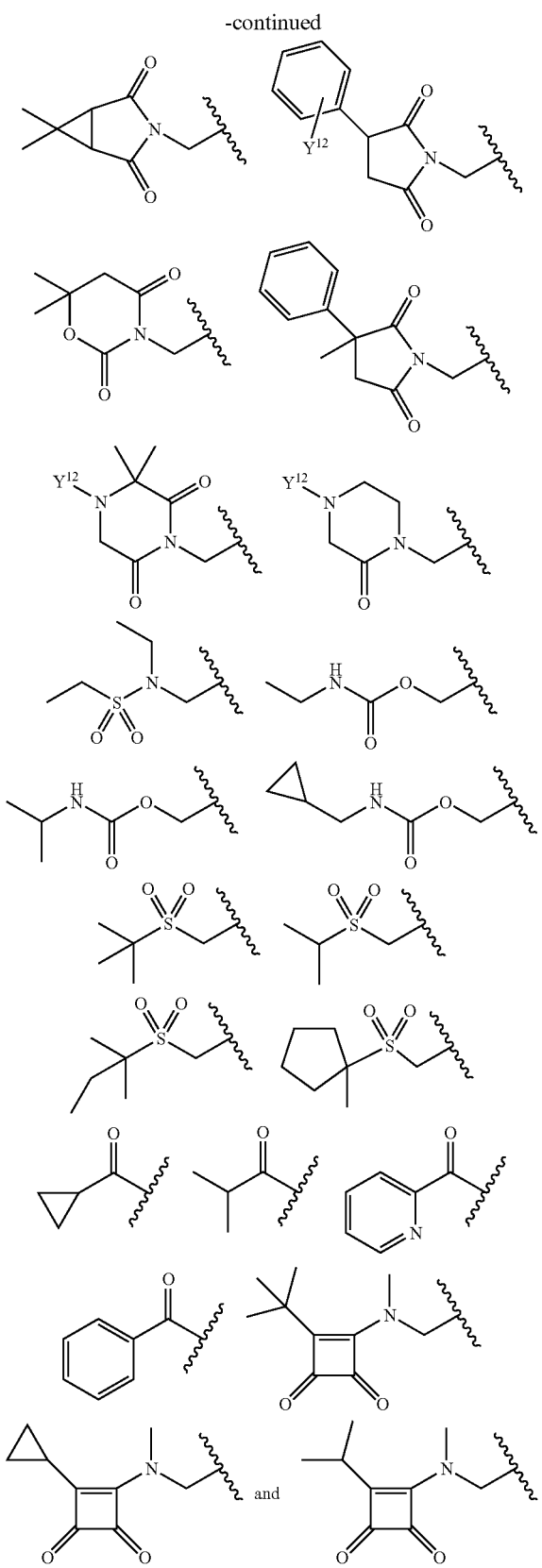
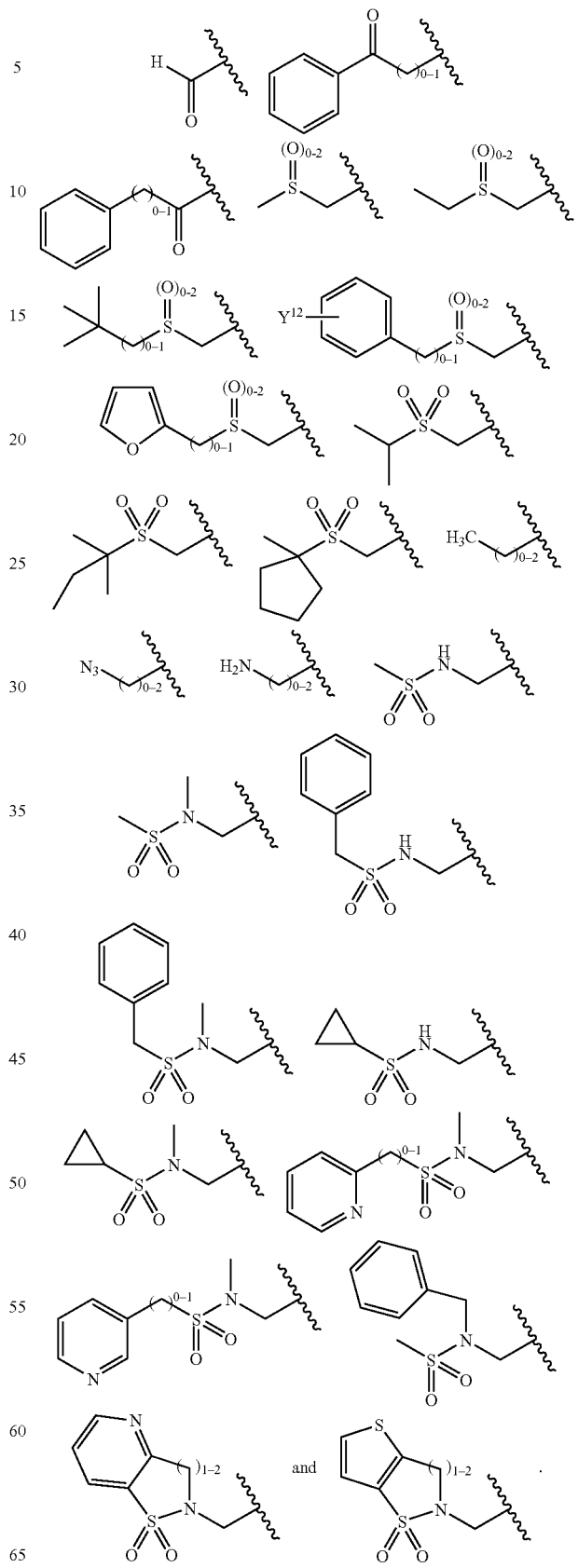
and $Y^{31}$ is selected from the group consisting of the following structures:

10. The compound according to claim 9, wherein $Y^{30}$ and $Y^{31}$ are independently selected from the group consisting of the following structures:
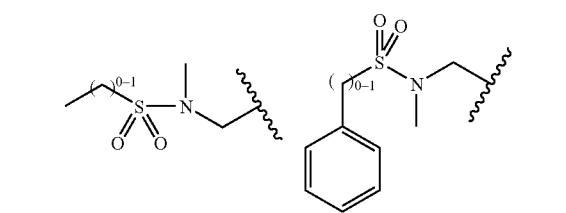
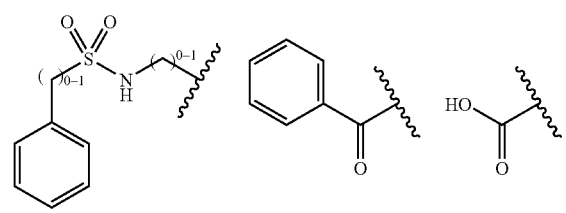
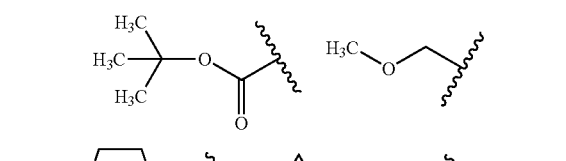
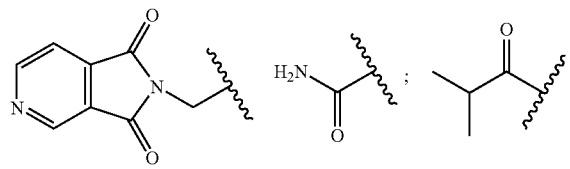
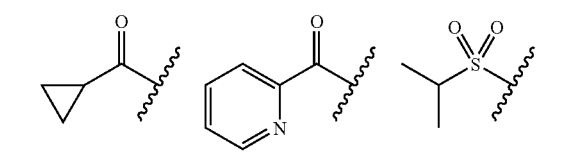
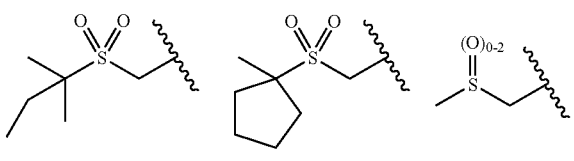
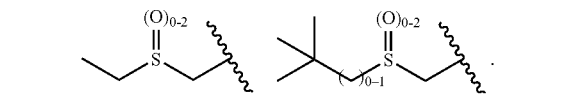
-continued
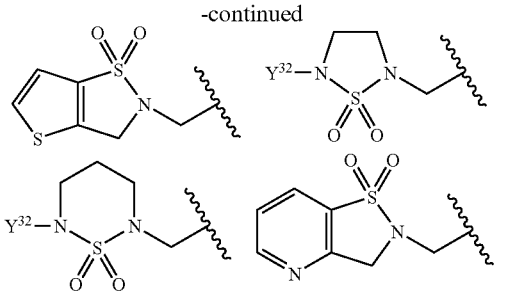
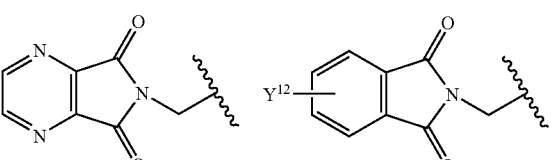
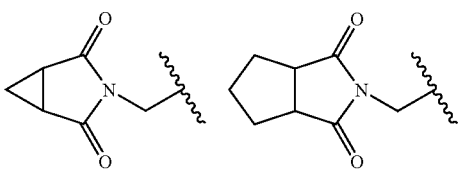
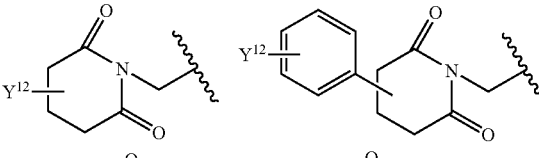
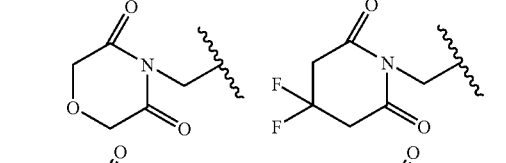
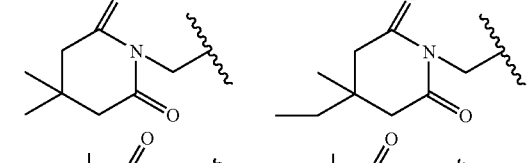
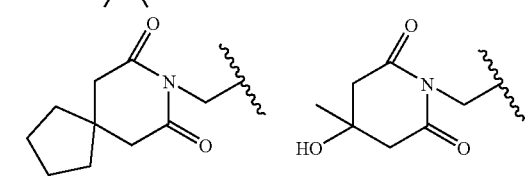
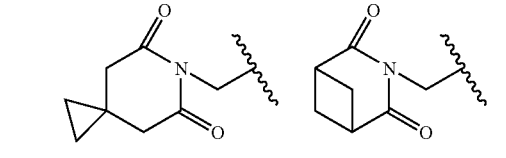

-continued
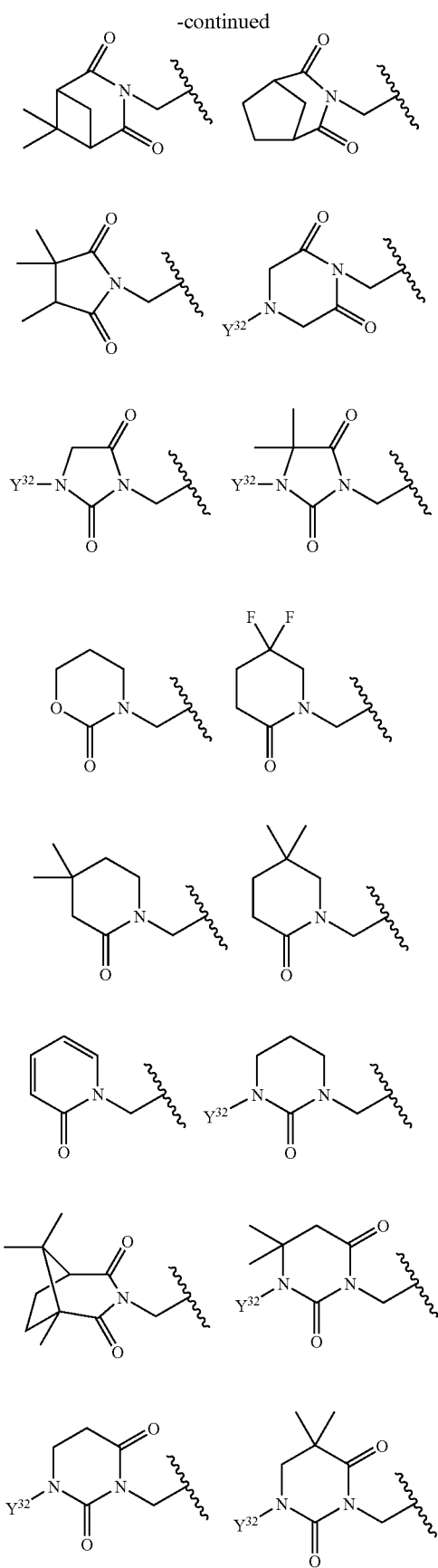
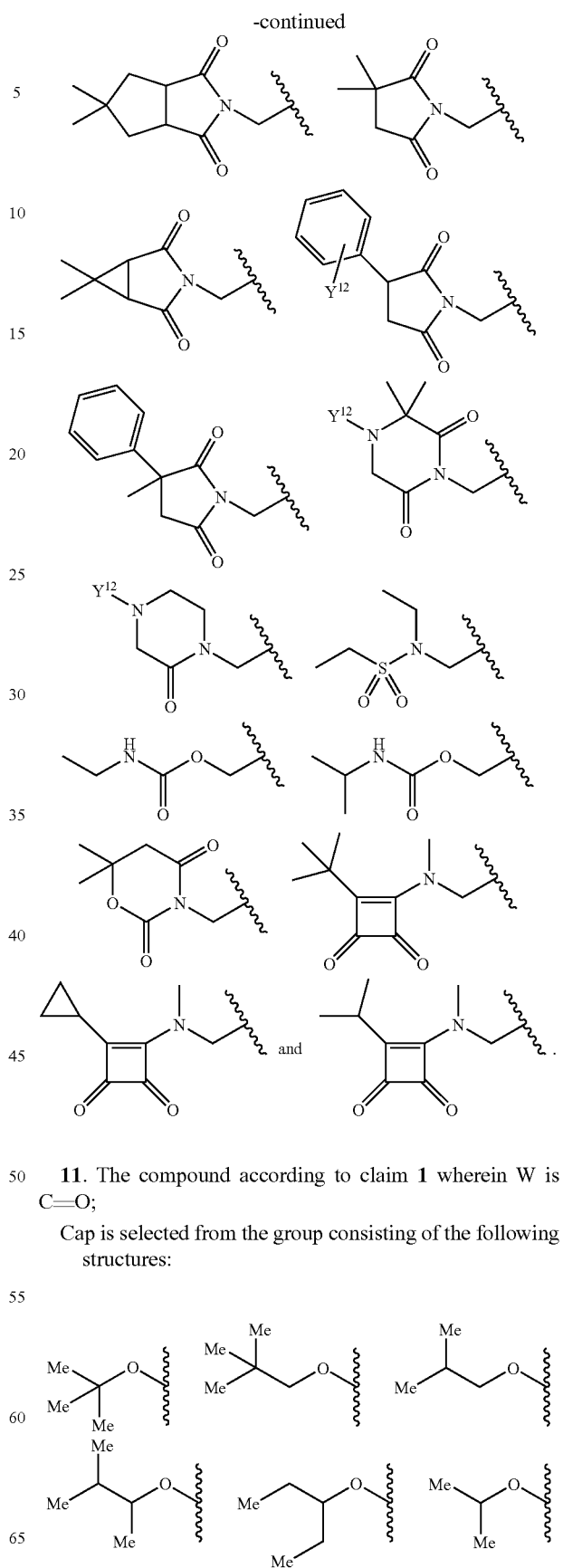
11. The compound according to claim 1 wherein W is C=O;
Cap is selected from the group consisting of the following structures:
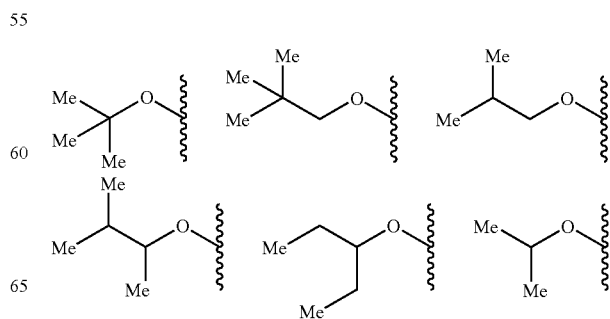

311
-continued
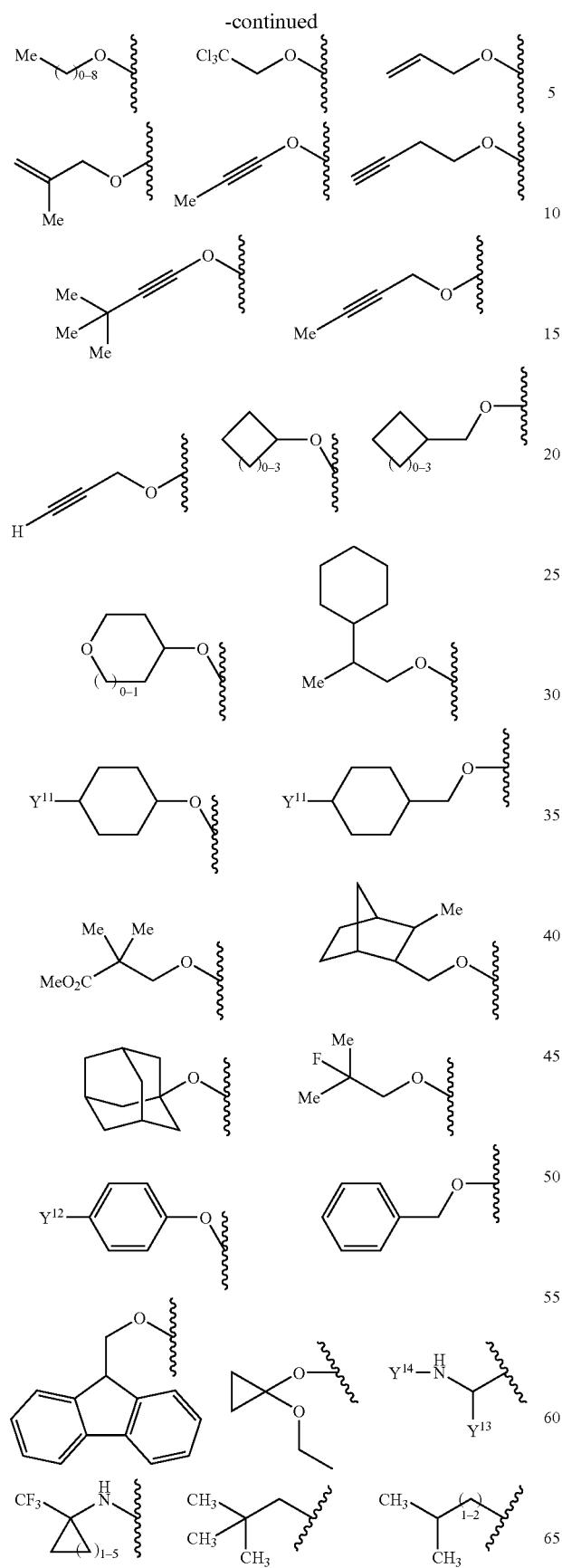
312
-continued
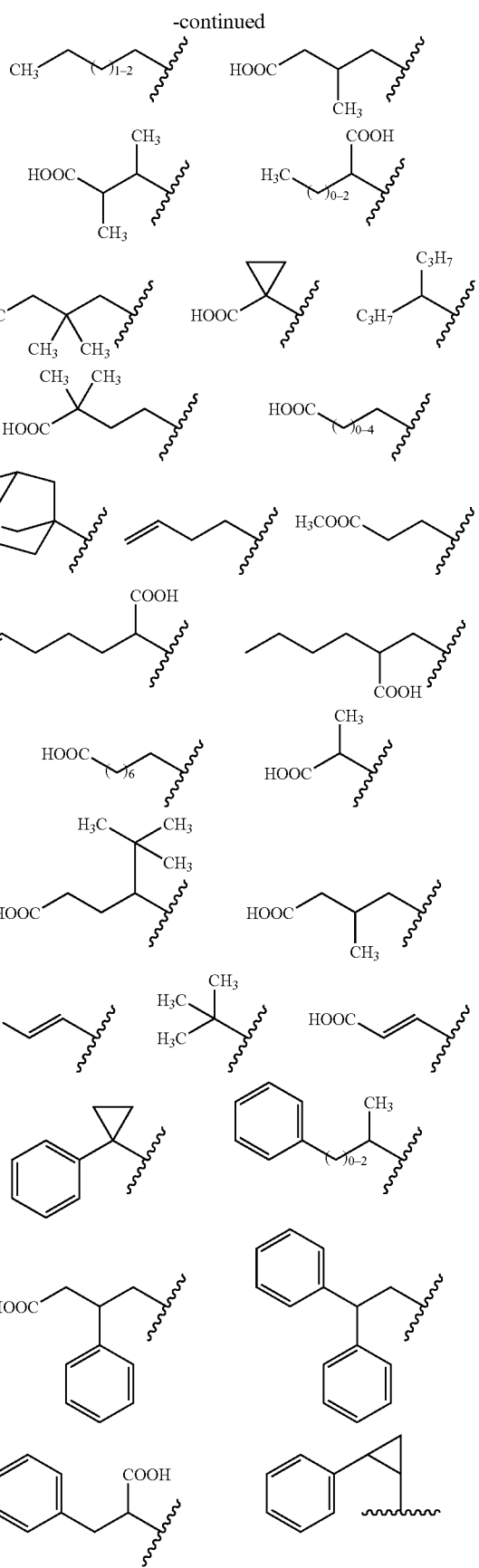

313
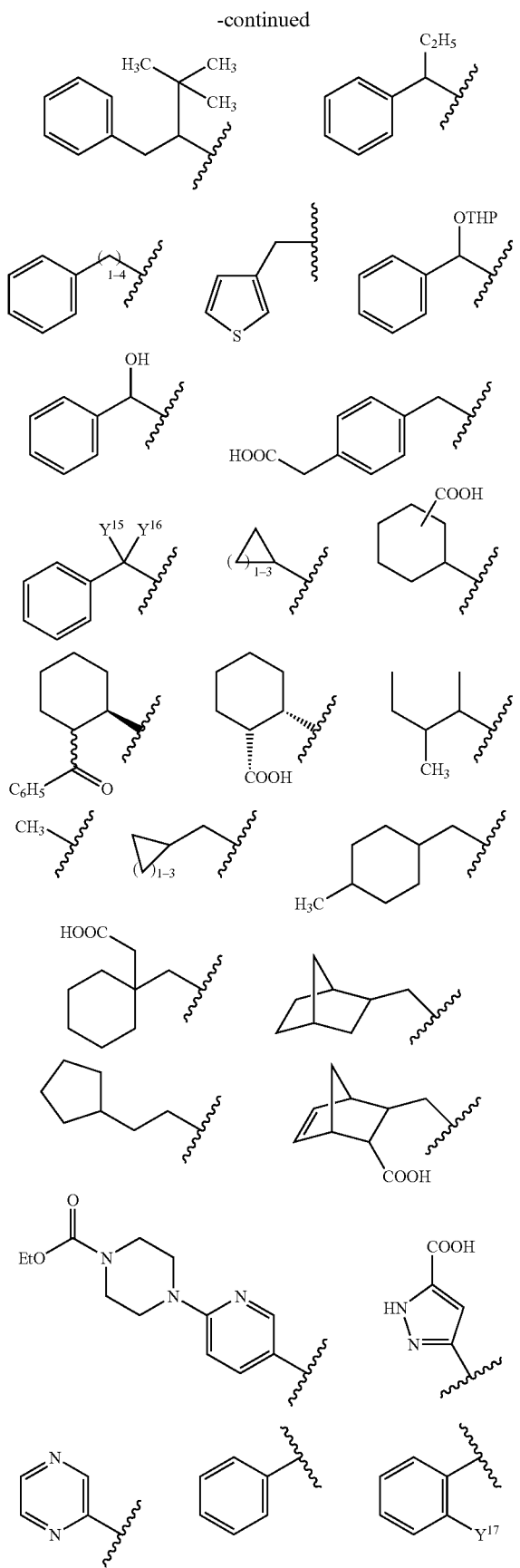
314
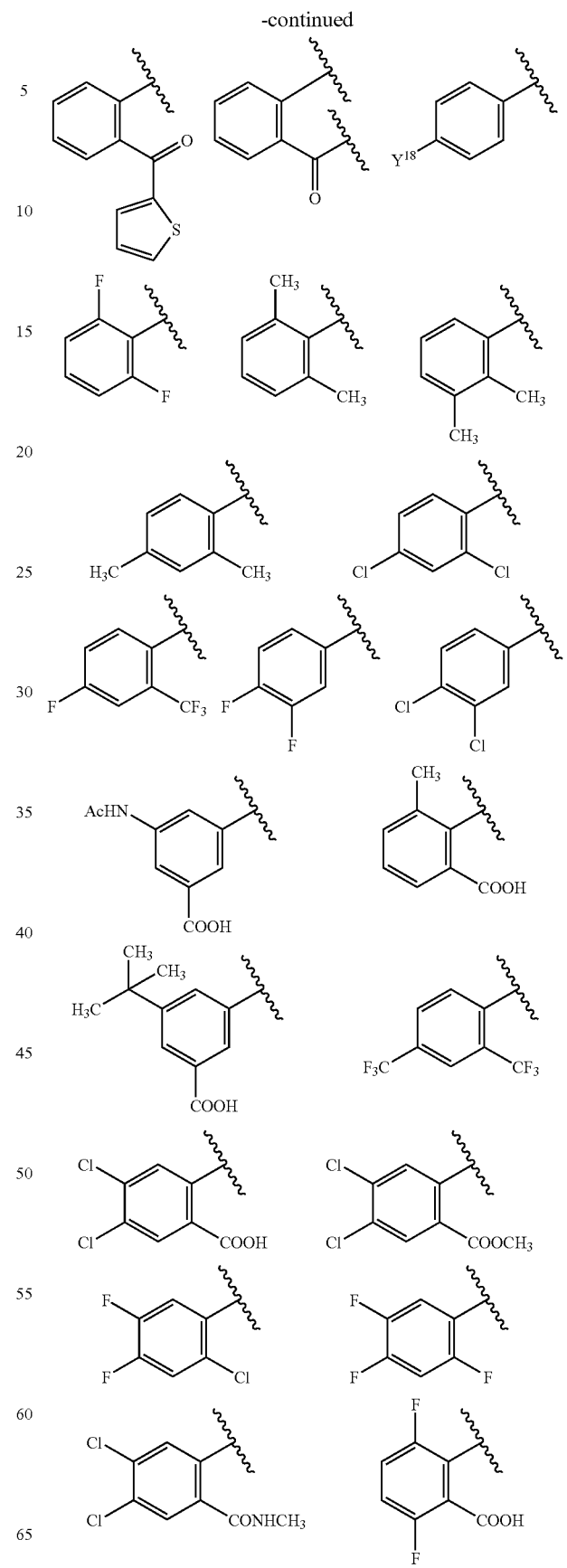

-continued
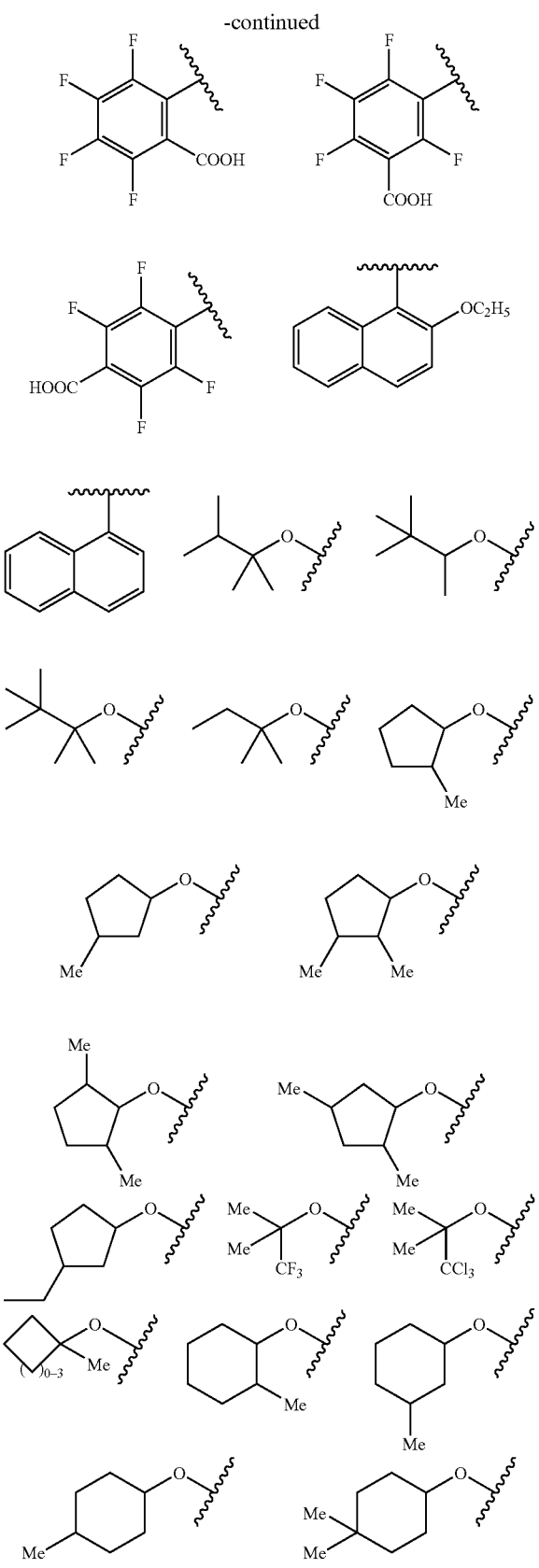
-continued
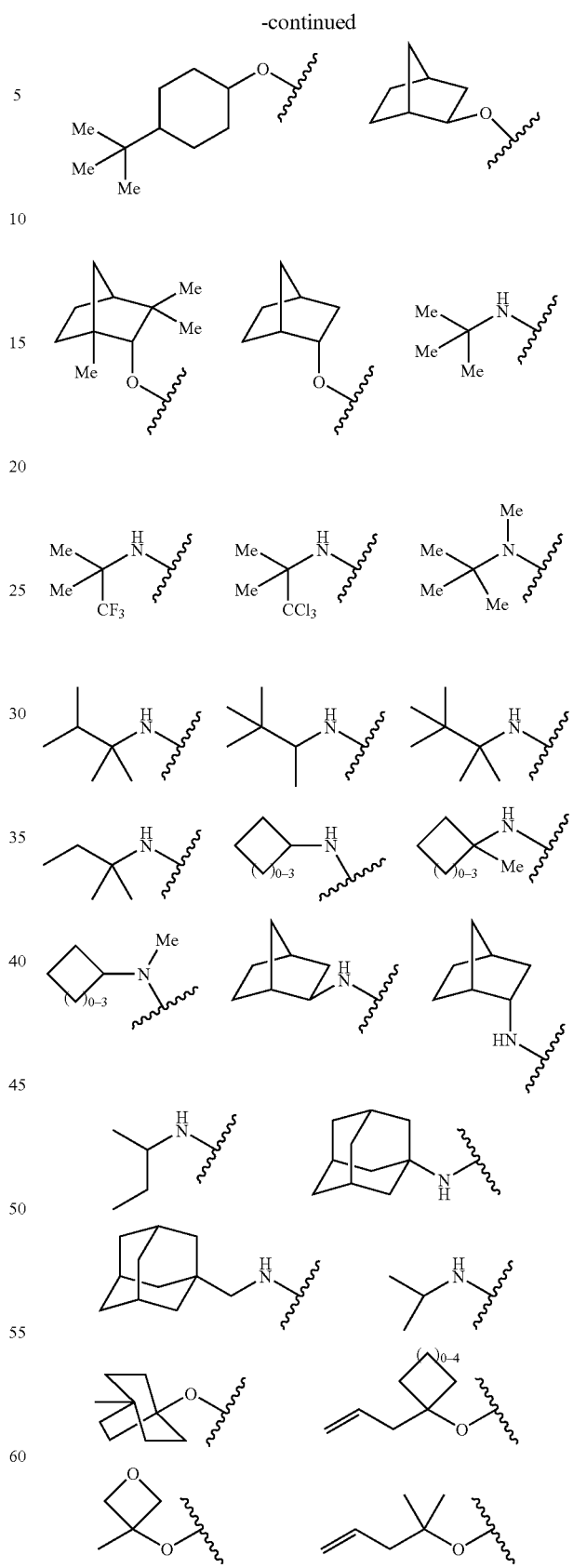

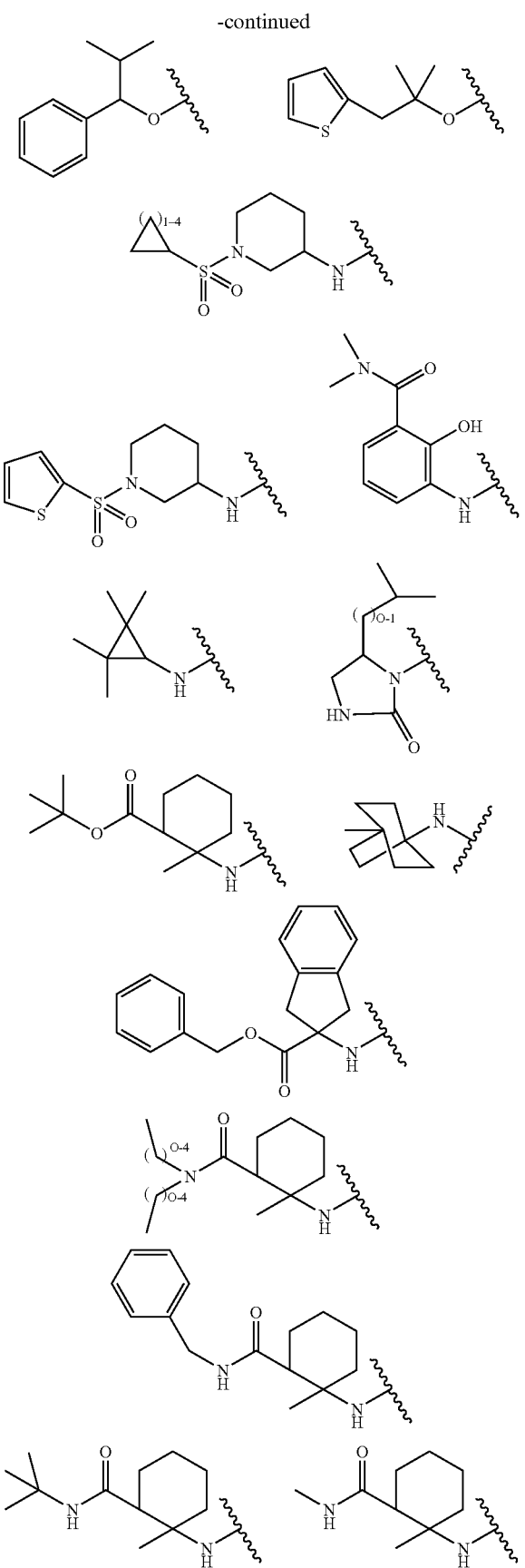
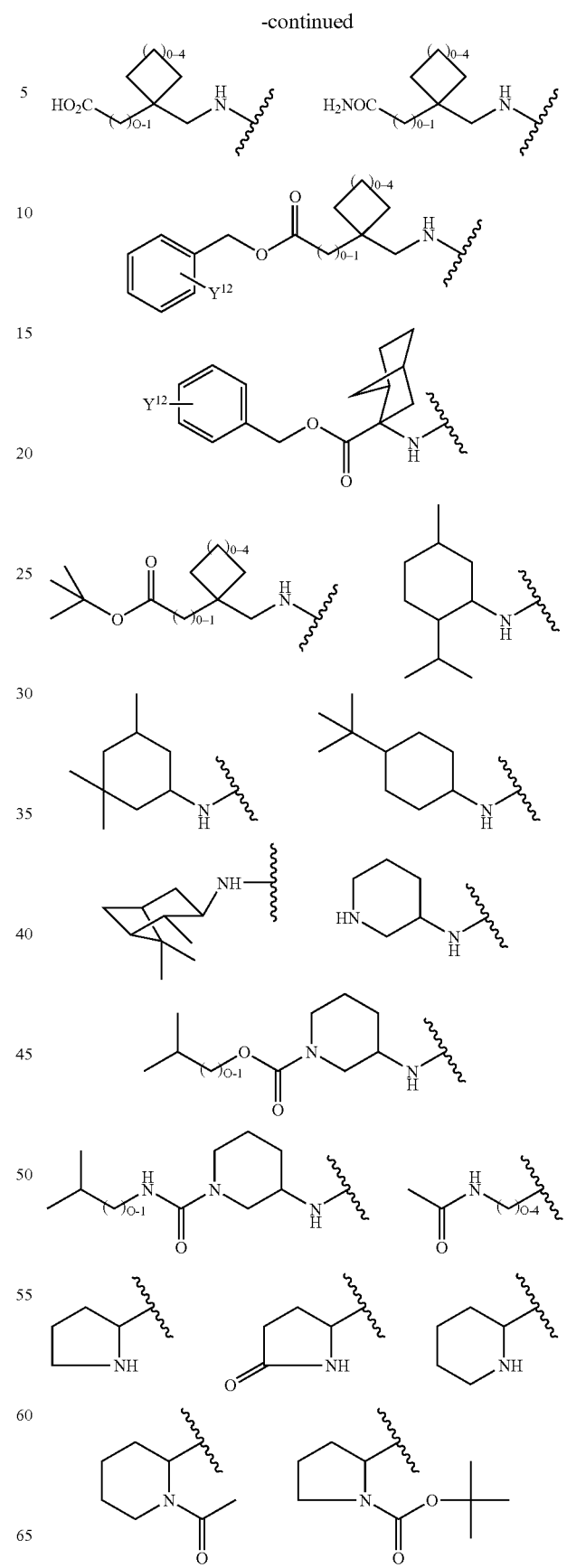

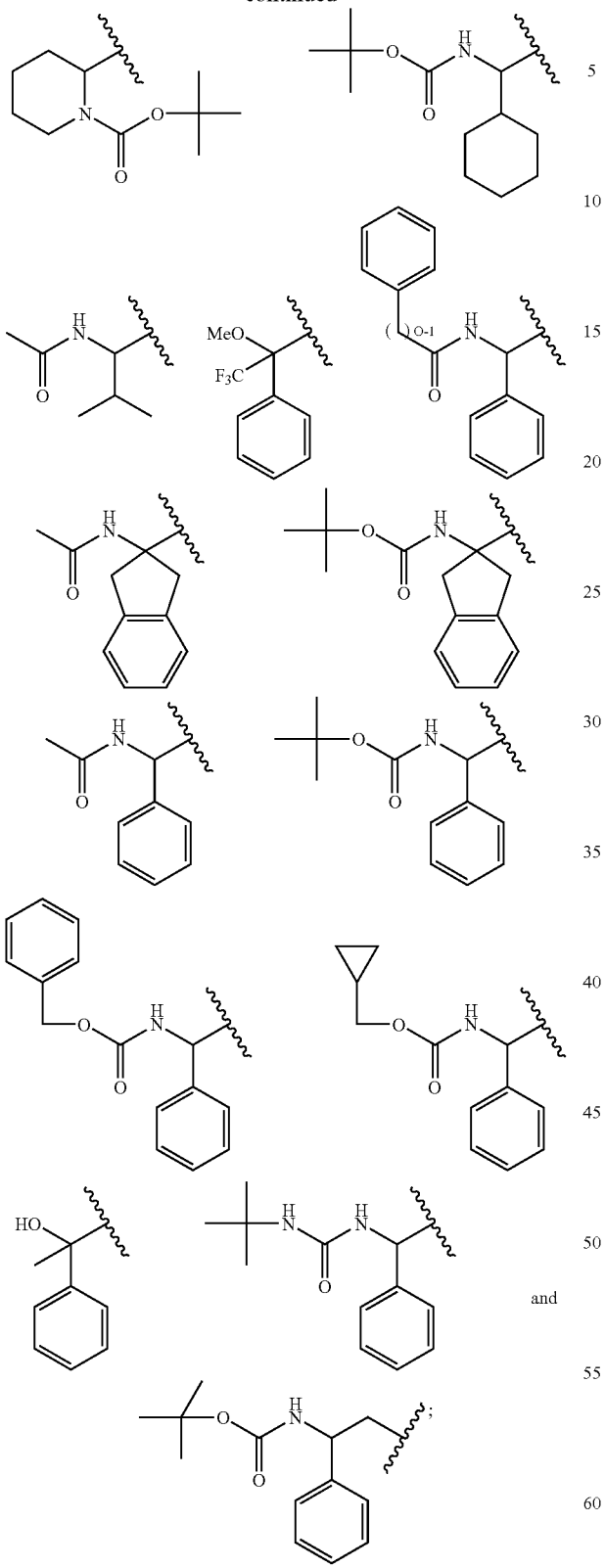

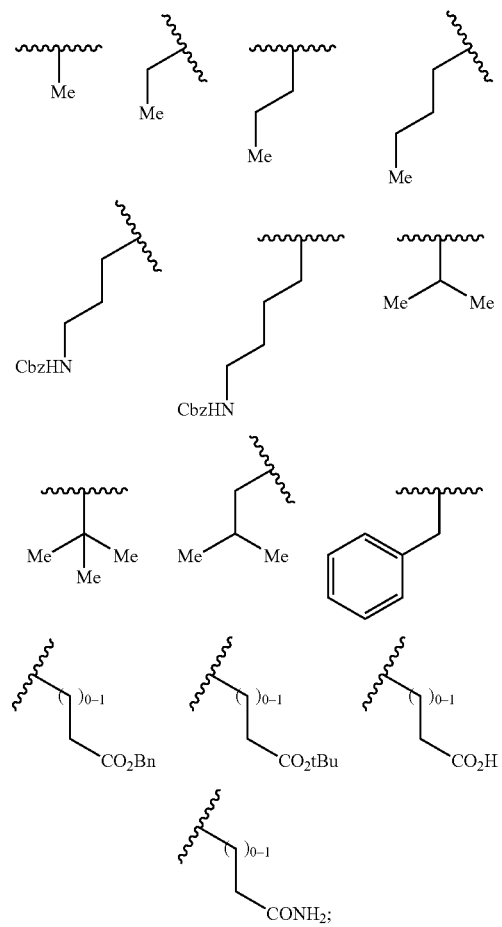

$Y^{12}$ is H, COOH, COOMe, OMe, F, Cl, Br, $NH_2$, $NHSO_2CH_3$, $NHCOCH_3$, $NO_2$, $SO_2NH_2$, $CF_3$, Me, OH or $CONH_2$;

$Y^{13}$ is selected from the following:

$Y^{14}$ is $MeSO_2$, Ac, Boc, iBoc, Cbz, or Alloc;

$Y^{15}$ and $Y^{16}$ are independently selected from the group consisting of: alkyl, aryl, heteroalkyl and heteroaryl;

$Y^{17}$ is $CF_3$, $NO_2$, $CONH_2$, OH, $COOCH_3$, $OCH_3$, $OC_6H_5$, $C_6H_5$, $COC_6H_5$, $NH_2$ or COOH; and $Y^{18}$ is $COOCH_3$, $NO_2$, $N(CH_3)_2$, F, $OCH_3$, $CH_2COOH$, COOH, $SO_2NH_2$, or $NHCOCH_3$.

12. The compound according to claim 11, wherein Gap is selected from the group consisting of the following structures:

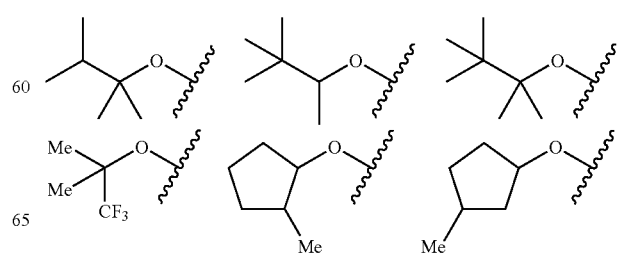

$Y^{11}$ is H, COOH, COOEt, OMe, Ph, OPh, NHMe, NHAc, NHPh, $CH(Me)_2$, 1-triazolyl, 1-imidazolyl or $NHCH_2COOH$;

-continued
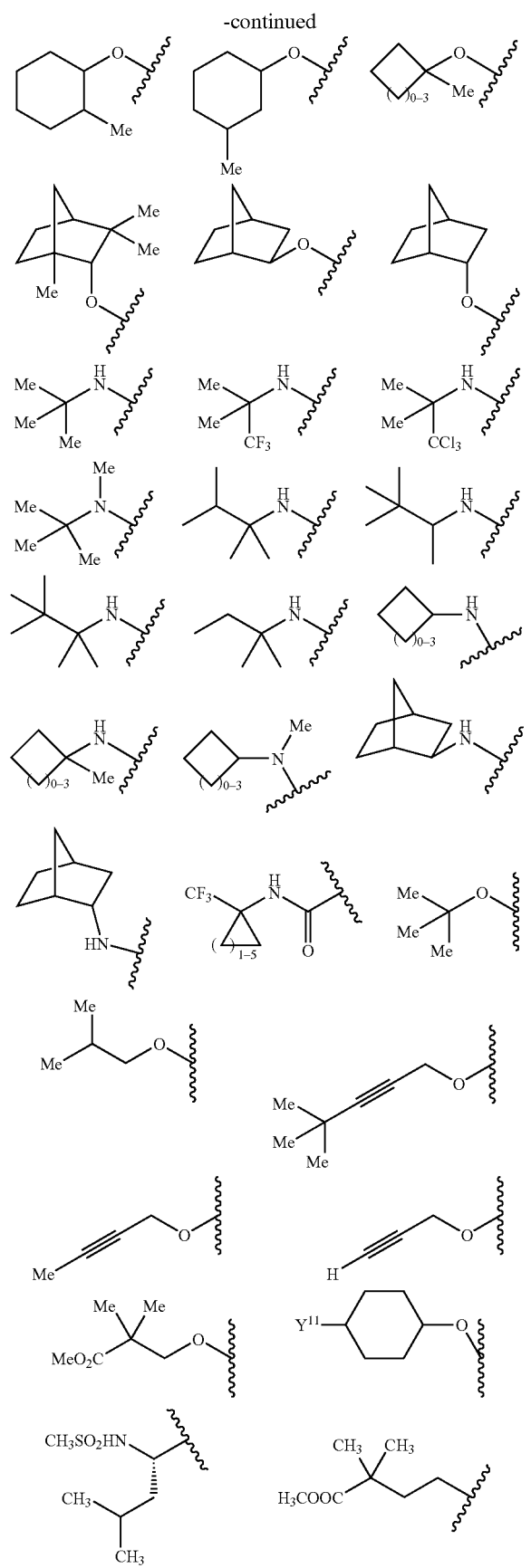
-continued
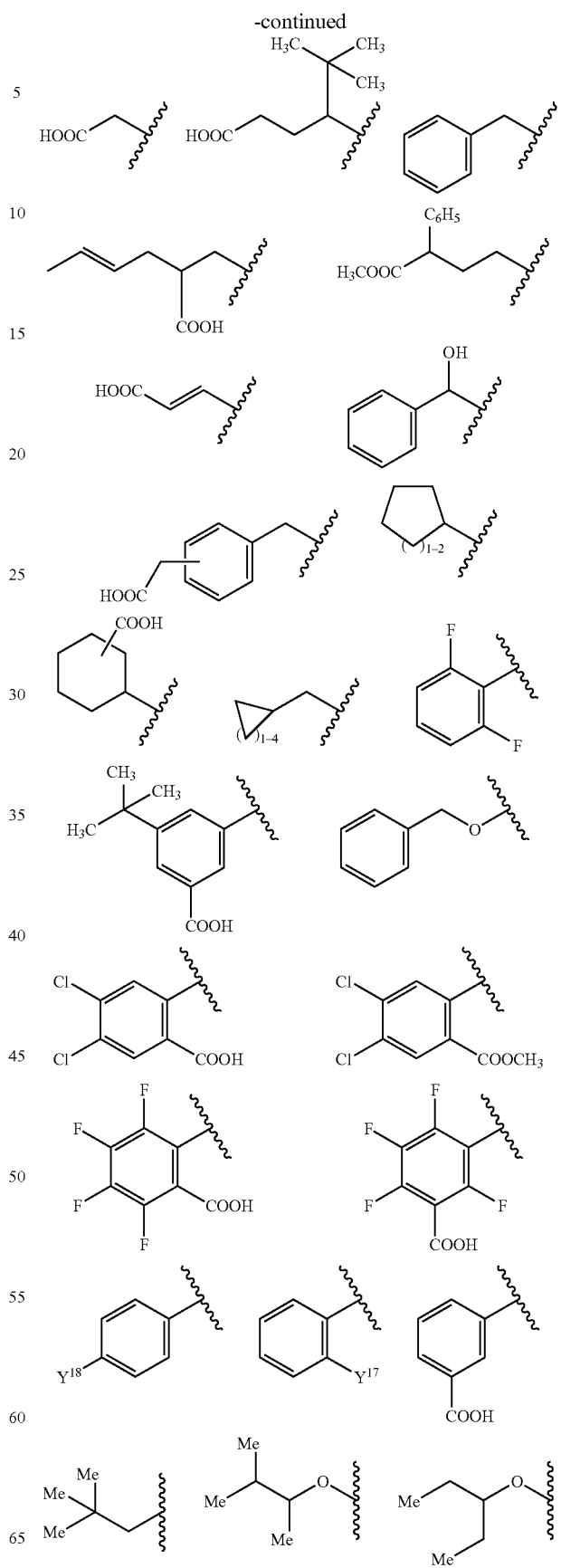

-continued
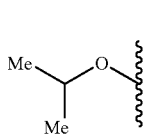 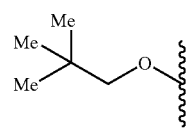
$Y^{17}$ is $CF_3$, $NO_2$, $CONH_2$, OH, $NH_2$ or COOH; and
$Y^{18}$ is F or COOH.
13. The compound according to claim 12, wherein Cap is selected from the group consisting of the following structures:
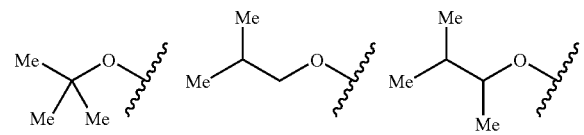
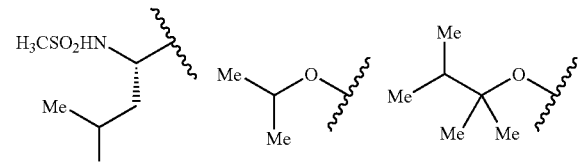
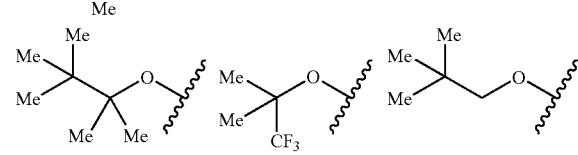
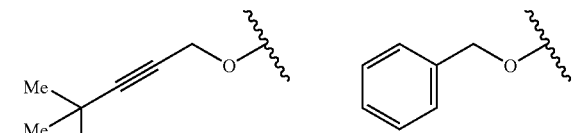
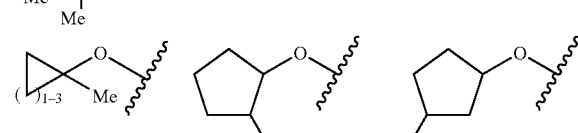
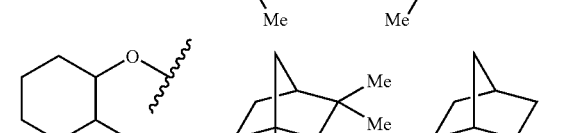
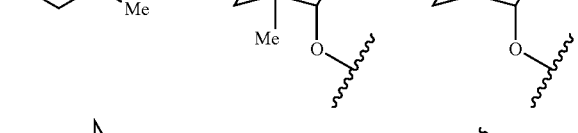
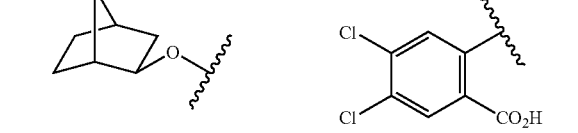
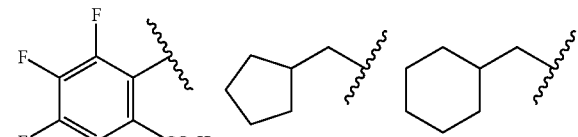
-continued
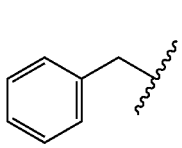 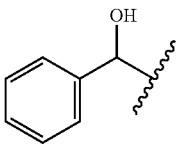 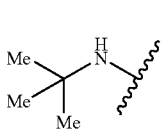
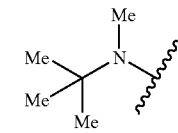 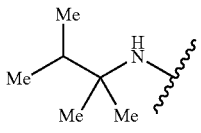
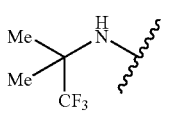 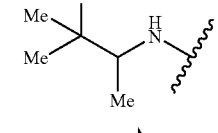
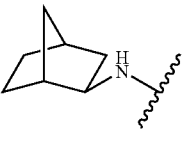
and
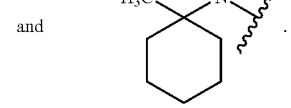
14. The compound according to claim 1, wherein W is C=O;
$R^3$ is selected from the group consisting of the following structures:
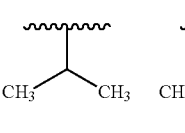 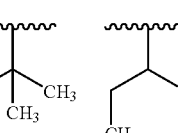 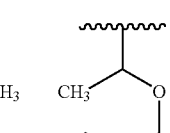
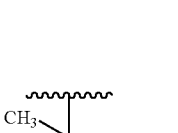 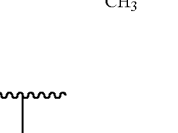 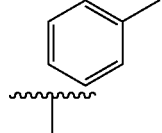
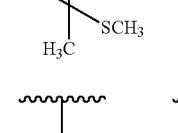 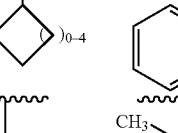 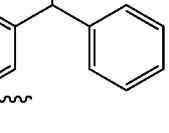
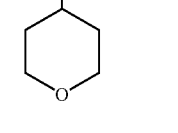 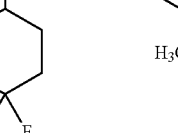 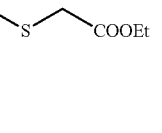
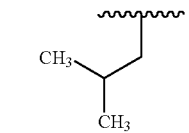 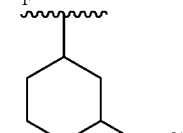 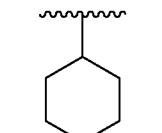

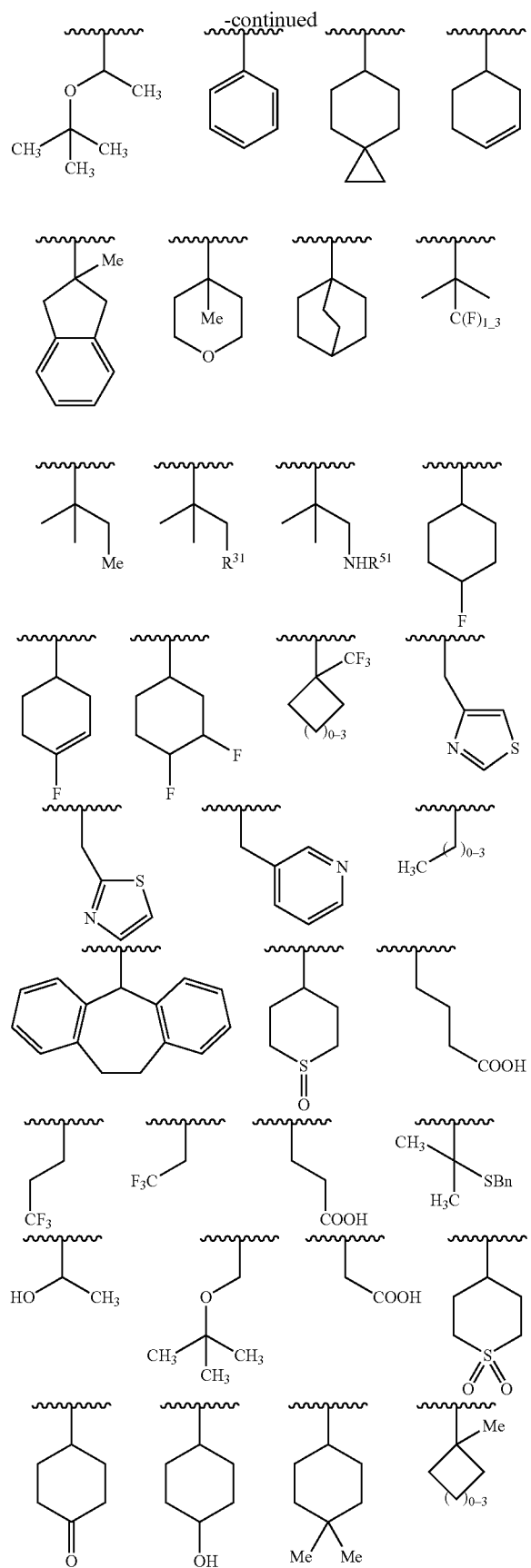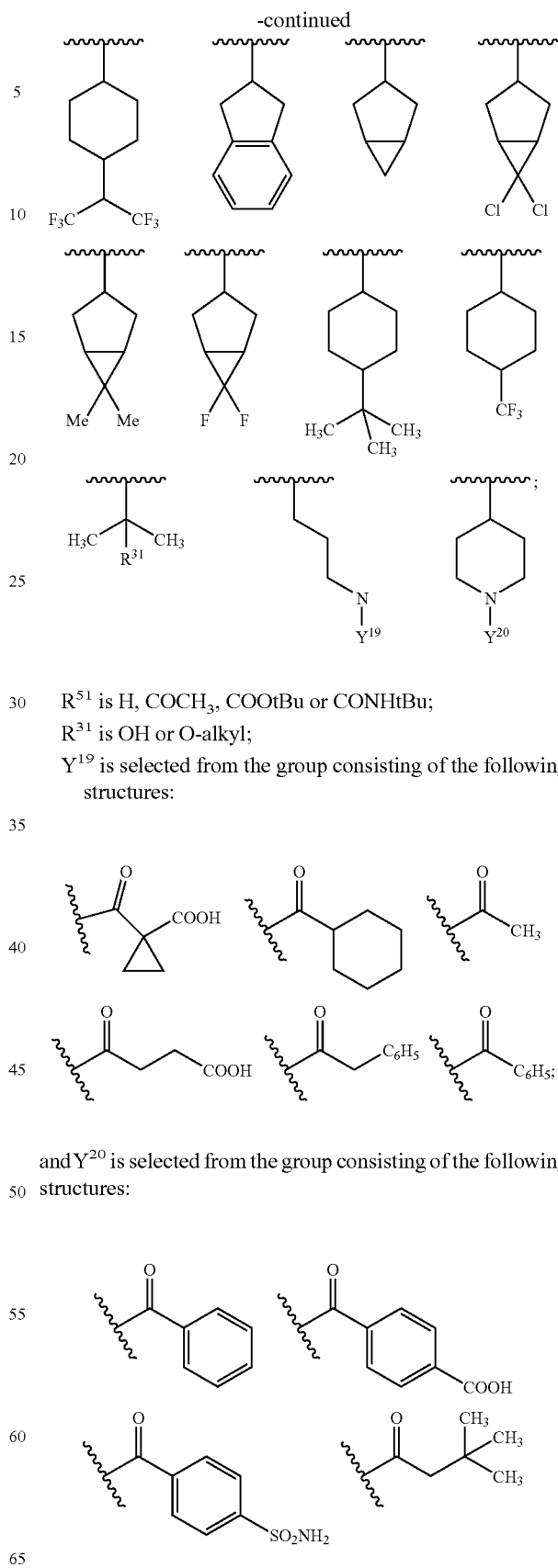
$R^{51}$ is H, $COCH_3$, $COOtBu$ or $CONHtBu$;
$R^{31}$ is OH or O-alkyl;
$Y^{19}$ is selected from the group consisting of the following structures:
and $Y^{20}$ is selected from the group consisting of the following structures:

-continued

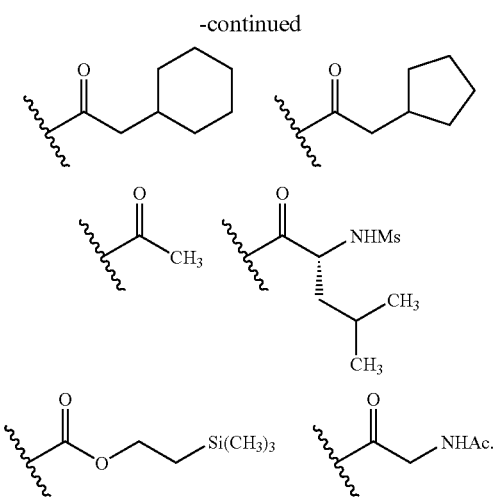

15. The compound according to claim 14, wherein $R^3$ is selected from the group consisting of the following structures:

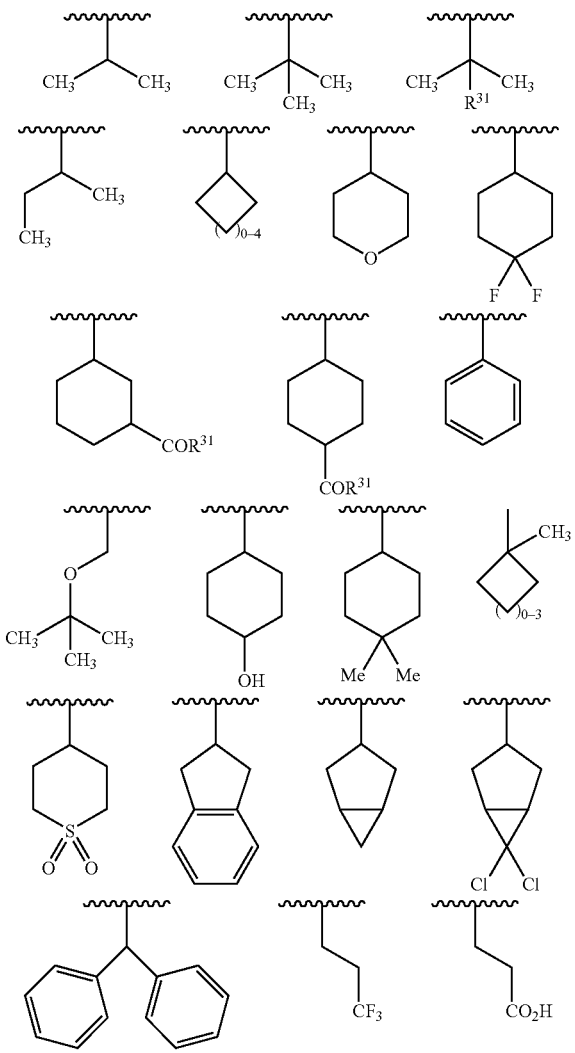

-continued

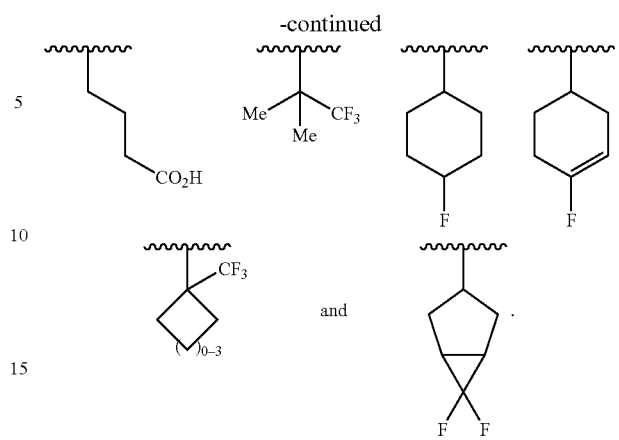

16. The compound according to claim 15, wherein $R^3$ is selected from the group consisting of the following structures:

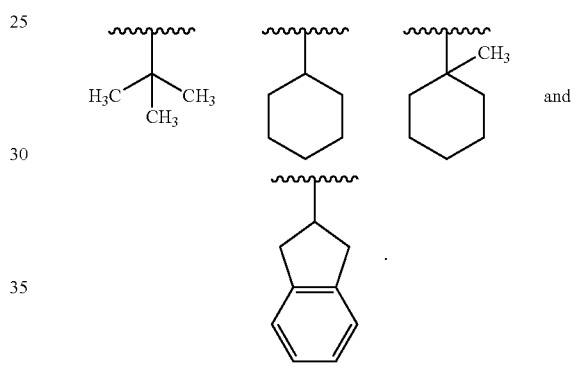

17. The compound according to claim 1, wherein W is C=O; P' is selected from the group consisting of the following structures:

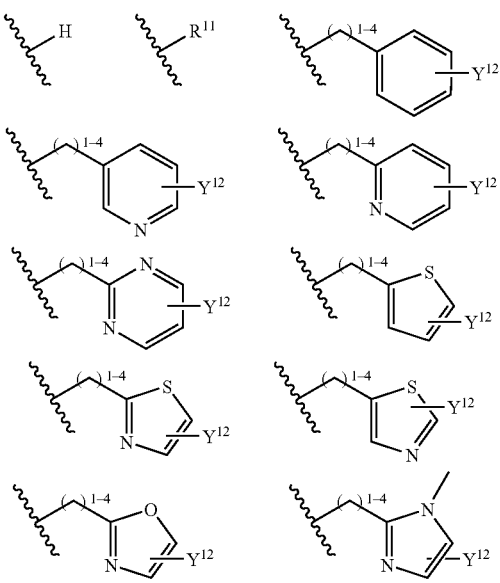

-continued

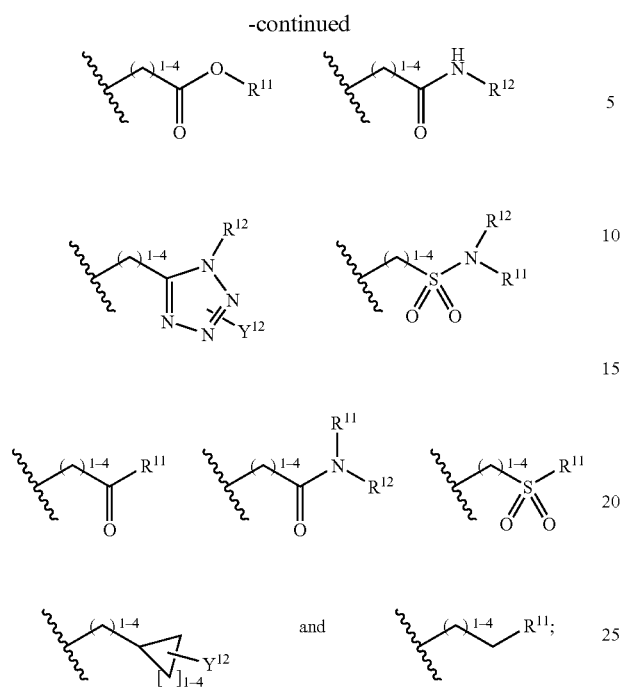

$R^{11}$ and $R^{12}$ are independently selected from the group consisting of: H, methyl, ethyl, propyl, propargyl, allyl, isopropyl, isobutyl, tert-butyl, benzyl, phenyl, 2-pyridyl, 3-pyridyl, 2-thiaphenyl, α-methylbenzyl, α,α-dimethylbenzyl, 1-methylcyclopropyl, 1-methylcyclopentyl and

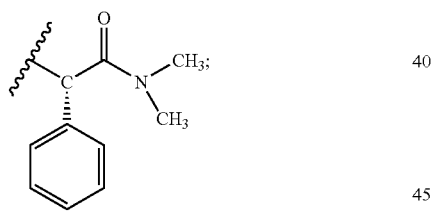

and $Y^{12}$ is one or more substituents independently selected from H, COOH, COOMe, OMe, F, Cl, Br, NH2, NHSO2CH3, CON(CH3)2, NHCOCH3, COOtBu, NO2, $SO_2NH_2$, $CF_3$, Me, Et, OH, $OCF_3$, and $CONH_2$.

18. The compound according to claim 17, wherein P' is selected from the group consisting of the following structures:

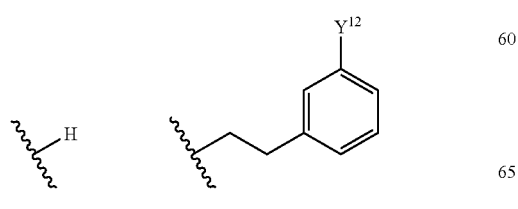

-continued

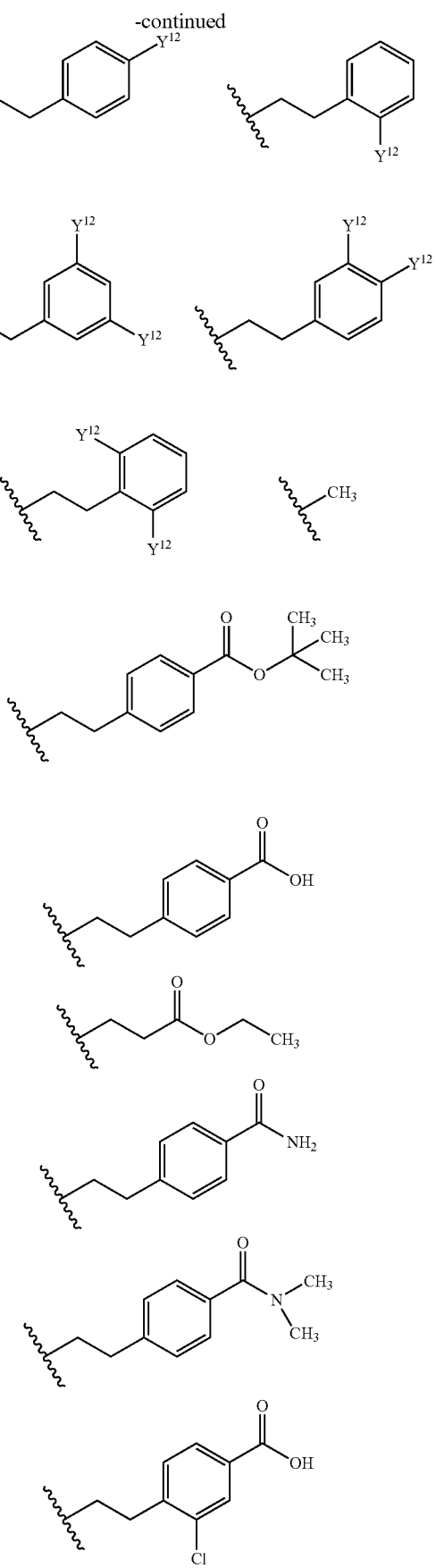

-continued
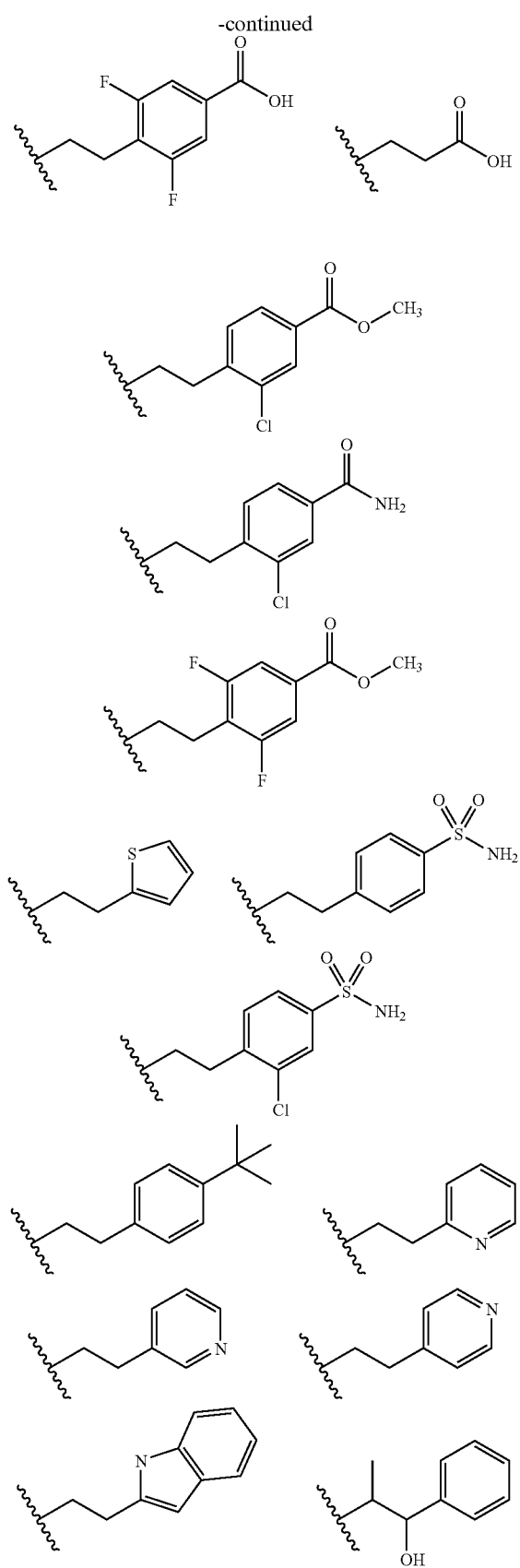
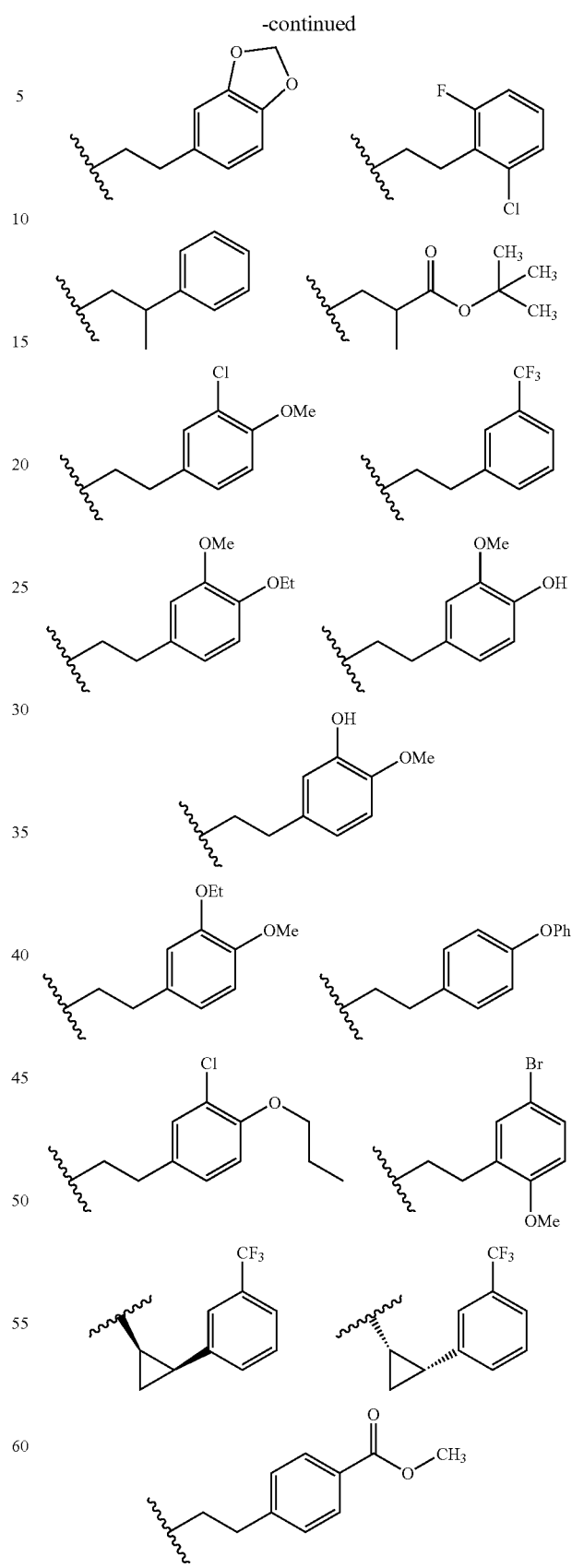

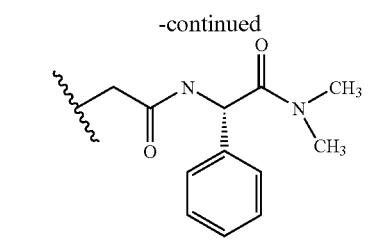
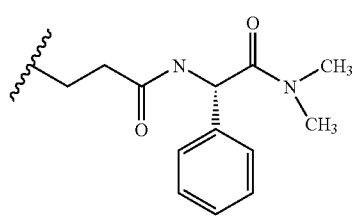
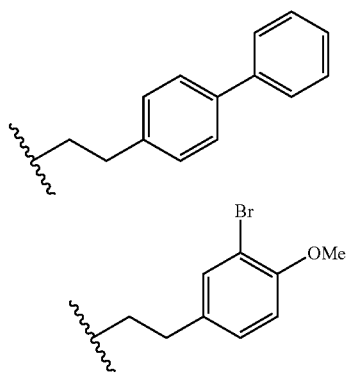
and
wherein $Y^{12}$ is selected from H, F, Cl, Br, Me, Et, OH, OMe, OEt, and $NH_2$.
19. The compound according to claim 18, wherein P' is selected from the group consisting of the following structures:
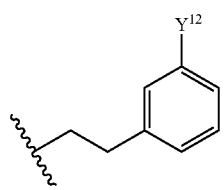 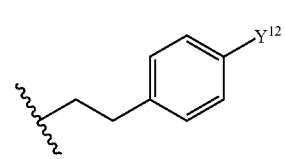
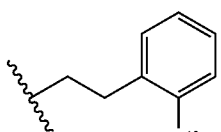 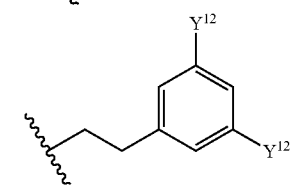
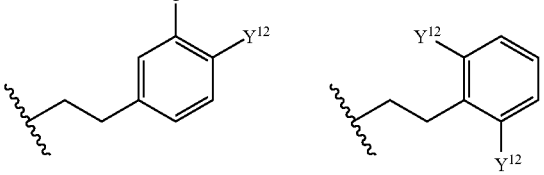
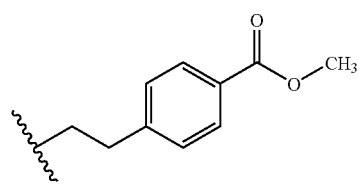
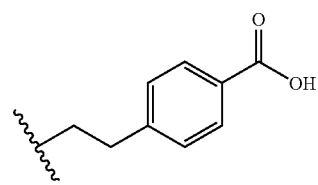
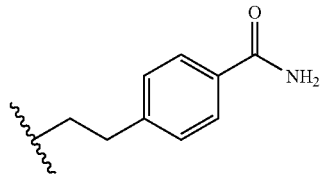
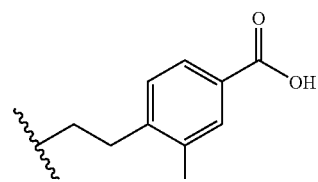
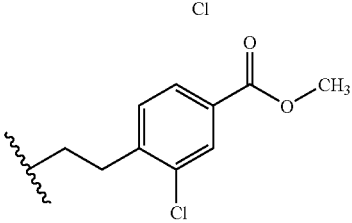
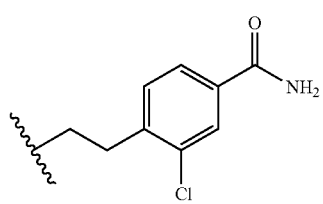
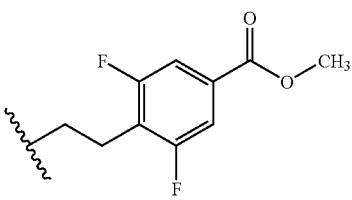
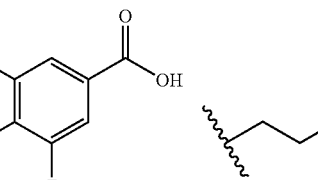

-continued
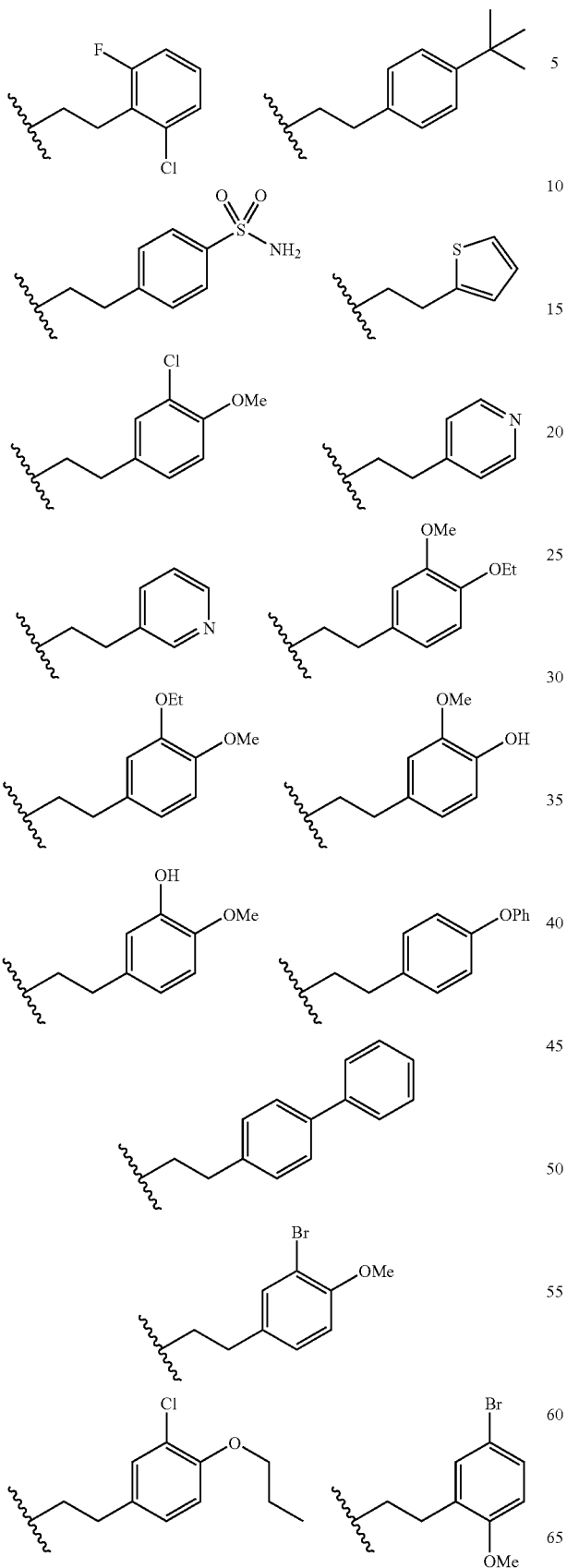
-continued
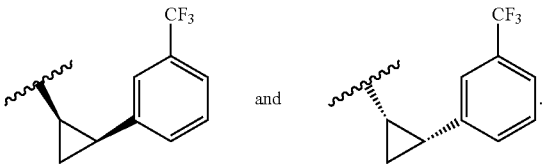
20. The compound of claim 1, represented by structural Formula 7:
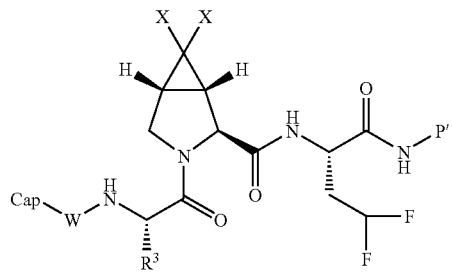
Formula 7
wherein X is $CH_3$, F, Cl or Br.
21. The compound according to Claim 20, wherein Cap is selected from the group consisting of the following structures:
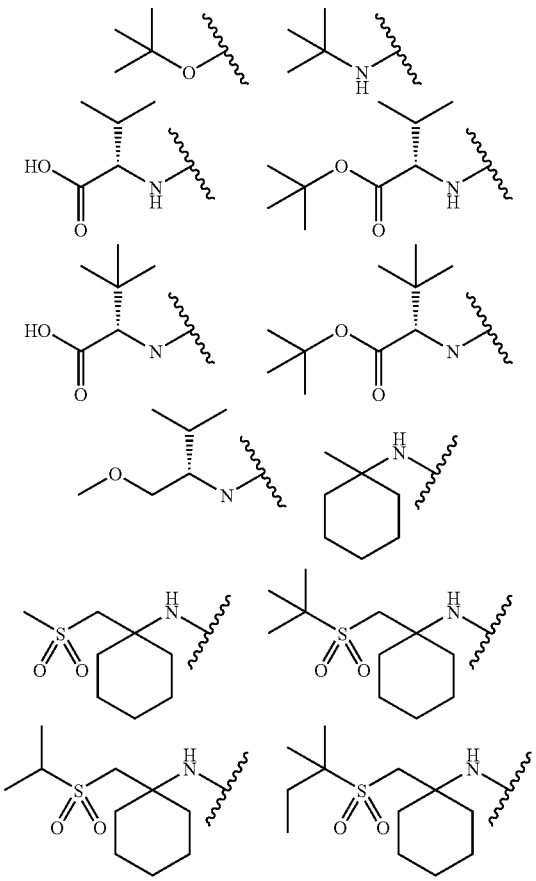

-continued
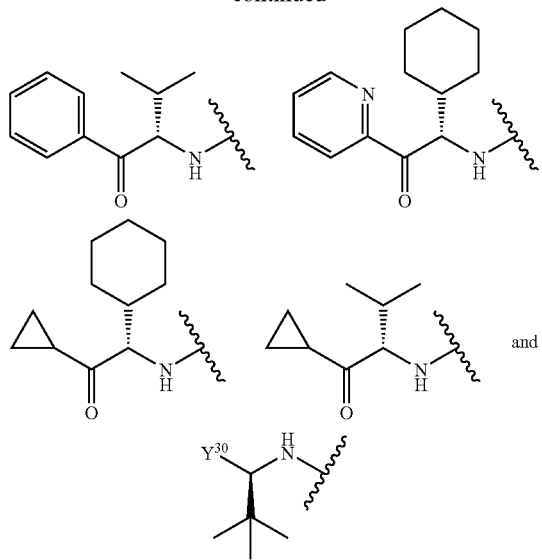
wherein $Y^{30}$ is selected from the group consisting of the following structures:
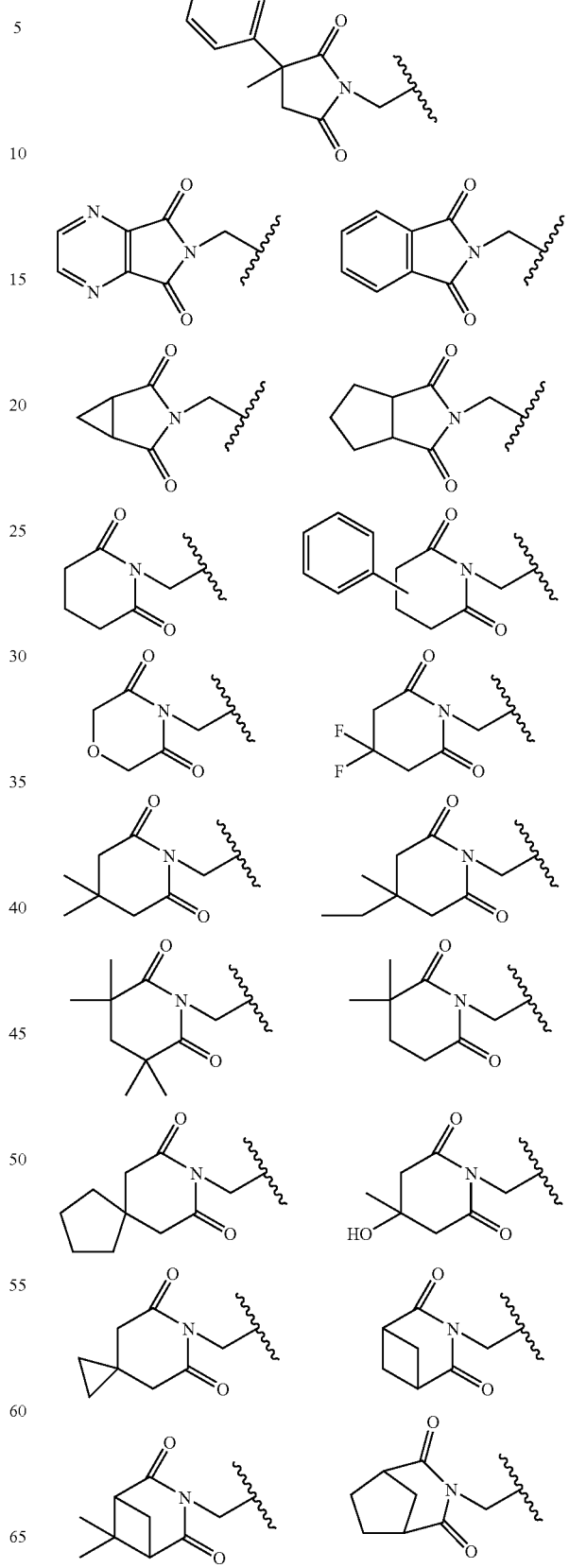
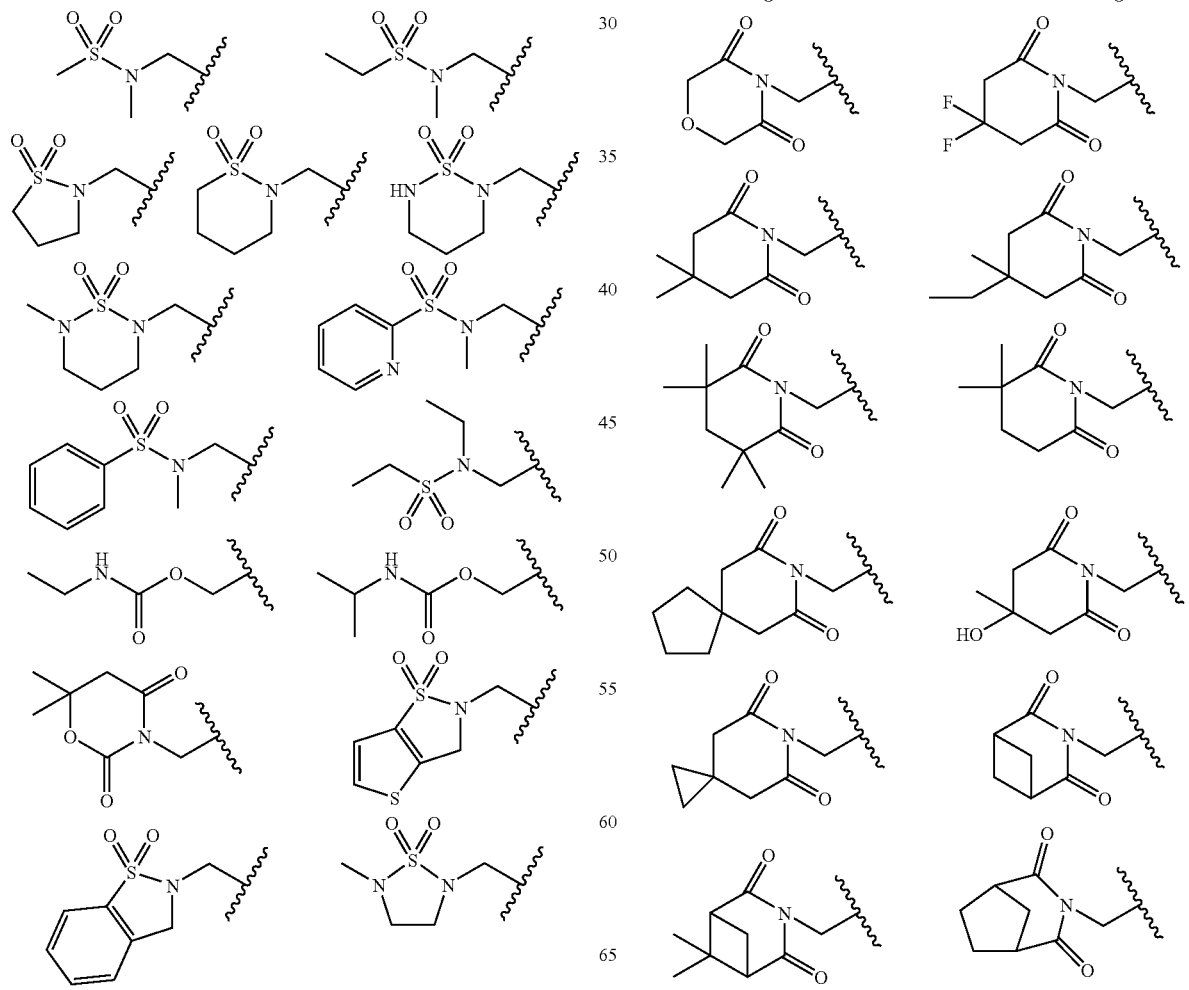

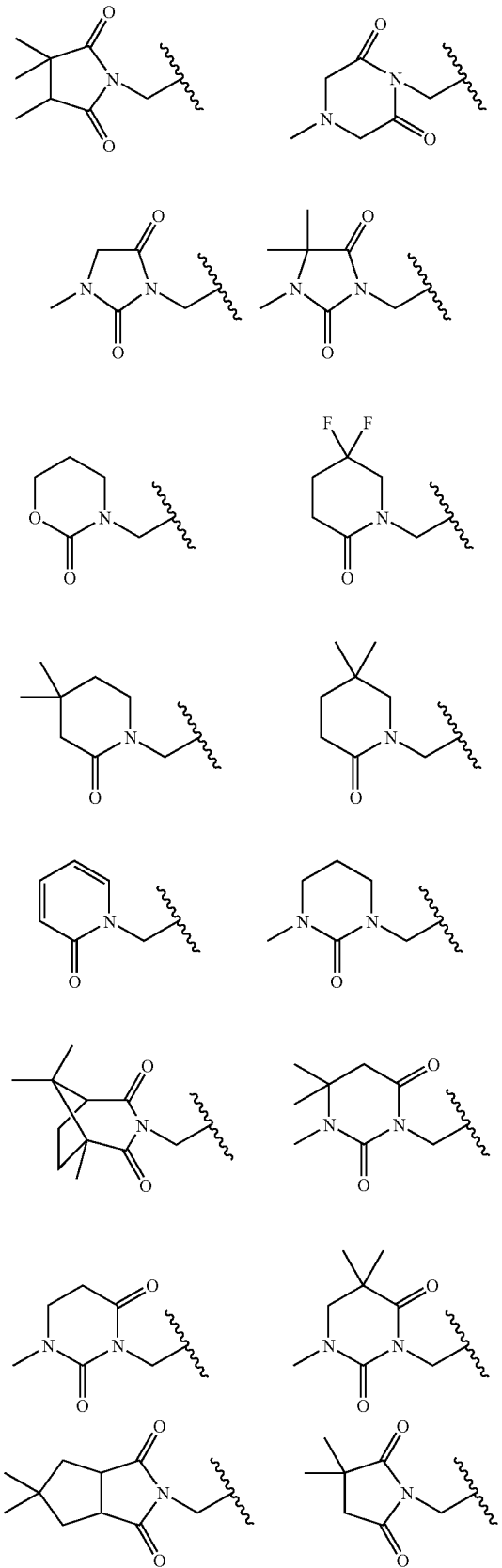
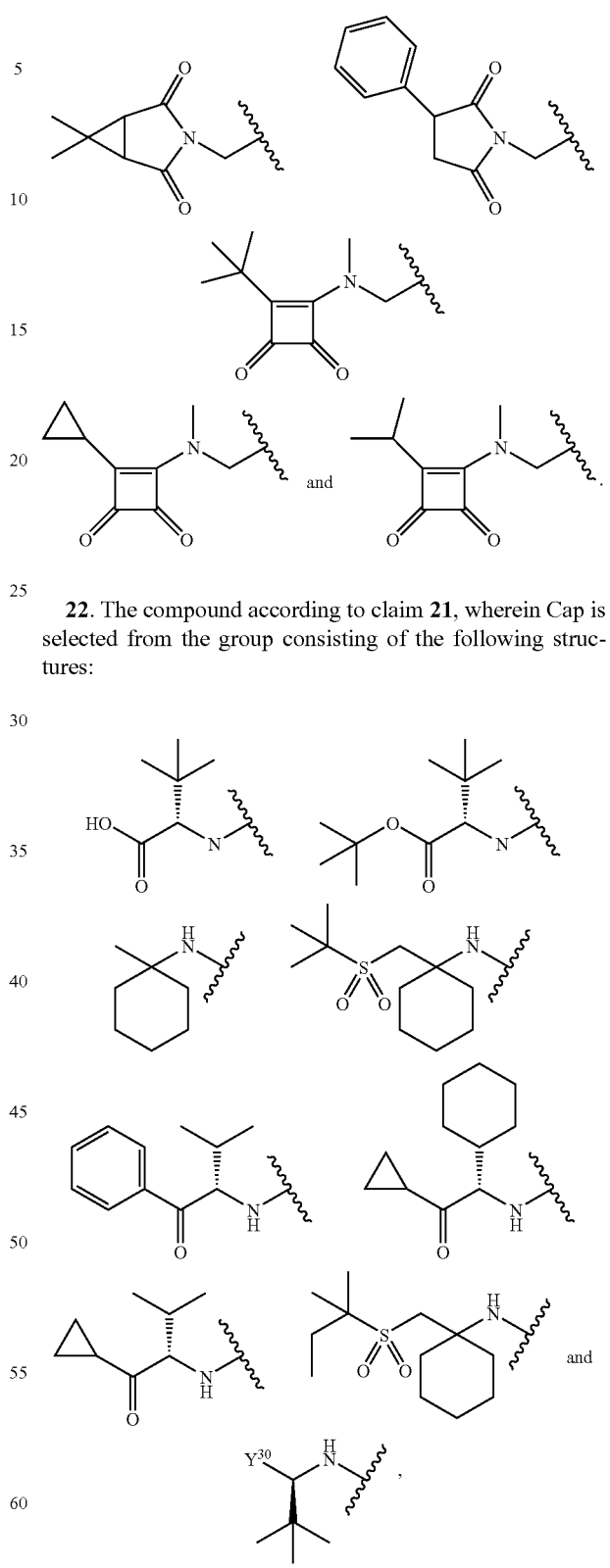
22. The compound according to claim 21, wherein Cap is selected from the group consisting of the following structures:
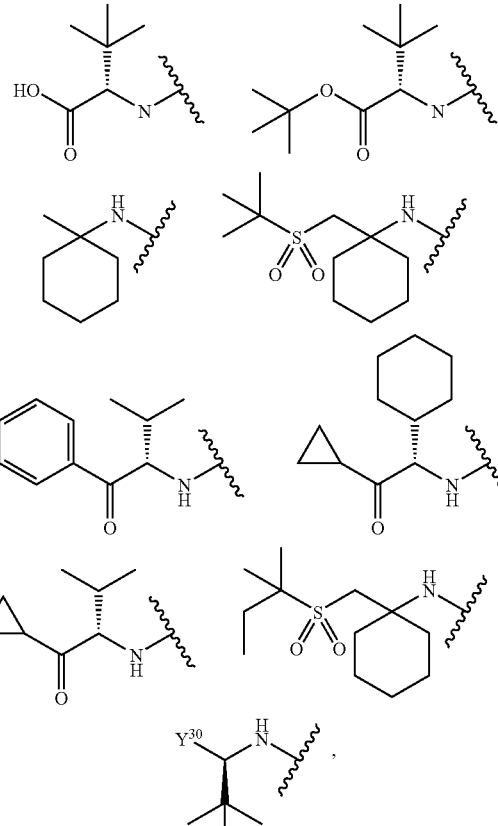
wherein $Y^{30}$ is selected from the group consisting of the following structures:

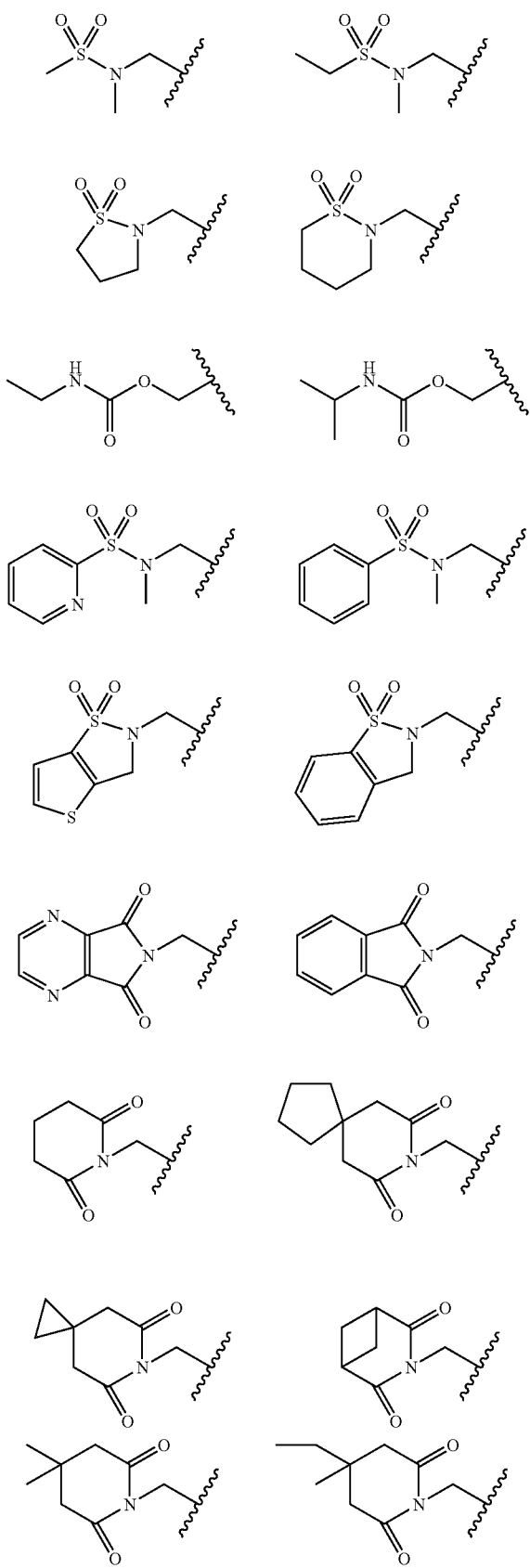
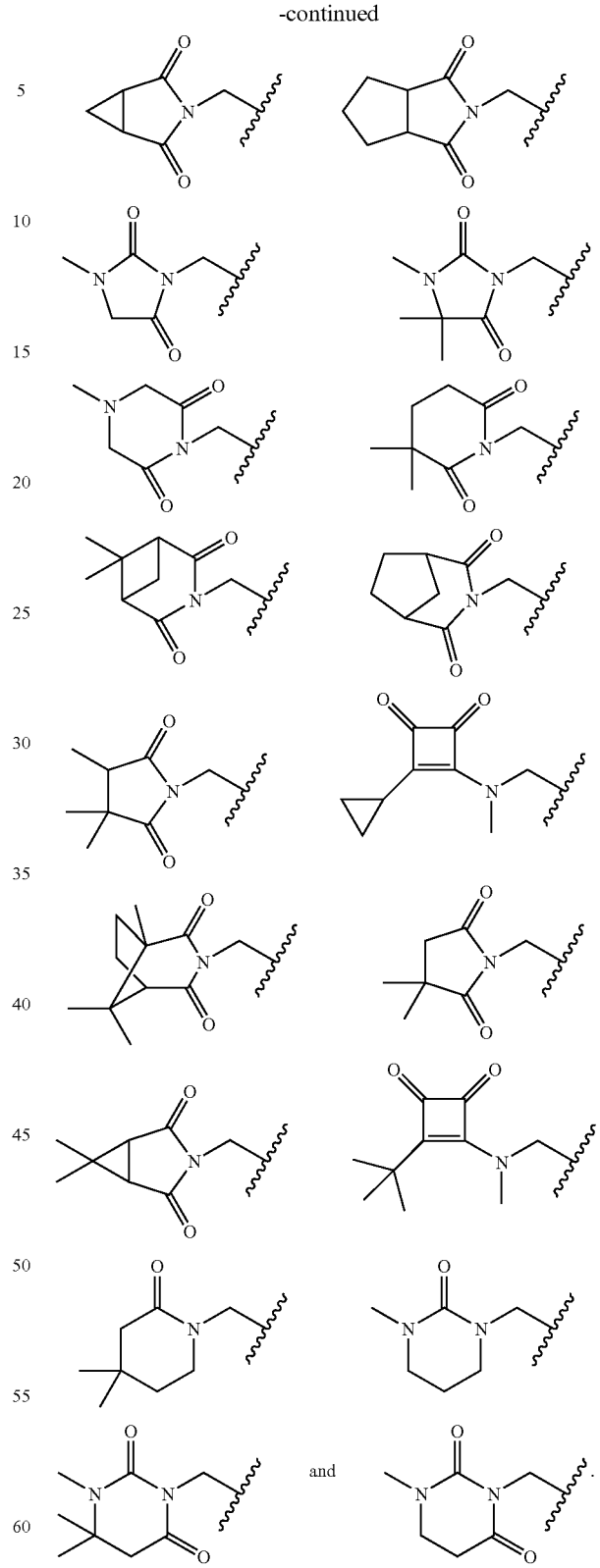
23. The compound according to claim 20, wherein P' is selected from the group consisting of the following structures:

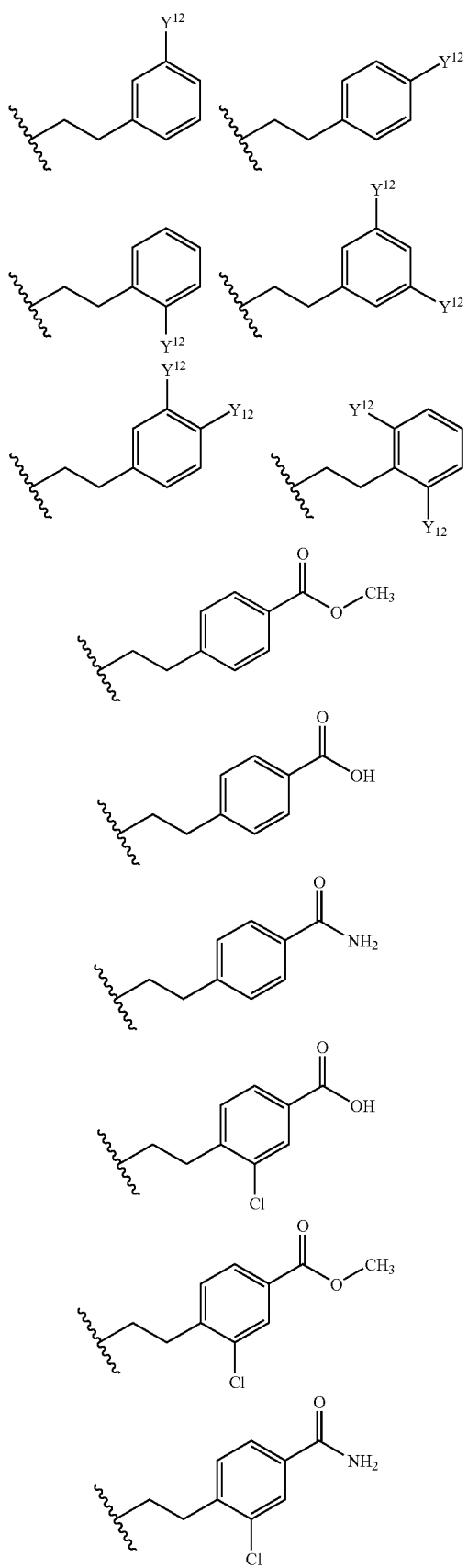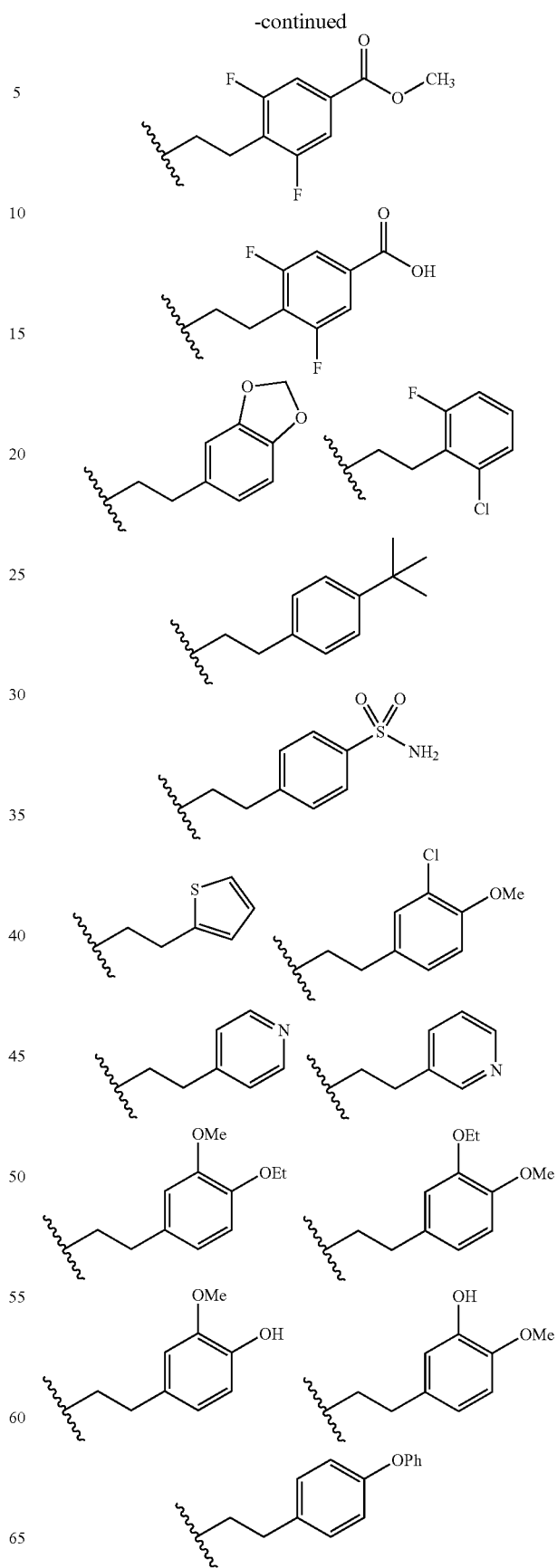

-continued
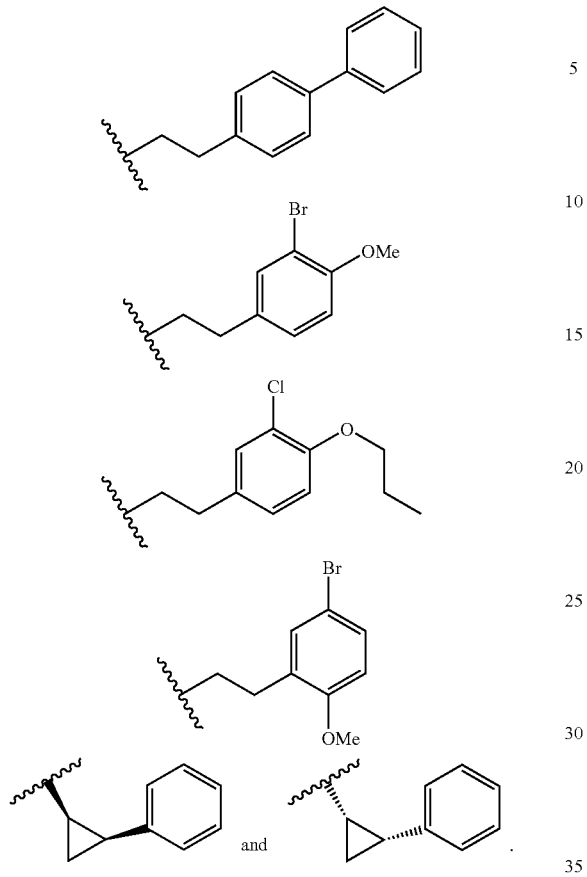
24. The compound according to claim 23, wherein P' is selected from the group consisting of the following structures:
-continued
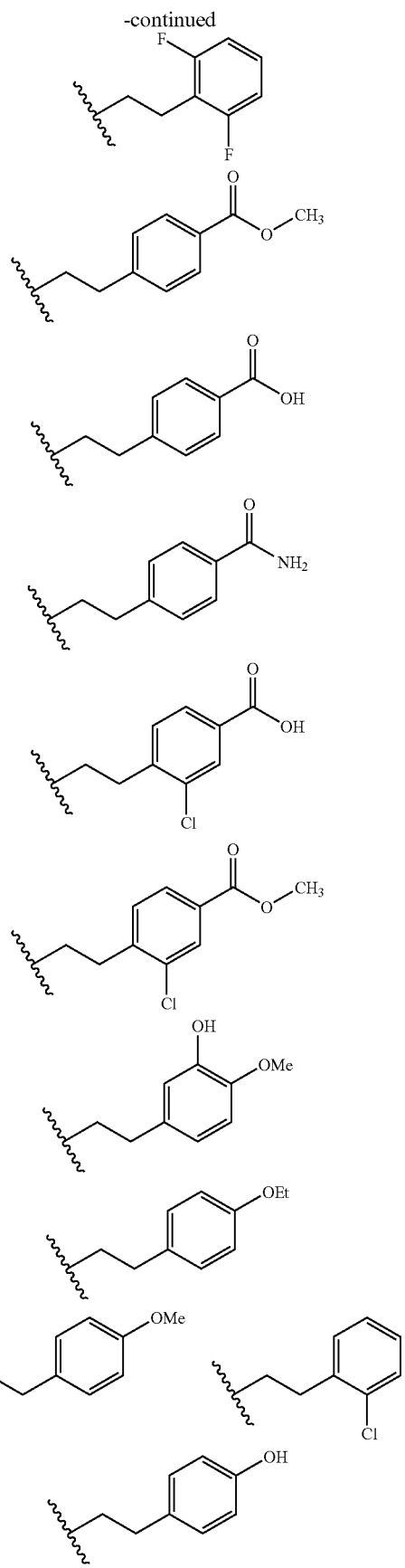

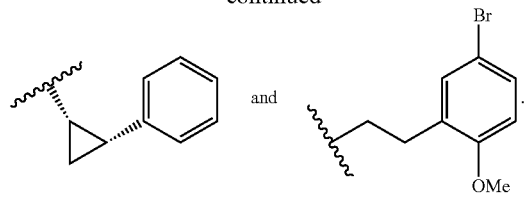 and
25. The compound according to claim 20, wherein W is C=O.
26. The compound according to claim 20, wherein $R_3$ is selected from the group consisting of the following structures:
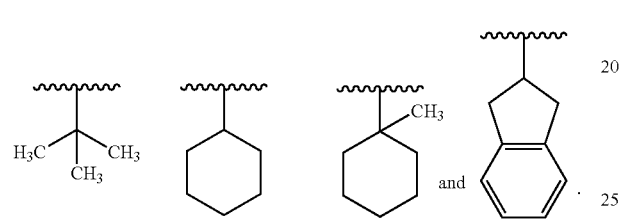
27. The compound according to claim 20, wherein Cap is selected from the group consisting of the following structures:
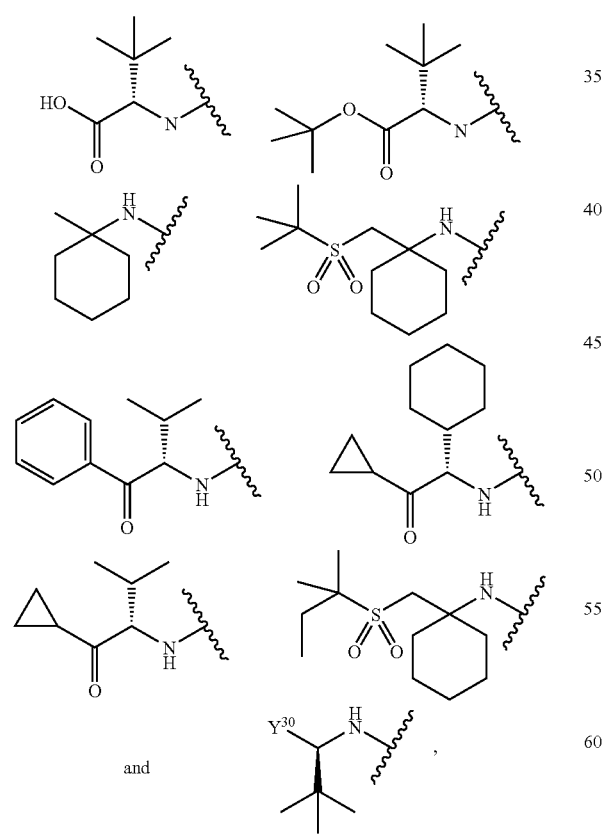
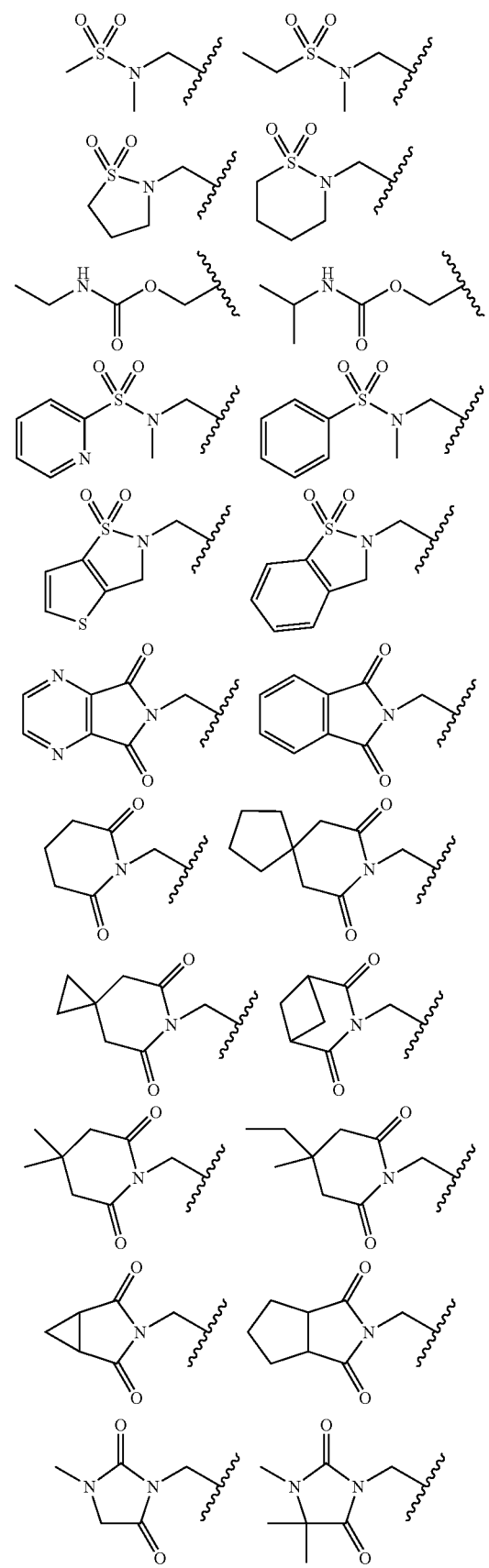
wherein $Y^{30}$ is selected from the group consisting of the following structures:

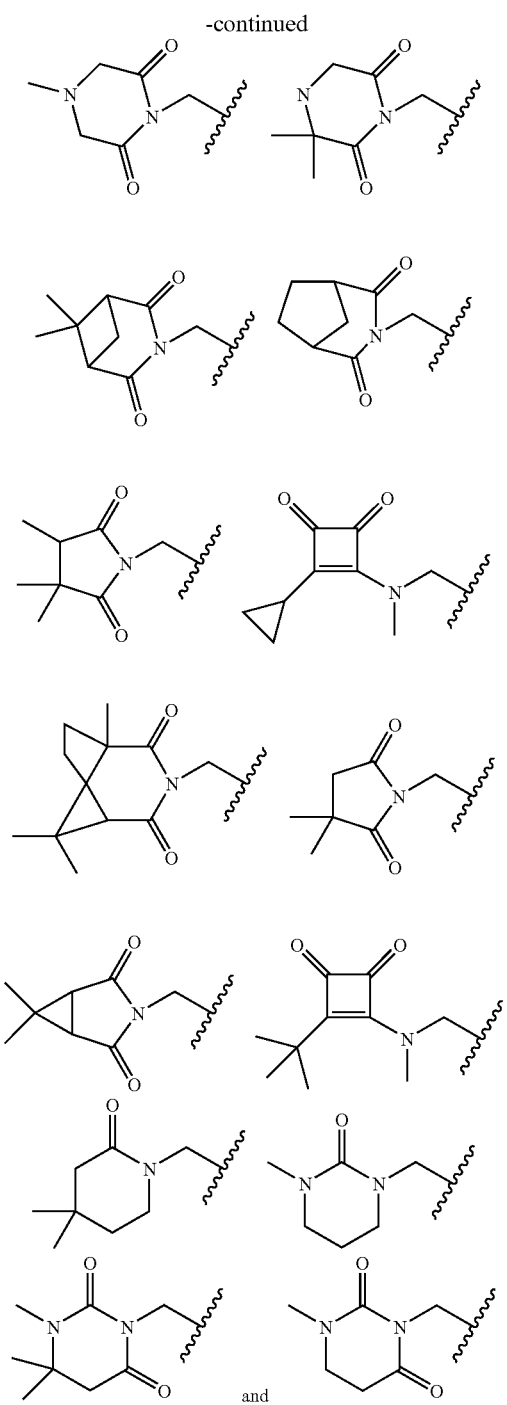
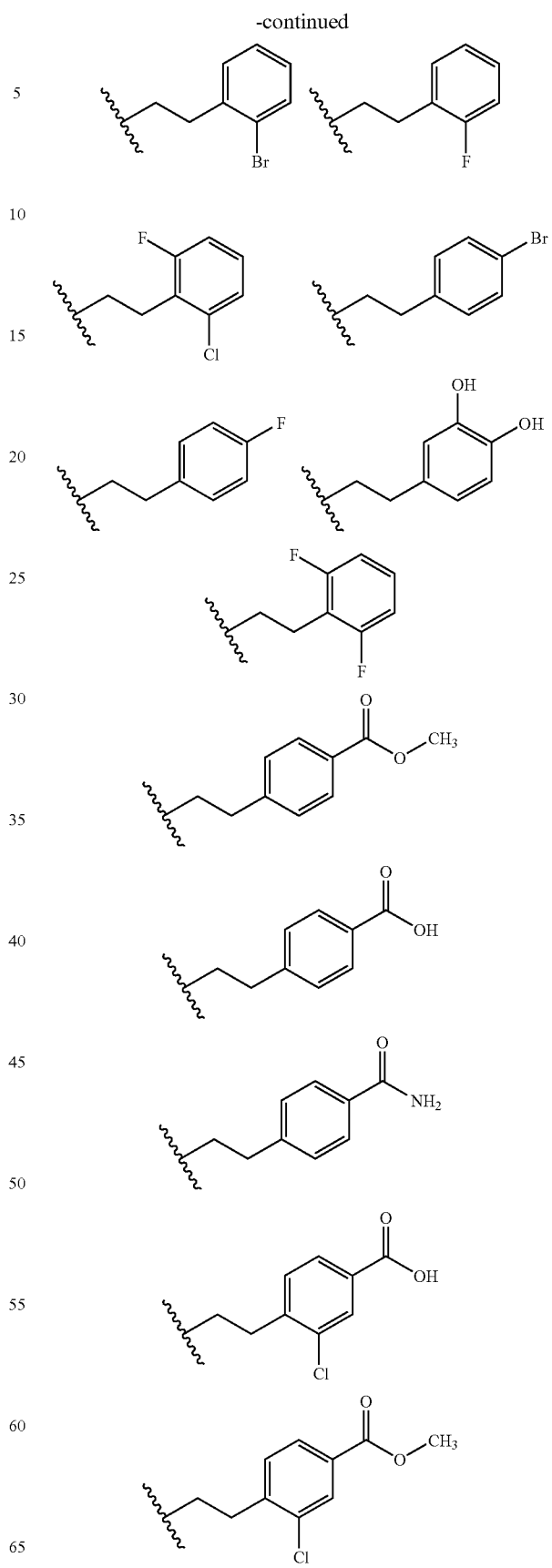
P' is selected from the group consisting of the following structures:
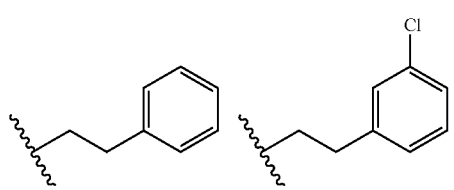

-continued
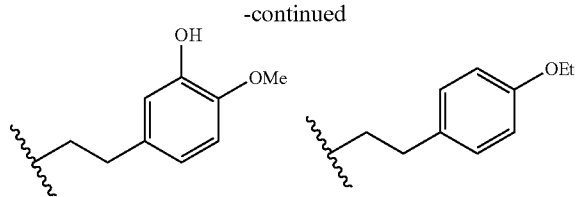
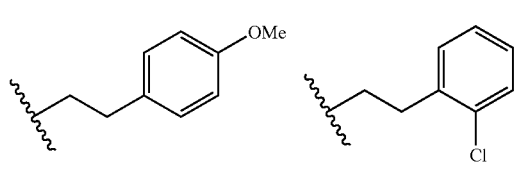
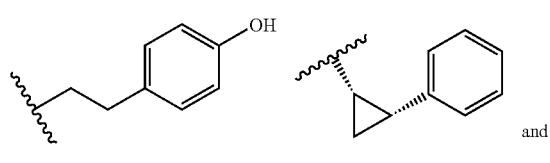
R³ is
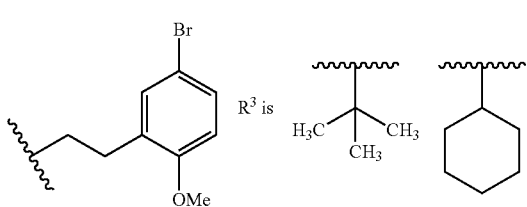
or
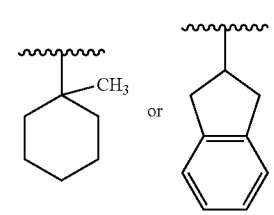
and W is C=O.
28. The compound according to claim 27, wherein Cap is selected from the group consisting of the following structures:
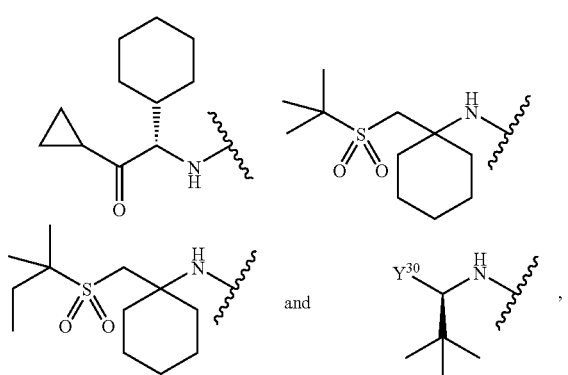
wherein Y³⁰ is selected from the group consisting of the following structures:
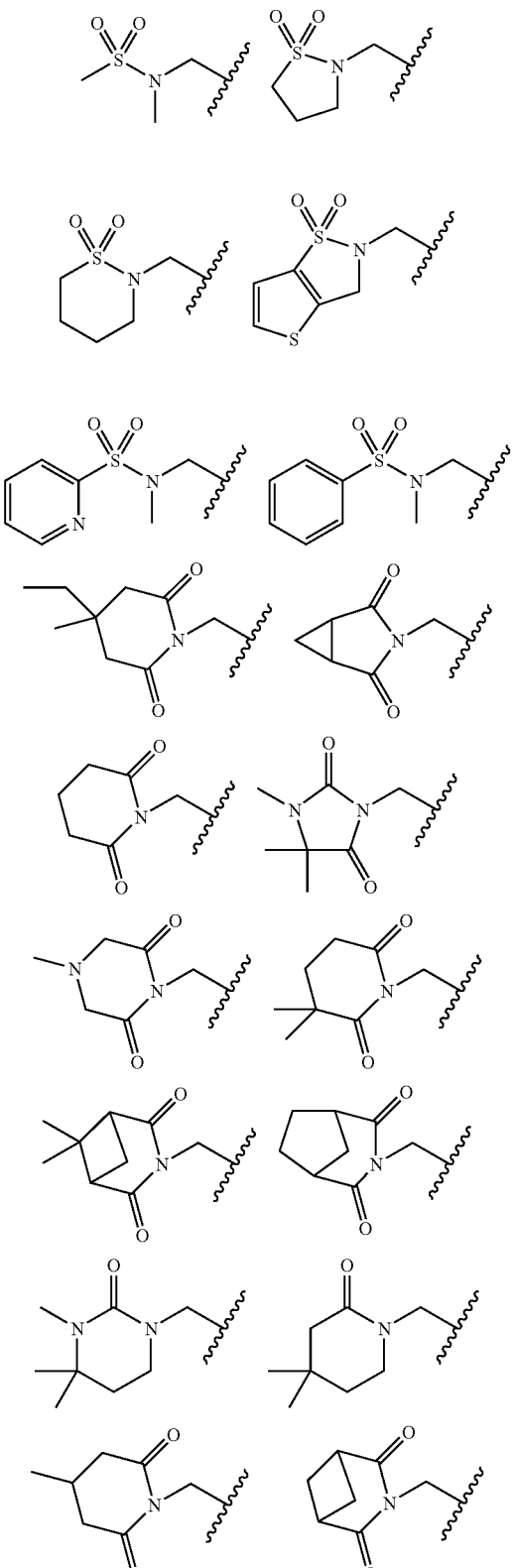

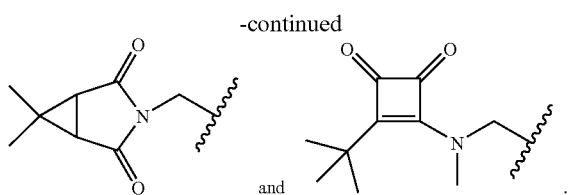
29. A compound selected from the following structures:
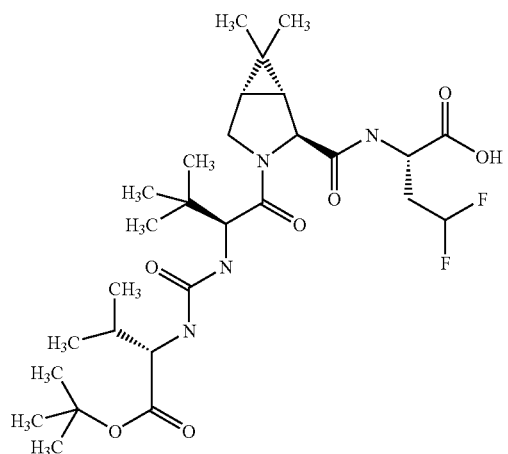
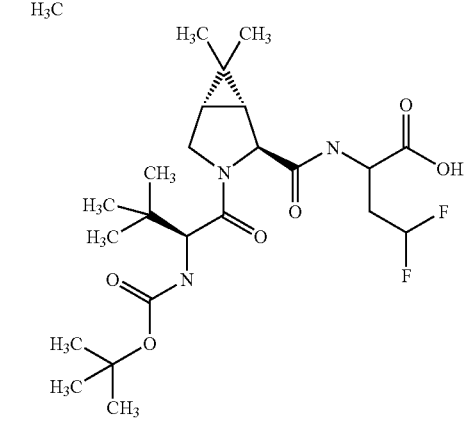
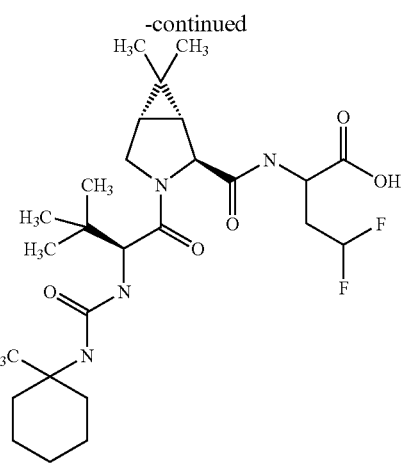
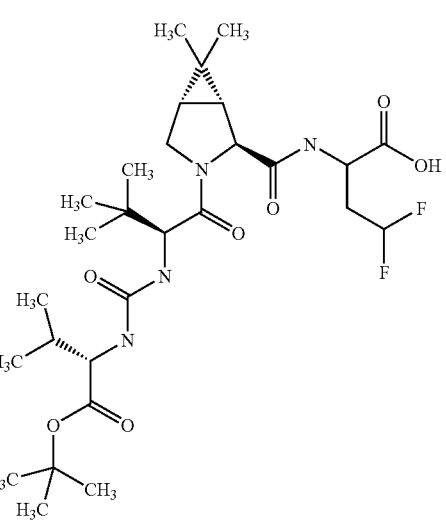
or a pharmaceutically acceptable salt thereof.
30. A compound selected from the following structures:
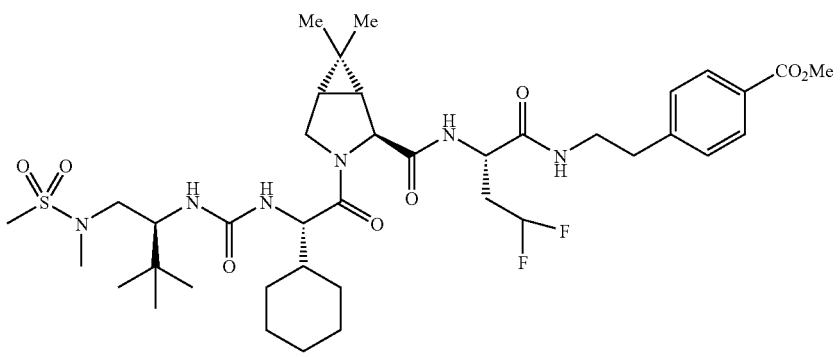

-continued
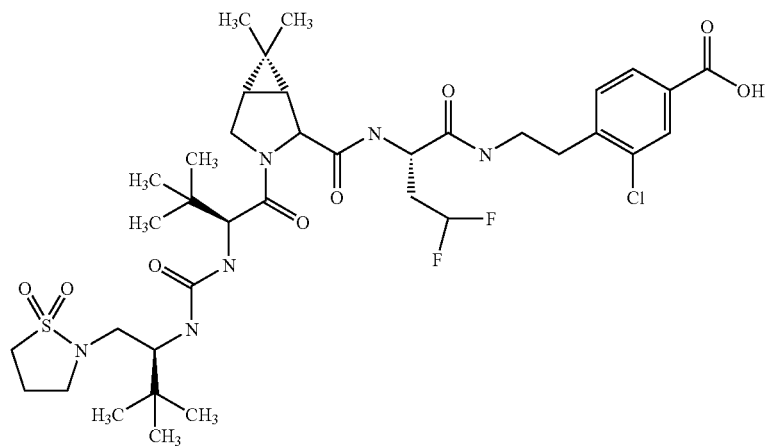
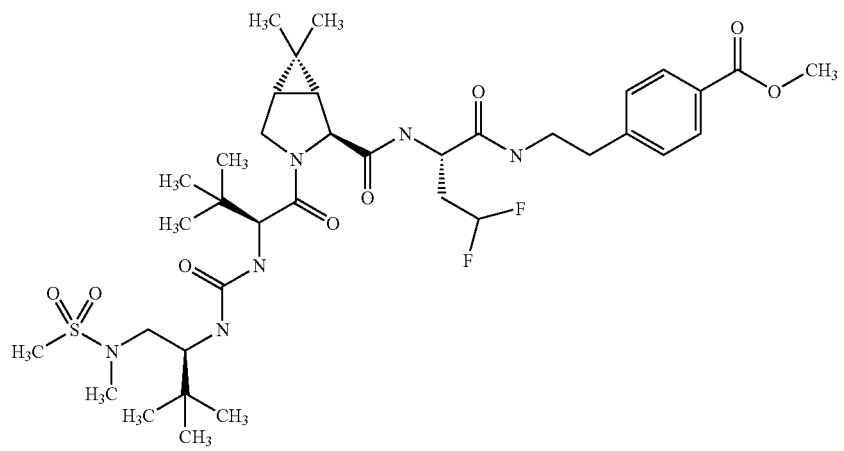
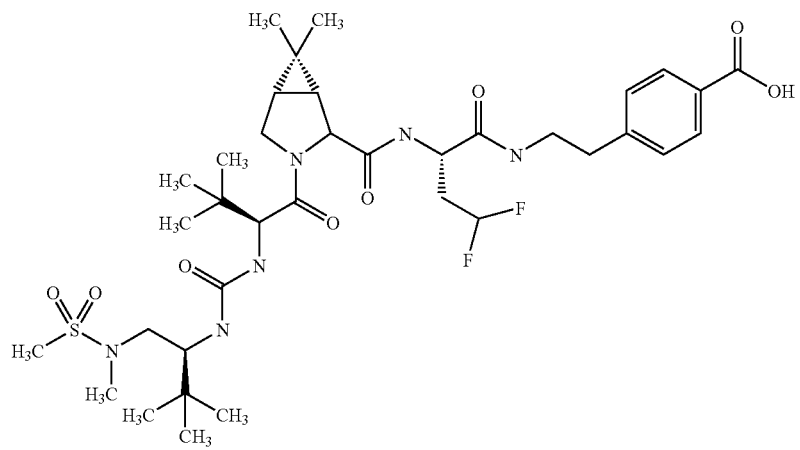

-continued
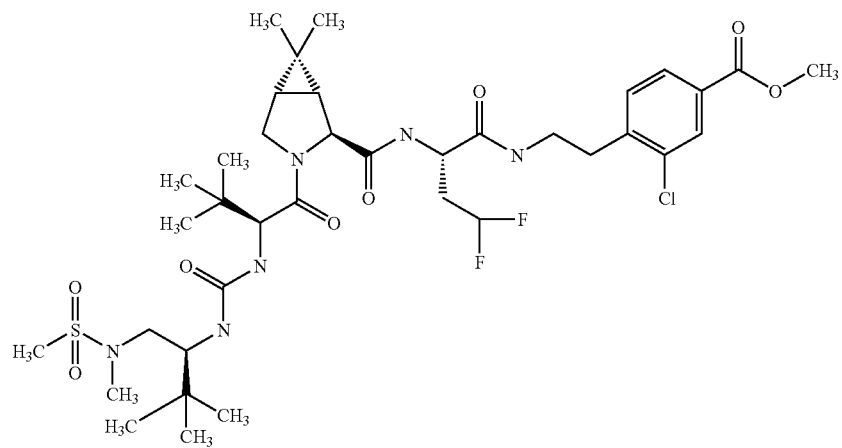
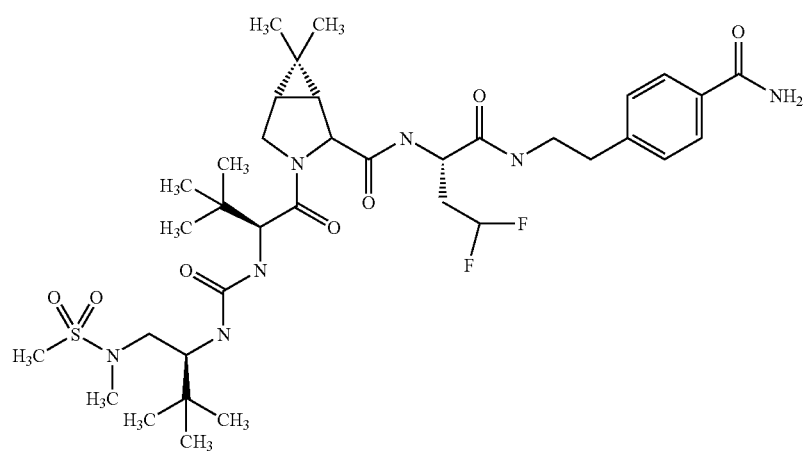
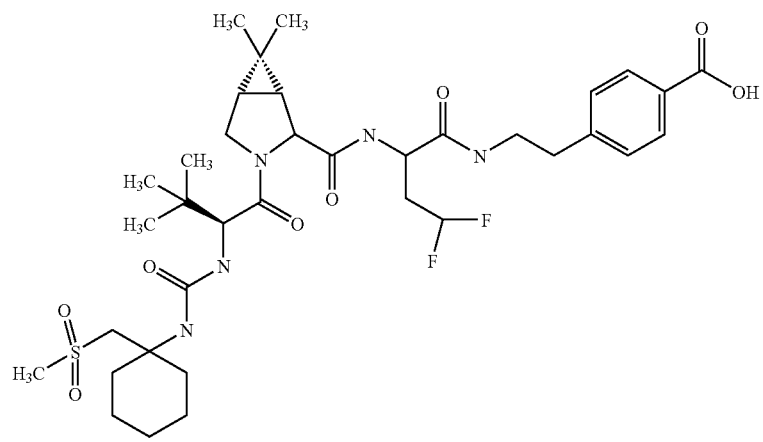

-continued
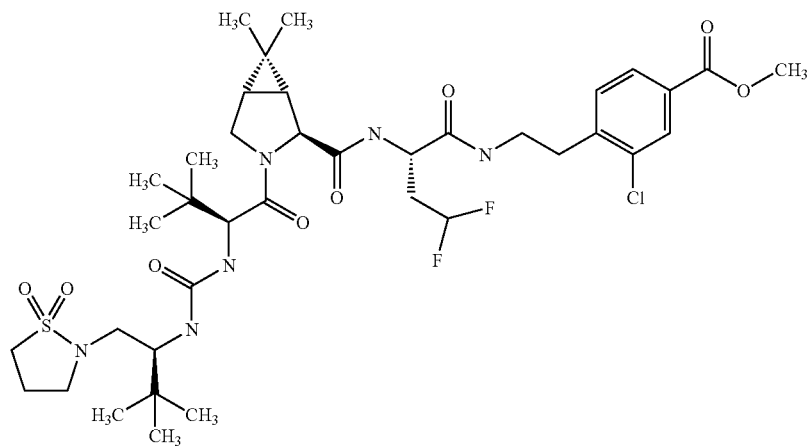
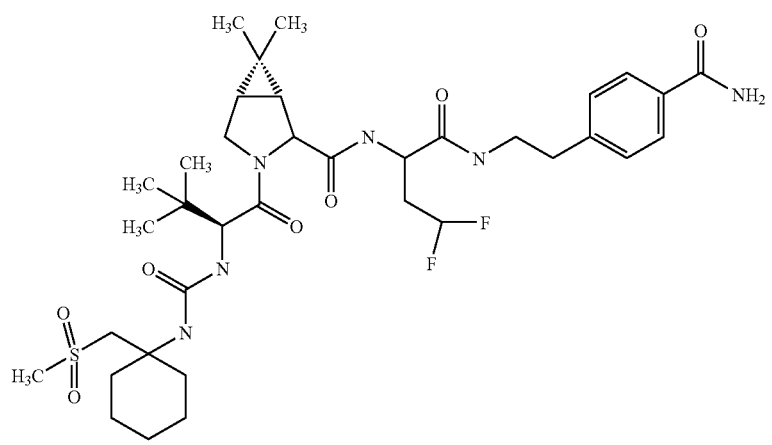
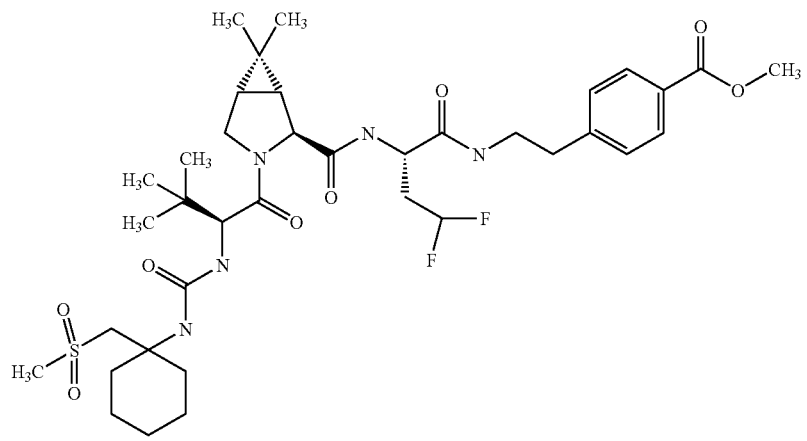

-continued
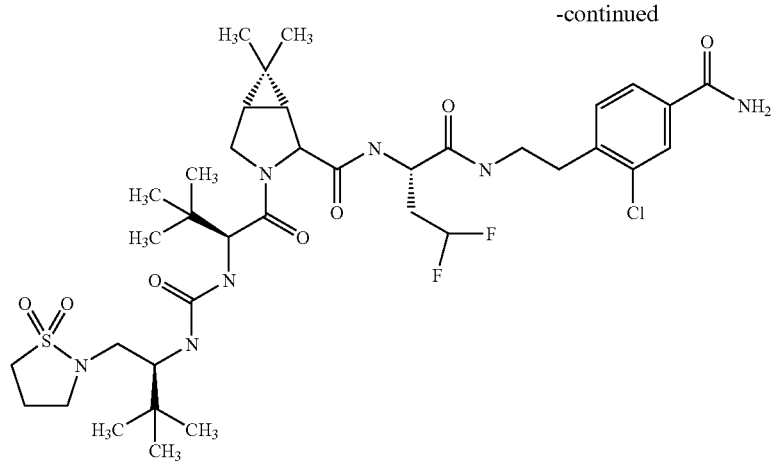
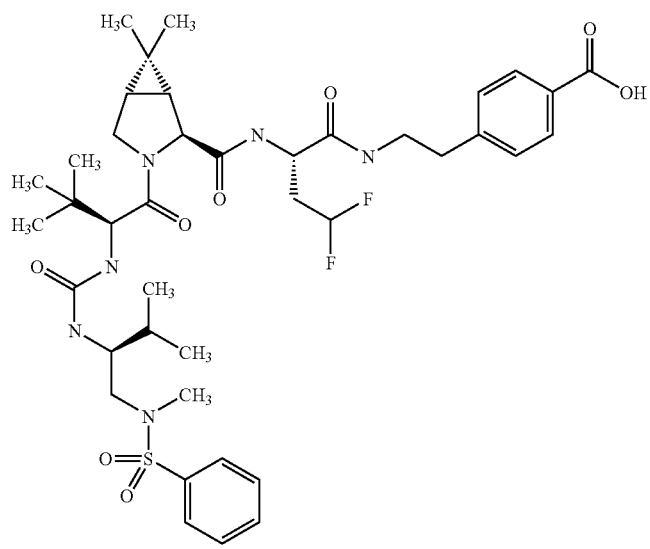
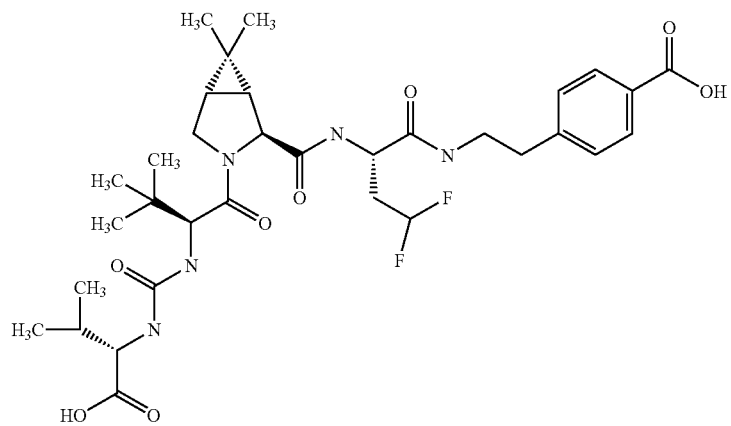

-continued
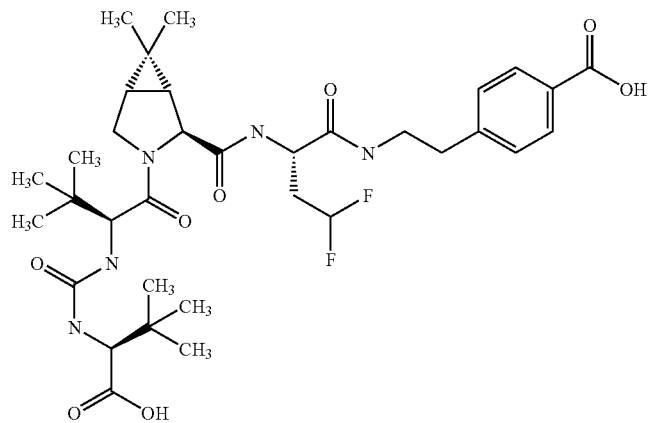
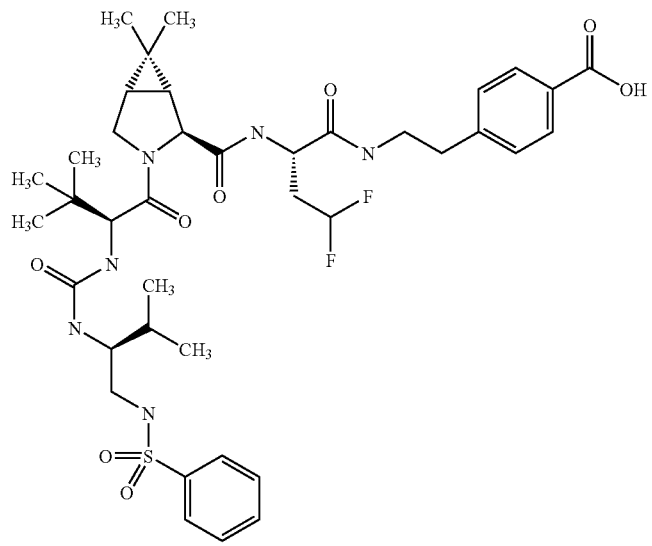
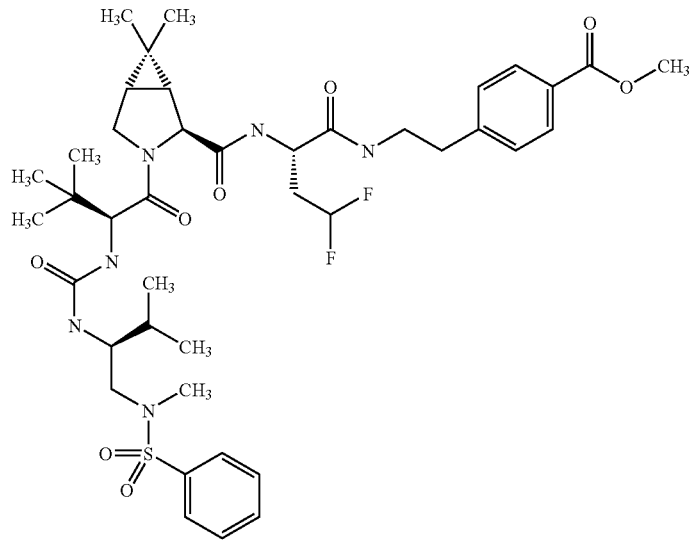

-continued
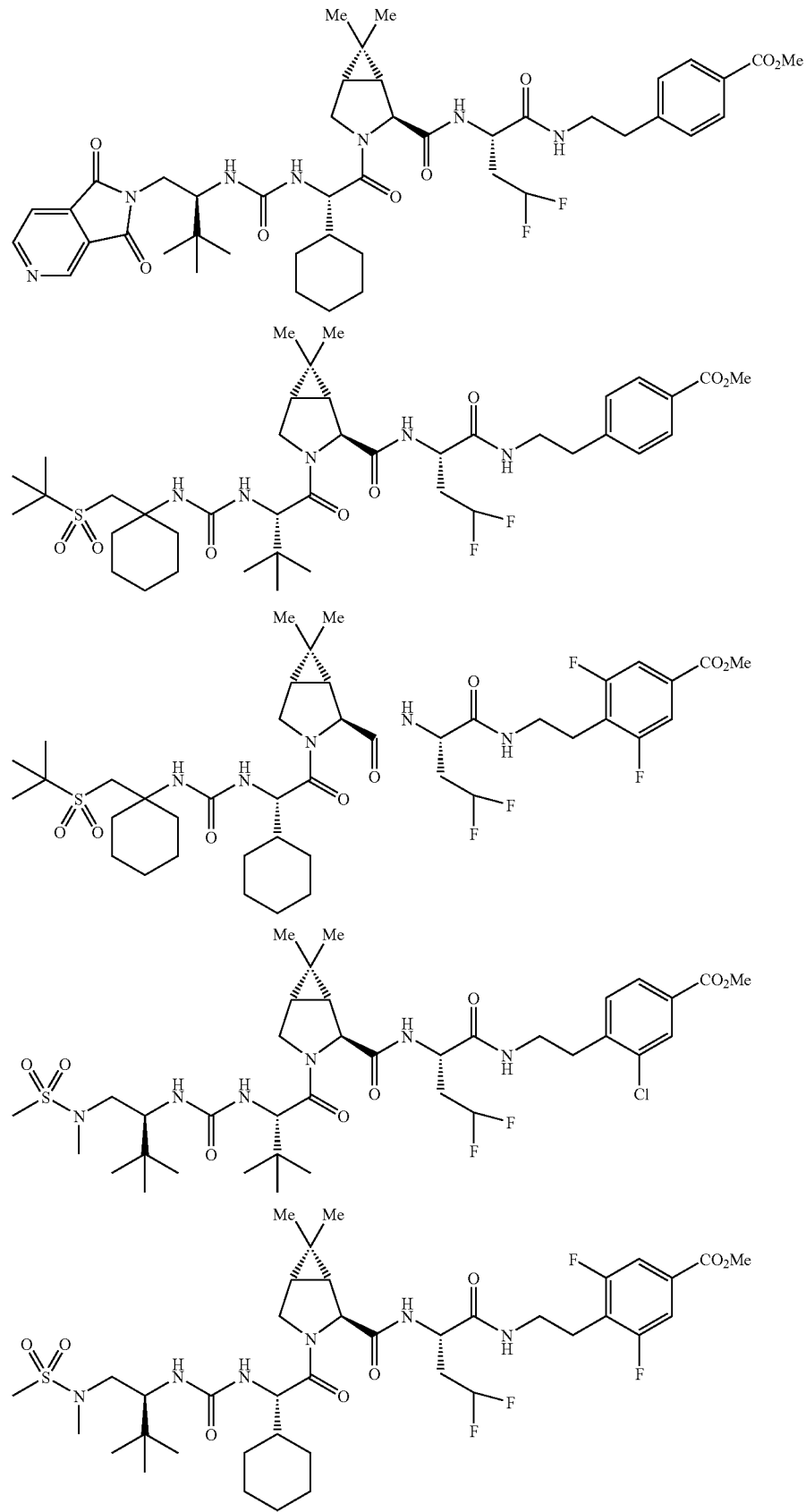

-continued
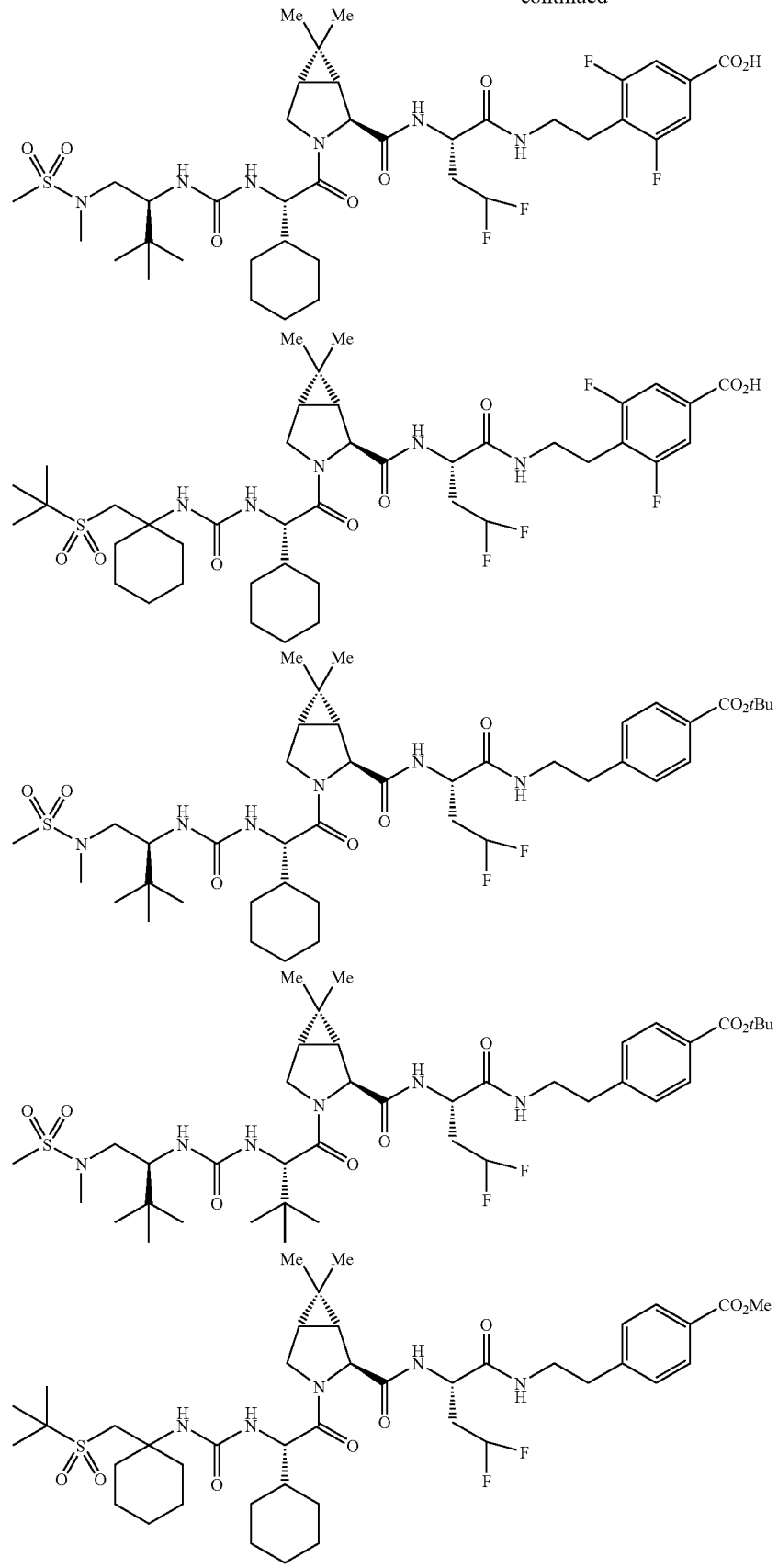

-continued
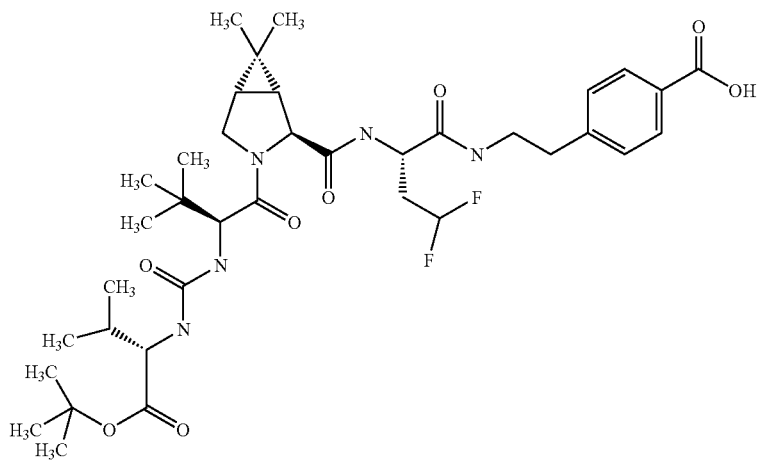
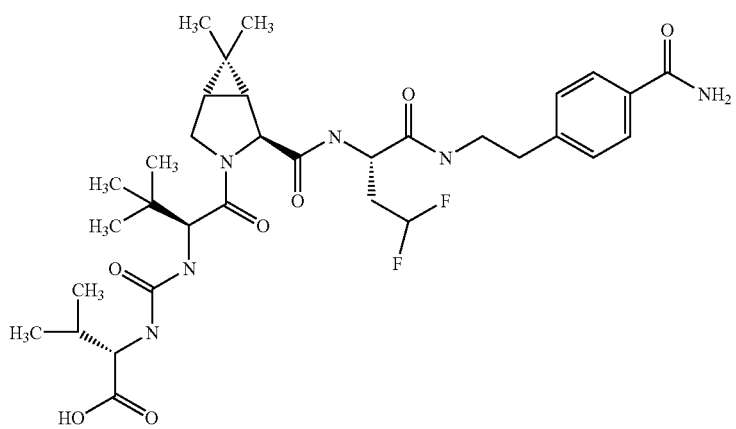
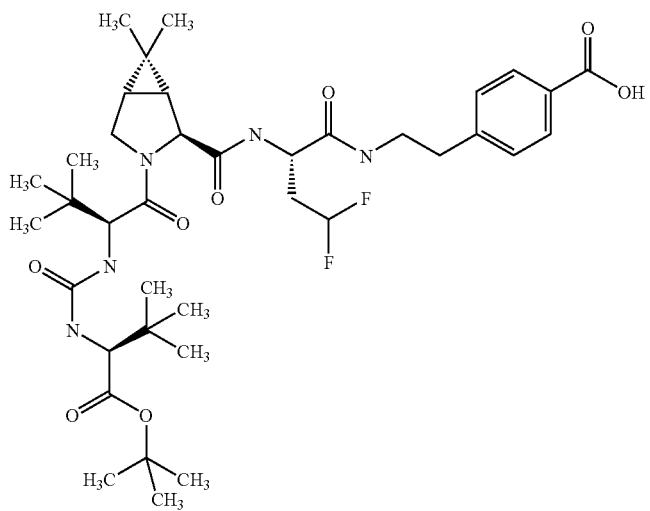

-continued
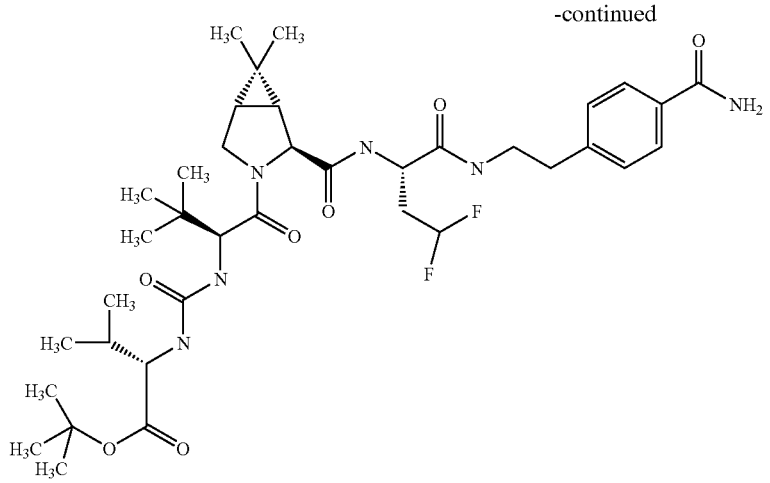
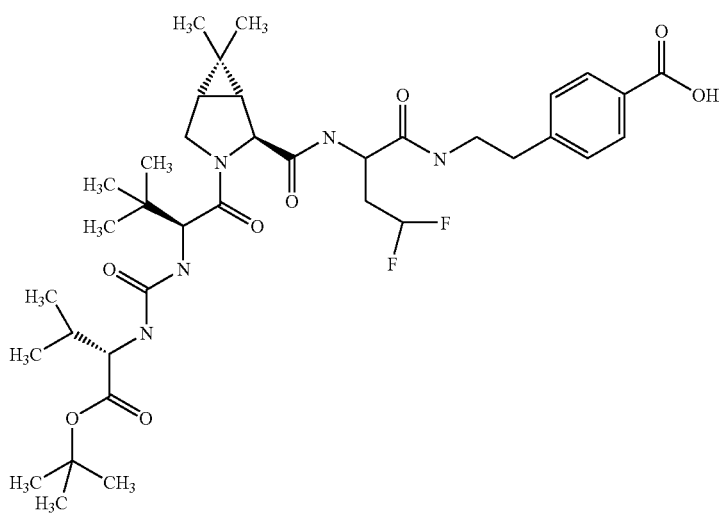
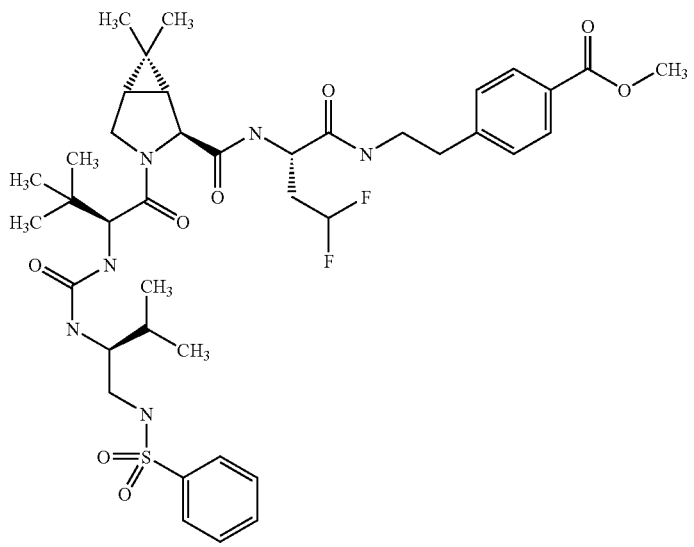

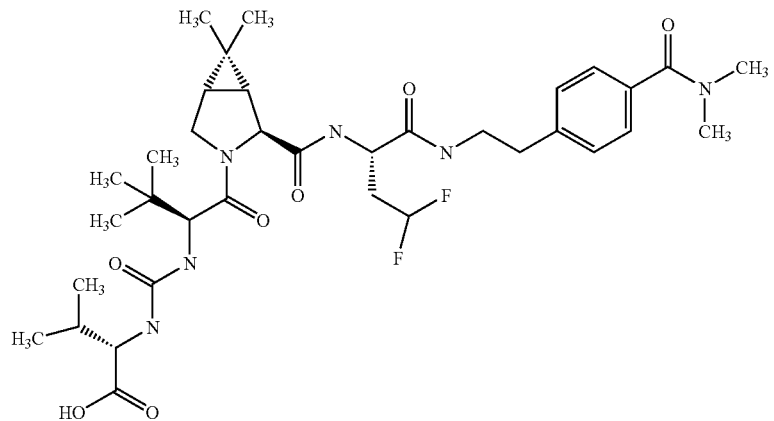
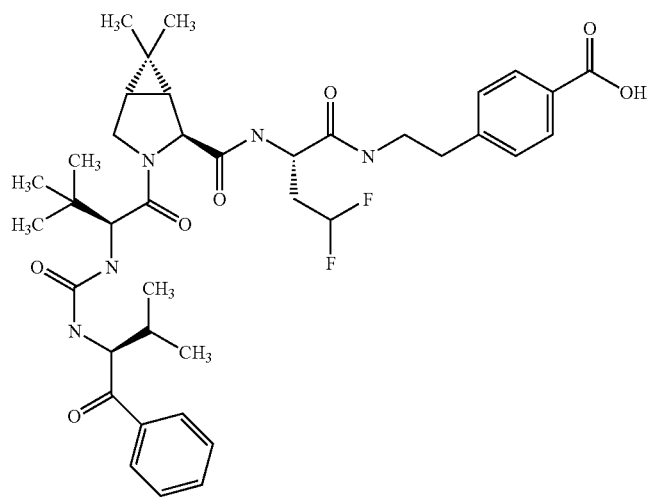
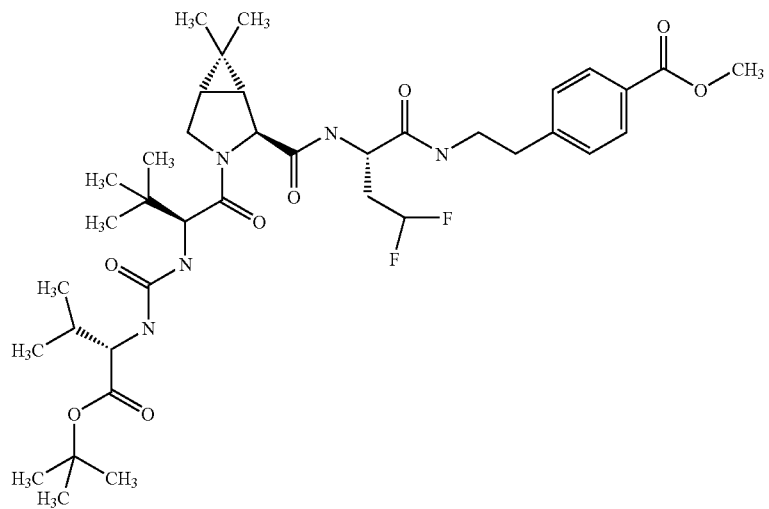

-continued
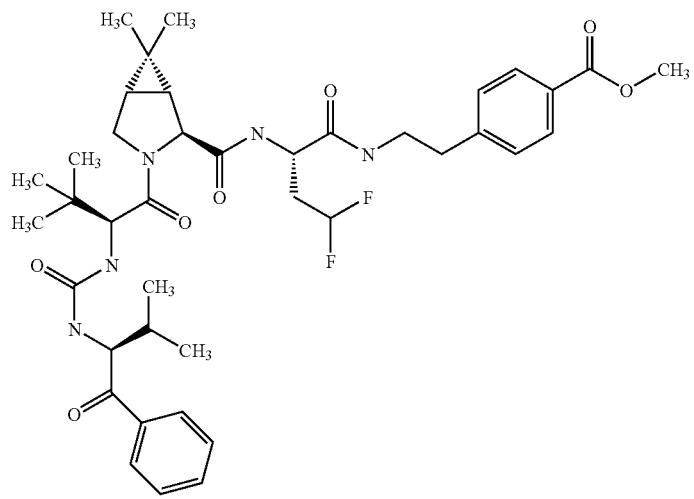
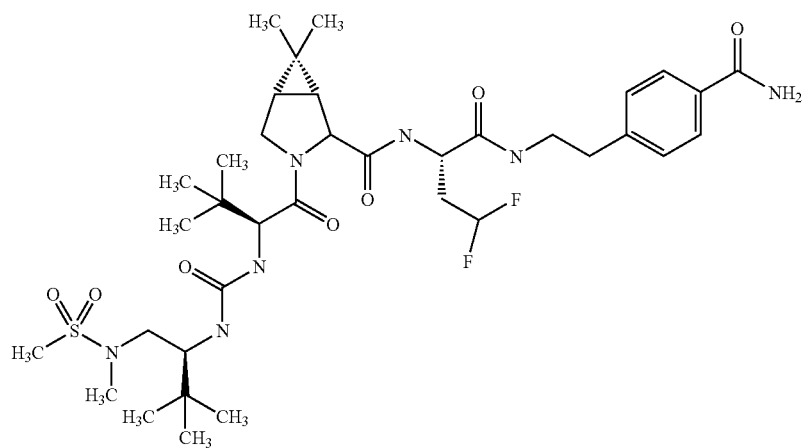
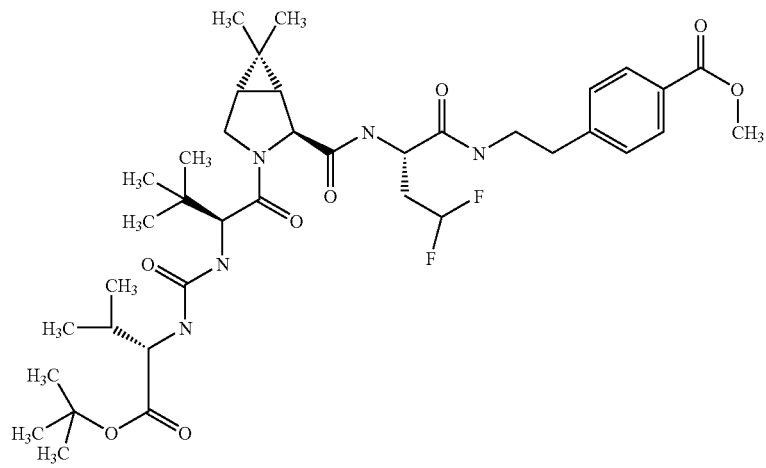

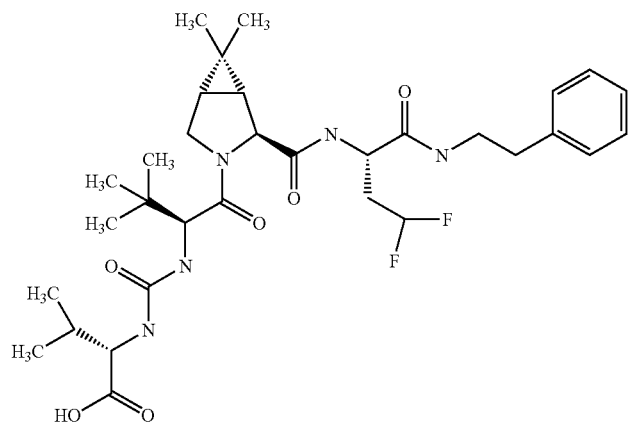
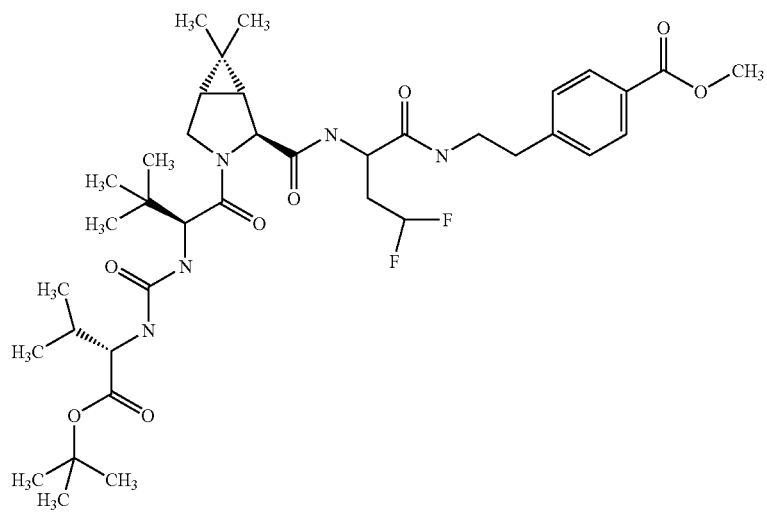
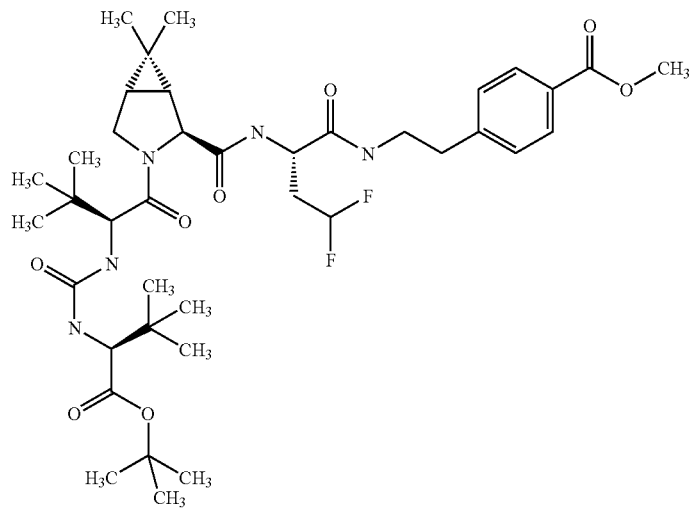

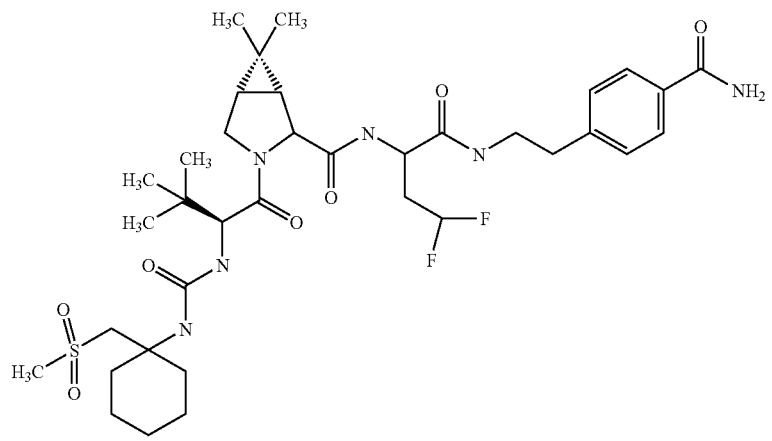
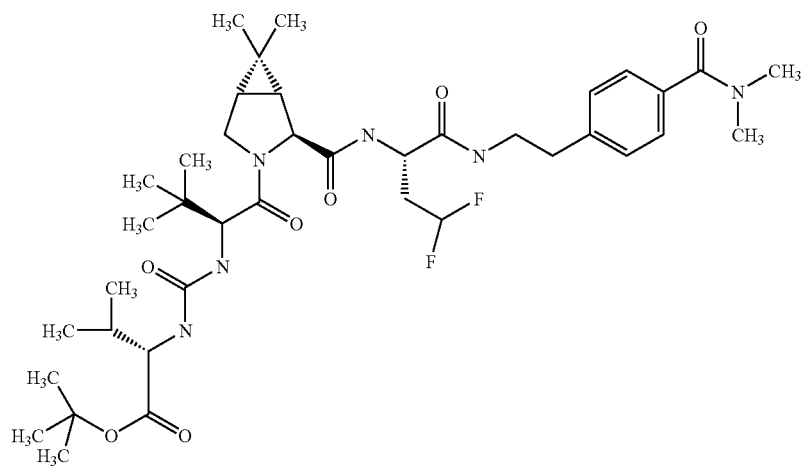
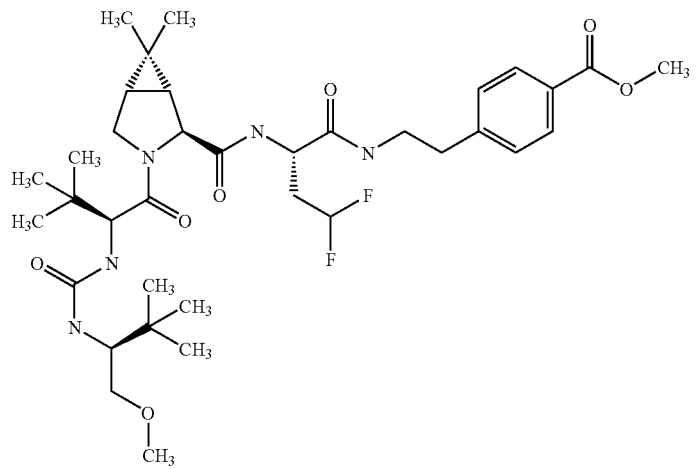

-continued
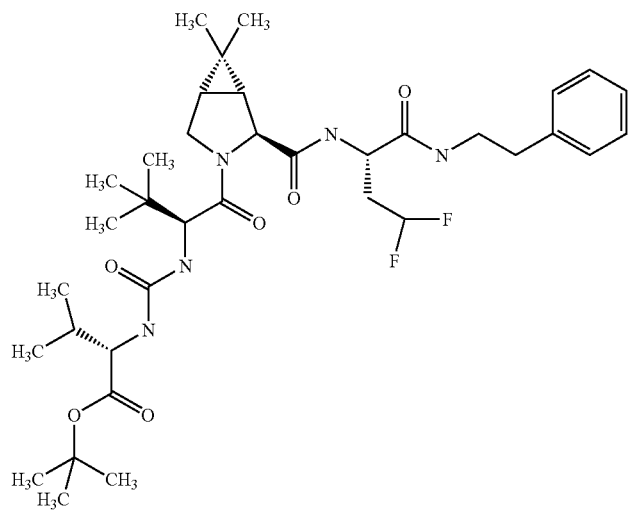
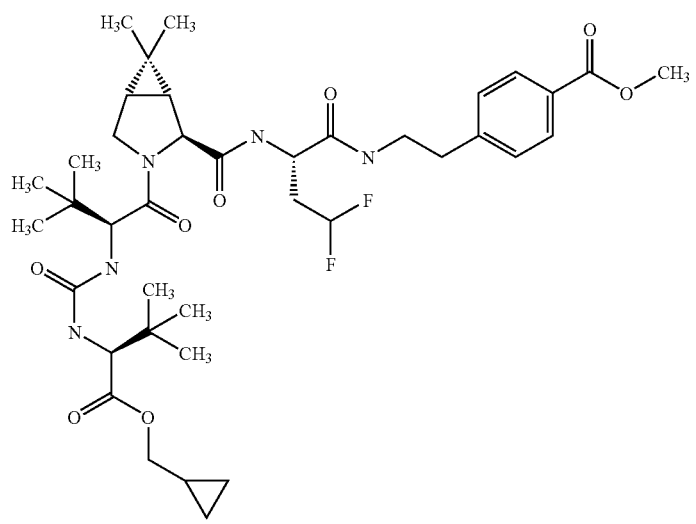
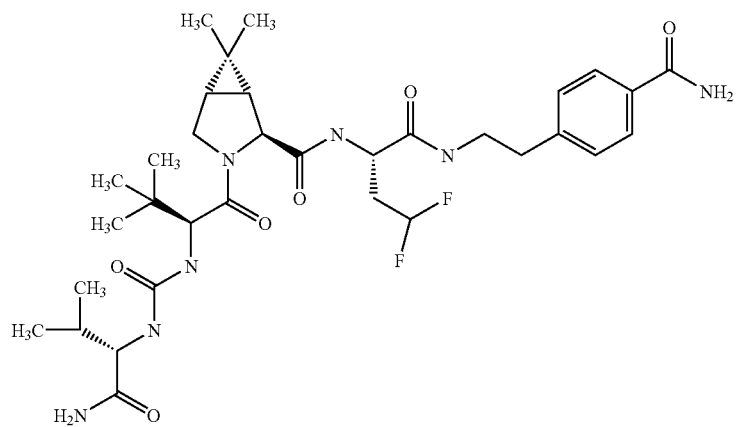

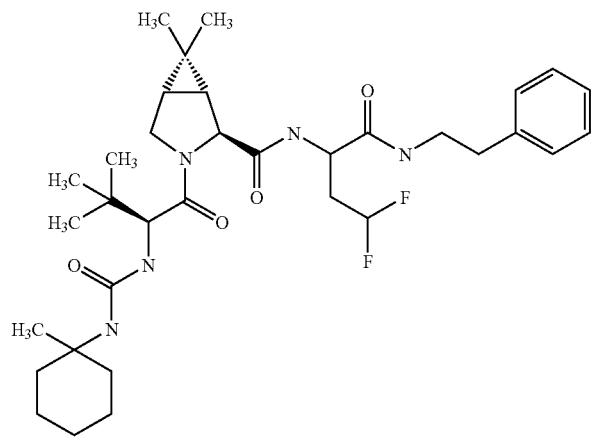
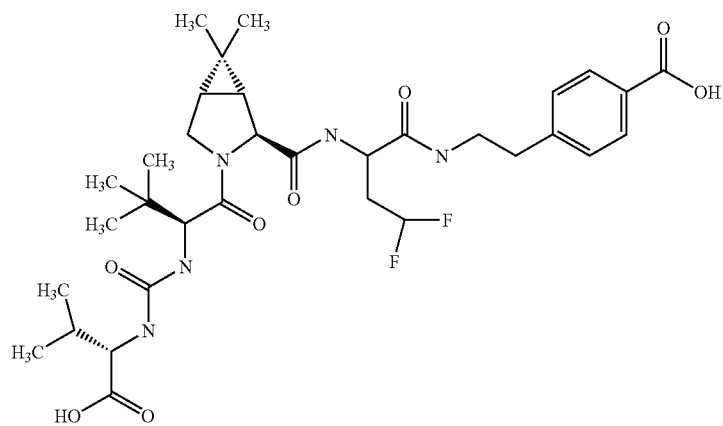
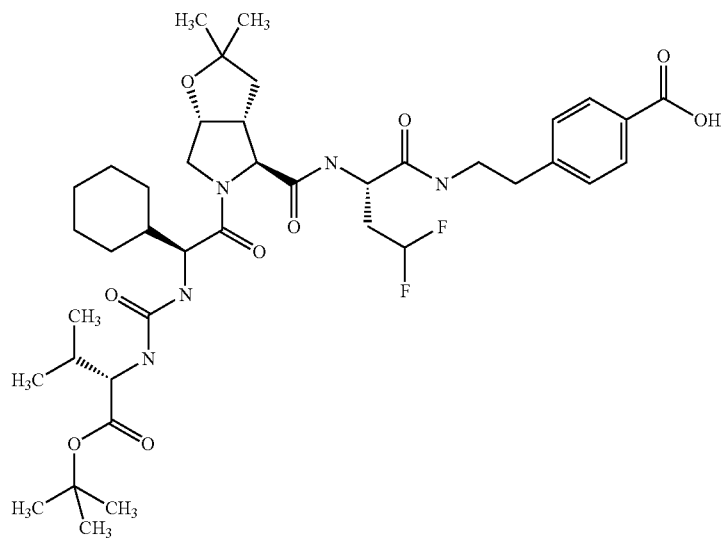

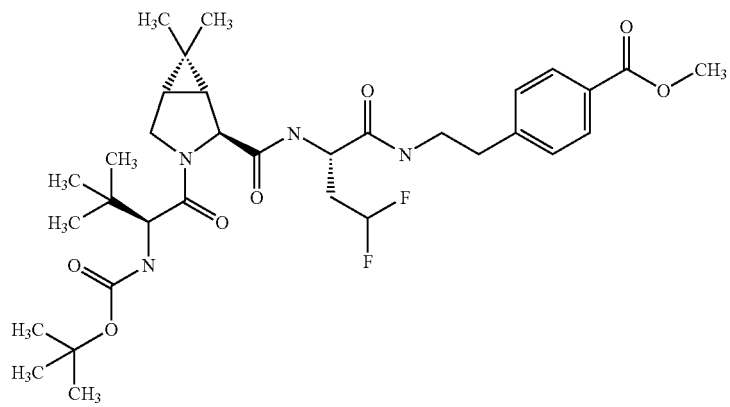
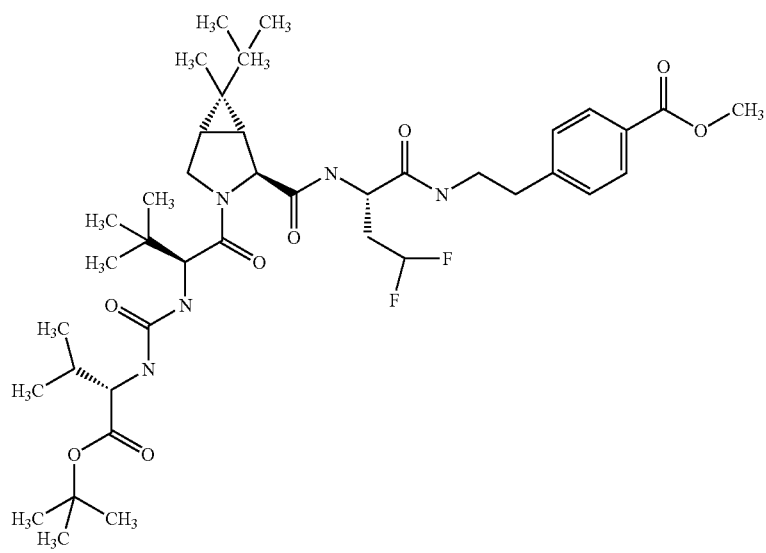
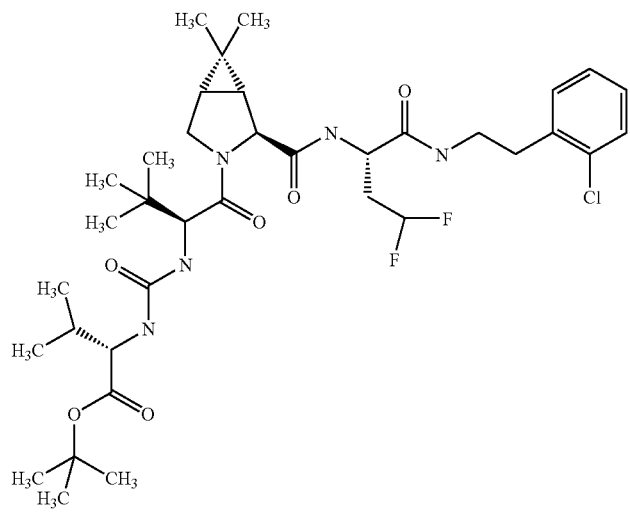

387
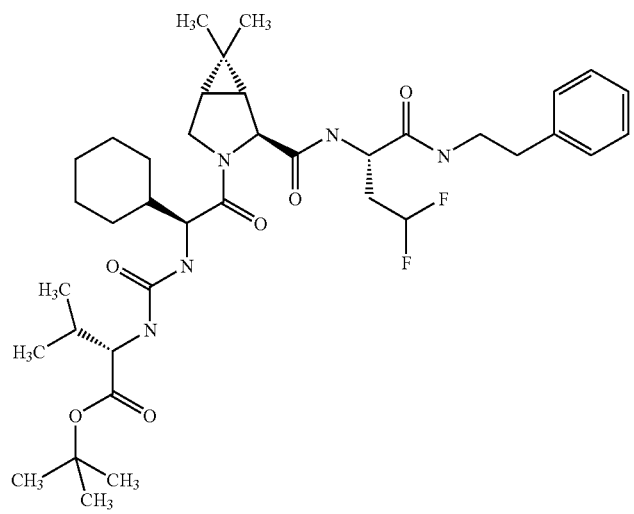
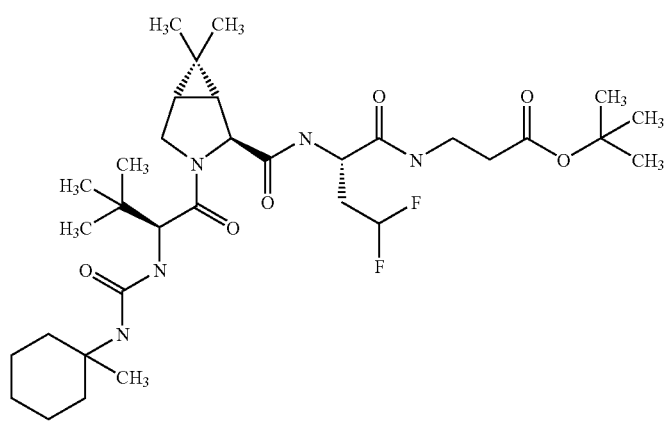
388
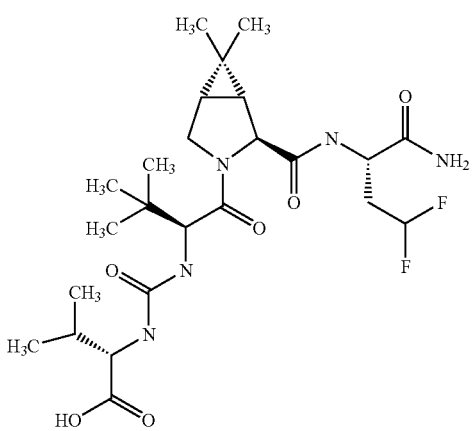
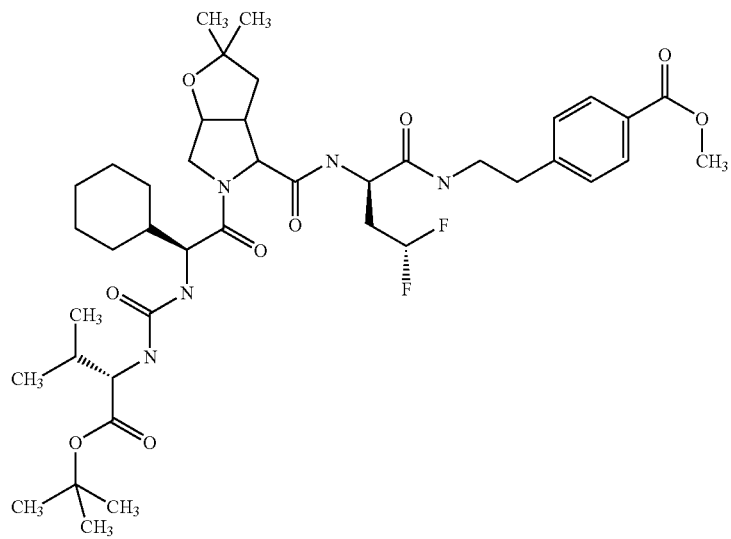

-continued
389
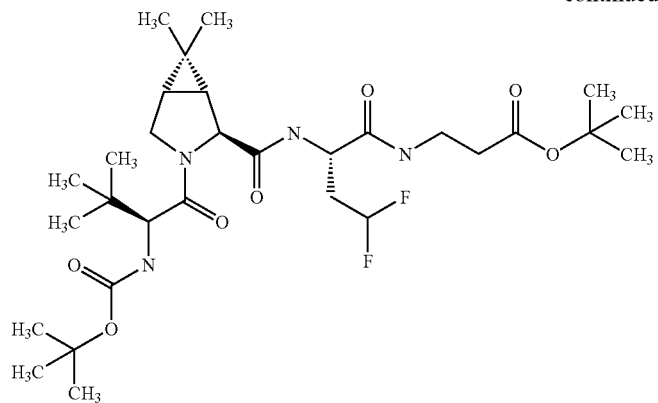
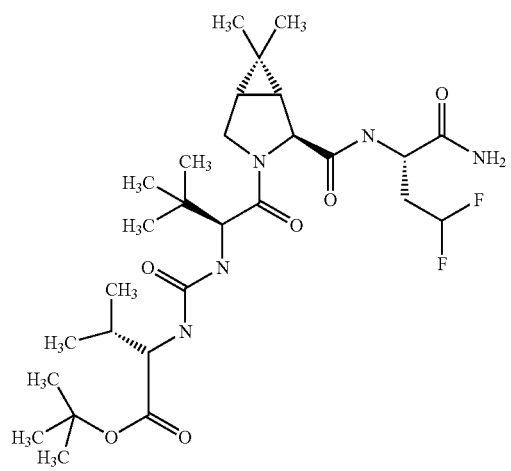
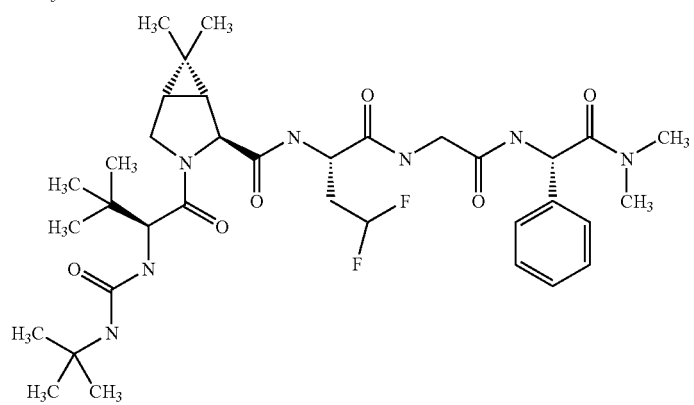
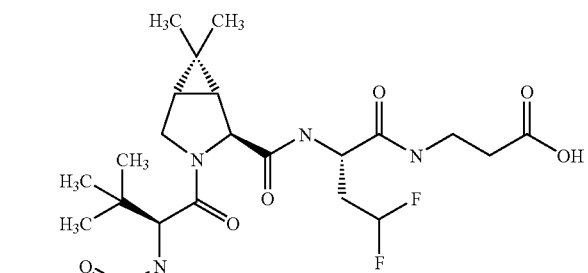
390
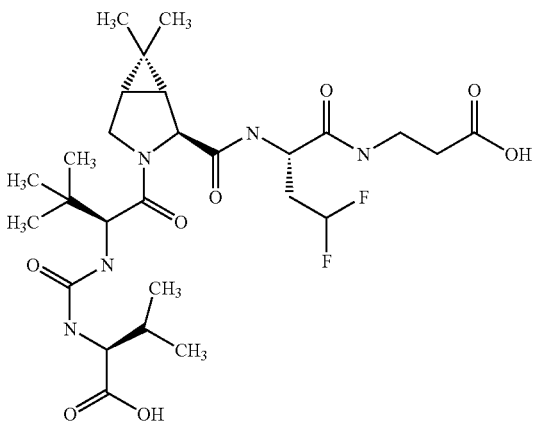
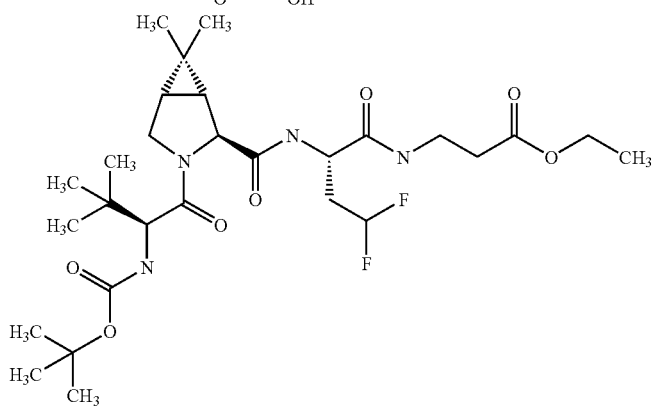
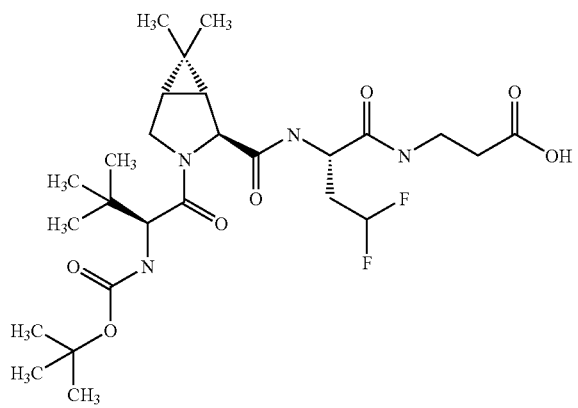

-continued
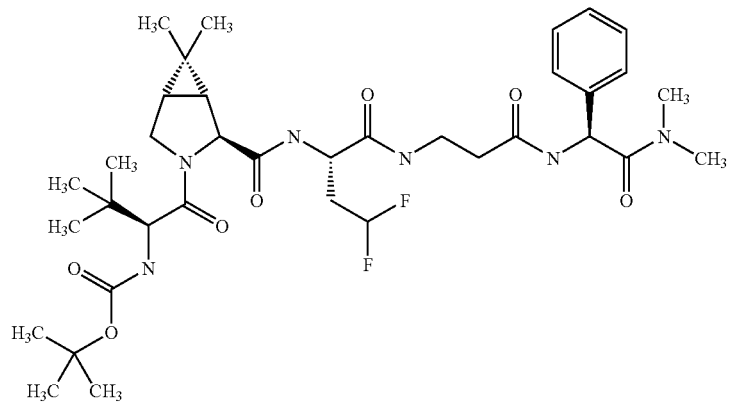
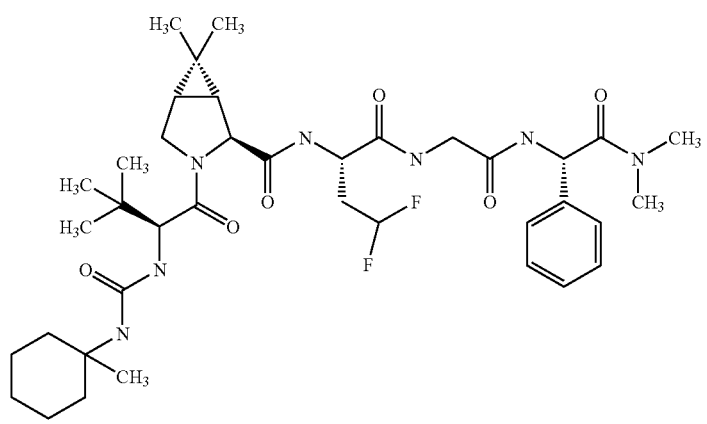
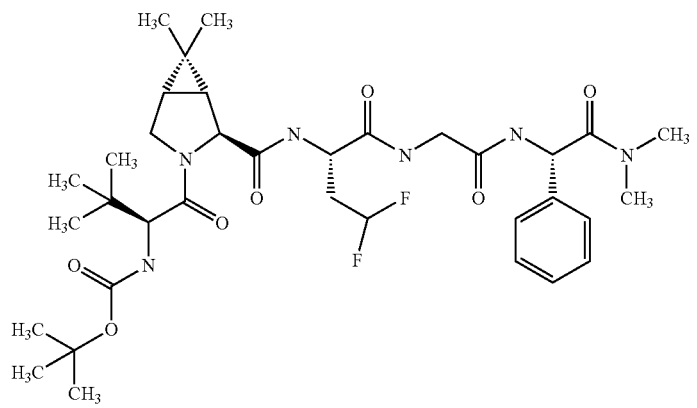

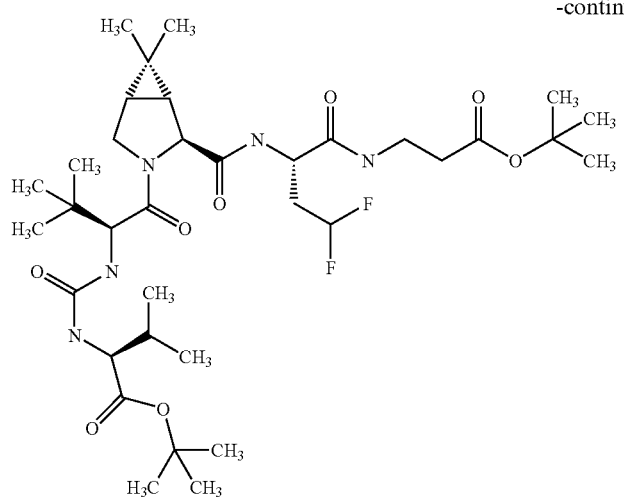
or a pharmaceutically acceptable salt thereof.
31. A compound selected from the following structures:
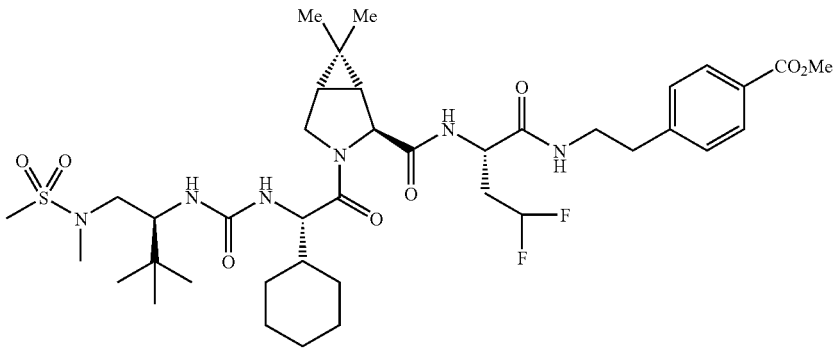
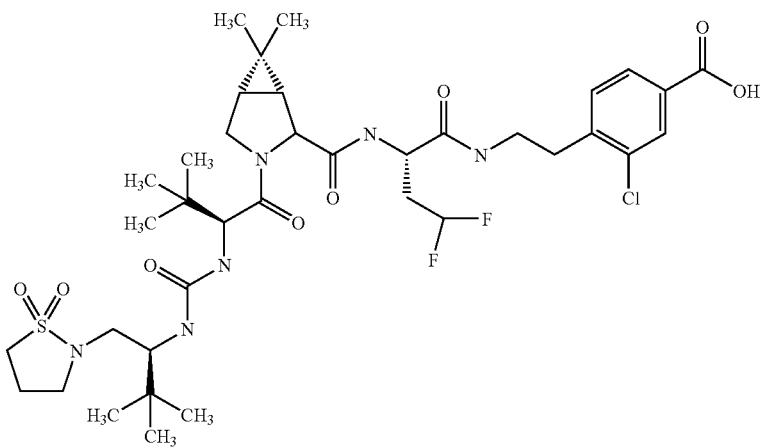

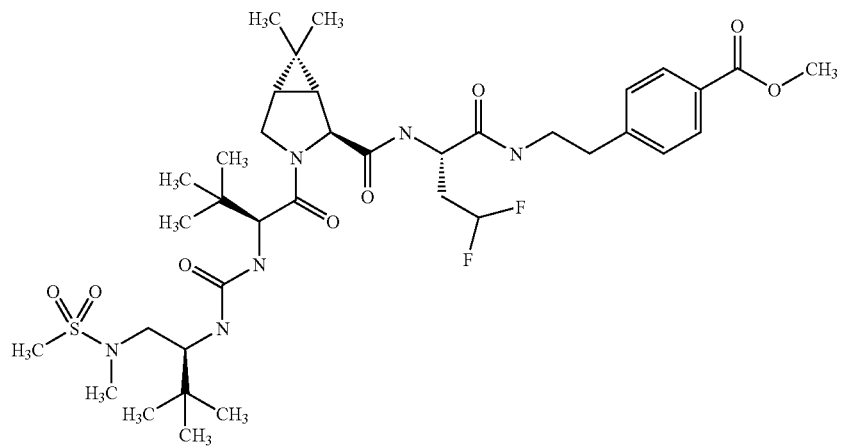
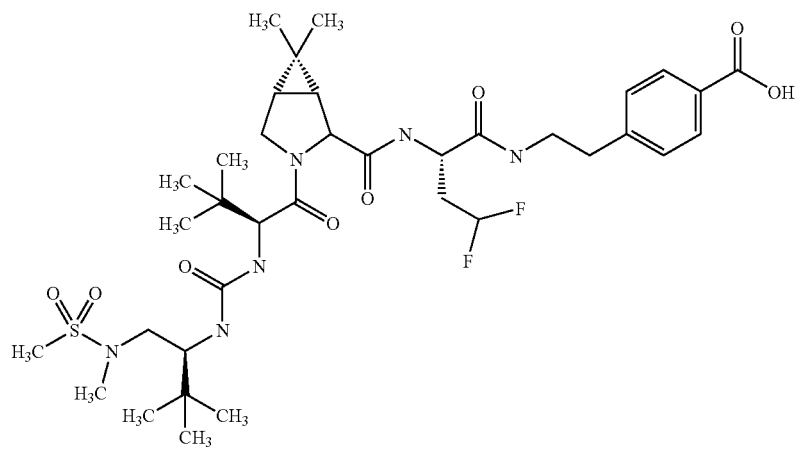
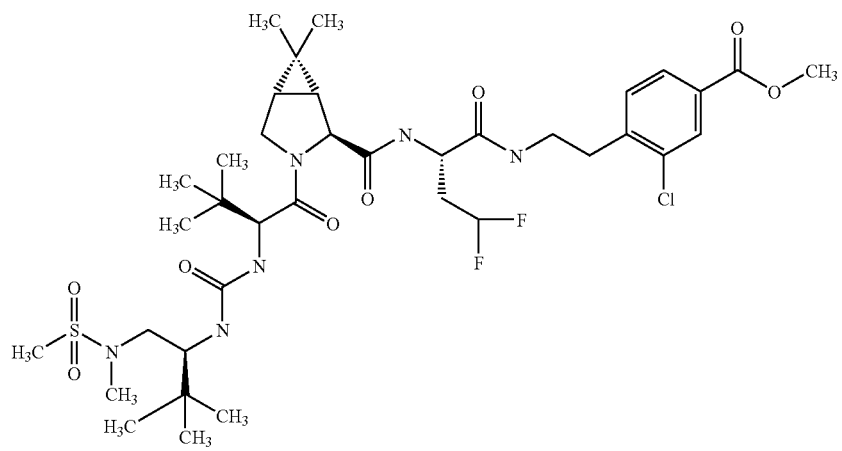

-continued
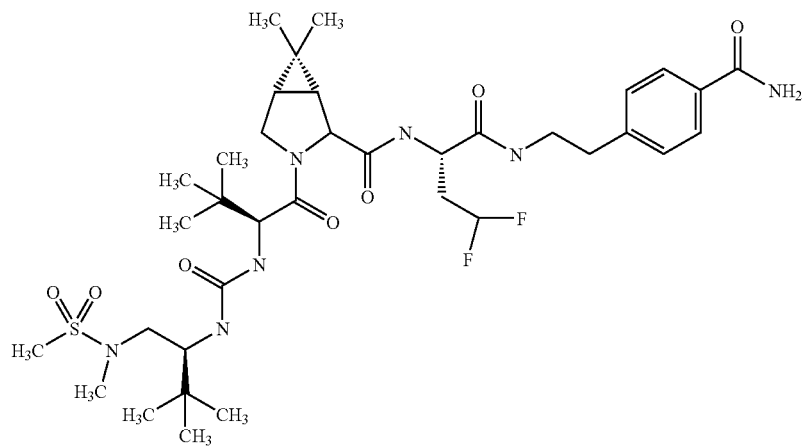
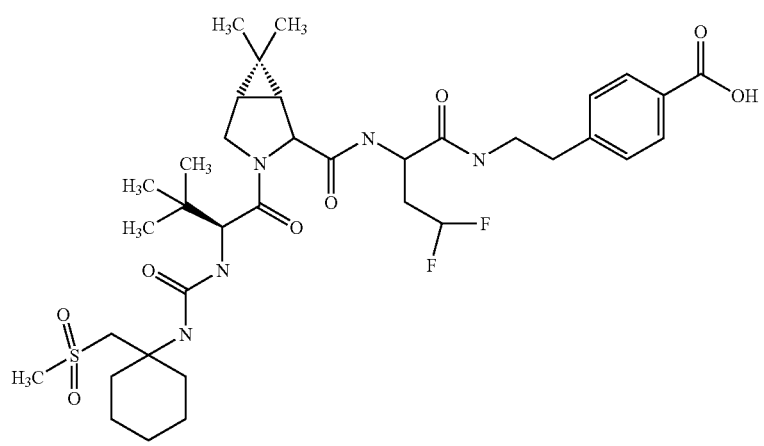
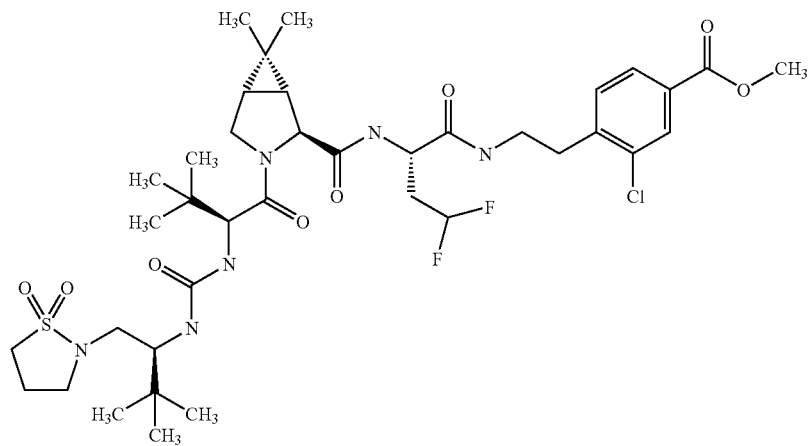

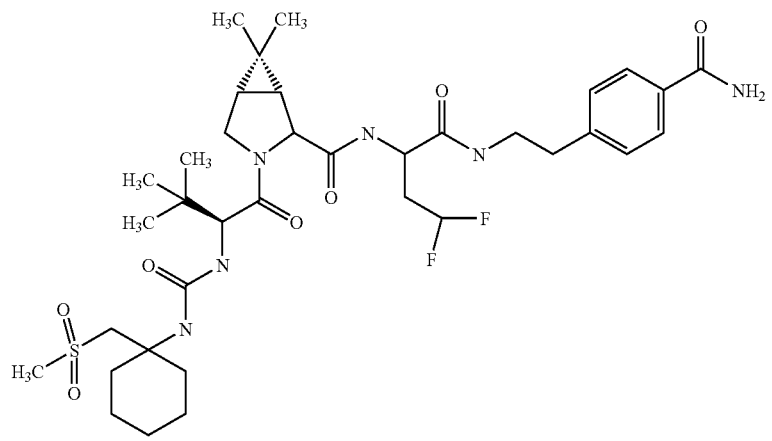
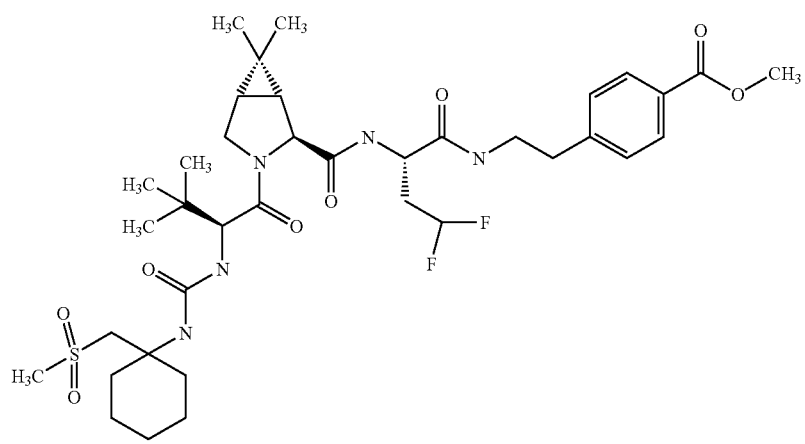
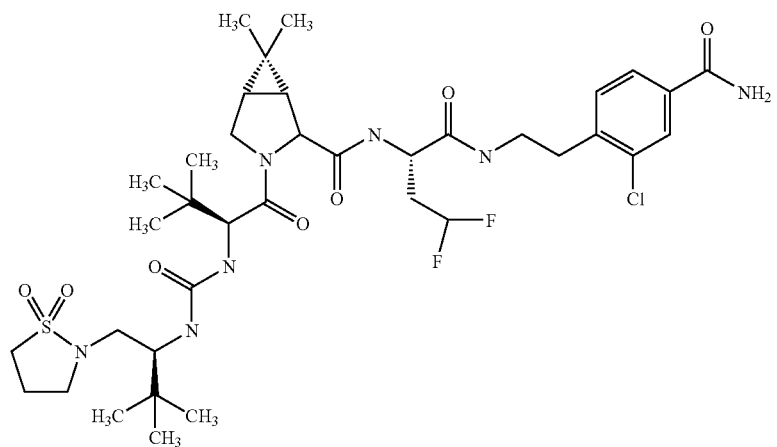

-continued
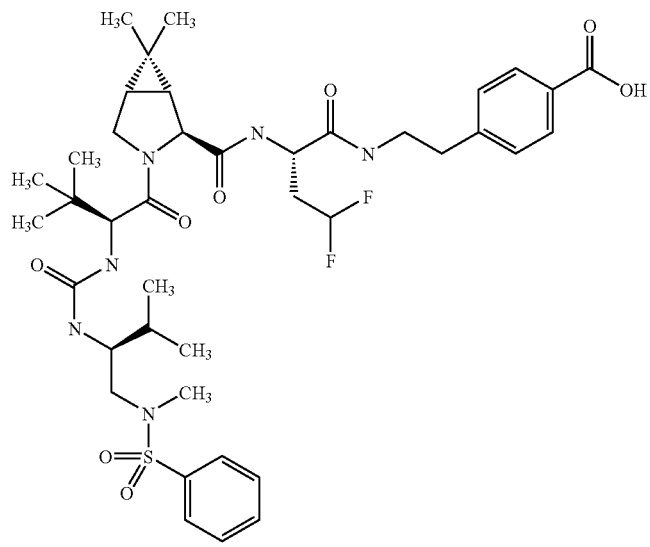
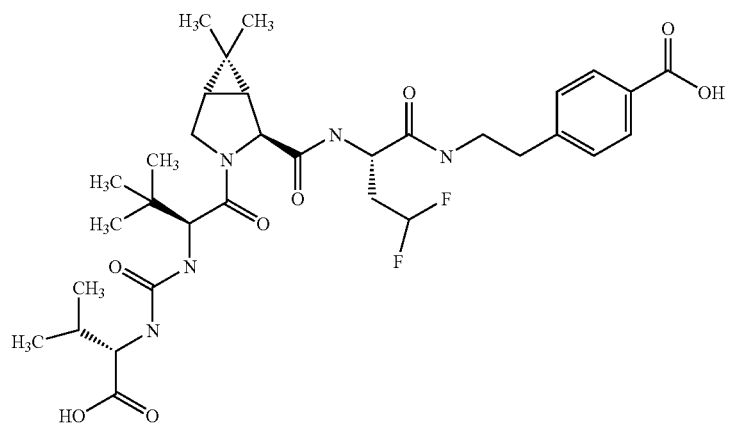
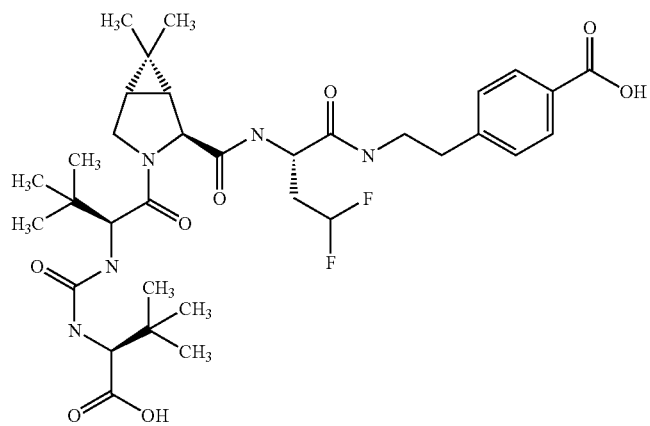

-continued

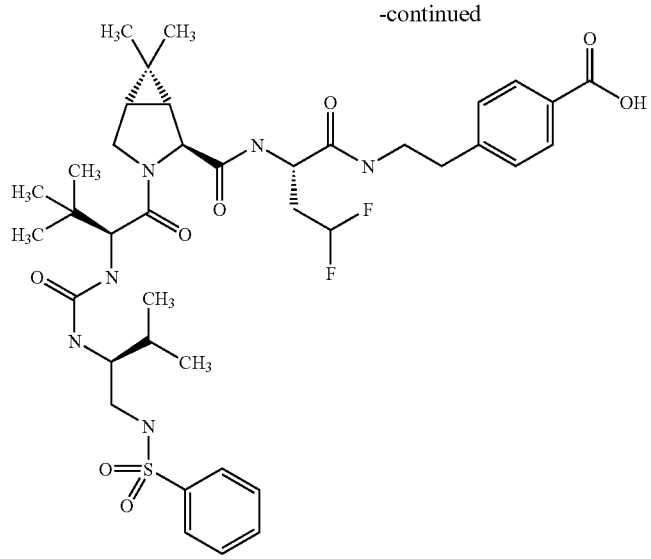

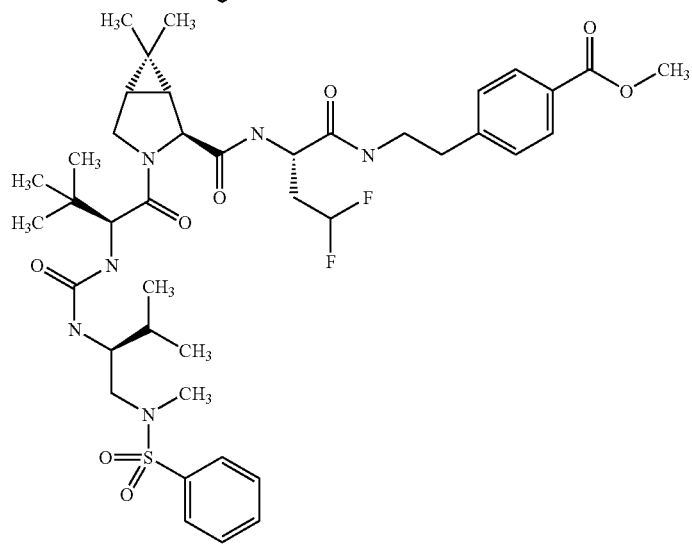

or a pharmaceutically acceptable salt thereof.

32. The compounds according to claim 1, with the proviso that when $R^1$ is O, P' is not H.

33. A pharmaceutical composition comprising as an active ingredient at least one compound of claim 1.

34. The pharmaceutical composition according to claim 33 additionally comprising a pharmaceutically acceptable carrier.

35. The pharmaceutical composition according to claim 34, additionally containing an antiviral agent.

36. The pharmaceutical composition according to claim 35, additionally containing an interferon or pegylated interferon.

37. The pharmaceutical composition according to claim 36, wherein said antiviral agent is ribavirin and said interferon is α-interferon.

38. A method of treating HCV infection, said method comprising administering to a patient in need of such treatment a pharmaceutical composition which comprises therapeutically effective amounts of a compound according to claim 1.

39. The method according to claim 38, wherein said administration is subcutaneous.

40. The method according to claim 38, wherein said administration is oral.

41. A compound of claim 1 in "purified" form.

* * * * *

UNITED STATES PATENT AND TRADEMARK OFFICE
CERTIFICATE OF CORRECTION

PATENT NO. : 7,449,447 B2
APPLICATION NO. : 10/925329
DATED : November 11, 2008
INVENTOR(S) : Chen et al.

It is certified that error appears in the above-identified patent and that said Letters Patent is hereby corrected as shown below:

Claim 1 at Column 275, line 63 delete "alkykaryl" and replace it with --alkyl-aryl--.

Claim 3 at Column 277, lines 25-35 delete the following:

" 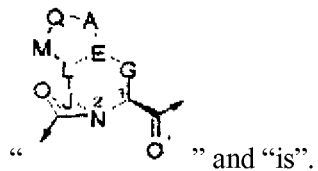 " and "is".

Claim 4 at Column 279, lines 39-50 delete the following:

" 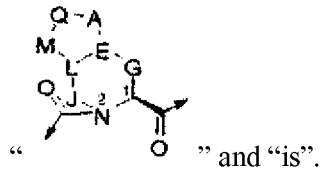 " and "is".

Claim 5 at Column 281, lines 1-14 delete the following:

" 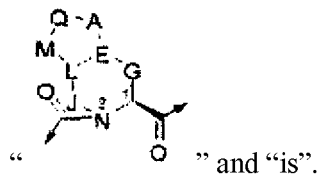 " and "is".

Claim 6 at Column 281, lines 45-54 delete the following:

" 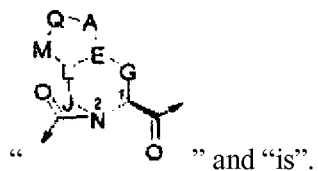 " and "is".

Claim 8 at Column 285, lines 29 replace "Y30" and replace it with --$Y^{30}$--.

UNITED STATES PATENT AND TRADEMARK OFFICE
CERTIFICATE OF CORRECTION

PATENT NO.        : 7,449,447 B2
APPLICATION NO.   : 10/925329
DATED             : November 11, 2008
INVENTOR(S)       : Chen et al.

It is certified that error appears in the above-identified patent and that said Letters Patent is hereby corrected as shown below:

Claim 8 at Column 288, lines 8-15 delete the following:

" 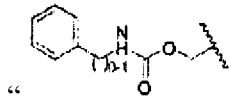 " and replace with the following:

-- 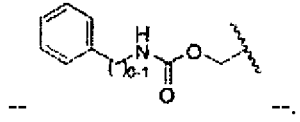 --.

Claim 8 at Column 292, lines 41-47 delete the following:

" 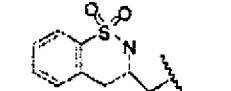 " and replace with the following:

-- 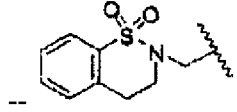 --.

Claim 8 at Column 292, lines 53-60 delete the following:

" 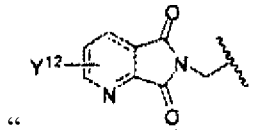 " and replace with the following:

-- 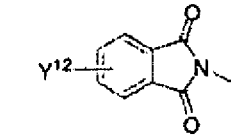 --.

UNITED STATES PATENT AND TRADEMARK OFFICE
CERTIFICATE OF CORRECTION

PATENT NO. : 7,449,447 B2
APPLICATION NO. : 10/925329
DATED : November 11, 2008
INVENTOR(S) : Chen et al.

It is certified that error appears in the above-identified patent and that said Letters Patent is hereby corrected as shown below:

Claim 11 at Column 311, lines 10-16 delete the following:

" 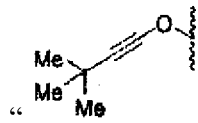 " and replace with the following:

-- 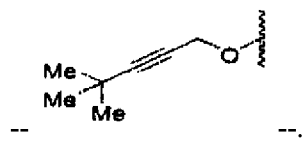 --.

Claim 12 at Column 320, line 52 delete "Gap" and replace it with --Cap--.

Claim 17 at Column 329, lines 9-14 delete the following:

" 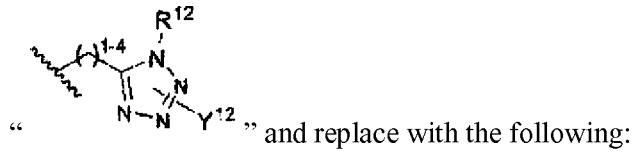 " and replace with the following:

-- 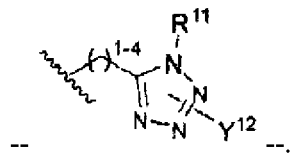 --.

Claim 17 at Column 329, line 51 delete "NHSO2CH3, CONH(CH3)2, NHCOCH3" and replace it with --$NHSO_2CH_3$, $CONH(CH_3)_2$, $NHCOCH_3$--.

Claim 17 at Column 329, line 52 delete "NO2" and replace it with --$NO_2$--.

Claim 18 at Column 332, lines 10-15 delete the following:

" 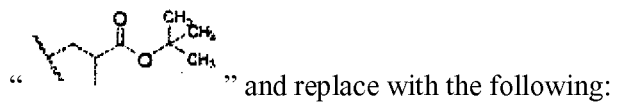 " and replace with the following:

-- 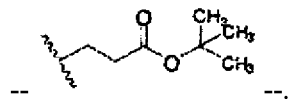 --.

UNITED STATES PATENT AND TRADEMARK OFFICE
CERTIFICATE OF CORRECTION

PATENT NO. : 7,449,447 B2
APPLICATION NO. : 10/925329
DATED : November 11, 2008
INVENTOR(S) : Chen et al.

It is certified that error appears in the above-identified patent and that said Letters Patent is hereby corrected as shown below:

Claim 21 at Column 336, lines 48-53 delete the following:

"  " and replace with the following:

-- 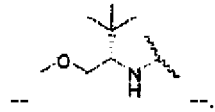 --.

Claim 28 at Column 352, lines 53-59 delete the following:

" 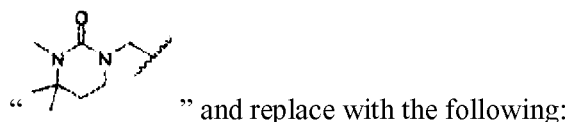 " and replace with the following:

-- 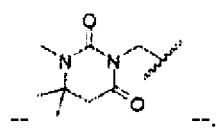 --.

Claim 30 at Column 355, lines 0-25 delete the following:

" 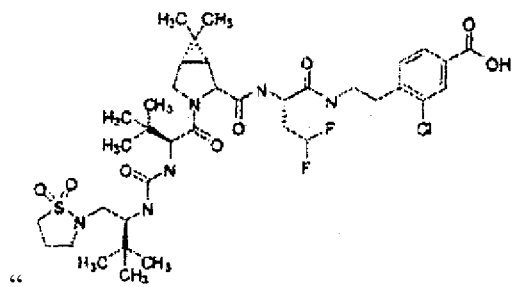 " and replace with the following:

--  --.

UNITED STATES PATENT AND TRADEMARK OFFICE
CERTIFICATE OF CORRECTION

PATENT NO. : 7,449,447 B2
APPLICATION NO. : 10/925329
DATED : November 11, 2008
INVENTOR(S) : Chen et al.

It is certified that error appears in the above-identified patent and that said Letters Patent is hereby corrected as shown below:

Claim 30 at Column 355, lines 55-65 delete the following:

" 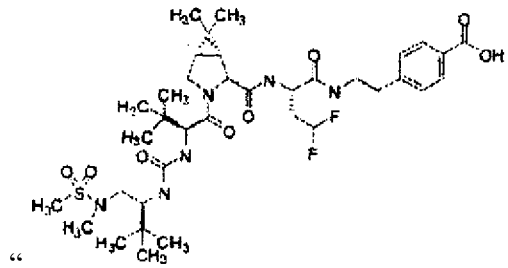 " and replace with the following:

-- 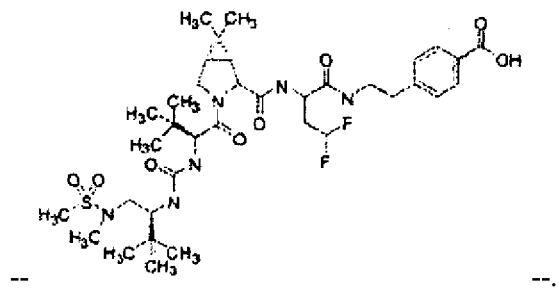 --.

Claim 30 at Column 357, lines 25-40 delete the following:

" 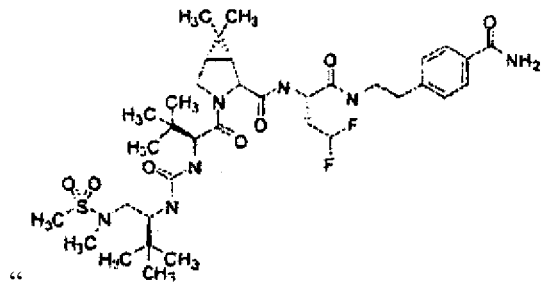 " and replace with the following:

-- 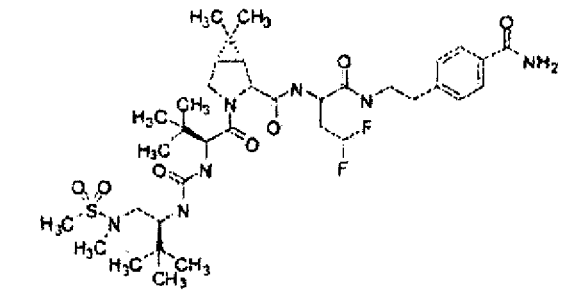 --.

UNITED STATES PATENT AND TRADEMARK OFFICE
CERTIFICATE OF CORRECTION

PATENT NO. : 7,449,447 B2  
APPLICATION NO. : 10/925329  
DATED : November 11, 2008  
INVENTOR(S) : Chen et al.

It is certified that error appears in the above-identified patent and that said Letters Patent is hereby corrected as shown below:

Claim 30 at Column 361, lines 0-25 delete the following:

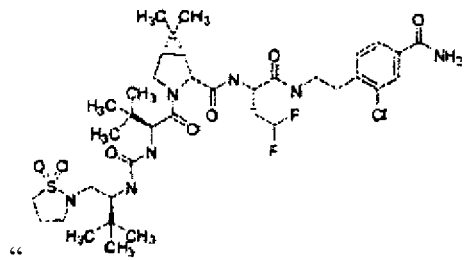

" and replace with the following:

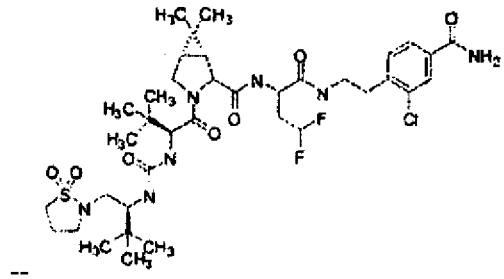

--.

Claim 30 at Column 365, lines 33-43 delete the following:

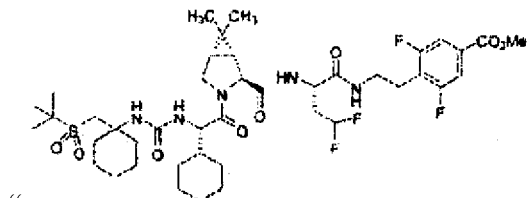

" and replace with the following:

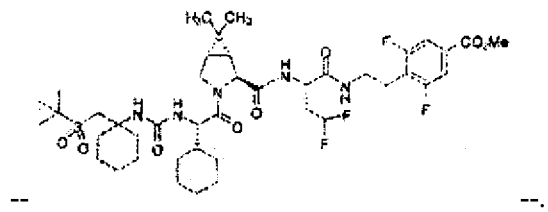

--.

UNITED STATES PATENT AND TRADEMARK OFFICE
CERTIFICATE OF CORRECTION

PATENT NO.      : 7,449,447 B2
APPLICATION NO. : 10/925329
DATED           : November 11, 2008
INVENTOR(S)     : Chen et al.

It is certified that error appears in the above-identified patent and that said Letters Patent is hereby corrected as shown below:

Claim 30 at Column 373, lines 53-65 delete the following:

"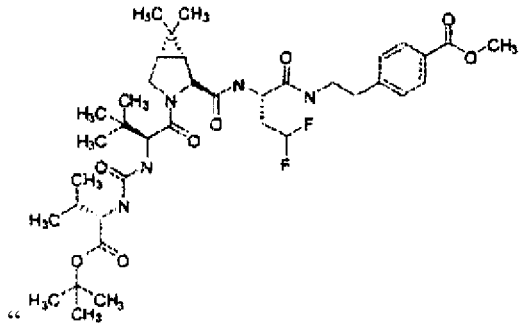" and replace with the following:

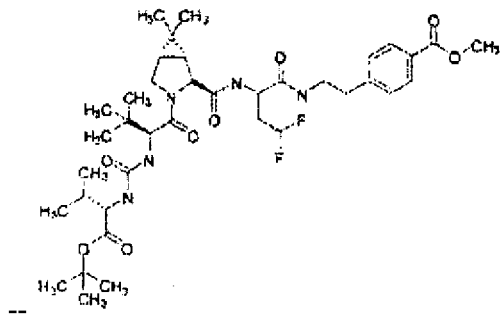
--.

Claim 30 at Column 375, lines 25-53 delete the following:

"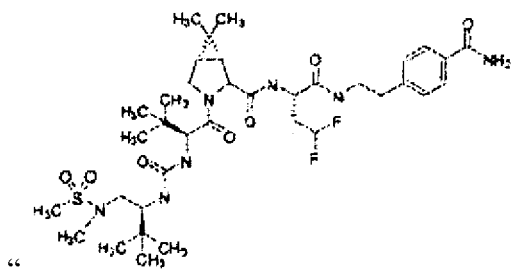" and replace with the following:

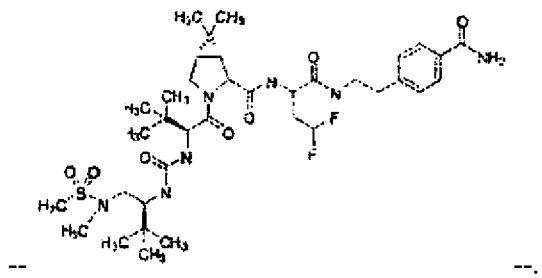
--.

UNITED STATES PATENT AND TRADEMARK OFFICE
CERTIFICATE OF CORRECTION

PATENT NO. : 7,449,447 B2
APPLICATION NO. : 10/925329
DATED : November 11, 2008
INVENTOR(S) : Chen et al.

It is certified that error appears in the above-identified patent and that said Letters Patent is hereby corrected as shown below:

Claim 30 at Column 377, lines 0-25 delete the following:

"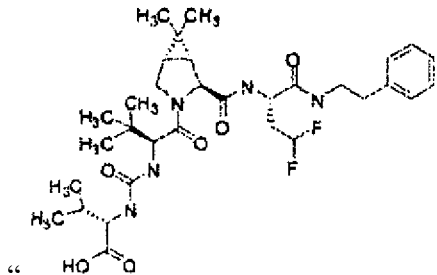 " and replace with the following:

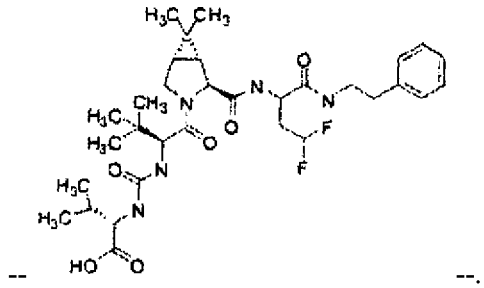 --.

Claim 30 at Column 381, lines 0-25 delete the following:

"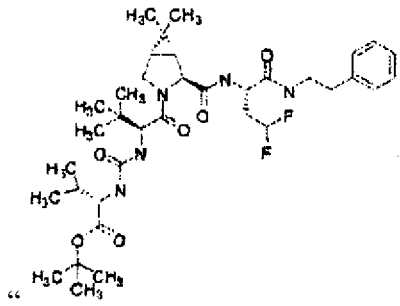 " and replace with the following:

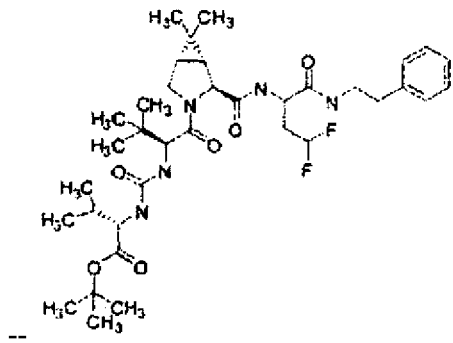 --.

UNITED STATES PATENT AND TRADEMARK OFFICE
CERTIFICATE OF CORRECTION

PATENT NO. : 7,449,447 B2
APPLICATION NO. : 10/925329
DATED : November 11, 2008
INVENTOR(S) : Chen et al.

It is certified that error appears in the above-identified patent and that said Letters Patent is hereby corrected as shown below:

Claim 30 at Column 385, lines 25-53 delete the following:

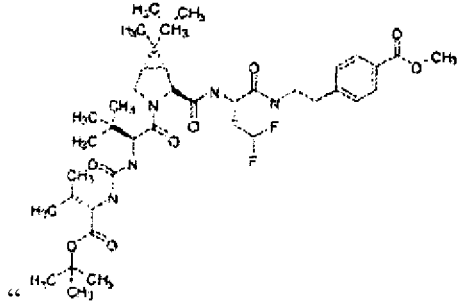

" and replace with the following:

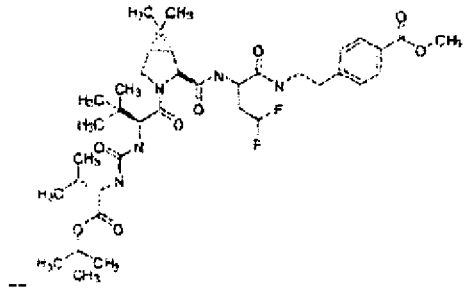

--.

Claim 30 at Column 385, lines 55-65 delete the following:

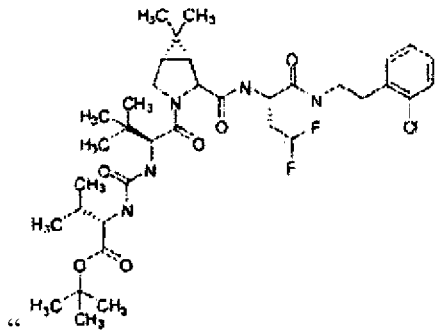

" and replace with the following:

UNITED STATES PATENT AND TRADEMARK OFFICE
CERTIFICATE OF CORRECTION

PATENT NO. : 7,449,447 B2  
APPLICATION NO. : 10/925329  
DATED : November 11, 2008  
INVENTOR(S) : Chen et al.

Page 10 of 12

It is certified that error appears in the above-identified patent and that said Letters Patent is hereby corrected as shown below:

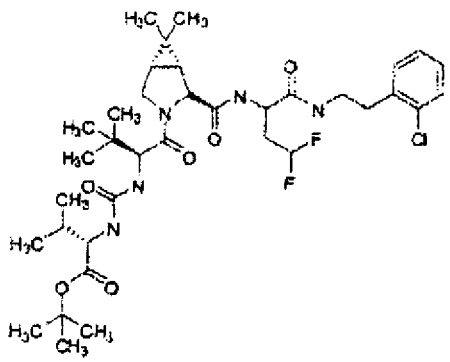

-- --.

Claim 30 at Column 387, lines 55-65 delete the following:

"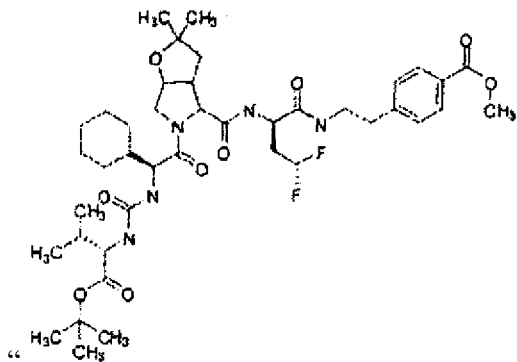" and replace with the following:

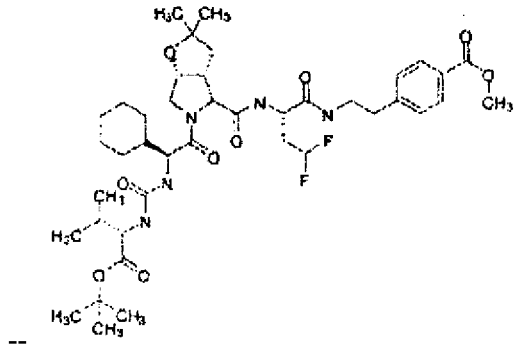

-- --.

UNITED STATES PATENT AND TRADEMARK OFFICE
CERTIFICATE OF CORRECTION

PATENT NO. : 7,449,447 B2
APPLICATION NO. : 10/925329
DATED : November 11, 2008
INVENTOR(S) : Chen et al.

It is certified that error appears in the above-identified patent and that said Letters Patent is hereby corrected as shown below:

Claim 31 at Column 394, lines 55-65 delete the following:

" 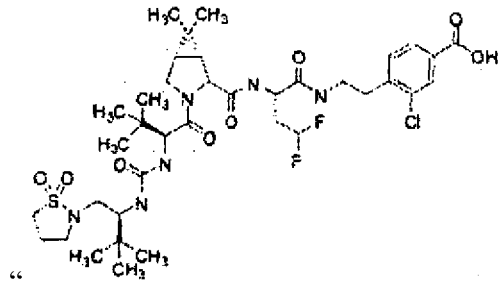 " and replace with the following:

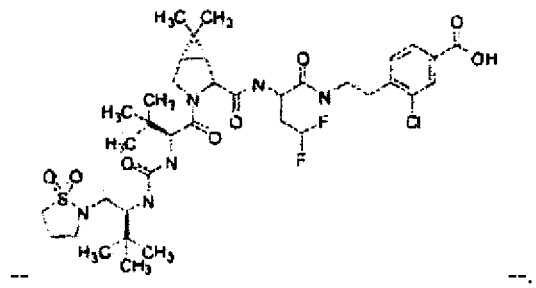 --.

Claim 31 at Column 395, lines 20-53 delete the following:

" 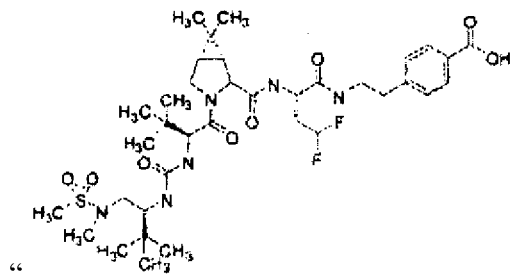 " and replace with the following:

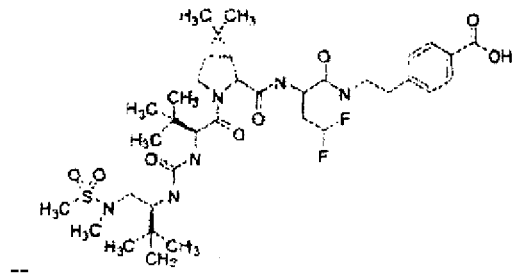 --.

UNITED STATES PATENT AND TRADEMARK OFFICE
CERTIFICATE OF CORRECTION

PATENT NO. : 7,449,447 B2  Page 12 of 12
APPLICATION NO. : 10/925329
DATED : November 11, 2008
INVENTOR(S) : Chen et al.

It is certified that error appears in the above-identified patent and that said Letters Patent is hereby corrected as shown below:

Claim 31 at Column 397, lines 0-20 delete the following:

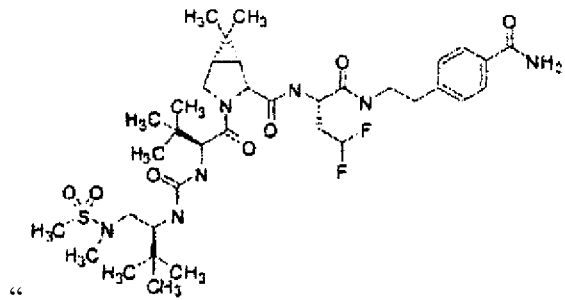

" and replace with the following:

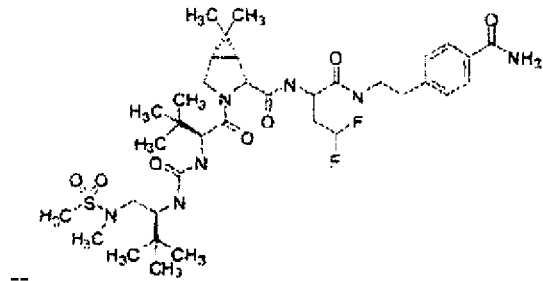

--.

Signed and Sealed this

Twenty-ninth Day of December, 2009

David J. Kappos
*Director of the United States Patent and Trademark Office*